(12) United States Patent
Park et al.

(10) Patent No.: US 12,082,500 B2
(45) Date of Patent: Sep. 3, 2024

(54) CONDENSED CYCLIC COMPOUND AND ORGANIC LIGHT-EMITTING DEVICE INCLUDING THE SAME

(71) Applicant: Samsung Display Co., Ltd, Yongin-si (KR)

(72) Inventors: Junha Park, Yongin-si (KR); Youngkook Kim, Yongin-si (KR); Munki Sim, Yongin-si (KR); Eunyoung Lee, Yongin-si (KR); Hyoyoung Lee, Yongin-si (KR); Eunjae Jeong, Yongin-si (KR); Seokhwan Hwang, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 482 days.

(21) Appl. No.: 15/371,066

(22) Filed: Dec. 6, 2016

(65) Prior Publication Data

US 2017/0179407 A1   Jun. 22, 2017

(30) Foreign Application Priority Data

Dec. 21, 2015 (KR) .................. 10-2015-0182792
Apr. 15, 2016 (KR) .................. 10-2016-0046499

(51) Int. Cl.
*H10K 85/60* (2023.01)
*C07D 221/18* (2006.01)
(Continued)

(52) U.S. Cl.
CPC ....... *H10K 85/6572* (2023.02); *C07D 221/18* (2013.01); *C07D 401/10* (2013.01);
(Continued)

(58) Field of Classification Search
CPC ............ H01L 51/0072; H01L 51/0067; C07F 9/5765; C07F 9/65583; C07F 9/6561; H10K 85/6572; H10K 85/654
See application file for complete search history.

(56) References Cited

U.S. PATENT DOCUMENTS 5,645,948 A   7/1997   Shi et al.
8,253,129 B2   8/2012   Kawamura
(Continued)

FOREIGN PATENT DOCUMENTS

JP   10-17860   1/1998
JP   11-87067   3/1999
(Continued)

OTHER PUBLICATIONS

Tang, "Organic electroluminescent diodes", Appl.Phys. Lett. ; 51, 913 (1987); doi: 10.1063/1.98799.
Adachi, Appl. Phys. Lett. "Confinement of charge carriers and molecular excitons within 5nmthick emitter layer in organic electroluminescent devices with a double heterostructure"; 57, 531 (1990); doi: 10.1063/1.103638.
(Continued)

*Primary Examiner* — Sean M DeGuire
(74) *Attorney, Agent, or Firm* — KILE PARK REED & HOUTTEMAN PLLC

(57) ABSTRACT

Provided are a condensed cyclic compound and an organic light-emitting device. The condensed cyclic compound is represented by Formula 1:
(Continued)

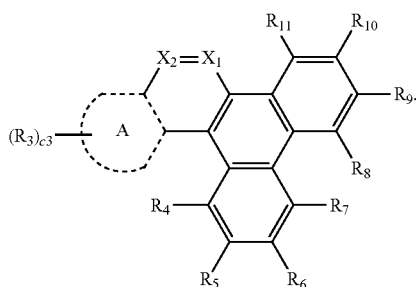

<Formula 1>

Details about the constituents of Formula 1 is disclosed.

16 Claims, 4 Drawing Sheets

(51) Int. Cl.
  *C07D 401/10*    (2006.01)
  *C07D 405/10*    (2006.01)
  *C07D 471/04*    (2006.01)
  *C07F 9/576*    (2006.01)
  *C07F 9/6558*    (2006.01)
  *C07F 9/6561*    (2006.01)
  *H10K 50/16*    (2023.01)
  *H10K 50/17*    (2023.01)
  *H10K 50/18*    (2023.01)

(52) U.S. Cl.
  CPC ......... *C07D 405/10* (2013.01); *C07D 471/04* (2013.01); *C07F 9/5765* (2013.01); *C07F 9/65583* (2013.01); *C07F 9/6561* (2013.01); *H10K 85/626* (2023.02); *H10K 85/654* (2023.02); *H10K 85/6574* (2023.02); *H10K 50/16* (2023.02); *H10K 50/171* (2023.02); *H10K 50/18* (2023.02)

(56) References Cited

U.S. PATENT DOCUMENTS

| | | | |
|---|---|---|---|
| 8,986,855 B2 | 3/2015 | Lim et al. | |
| 9,005,771 B2 | 4/2015 | Ma et al. | |
| 9,028,978 B2 | 5/2015 | Kim et al. | |
| 10,069,083 B2 | 9/2018 | Jeong et al. | |
| 2007/0170419 A1* | 7/2007 | Gerhard | H01L 51/5048 |
| | | | 313/506 |
| 2007/0241670 A1* | 10/2007 | Sapochak | C07F 9/65517 |
| | | | 313/504 |
| 2014/0103325 A1 | 4/2014 | Shin et al. | |
| 2016/0204357 A1* | 7/2016 | Jang | C07D 401/14 |
| | | | 257/40 |

FOREIGN PATENT DOCUMENTS

| | | | |
|---|---|---|---|
| JP | 2002-63989 | 2/2002 | |
| JP | 4060669 B2 | 12/2007 | |
| KR | 10-0525408 | 11/2005 | |
| KR | 10-2010-0088613 | 8/2010 | |
| KR | 10-2011-0077871 | 7/2011 | |
| KR | 10-2012-0023780 | 3/2012 | |
| KR | 10-2012-0122982 | 7/2012 | |
| KR | 10-2012-0138673 | 12/2012 | |
| KR | 10-2013-0000230 | 1/2013 | |
| KR | 10-2013-0007162 | 1/2013 | |
| KR | 10-2013-0135178 A | 10/2013 | |
| KR | 1558495 B * | 11/2014 | ........... C07D 209/44 |
| KR | 10-2015-0051119 | 11/2015 | |
| KR | 10-2015-0139125 | 12/2015 | |

OTHER PUBLICATIONS

Sakamoto, "Synthesis, Characterization, and Electron-Transport", J. Am. Chem. Soc. 2000, 122, 1832-1833.
Yamaguchi, "Diphenylamino-Substituted 2,5-Diarylsiloles for Single-Layer Organic Electroluminescent Devices", Chem. Lett., 98 (2001).
Johansson, "Solid-State Amplified Spontaneous Emission in Some Spiro-Type Molecules: A New Concept for the Design of Solid State Lasing Molecules" Adv. Mater., 10, 1136 (1998).
Tao, "Sharp green electroluminescence from 1H-pyrazolo[3,4-b]quinoline-based light-emitting diodes", Appl. Phys. Lett., 77, 1575 (2000).

* cited by examiner

| |
|---|
| 190 |
| 150 |
| 110 |

| 190 |
|-----|
| 150 |
| 110 |
| 210 |

| 220 |
|---|
| 190 |
| 150 |
| 110 |

| |
|---|
| 220 |
| 190 |
| 150 |
| 110 |
| 210 |

CONDENSED CYCLIC COMPOUND AND ORGANIC LIGHT-EMITTING DEVICE INCLUDING THE SAME

CROSS-REFERENCE TO RELATED APPLICATIONS

This application claims the benefit of Korean Patent Application Nos. 10-2015-0182792 filed on Dec. 21, 2015, and 10-2016-0046499 filed on Apr. 15, 2016 in the Korean Intellectual Property Office, the disclosure of which are incorporated herein in their entirety by reference.

BACKGROUND

1. Field

One or more embodiments relate to a condensed cyclic compound and an organic light-emitting device including the same.

SUMMARY

Organic light-emitting devices are self-emission devices that offer advantages such as wide viewing angles, high contrast ratios, short response times, and excellent luminance, driving voltage, and response speed characteristics, and produce full-color images.

The organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. Then, the excitons are transitioned from an excited state to a ground state, thereby generating light.

SUMMARY

One or more embodiments include a novel condensed cyclic compound and an organic light-emitting device including the same.

Additional aspects will be set forth in part in the description which follows and, in part, will be apparent from the description, or may be learned by practice of the presented embodiments.

According to one or more embodiments, a condensed cyclic compound is represented by Formula 1:

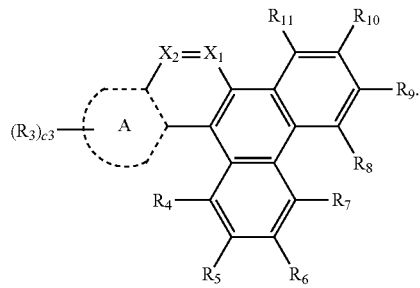

<Formula 1>

In Formula 1, ring A may be selected from a $C_5$-$C_{30}$ carbocyclic ring and a $C_2$-$C_{30}$ heterocyclic ring, $X_1$ may be $C(R_1)$ or N, $X_2$ may be $C(R_2)$ or N, at least one of $X_1$ and $X_2$ may be N, $R_1$ to $R_{11}$ may each independently be a group represented by one of Formulae 2-1 to 2-5 group, hydrogen, deuterium, —F, —Cl, —Br, —I, a hydroxyl group, a cyano group, a nitro group, a hydrazino group, a hydrazono group, substituted or unsubstituted $C_1$-$C_{60}$ alkyl group, substituted or unsubstituted $C_2$-$C_{60}$ alkenyl group, substituted or unsubstituted $C_2$-$C_{60}$ alkynyl group, substituted or unsubstituted $C_1$-$C_{60}$ alkoxy group, substituted or unsubstituted $C_3$-$C_{10}$ cycloalkyl group, substituted or unsubstituted $C_1$-$C_{10}$ heterocycloalkyl group, substituted or unsubstituted $C_3$-$C_{10}$ cycloalkenyl group, substituted or unsubstituted $C_1$-$C_{10}$ heterocycloalkenyl group, substituted or unsubstituted $C_6$-$C_{60}$ aryl group, substituted or unsubstituted $C_6$-$C_{60}$ aryloxy group, substituted or unsubstituted $C_6$-$C_{60}$ arylthio group, substituted or unsubstituted $C_1$-$C_{60}$ heteroaryl group, substituted or unsubstituted monovalent non-aromatic condensed polycyclic group, substituted or unsubstituted monovalent non-aromatic condensed heteropolycyclic group, —$Si(Q_1)(Q_2)(Q_3)$, —$B(Q_1)(Q_2)$, —$C(=O)(Q_1)$, —$S(=O)_2(Q_1)$, and —$P(=O)(Q_1)(Q_2)$:

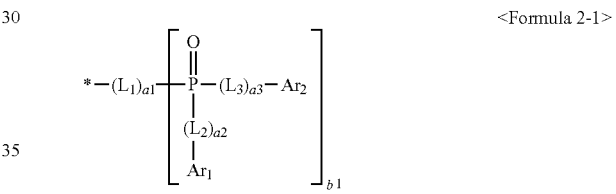

<Formula 2-1>

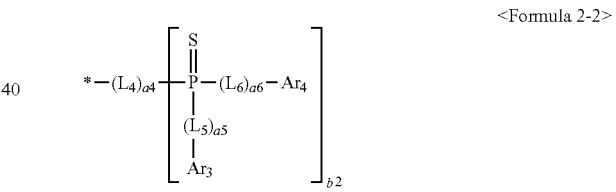

<Formula 2-2>

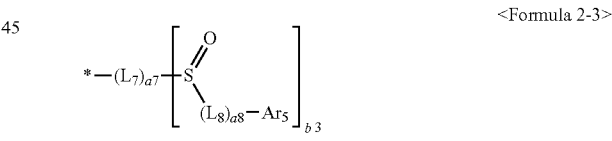

<Formula 2-3>

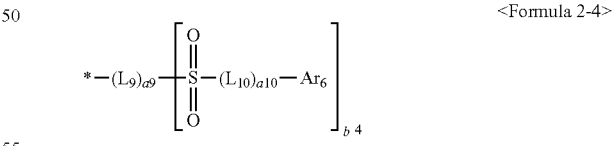

<Formula 2-4>

\*—$(L_{11})_{a11}$—$Ar_7$, <Formula 2-5>

$L_1$ to $L_{11}$ may each independently be selected from a substituted or unsubstituted $C_3$-$C_{10}$ cycloalkylene group, substituted or unsubstituted $C_1$-$C_{10}$ heterocycloalkylene group, substituted or unsubstituted $C_3$-$C_{10}$ cycloalkenylene group, substituted or unsubstituted $C_1$-$C_{10}$ heterocycloalkenylene group, substituted or unsubstituted $C_6$-$C_{60}$ arylene group, substituted or unsubstituted $C_1$-$C_{60}$ heteroarylene group, substituted or unsubstituted divalent non-aromatic condensed polycyclic group, and a substituted or unsubstituted divalent non-aromatic condensed heteropolycyclic group, a1 to a11 may each independently be 0, 1, 2, 3, 4, or 5, $Ar_1$ to $Ar_7$ may be a substituted or unsubstituted $C_1$-$C_{60}$ alkyl group, substituted or unsubstituted $C_2$-$C_{60}$ alkenyl group, substituted or unsubstituted $C_2$-$C_{60}$ alkynyl group, substituted or unsubstituted $C_1$-$C_{60}$ alkoxy group, substituted or unsubstituted $C_3$-$C_{10}$ cycloalkyl group, substituted or unsubstituted $C_1$-$C_{10}$ heterocycloalkyl group, substituted or unsubstituted $C_3$-$C_{10}$ cycloalkenyl group, substituted or unsubstituted $C_1$-$C_{10}$ heterocycloalkenyl group, substituted or unsubstituted $C_6$-$C_{60}$ aryl group, substituted or unsubstituted $C_1$-$C_{60}$ heteroaryl group, substituted or unsubstituted monovalent non-aromatic condensed polycyclic group, and a substituted or unsubstituted monovalent non-aromatic condensed heteropolycyclic group, b1 to b4 may each independently be 1, 2, or 3, c3 may be 0, 1, 2, 3, 4, 5, or 6, at least one of substituent or substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{11})(Q_{12})(Q_{13})$, —N$(Q_{11})(Q_{12})$, —B$(Q_{11})(Q_{12})$, —C$(=O)(Q_{11})$, —S$(=O)_2(Q_{11})$, and —P$(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{21})(Q_{22})(Q_{23})$, —N$(Q_{21})(Q_{22})$, —B$(Q_{21})(Q_{22})$, —C$(=O)(Q_{21})$, —S$(=O)_2(Q_{21})$, and —P$(=O)(Q_{21})(Q_{22})$; and —Si$(Q_{31})(Q_{32})(Q_{33})$, —N$(Q_{31})(Q_{32})$, —B$(Q_{31})(Q_{32})$, —C$(=O)(Q_{31})$, —S$(=O)_2(Q_{31})$ and —P$(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ ≙ each independently hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to a neighboring atom.

According to another aspect, an organic light-emitting device includes a first electrode; a second electrode facing the first electrode; and an organic layer that is disposed between the first electrode and the second electrode and includes an emission layer, wherein the organic layer includes at least one of condensed cyclic compounds represented by Formula 1.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic cross-sectional view of an organic light-emitting device according to an embodiment;

FIG. 2 is a schematic cross-sectional view of an organic light-emitting device according to an embodiment;

FIG. 3 is a schematic cross-sectional view of an organic light-emitting device according to an embodiment; and FIG. 4 is a schematic cross-sectional view of an organic light-emitting device according to an embodiment;

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

A condensed cyclic compound according to an embodiment of the present disclosure is represented by Formula 1:

<Formula 1>

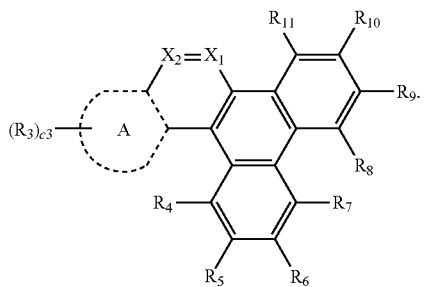

Ring A in Formula 1 may be selected from a $C_5$-$C_{30}$ carbocyclic ring and a $C_2$-$C_{30}$ heterocyclic ring. For example, ring A may be selected from a benzene group, a pyridine group, a pyridazine group, a pyrimidine group, a pyrazine group, a naphthalene group, a quinoline group, an isoquinoline group, a cinnoline group, a quinazoline group, a quinoxaline group, a naphthyridine group, an anthracene group, a phenanthrene group, a benzoquinoline group, a phenanthridine group, an acridine group, a phenanthroline group, and a phenazine group. In one embodiment, ring A may be selected from a benzene group, a pyridine group, a naphthalene group, a quinoline group, and an isoquinoline group, but embodiments of the present disclosure are not limited thereto.

In Formula 1, $X_1$ may be $C(R_1)$ or N, $X_2$ may be $C(R_2)$ or N, and at least one of $X_1$ and $X_2$ may be N.

$R_1$ to $R_{11}$ in Formula 1 may each independently be selected from the group represented by one of Formulae 2-1 to 2-5, hydrogen, deuterium, —F, —Cl, —Br, —I, a hydroxyl group, a cyano group, a nitro group, a hydrazino group, a hydrazono group, substituted or unsubstituted $C_1$-$C_{60}$ alkyl group, substituted or unsubstituted $C_2$-$C_{60}$ alkenyl group, substituted or unsubstituted $C_2$-$C_{60}$ alkynyl group, substituted or unsubstituted $C_1$-$C_{60}$ alkoxy group, substituted or unsubstituted $C_3$-$C_{10}$ cycloalkyl group, substituted or unsubstituted $C_1$-$C_{10}$ heterocycloalkyl group, substituted or unsubstituted $C_3$-$C_{10}$ cycloalkenyl group, substituted or unsubstituted $C_1$-$C_{10}$ heterocycloalkenyl group, substituted or unsubstituted $C_6$-$C_{60}$ aryl group, substituted or unsubstituted $C_6$-$C_{60}$ aryloxy group, substituted or unsubstituted $C_6$-$C_{60}$ arylthio group, substituted or unsubstituted $C_1$-$C_{60}$ heteroaryl group, substituted or unsubstituted monovalent non-aromatic condensed polycyclic group, substituted or unsubstituted monovalent non-aromatic condensed heteropolycyclic group, —Si($Q_1$)($Q_2$)($Q_3$), —B($Q_1$)($Q_2$), —C(=O)($Q_1$), —S(=O)$_2$($Q_1$), and —P(=O)($Q_1$)($Q_2$), wherein $Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group:

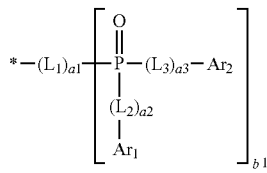

<Formula 2-1>

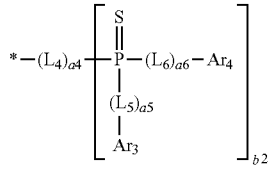

<Formula 2-2>

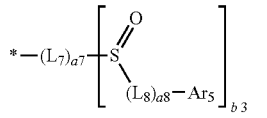

<Formula 2-3>

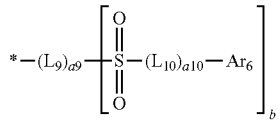

<Formula 2-4>

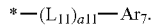

<Formula 2-5>

\* in Formulae 2-1 to 2-5 indicates a binding site to a neighboring atom.

$L_1$ to $L_{11}$ in Formulae 2-1 to 2-5 may each independently be selected from a substituted or unsubstituted $C_3$-$C_{10}$ cycloalkylene group, substituted or unsubstituted $C_1$-$C_{10}$ heterocycloalkylene group, substituted or unsubstituted $C_3$-$C_{10}$ cycloalkenylene group, substituted or unsubstituted $C_1$-$C_{10}$ heterocycloalkenylene group, substituted or unsubstituted $C_6$-$C_{60}$ arylene group, substituted or unsubstituted $C_1$-$C_{60}$ heteroarylene group, substituted or unsubstituted divalent non-aromatic condensed polycyclic group, and a substituted or unsubstituted divalent non-aromatic condensed heteropolycyclic group. For example, $L_1$ to $L_{11}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzosilolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzosilolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, —Si($Q_{31}$)($Q_{32}$)($Q_{33}$), —N($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and a carbazolyl group.

In one embodiment, $L_1$ to $L_{11}$ may each independently be selected from groups represented by Formulae 3-1 to 3-25:

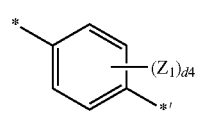

Formular 3-1

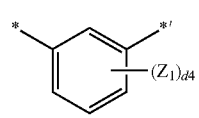

Formular 3-2

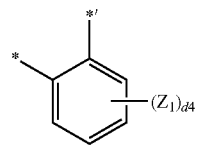

Formular 3-3

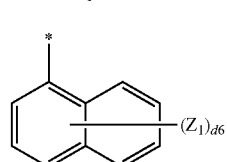

Formular 3-4

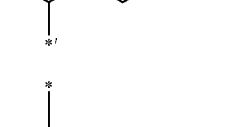

Formular 3-5

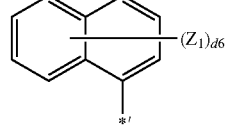

Formular 3-6

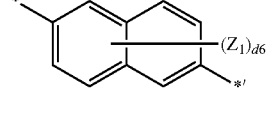

Formular 3-7

-continued
Formular 3-8
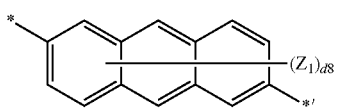
Formular 3-9
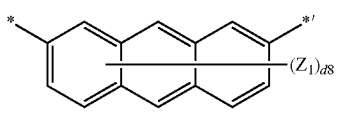
Formular 3-10
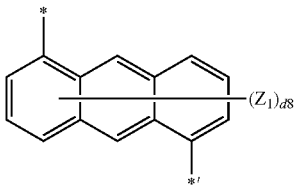
Formular 3-11
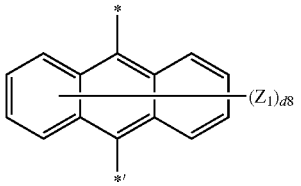
Formular 3-12
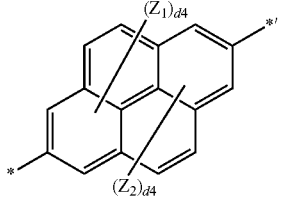
Formular 3-13
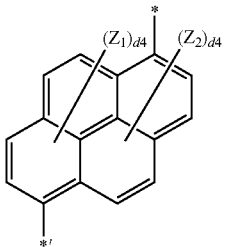
Formular 3-14
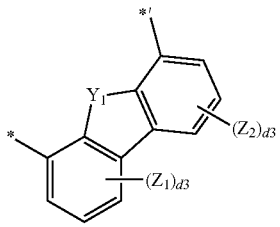
Formular 3-15
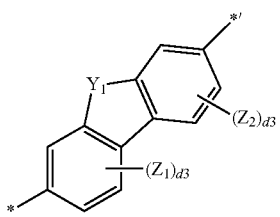
-continued
Formular 3-16
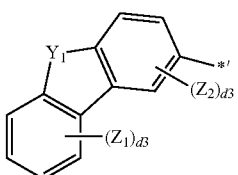
Formular 3-17
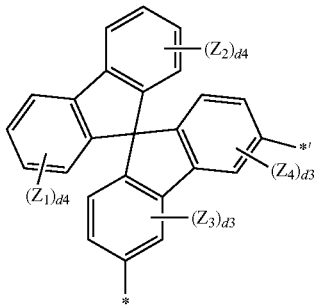
Formular 3-18
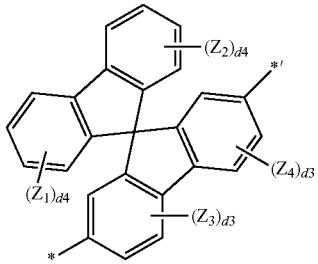
Formular 3-19
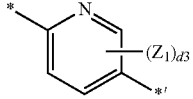
Formular 3-20
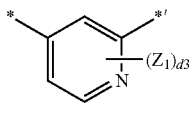
Formular 3-21
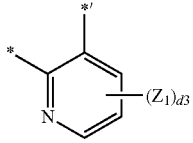
Formular 3-22
Formular 3-23
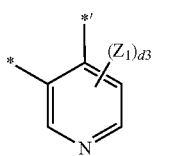
Formular 3-24

-continued

Formular 3-25

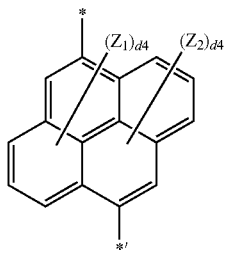

In Formulae 3-1 to 3-25, $Y_1$ may be O, S, $C(Z_5)(Z_6)$, $N(Z_7)$, or $Si(Z_5)(Z_9)$, $Z_1$ to $Z_9$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a pyridinyl group, a pyrazinyl group, a pyrimidinyl group, a pyridazinyl group, a triazinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, d3 may be an integer from 1 to 3, d4 may be an integer from 1 to 4, d6 may be an integer from 1 to 6, d8 may be an integer from 1 to 8, and

* and *' each indicate a binding site to a neighboring atom. For example, $L_1$ to $L_{11}$ may each independently be selected from groups represented by Formulae 4-1 to 4-19, but embodiments of the present disclosure are not limited thereto:

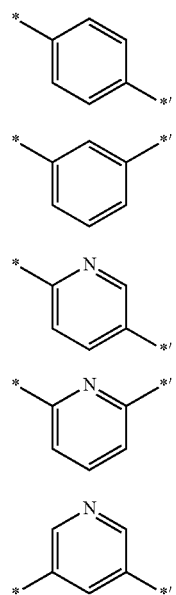

Formular 4-1

Formular 4-2

Formular 4-3

Formular 4-4

Formular 4-5

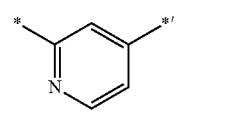

Formular 4-6

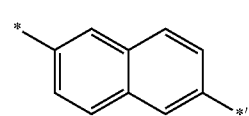

Formular 4-7

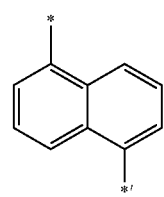

Formular 4-8

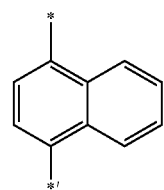

Formular 4-9

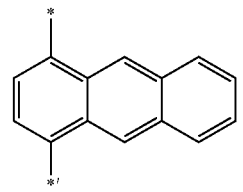

Formular 4-10

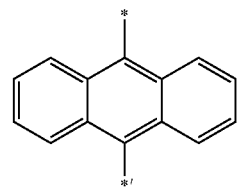

Formular 4-11

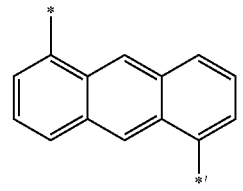

Formular 4-12

Formular 4-13

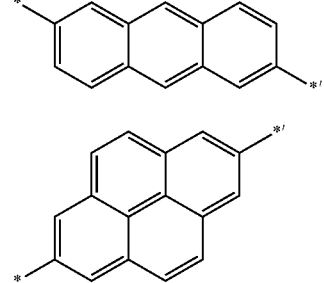

Formular 4-14

-continued

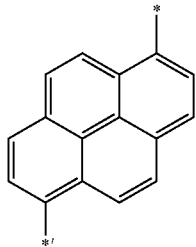
Formular 4-15

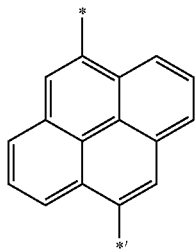
Formular 4-16

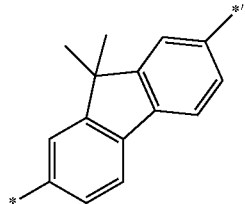
Formular 4-17

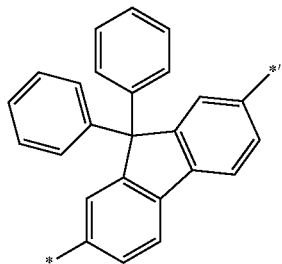
Formular 4-18

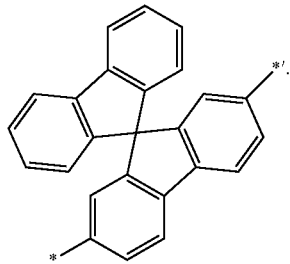
Formular 4-19

* and *' in Formulae 4-1 to 4-19 each indicate a binding site to a neighboring atom.

a1 to a11 in Formulae 2-1 to 2-5 may each independently be 0, 1, 2, 3, 4, or 5.

a1 indicates the number of $L_1(s)$, wherein, when a1 is 0, *-$(L_1)_{a1}$-*' indicates a single bond, and when a1 is two or more, two or more $L_1(s)$ may be identical to or different from each other. a2 to a11 may be understood by referring to the description of a1 and the structures of Formulae 2-1 to 2-5. For example, a1 to a10 may each independently be 0, 1, 2, or 3, but embodiments of the present disclosure are not limited thereto.

$Ar_1$ to $Ar_7$ in Formulae 2-1 to 2-5 may be selected from a substituted or unsubstituted $C_1$-$C_{60}$ alkyl group, substituted or unsubstituted $C_2$-$C_{60}$ alkenyl group, substituted or unsubstituted $C_2$-$C_{60}$ alkynyl group, substituted or unsubstituted $C_1$-$C_{60}$ alkoxy group, substituted or unsubstituted $C_3$-$C_{10}$ cycloalkyl group, substituted or unsubstituted $C_1$-$C_{10}$ heterocycloalkyl group, substituted or unsubstituted $C_3$-$C_{10}$ cycloalkenyl group, substituted or unsubstituted $C_1$-$C_{10}$ heterocycloalkenyl group, substituted or unsubstituted $C_6$-$C_{60}$ aryl group, substituted or unsubstituted $C_1$-$C_{60}$ heteroaryl group, substituted or unsubstituted monovalent non-aromatic condensed polycyclic group, and a substituted or unsubstituted monovalent non-aromatic condensed heteropolycyclic group. For example, $Ar_1$ to $Ar_7$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a benzonaphthofuranyl group, a dinaphthofuranyl group, a benzonaphthothiophenyl group, a dinaphthothiophenyl group, a benzonaphthosilolyl group, and a dinaphthosilolyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a benzonaphthofuranyl group, a dinaphthofuranyl group, a benzonaphthothiophenyl group, a dinaphthothiophenyl group, a benzonaphthosilolyl group, and a dinaphthosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzosilolyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a benzonaphthofuranyl group, a dinaphthofuranyl group, a benzonaphthothiophenyl group, a dinaphthothiophenyl group, a benzonaphthosilolyl group, a dinaphthosilolyl group, —Si($Q_{31}$)($Q_{32}$)($Q_{33}$), —N($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and a carbazolyl group.

In one embodiment, $Ar_1$ to $Ar_7$ may each independently be selected from groups represented by Formulae 5-1 to 5-25:

Formular 5-14 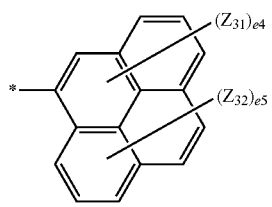

Formular 5-15 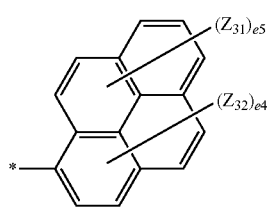

Formular 5-16 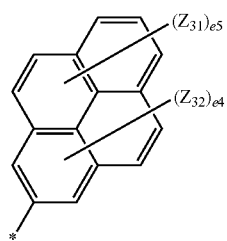

Formular 5-17 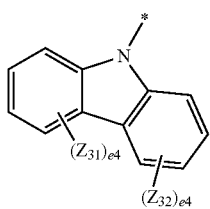

Formular 5-18 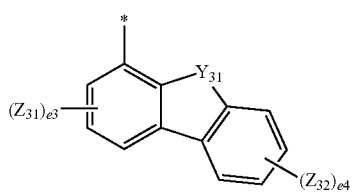

Formular 5-19 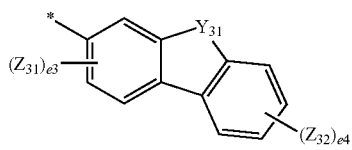

Formular 5-20 

Formular 5-21 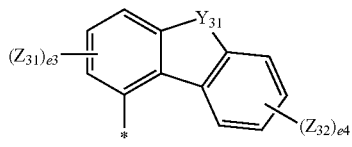

Formular 5-22 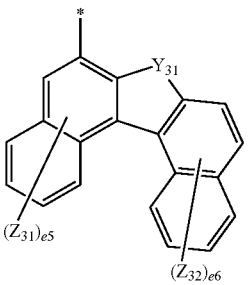

Formular 5-23 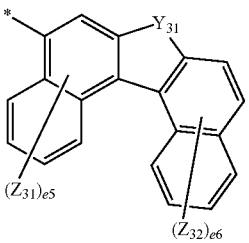

Formular 5-24 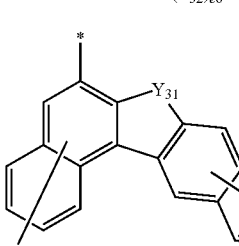

Formular 5-25 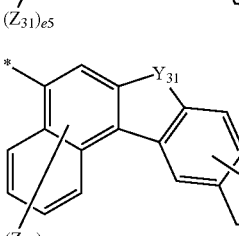

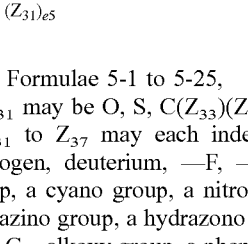

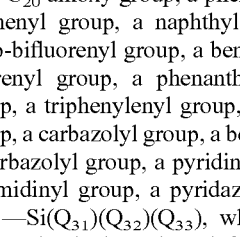

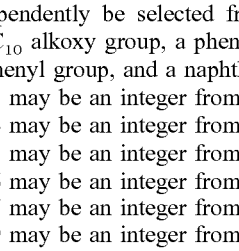

In Formulae 5-1 to 5-25, $Y_{31}$ may be O, S, $C(Z_{33})(Z_{34})$, $N(Z_{35})$, or $Si(Z_{36})(Z_{37})$, $Z_{31}$ to $Z_{37}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a pyridinyl group, a pyrazinyl group, a pyrimidinyl group, a pyridazinyl group, a triazinyl group, and —$Si(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, e3 may be an integer from 1 to 3,
e4 may be an integer from 1 to 4,
e5 may be an integer from 1 to 5,
e6 may be an integer from 1 to 6,
e7 may be an integer from 1 to 7,
e9 may be an integer from 1 to 9, and \* indicates a binding site to a neighboring atom. For example, Ar₁ to Ar₇ may each independently be selected from groups represented by Formulae 6-1 to 6-18, but embodiments of the present disclosure are not limited thereto:

Formular 6-1
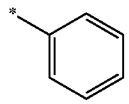

Formular 6-2
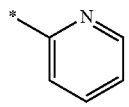

Formular 6-3
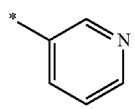

Formular 6-4
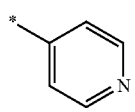

Formular 6-5
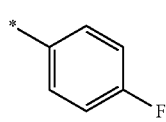

Formular 6-6
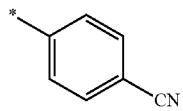

Formular 6-7
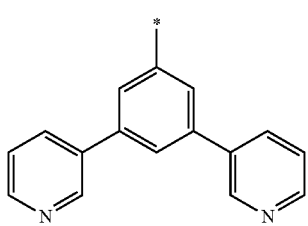

Formular 6-8
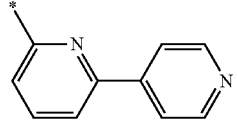

Formular 6-9
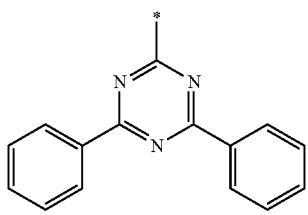

Formular 6-10
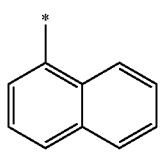

-continued

Formular 6-11
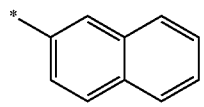

Formular 6-12
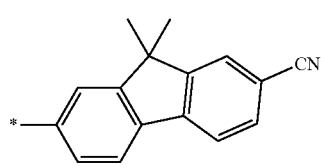

Formular 6-13
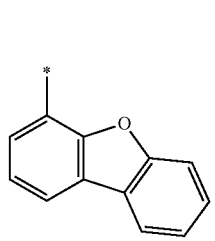

Formular 6-14
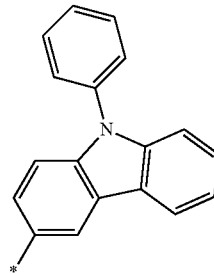

Formular 6-15
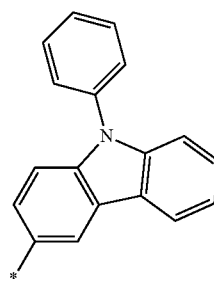

Formular 6-16

Formular 6-17
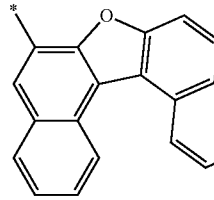

Formular 6-18

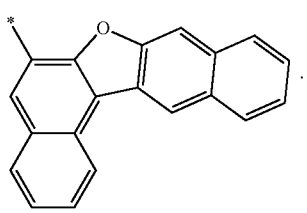

* in Formulae 6-1 to 6-18 indicates a binding site to a neighboring atom.

b1 to b4 in Formulae 2-1 to 2-4 may each independently be 1, 2, or 3. For example, b1 to b4 may be 1, but embodiments of the present disclosure are not limited thereto.

In one embodiment, $R_1$ to $R_{11}$ may each independently be selected from:

the group represented by one of Formulae 2-1 to 2-5, hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, —Si($Q_{31}$)($Q_{32}$)($Q_{33}$), —N($Q_{31}$)($Q_{32}$), —C(=O)($Q_{31}$), —S(=O)$_2$($Q_{31}$), and —P(=O)($Q_{31}$)($Q_{32}$); and —Si($Q_1$)($Q_2$)($Q_3$), —N($Q_1$)($Q_2$), —B($Q_1$)($Q_2$), —C(=O)($Q_1$), —S(=O)$_2$($Q_1$) and —P(=O)($Q_1$)($Q_2$), wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, and a carbazolyl group.

In one embodiment, $R_1$ to $R_{11}$ may each independently be selected from:

the group represented by one of Formulae 2-1 to 2-5, hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, —Si($Q_1$)($Q_2$)($Q_3$), —N($Q_1$)($Q_2$), —C(=O)($Q_1$), —S(=O)$_2$($Q_1$), and —P(=O)($Q_1$)($Q_2$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

c3 in Formula 1 may be 0, 1, 2, 3, 4, 5, or 6. c3 indicates the number of $R_3$(s), wherein, when c3 is two or more, two or more $R_3$(s) may be identical to or different from each other. For example, c3 may be 0, 1, 2, or 3, but embodiments of the present disclosure are not limited thereto.

In one embodiment, in Formula 1, $X_1$ may be N, $X_2$ may be C($R_2$), $R_2$ may be selected from groups represented by Formulae 2-1 to 2-5, and $R_3$ to $R_{11}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, and a dibenzocarbazolyl group.

In one embodiment, in Formula 1, $X_1$ may be C($R_1$), $X_2$ may be N, $R_1$ may be selected from groups represented by Formulae 2-1 to 2-5, and $R_3$ to $R_{11}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, and a dibenzocarbazolyl group.

In one embodiment, in Formula 1, $R_3$ may be selected from groups represented by Formulae 2-1 to 2-5, $R_1$, $R_2$ and $R_4$ to $R_{11}$ may each independently be selected from the group represented by Formula 2-5, hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, and a dibenzocarbazolyl group.

In one embodiment, Formula 1 may be represented by one of Formulae 1A to 1S:

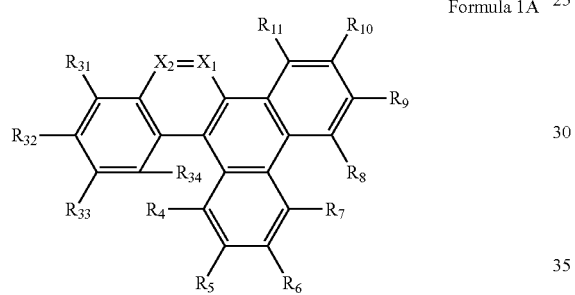

Formula 1A

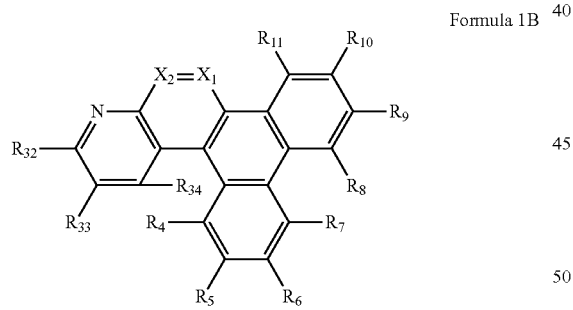

Formula 1B


Formula 1C

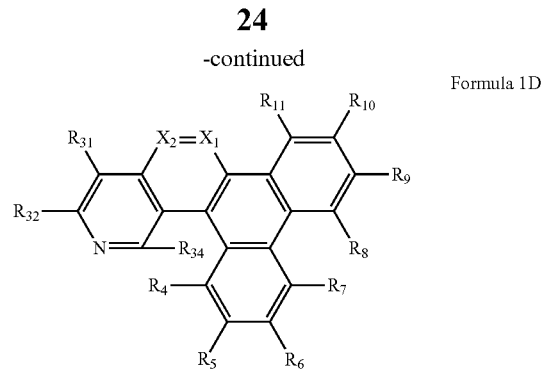

Formula 1D

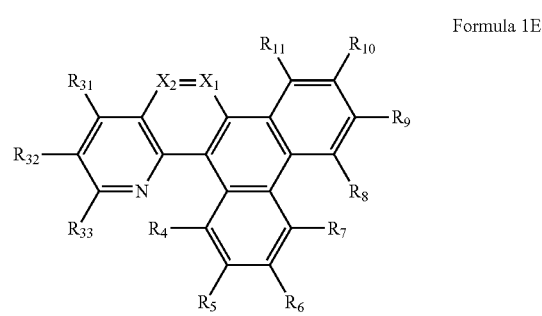

Formula 1E

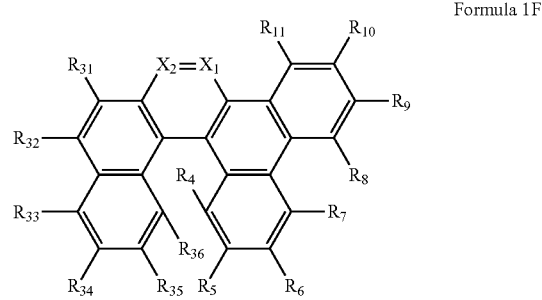

Formula 1F

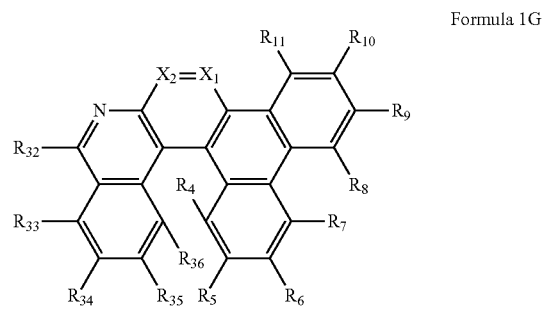

Formula 1G

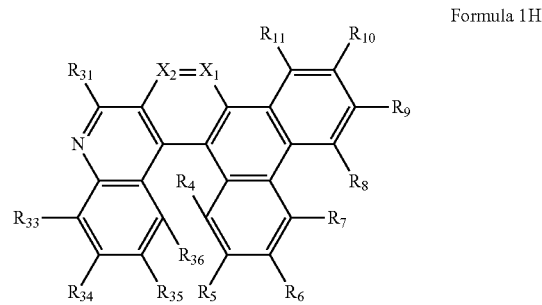

Formula 1H

Formula 1I
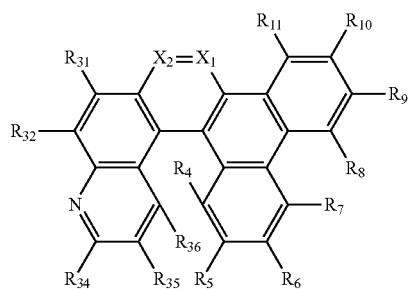
Formula 1J
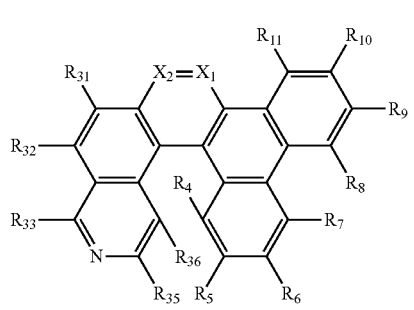
Formula 1K
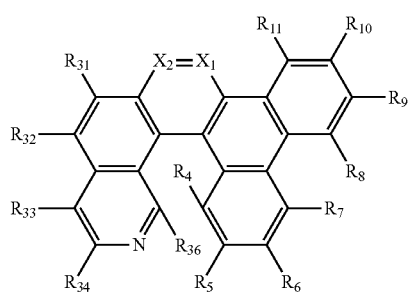
Formula 1L
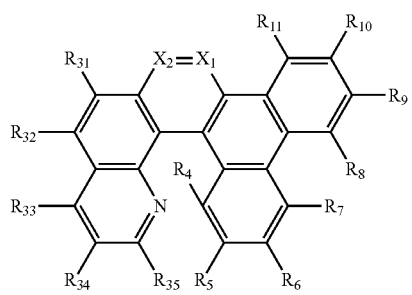
Formula 1M
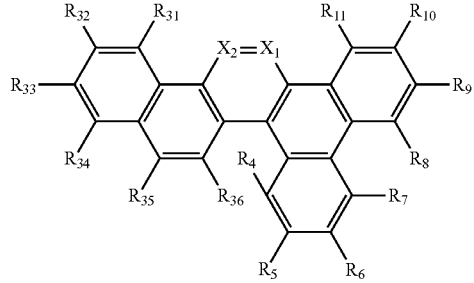
Formula 1N
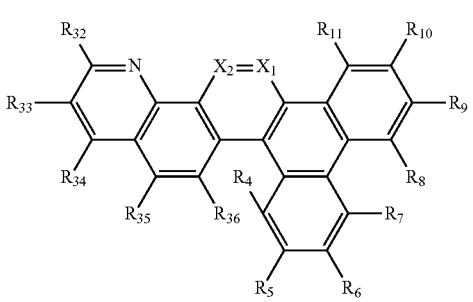
Formula 1O
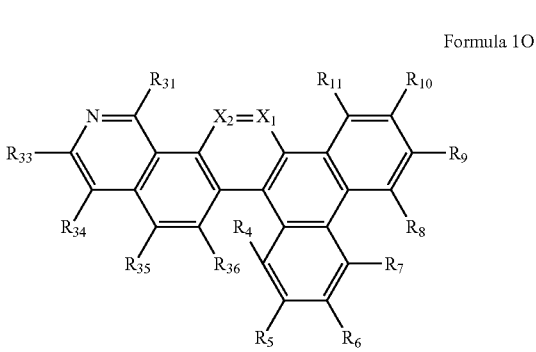
Formula 1P
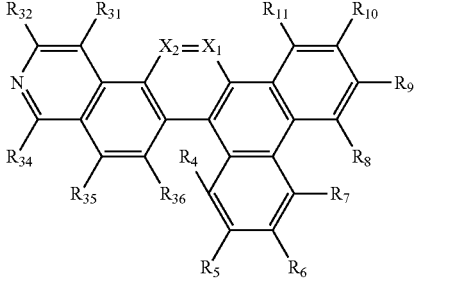
Formula 1Q
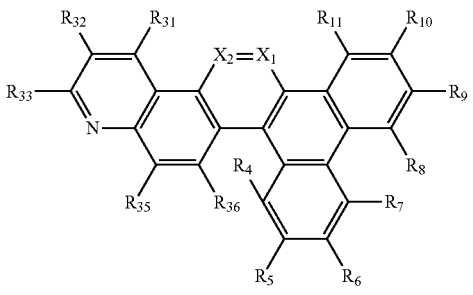
Formula 1R
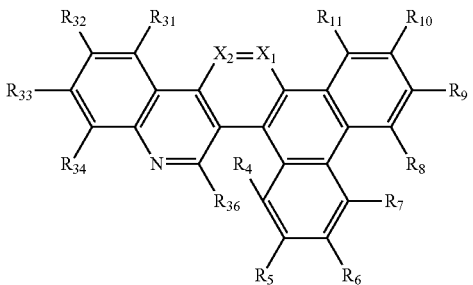

-continued

Formula 1S

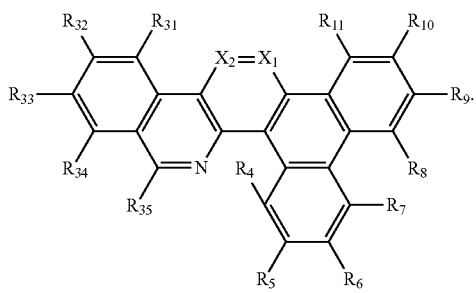

In Formulae 1A to 1S, $R_{31}$ to $R_{36}$ may be the same as described in connection with $R_3$, and $X_1$, $X_2$, and $R_3$ to $R_{11}$ are the same as described above.

In one embodiment, in Formulae 1A to 1S, $X_1$ may be N, $X_2$ may be $C(R_2)$, and $R_2$ may be selected from groups represented by Formulae 2-1 to 2-5. For example, in Formulae 1A to 1S, $X_1$ may be N, $X_2$ may be $C(R_2)$, $R_2$ may be selected from groups represented by Formulae 2-1 to 2-5, $R_{31}$ to $R_{36}$ and $R_4$ to $R_{11}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, and a dibenzocarbazolyl group.

In one embodiment, in Formulae 1A to 1S, $X_1$ may be $C(R_1)$, $X_2$ may be N, and $R_1$ may be selected from groups represented by Formulae 2-1 to 2-5. For example, in Formulae 1A to 1S, $X_1$ may be $C(R_1)$, $X_2$ may be N, $R_1$ may be selected from groups represented by Formulae 2-1 to 2-5, and $R_{31}$ to $R_{36}$ and $R_4$ to $R_{11}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, and a dibenzocarbazolyl group.

In one embodiment, in Formulae 1A, 1B, 1D to 1G, 1I to 1N, and 1P to 1S, $X_1$ may be N, $X_2$ may be $C(R_2)$, and $R_{32}$ may be selected from groups represented by Formulae 2-1 to 2-5. For example, in Formulae 1A, 1B, 1D to 1G, 1I to 1N, and 1P to 1S, $X_1$ may be N, $X_2$ may be $C(R_2)$, $R_{32}$ may be selected from groups represented by Formulae 2-1 to 2-5, and $R_2$, $R_{31}$, $R_{33}$ to $R_{36}$ and $R_4$ to $R_{11}$ may each independently be selected from the group represented by Formula 2-5, hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, and a dibenzocarbazolyl group.

In one embodiment, in Formulae 1A, 1B, 1D to 1G, 1I to 1N, and 1P to 1S, $X_1$ may be $C(R_1)$, $X_2$ may be N, and $R_{32}$ may be selected from groups represented by Formulae 2-1 to 2-5. For example, in Formulae 1A, 1B, 1D to 1G, 1I to 1N, and 1P to 1S, $X_1$ may be $C(R_1)$, $X_2$ may be N, $R_{32}$ may be selected from groups represented by Formulae 2-1 to 2-5, $R_1$, $R_{31}$, $R_{33}$ to $R_{36}$, and $R_4$ to $R_{11}$ may each independently be selected from the group represented by Formula 2-5, hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, and a dibenzocarbazolyl group.

The condensed cyclic compound represented by Formula 1 may be one of Compounds 1 to 192, but embodiments of the present disclosure are not limited thereto:

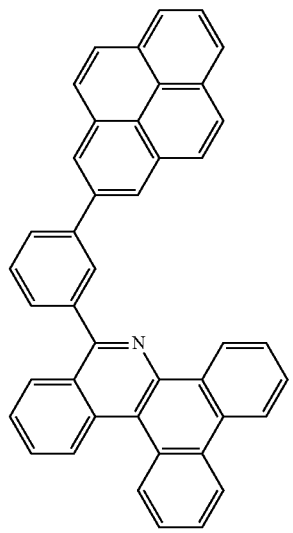

1

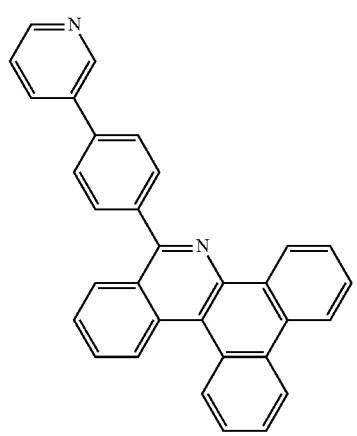

2

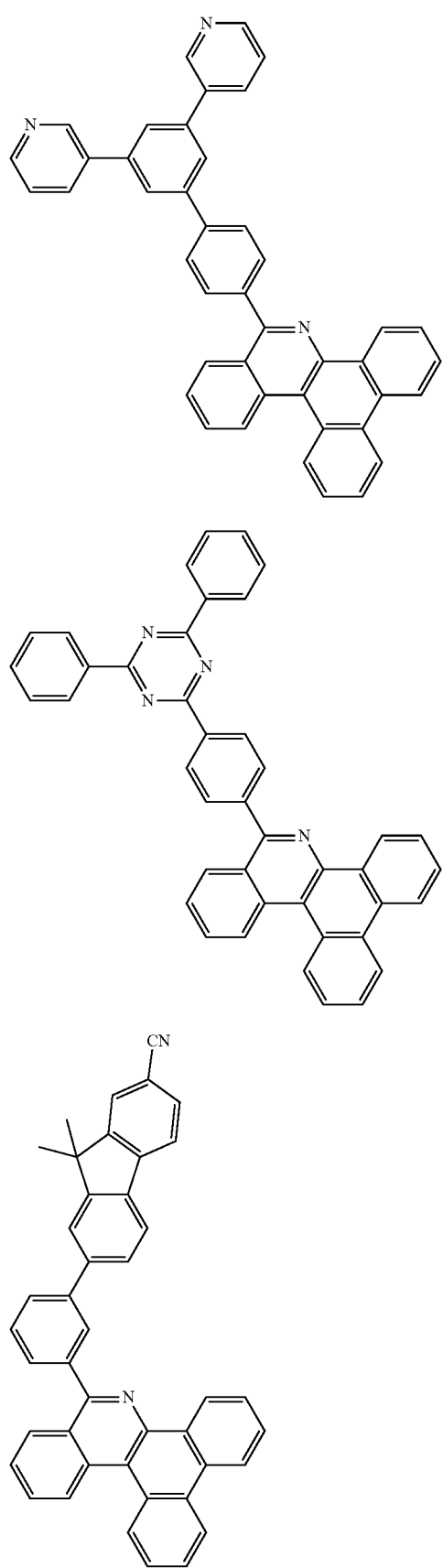
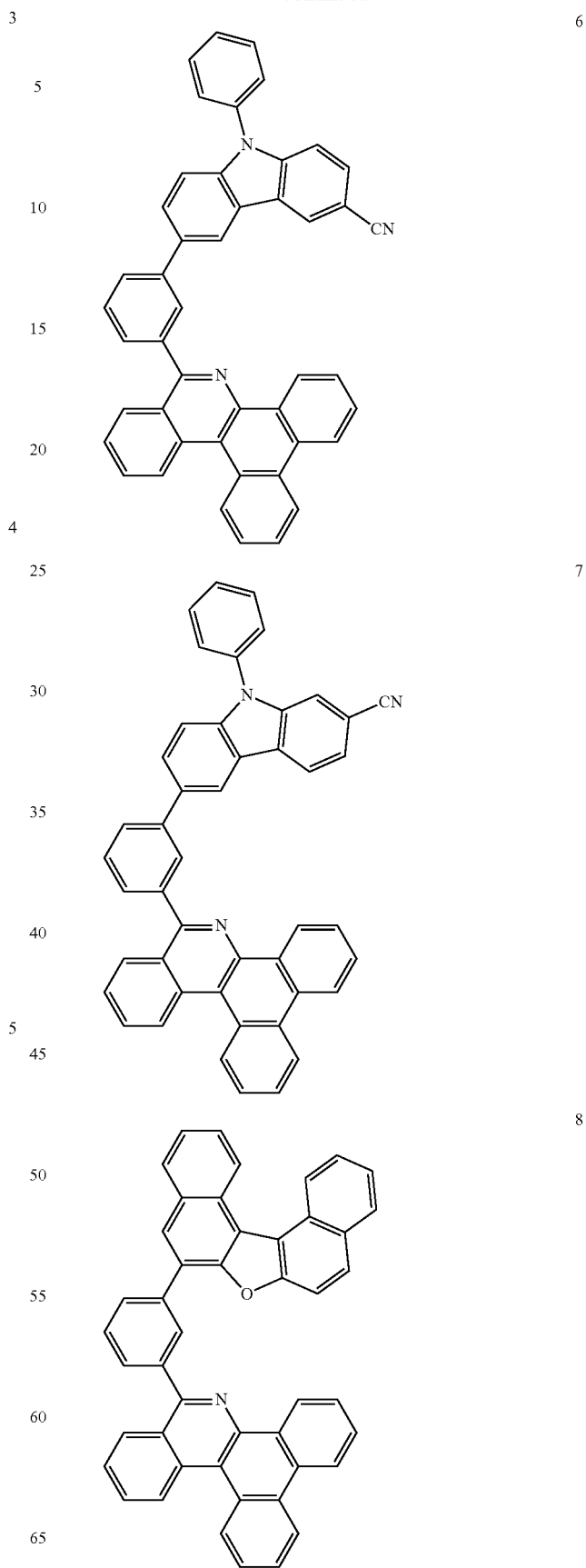

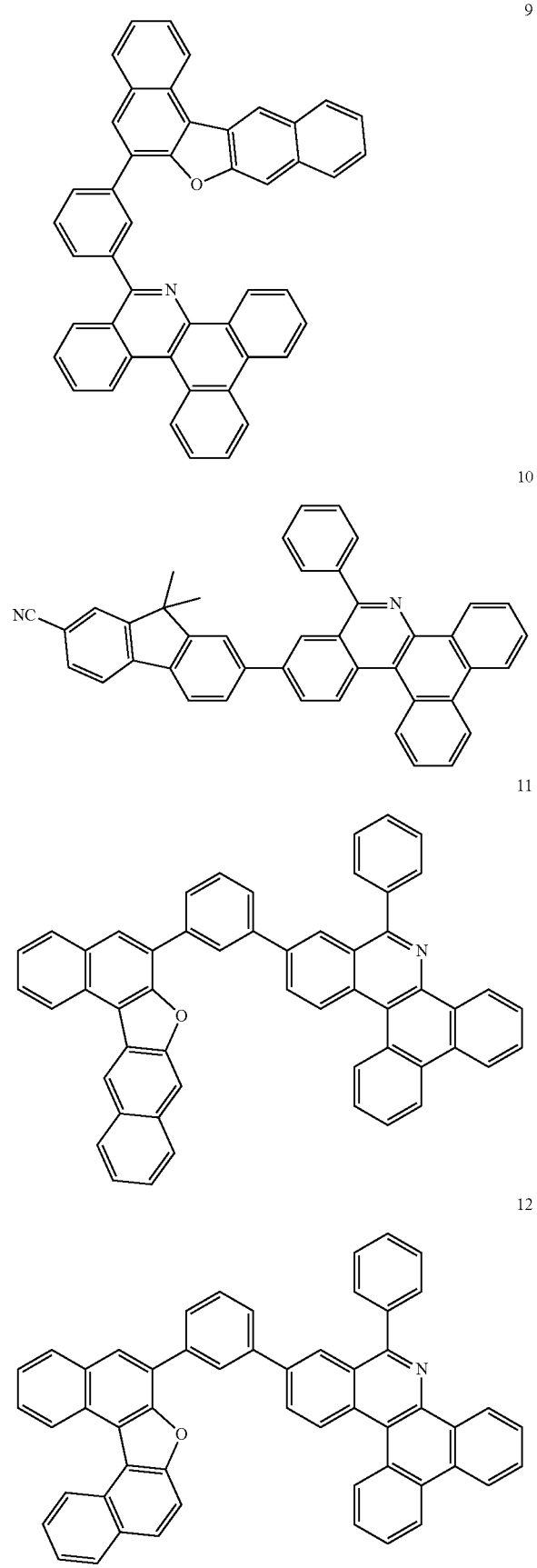
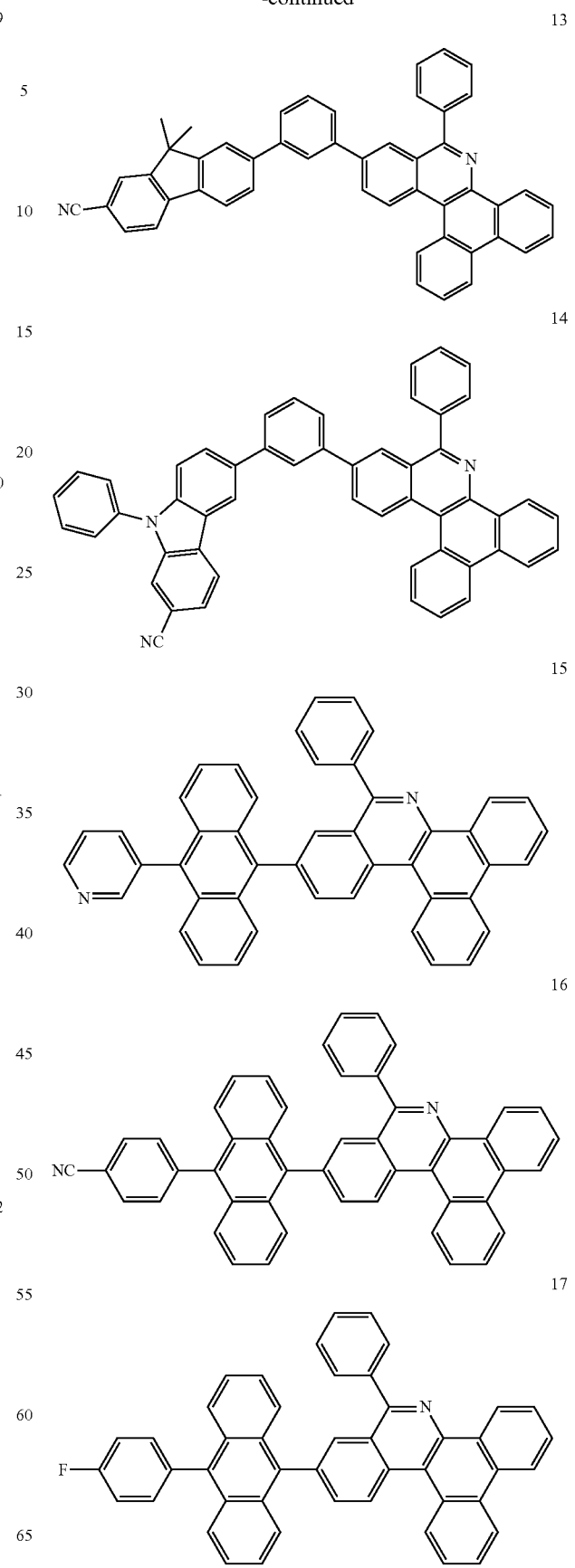

18
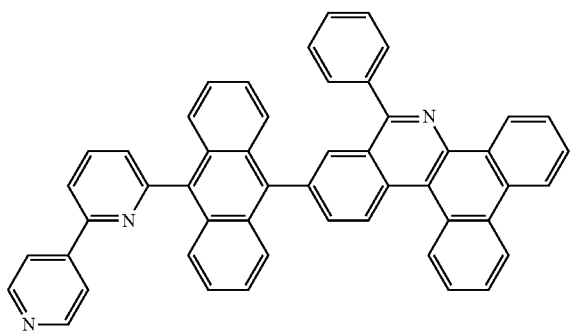
19
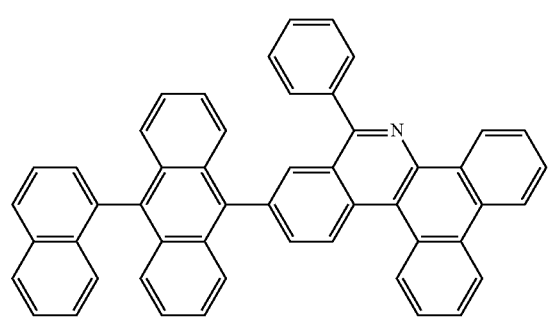
20
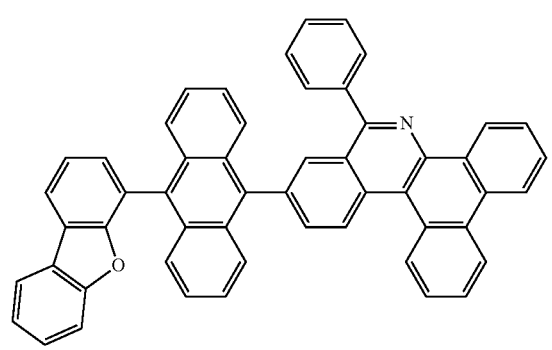
21
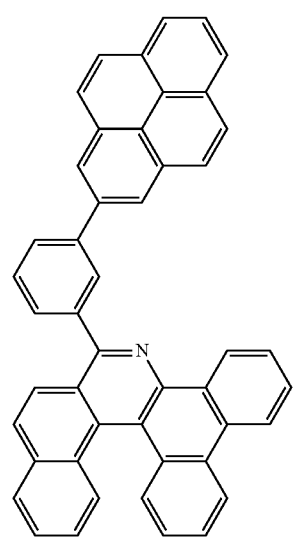
22
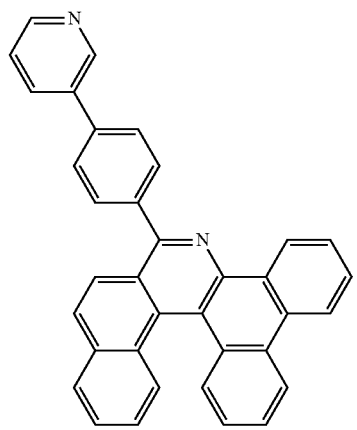
23
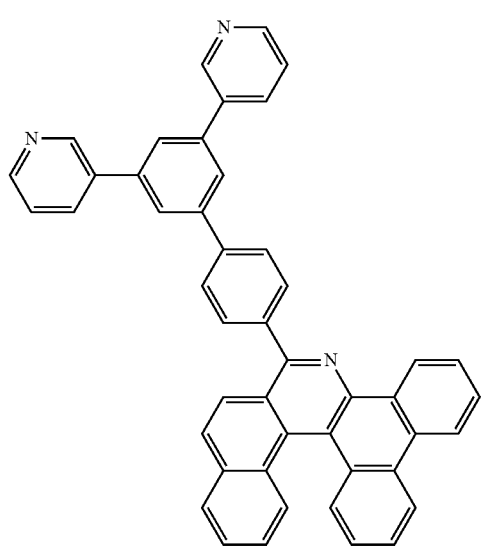
24
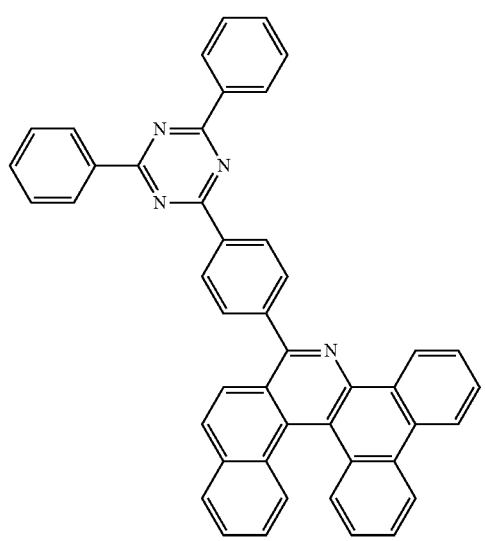

25
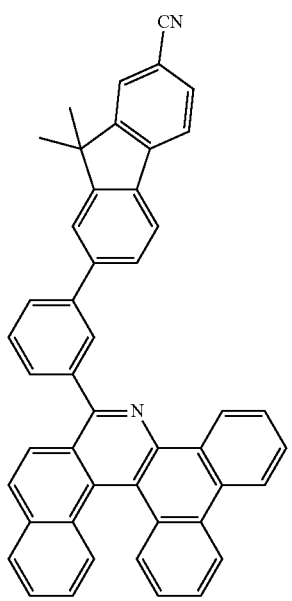
26
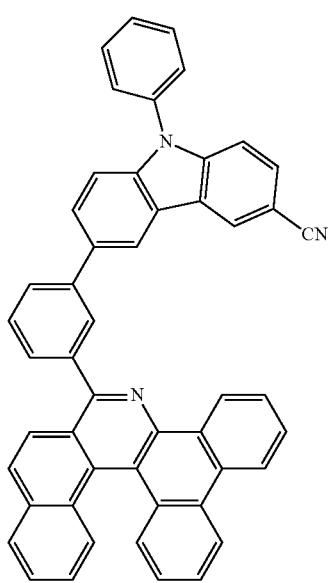
27
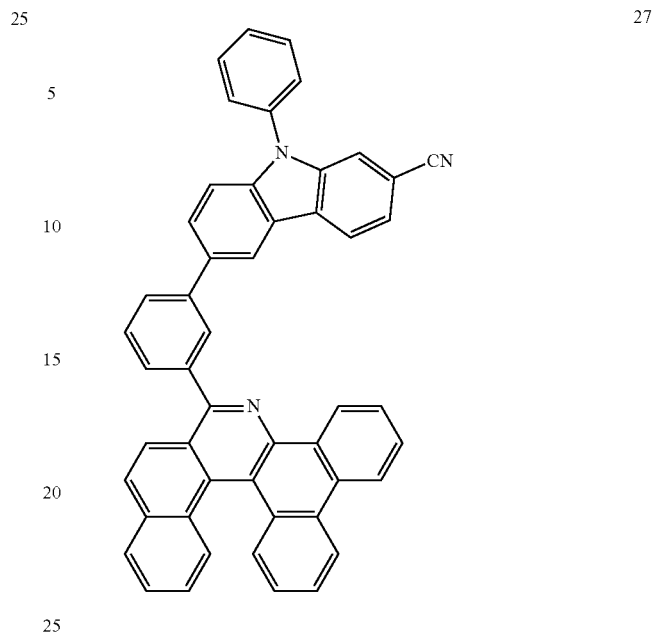
28
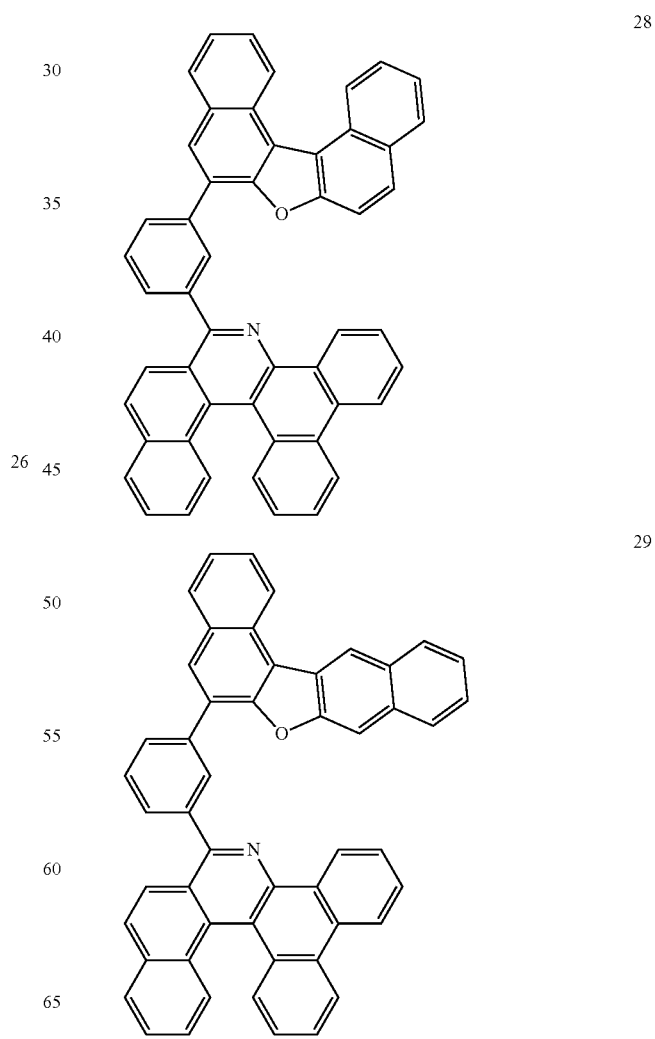
29

30
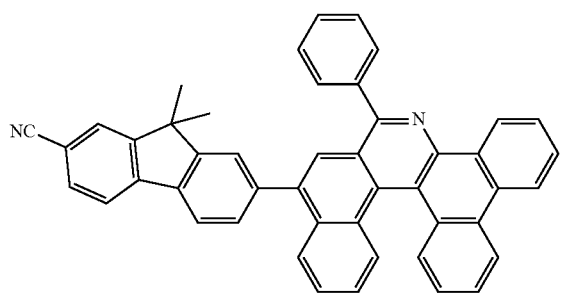
31
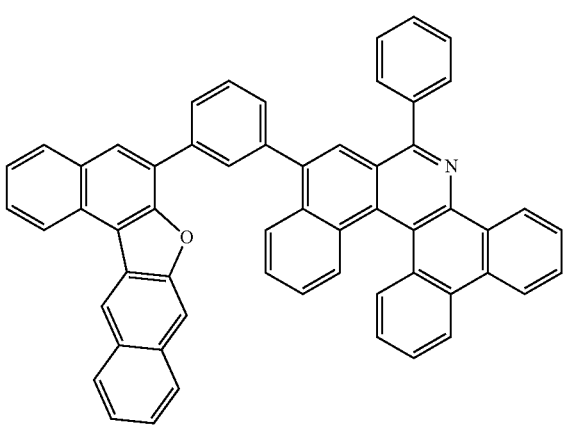
32
33
34
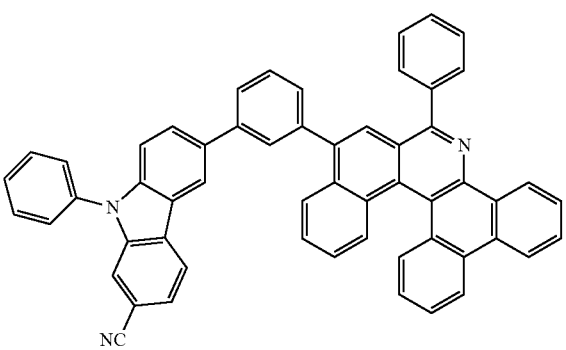
35
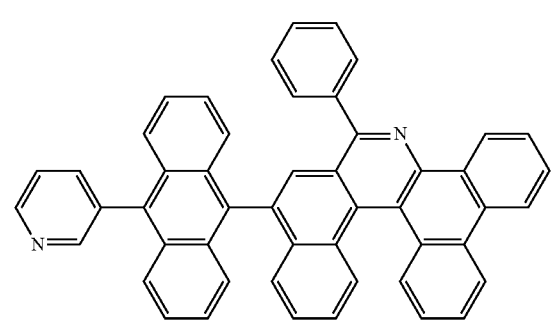
36
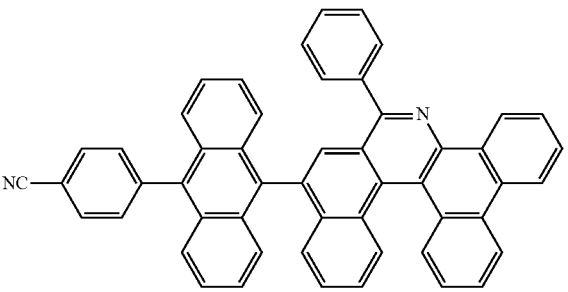
37
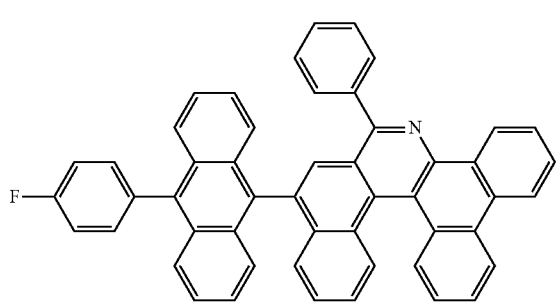

-continued
38
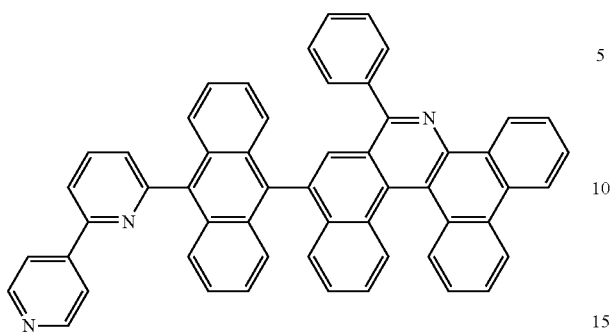
39
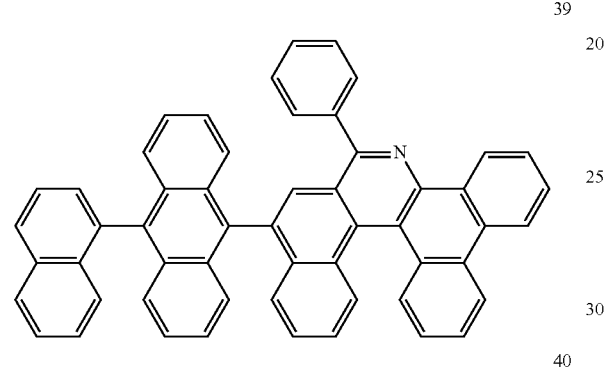
40
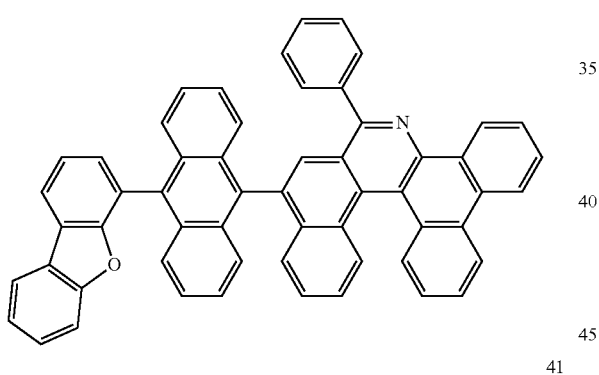
41
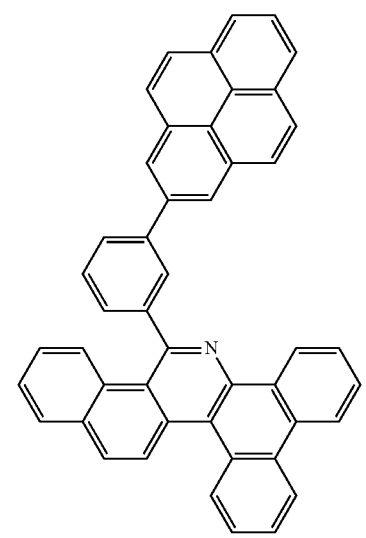
-continued
42
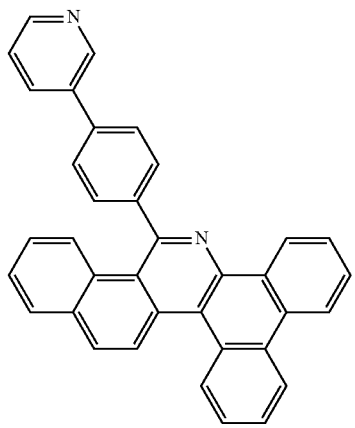
43
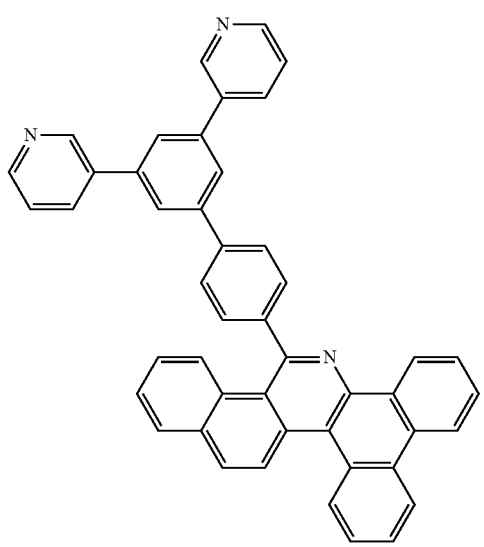
44
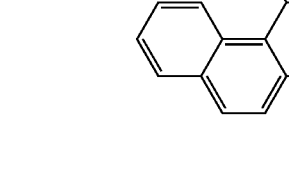

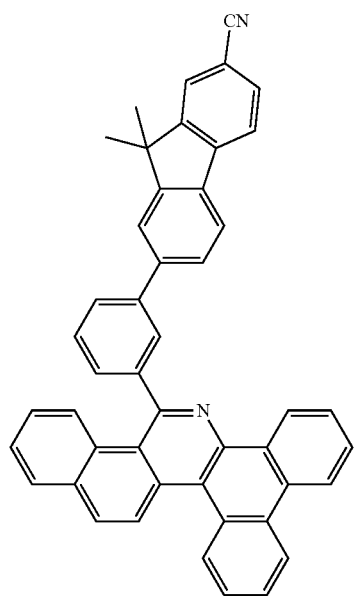
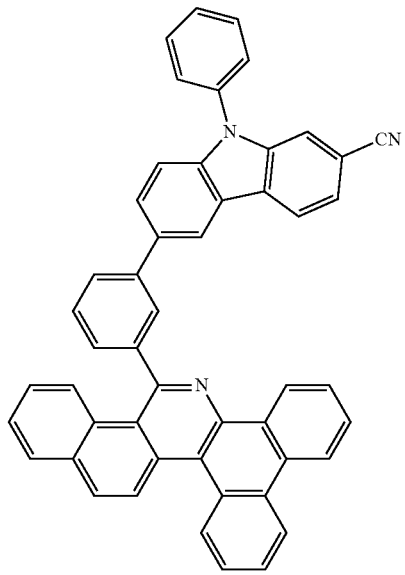
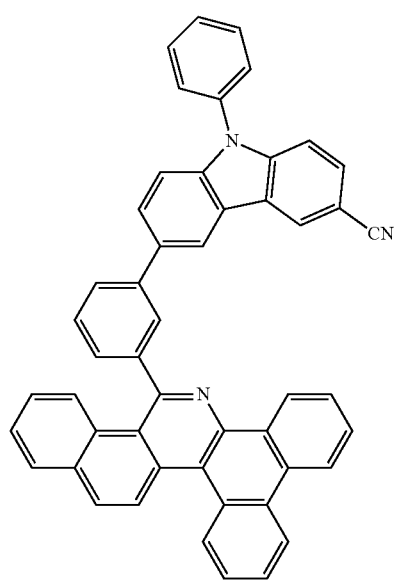
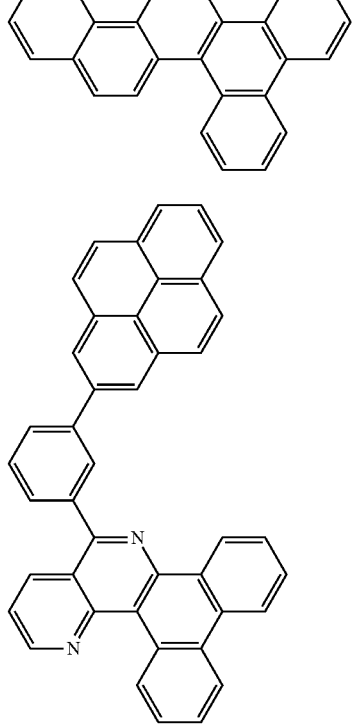

50
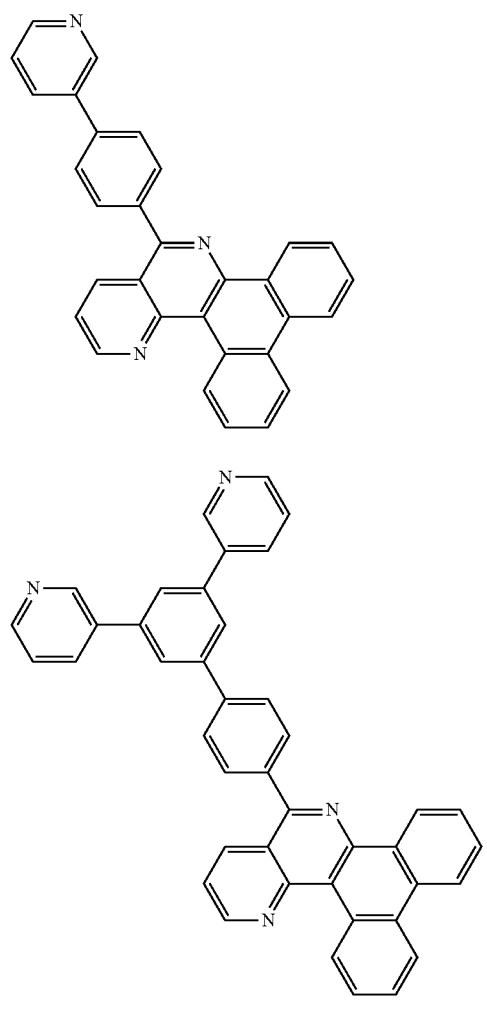
51
52
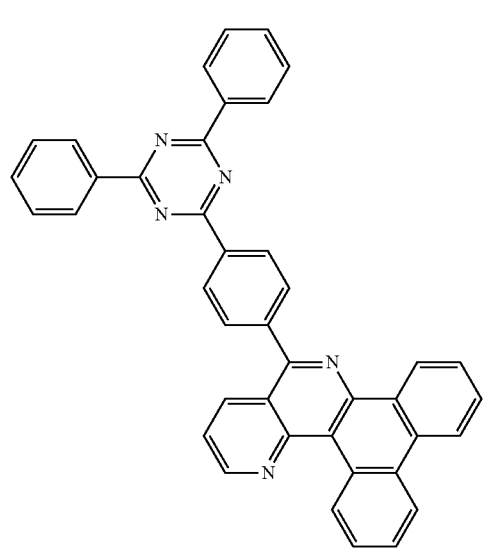
53
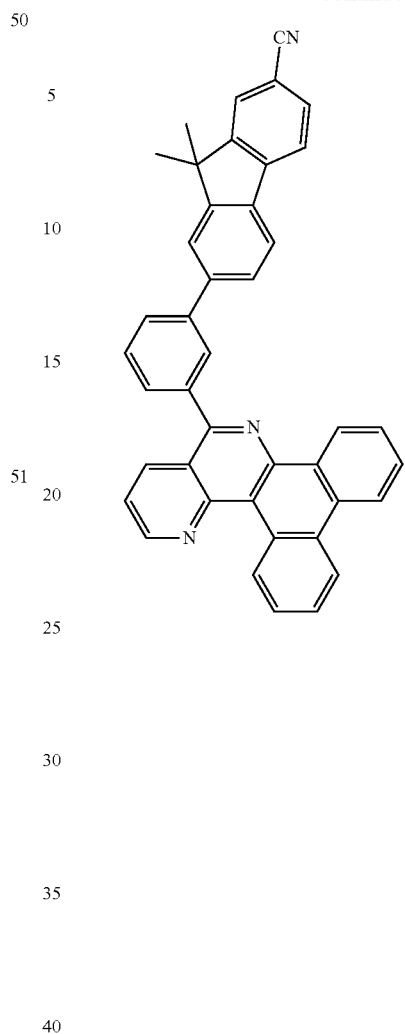
54
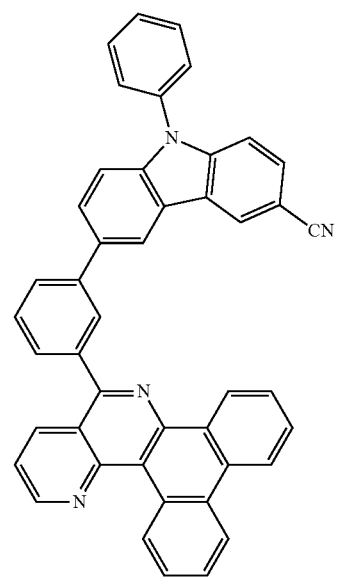

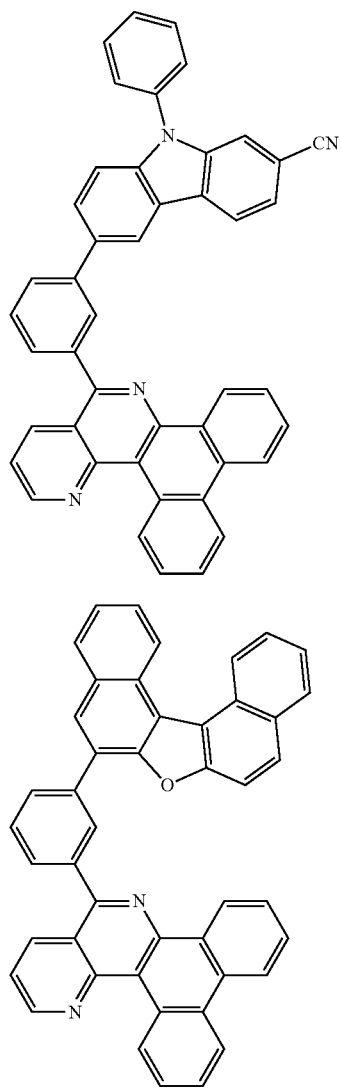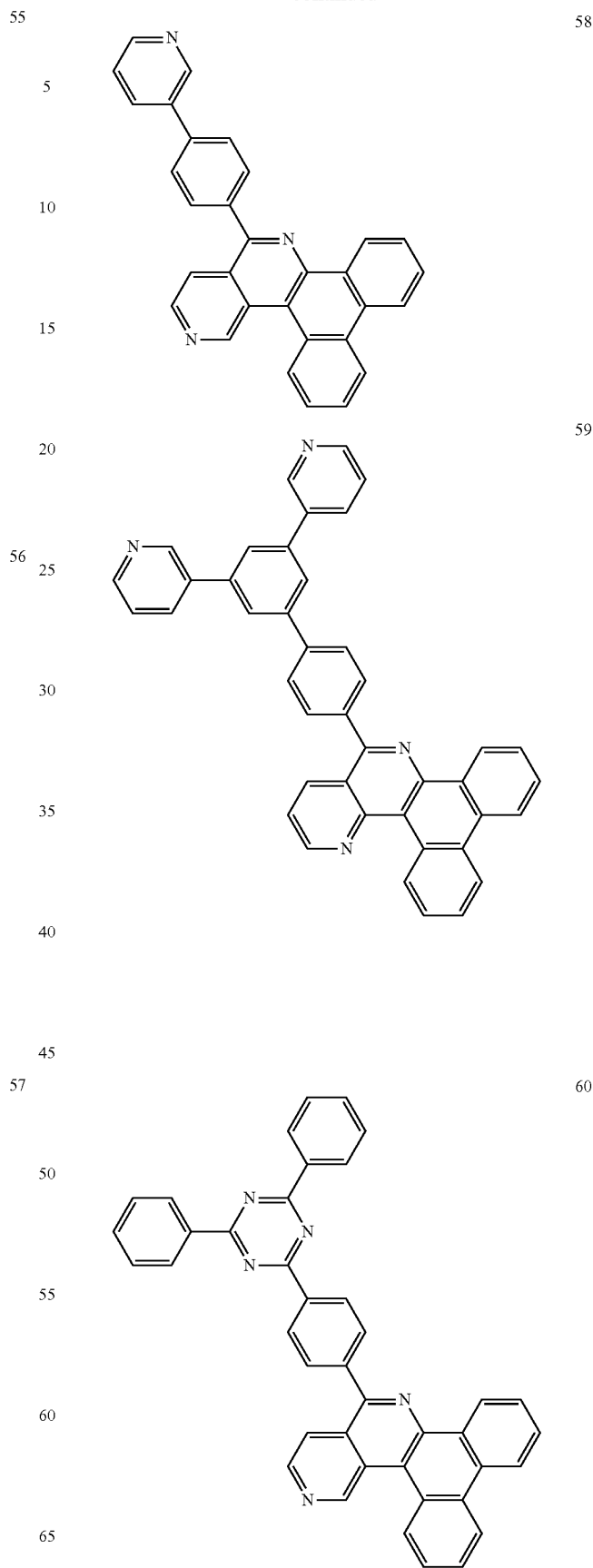

61
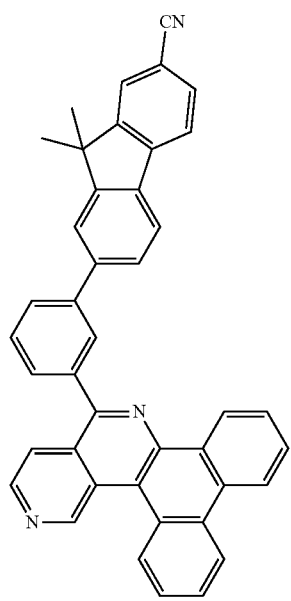
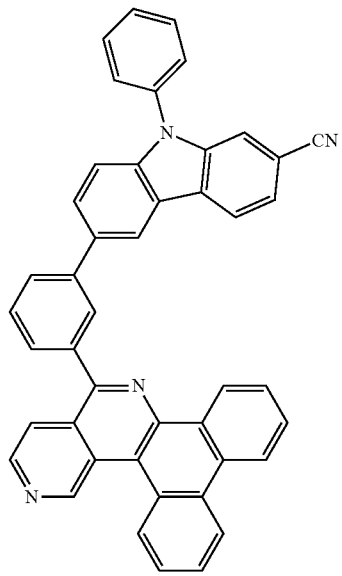
63
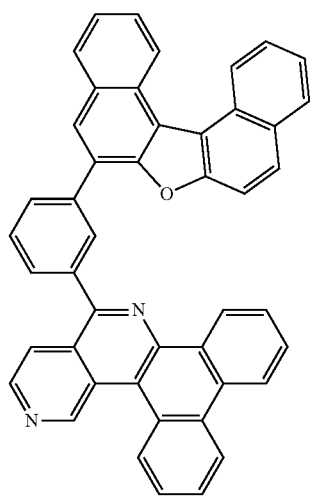
64
62
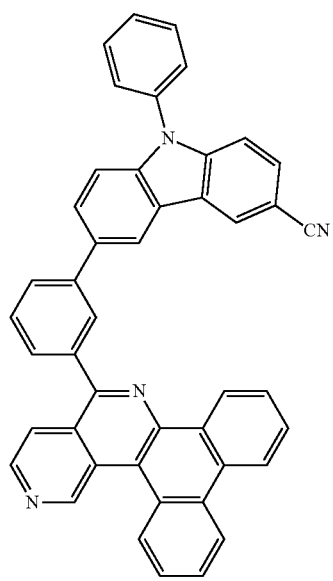
65
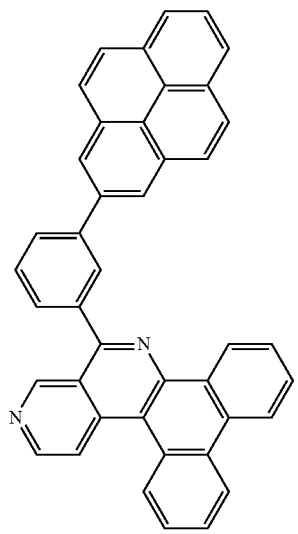

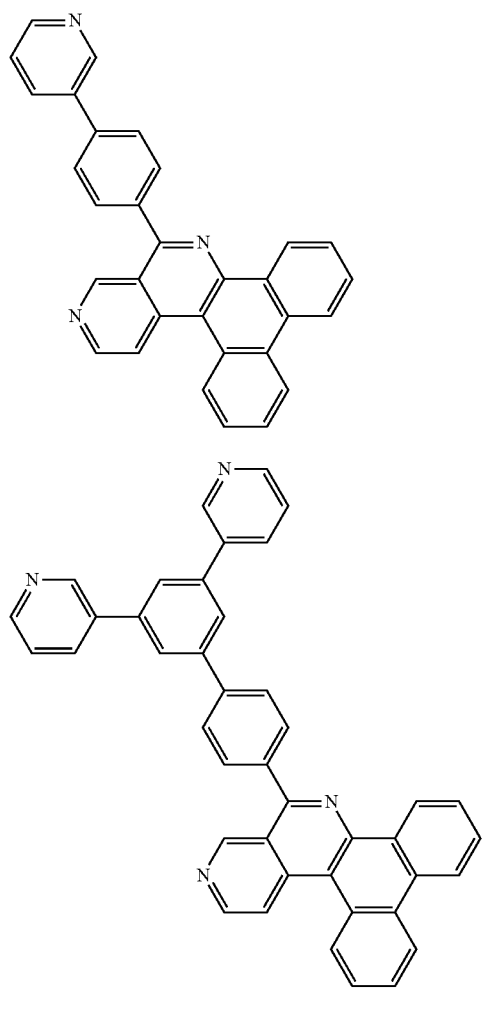
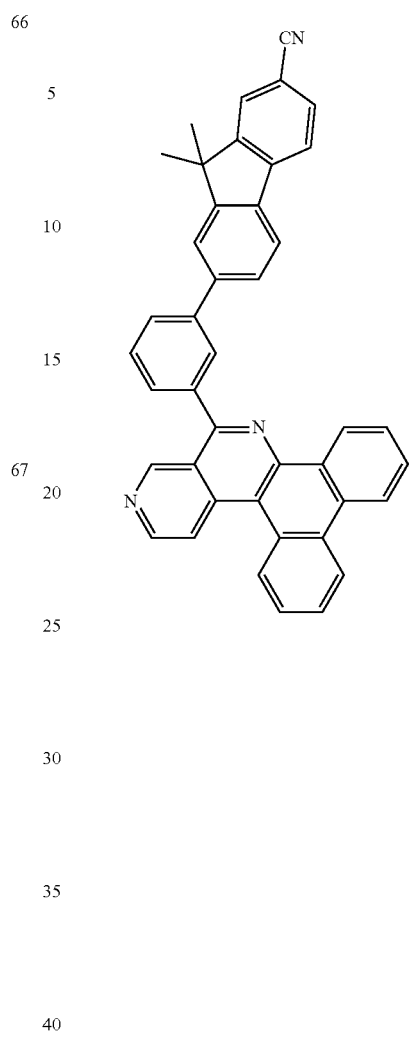
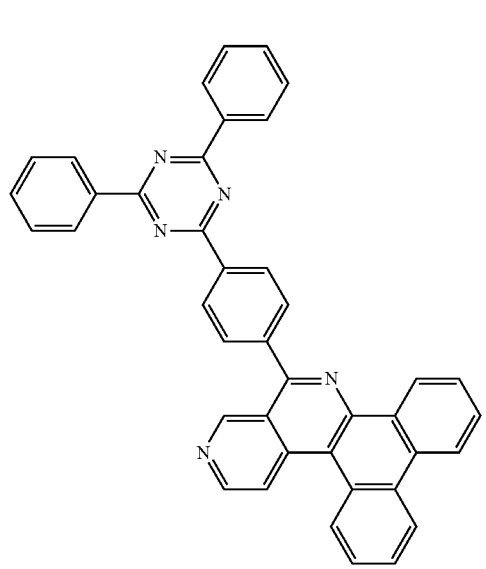
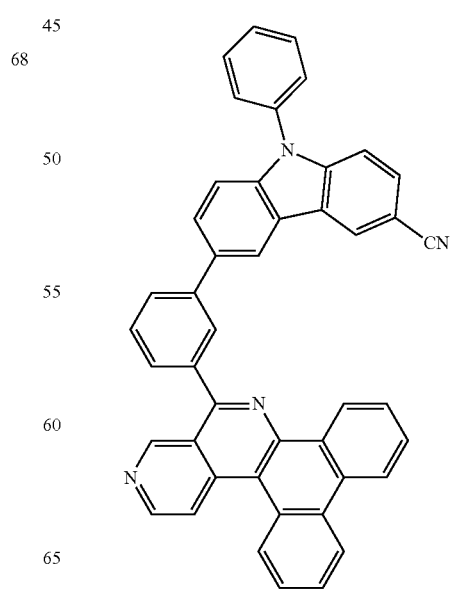

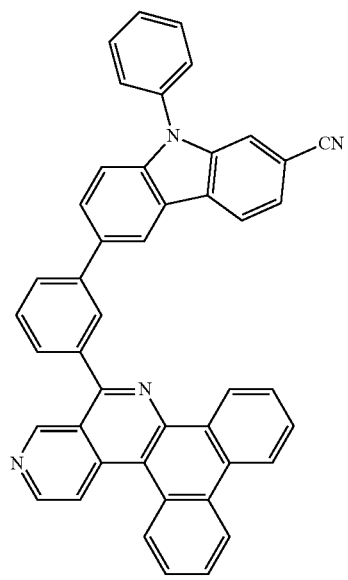
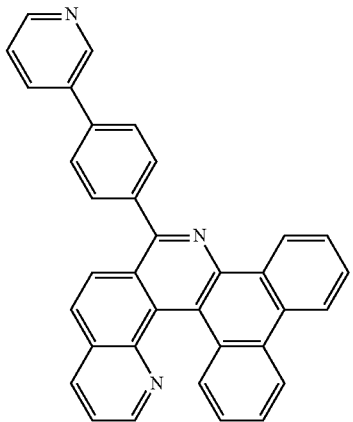
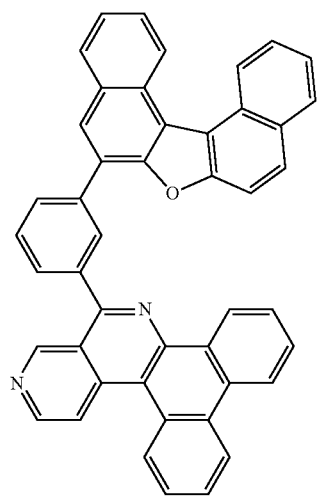
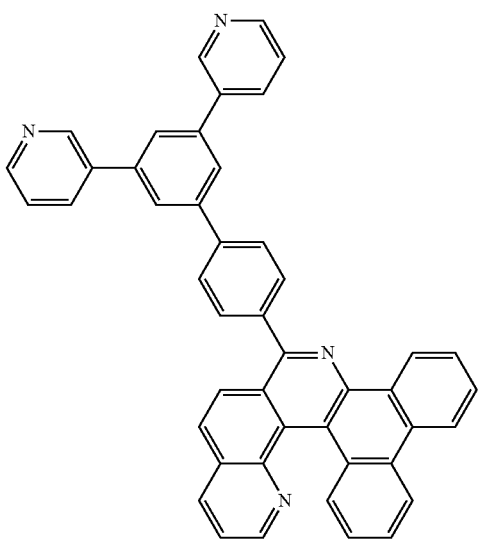
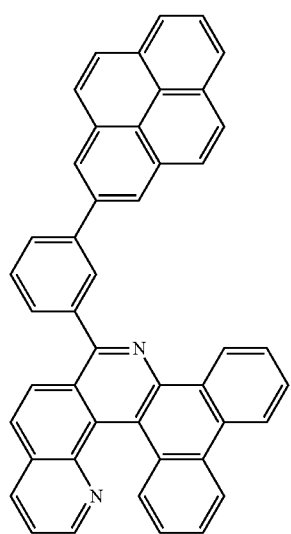
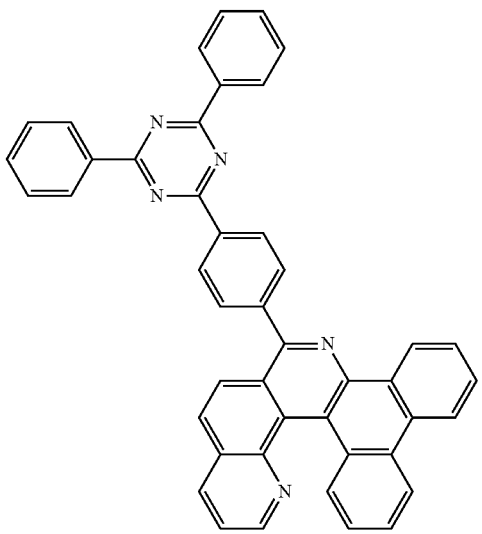

77
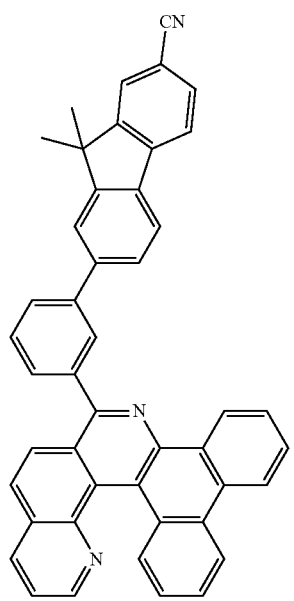
78
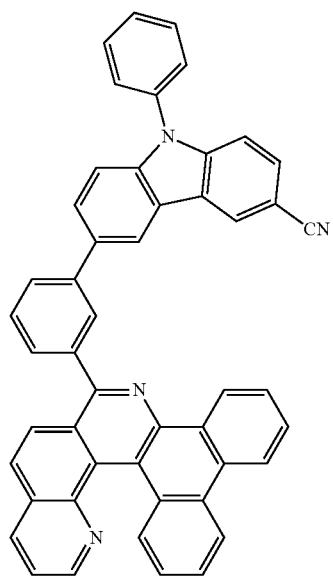
79
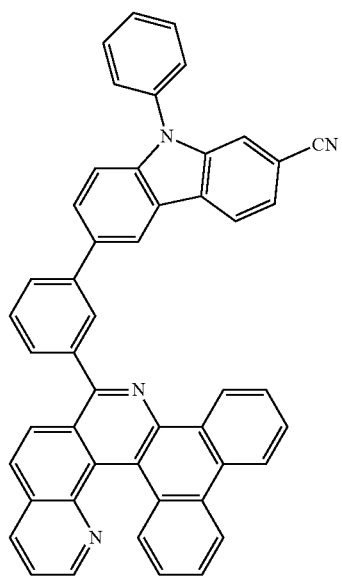
80
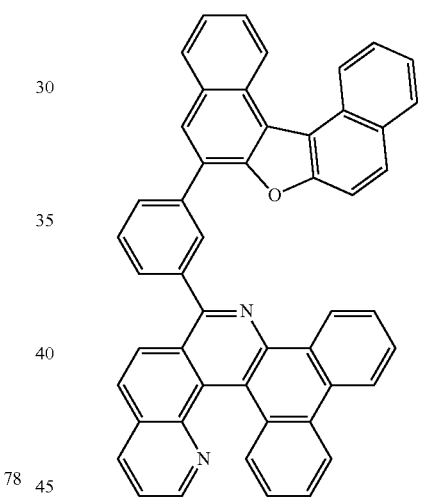
81
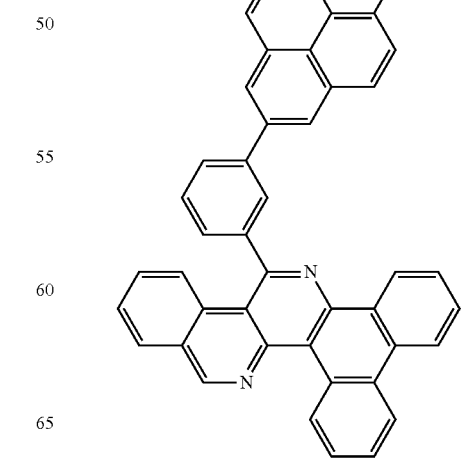

82
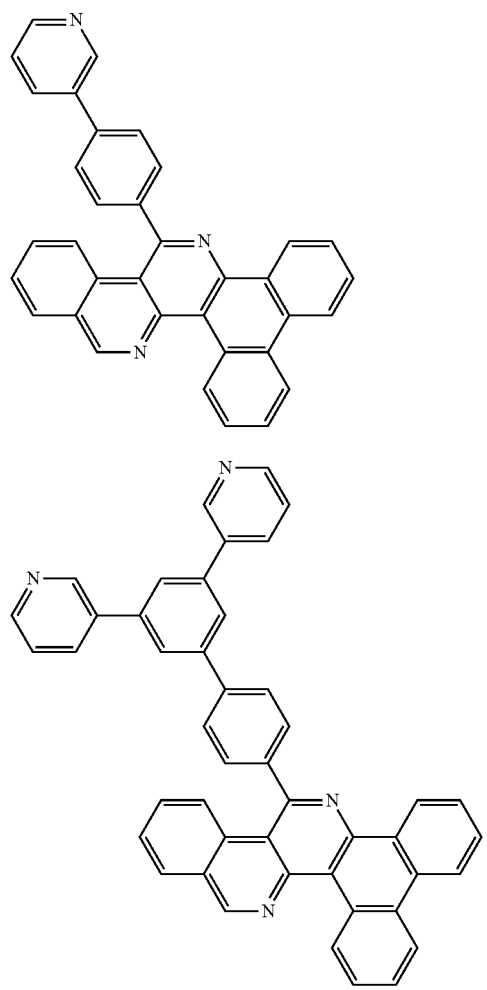
83
84
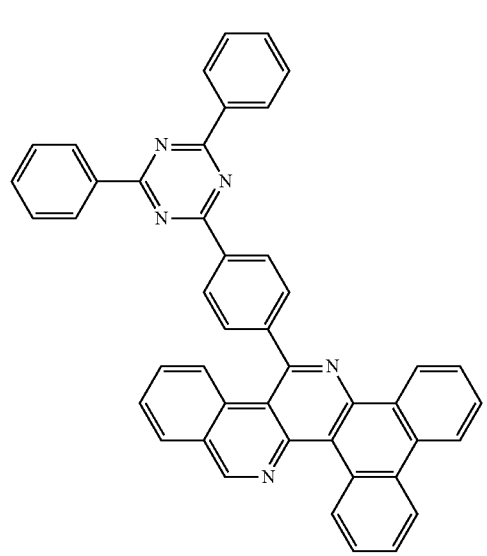
85
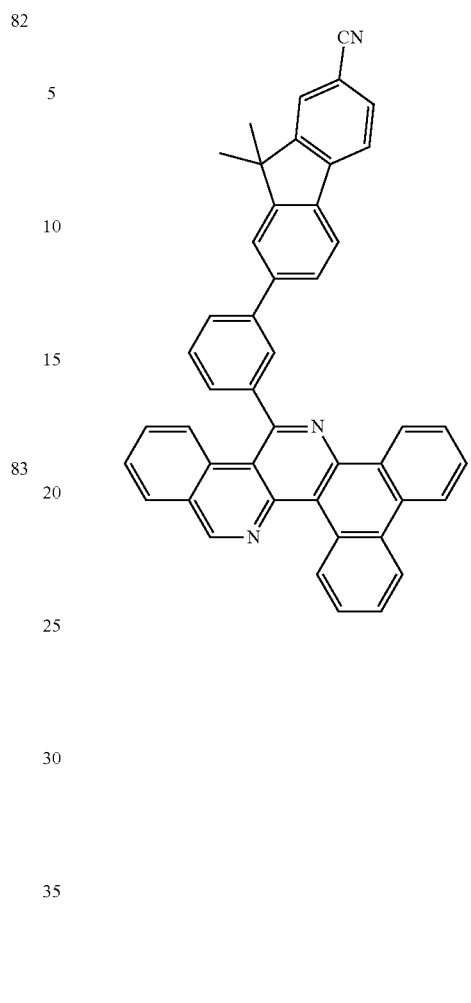
86
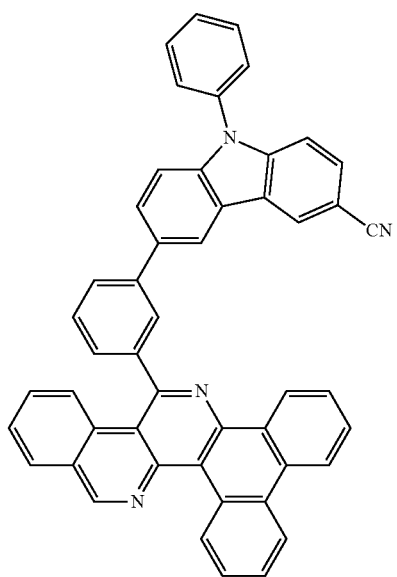

87
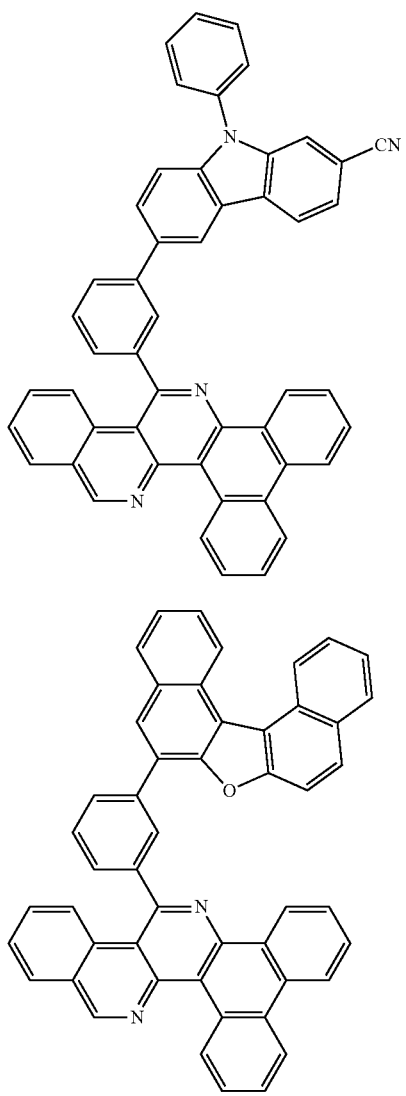
88
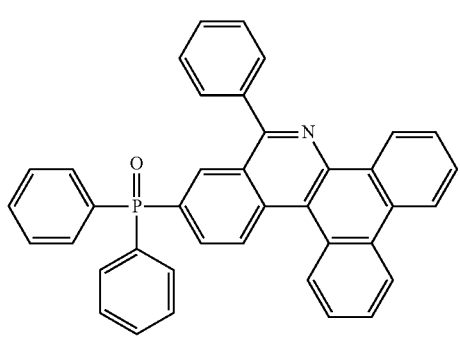
89
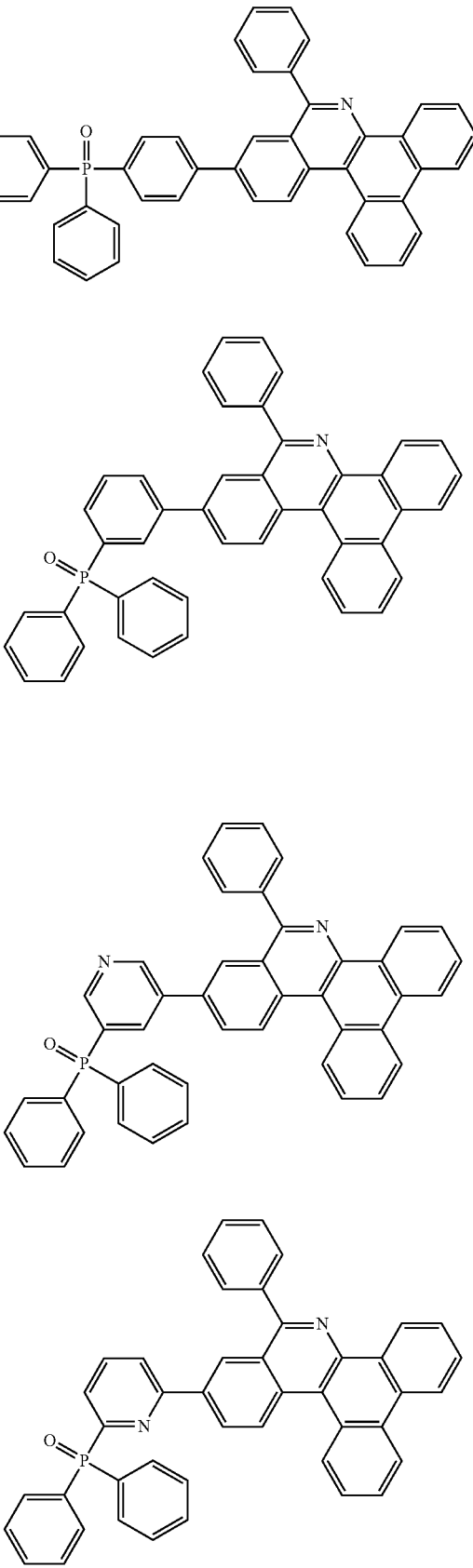
90
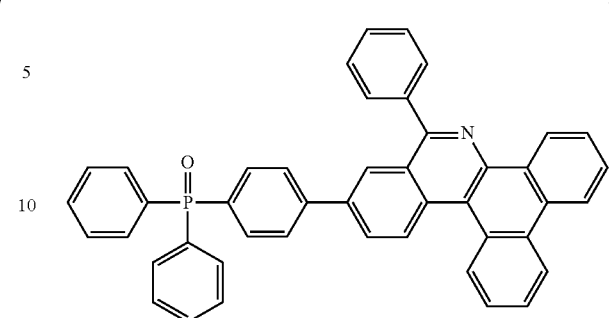
91
92
93

-continued
94
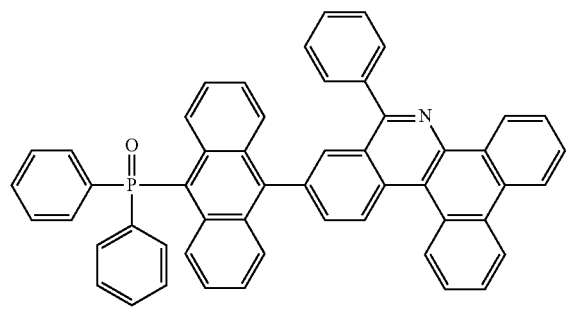
95
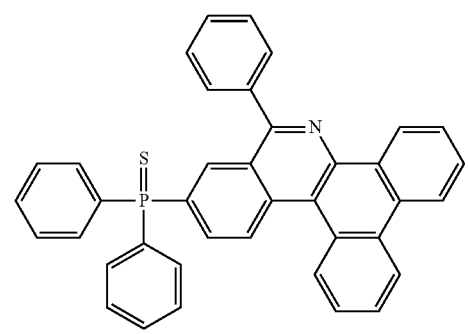
96
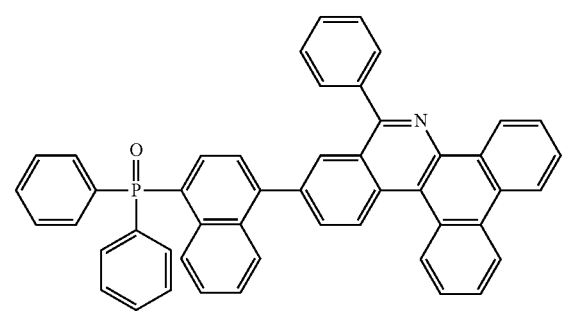
97
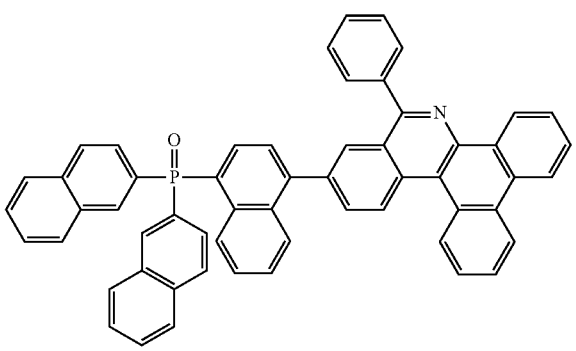
98
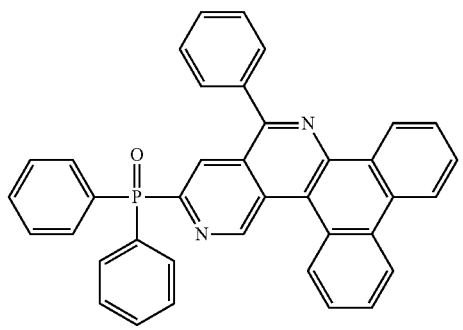
99
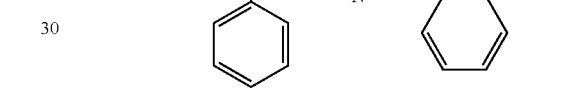
100
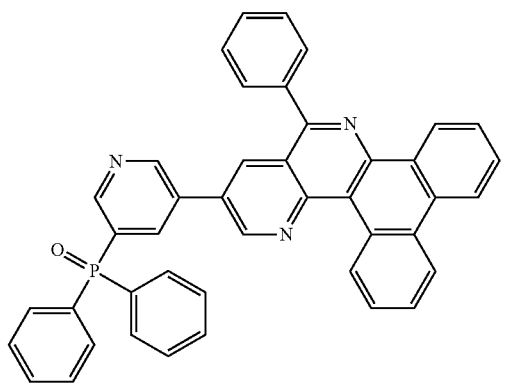
101
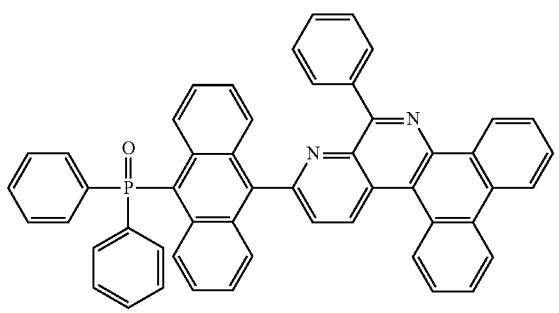

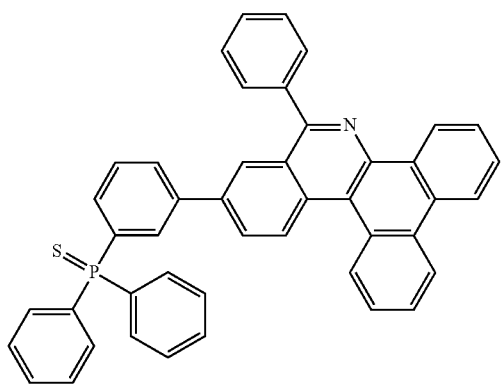
102
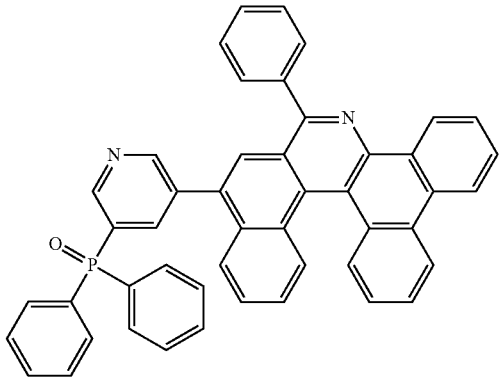
106
103
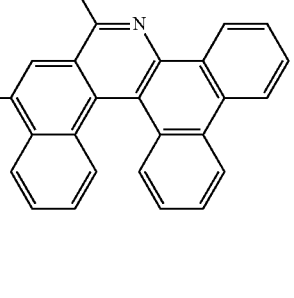
107
104
108
105
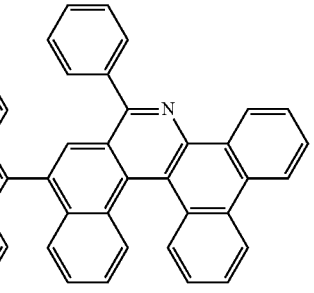
109
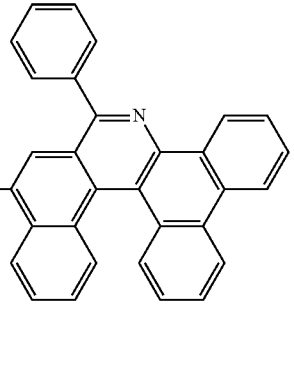

110
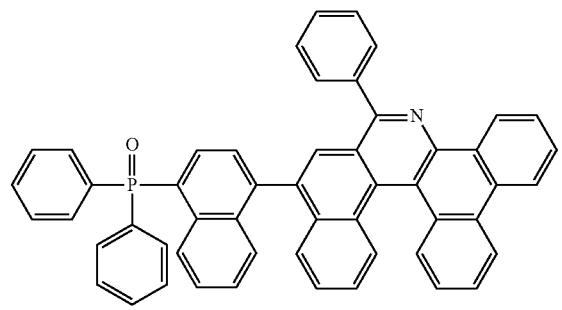
111
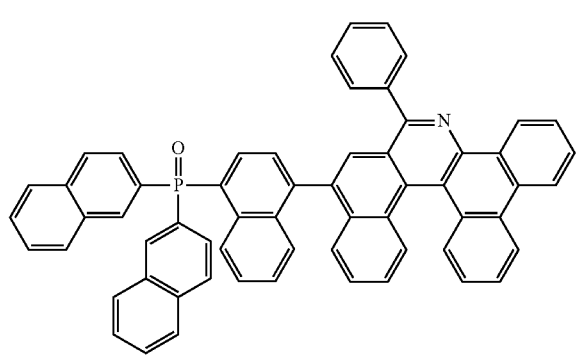
112
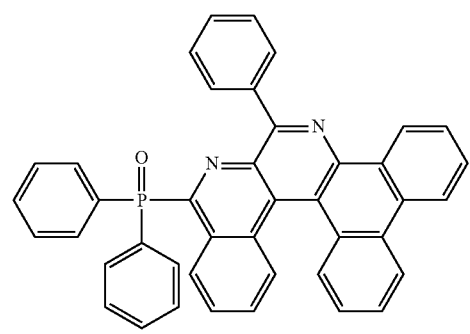
113
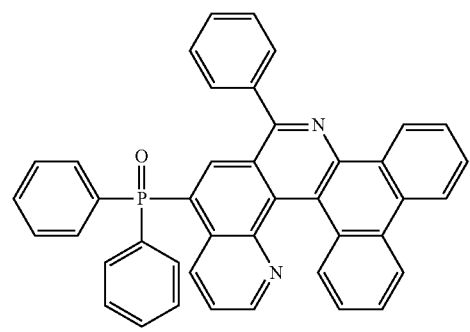
114
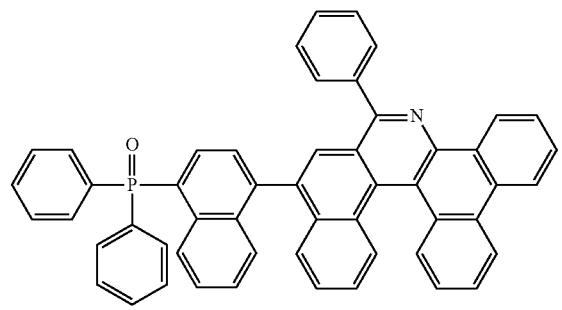
115
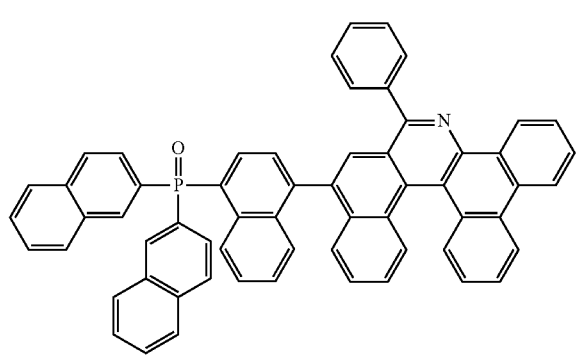
116
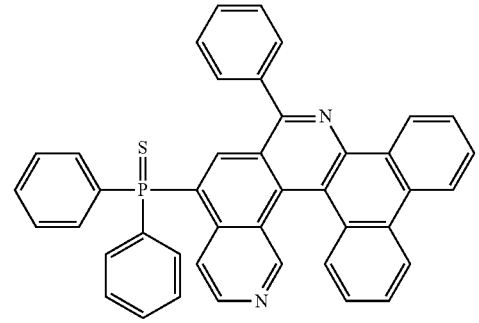
117
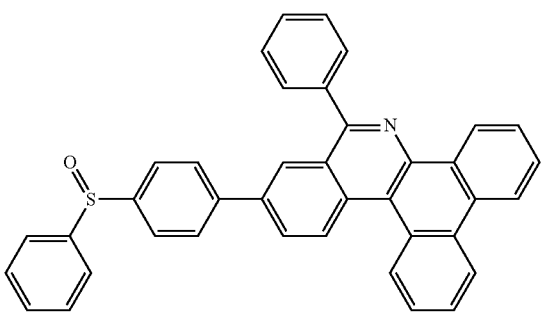

118
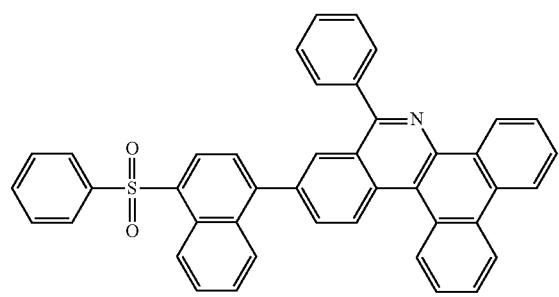
122
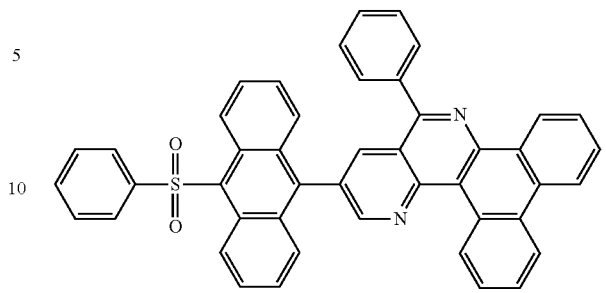
119
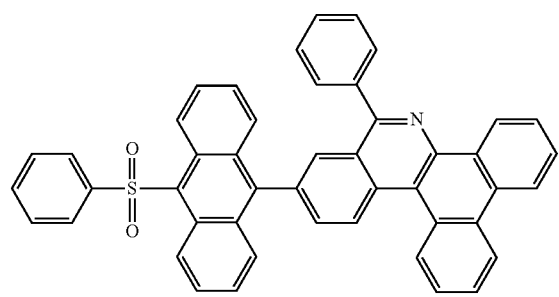
123
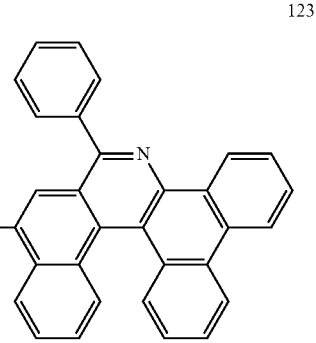
120
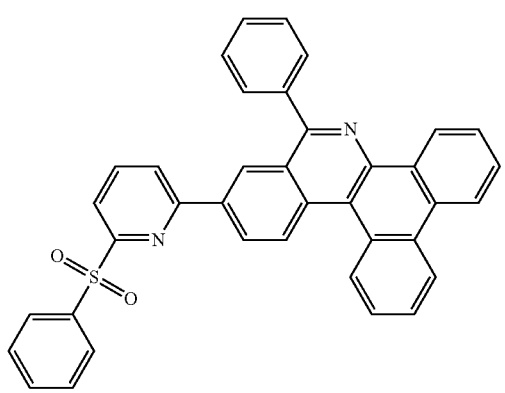
124
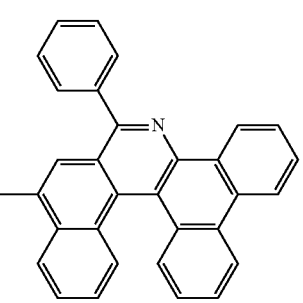
121
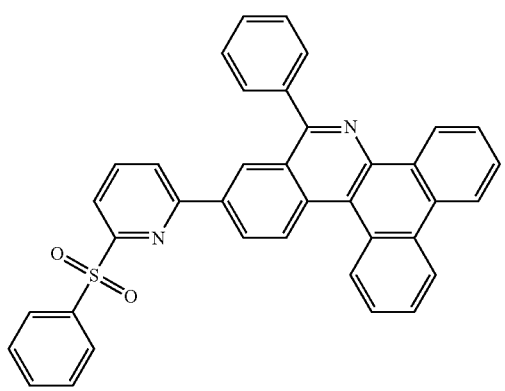
125
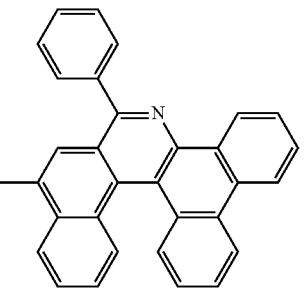

126
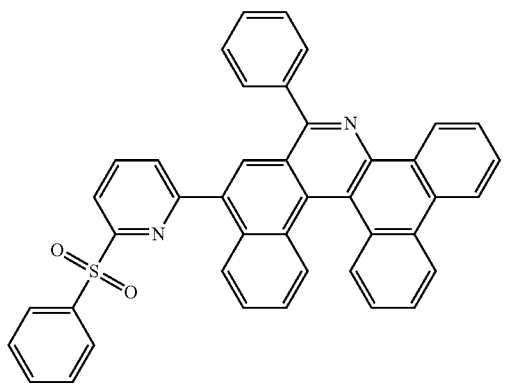
127
130
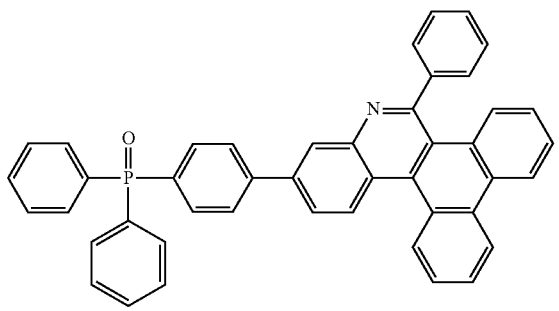
131
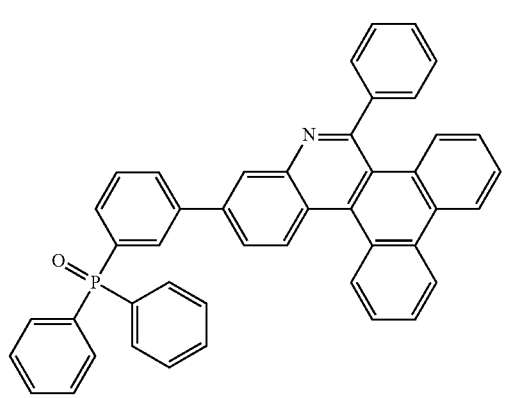
128
132
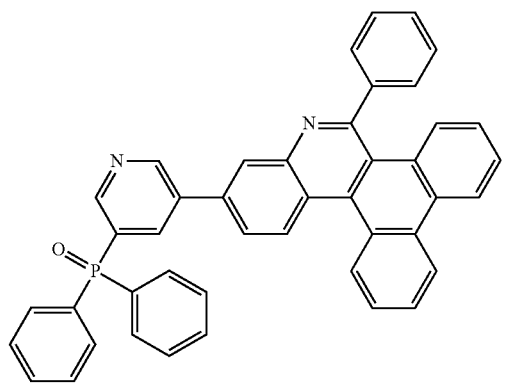
129
133
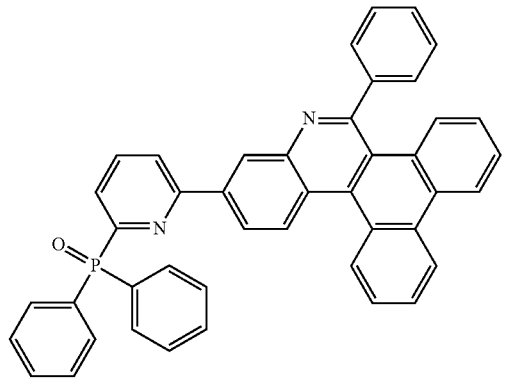

134
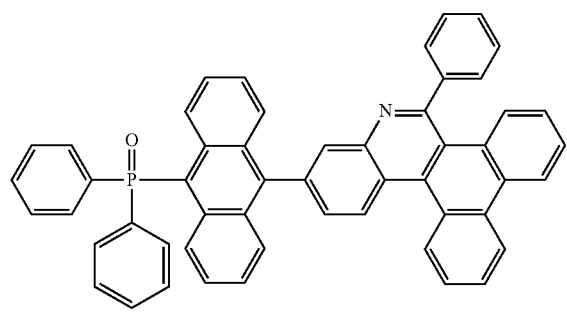
138
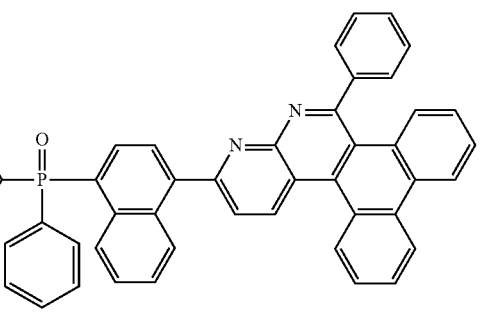
135
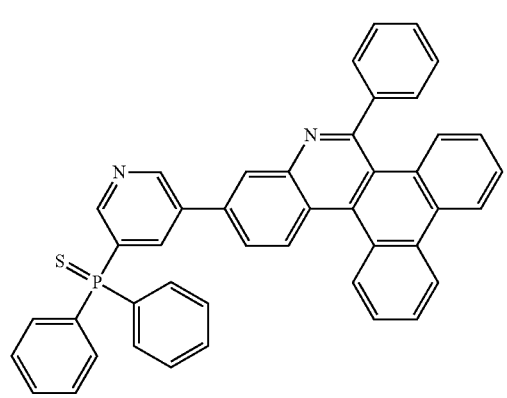
139
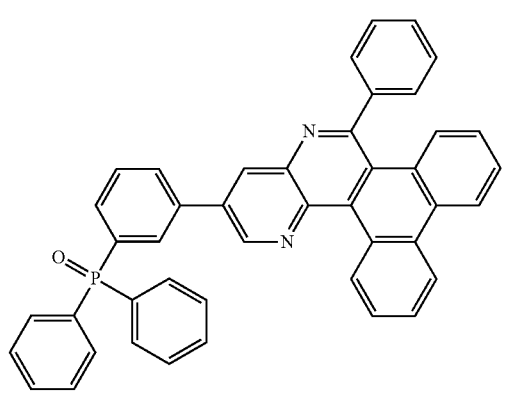
136
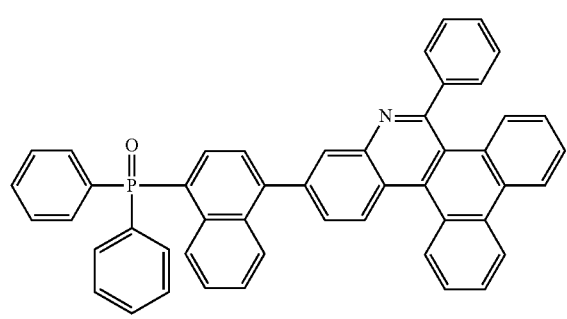
140
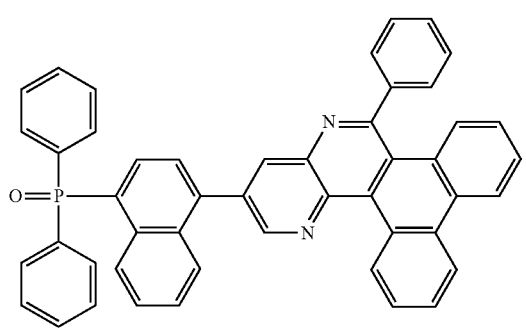
137
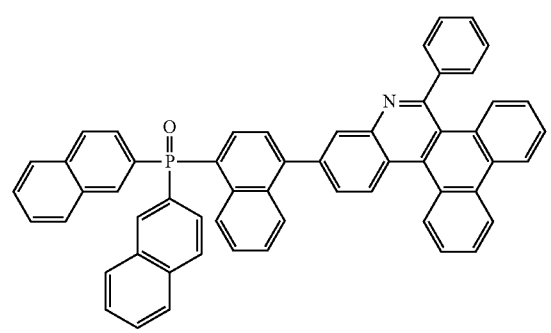
141
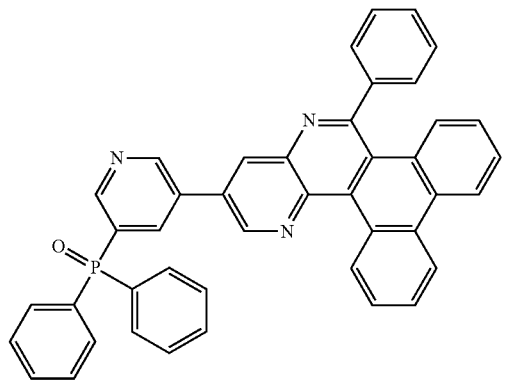

142
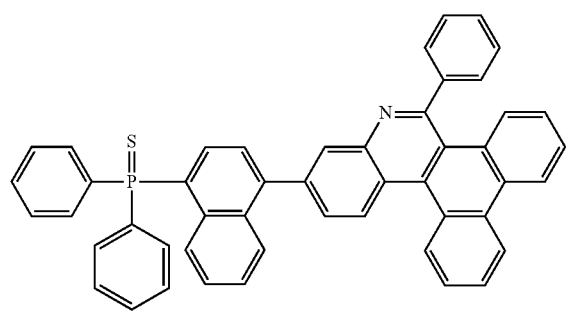
143
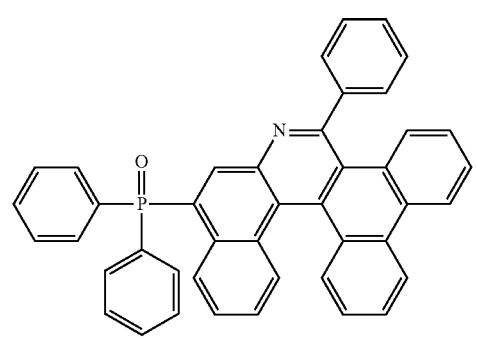
144
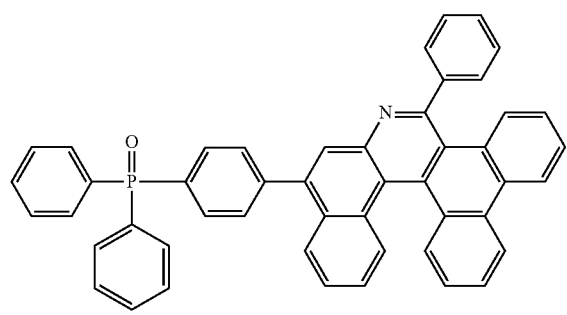
145
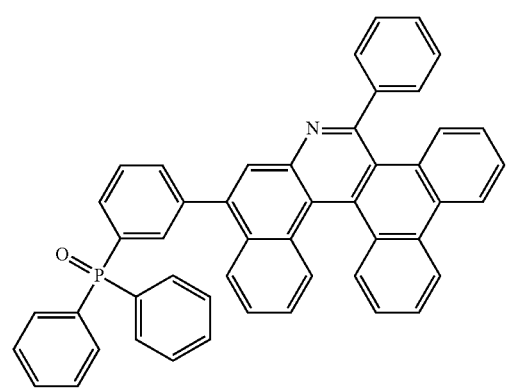
146
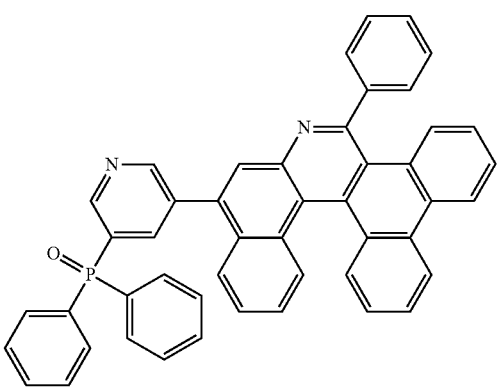
147
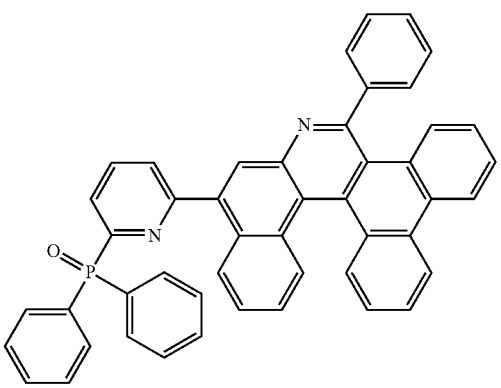
148
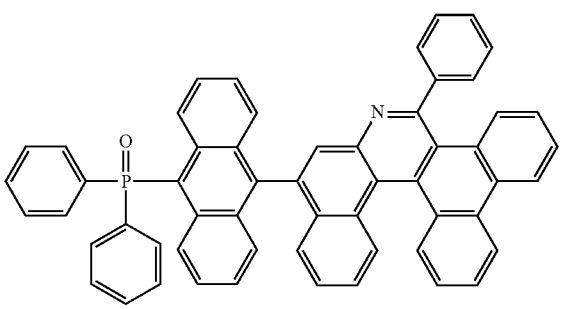
149
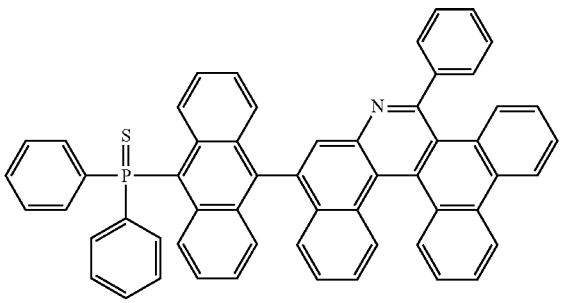

150
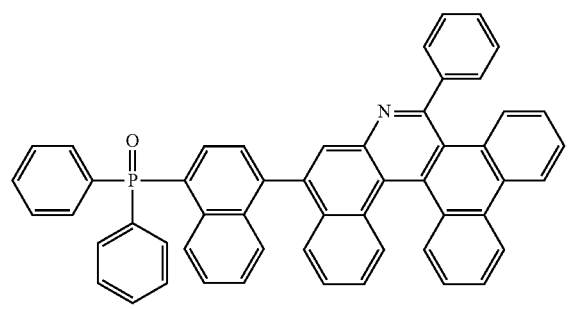
151
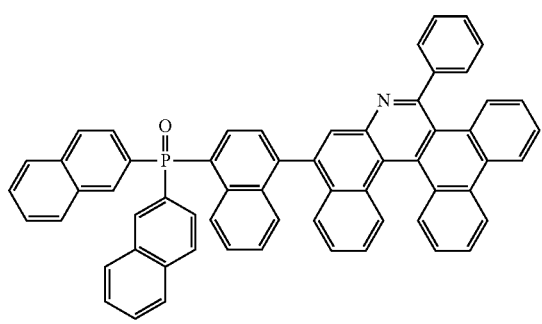
152
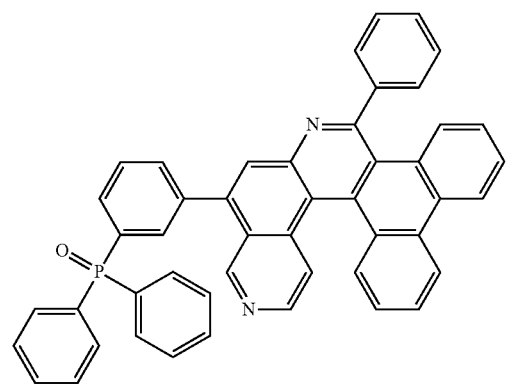
153
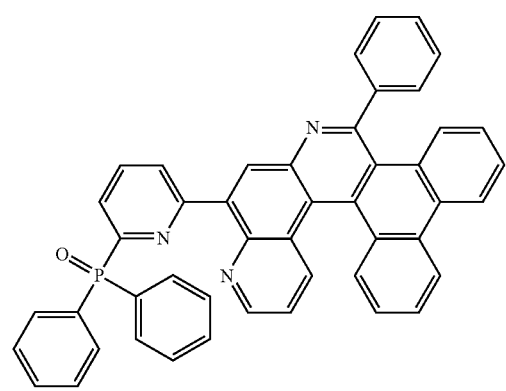
154
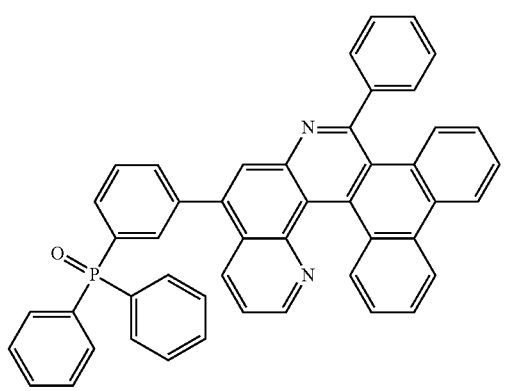
155
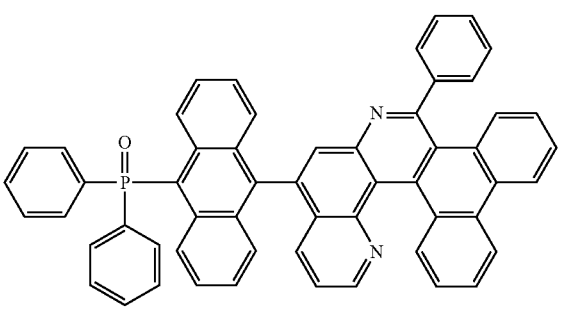
156
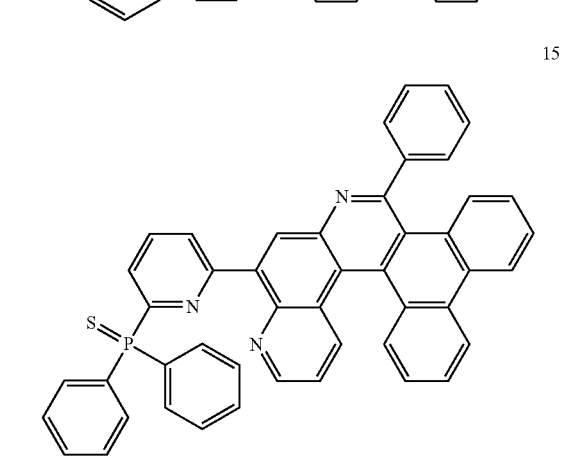
157
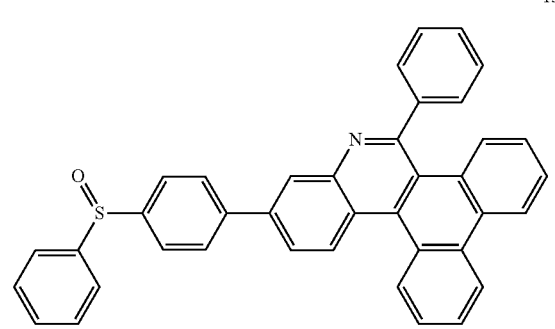

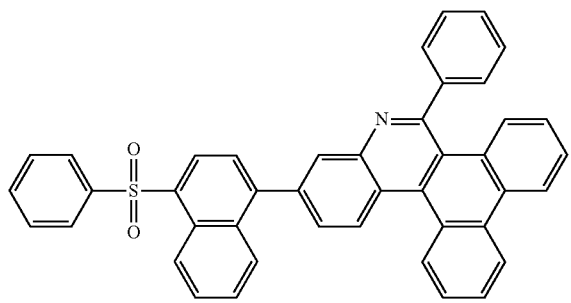
158
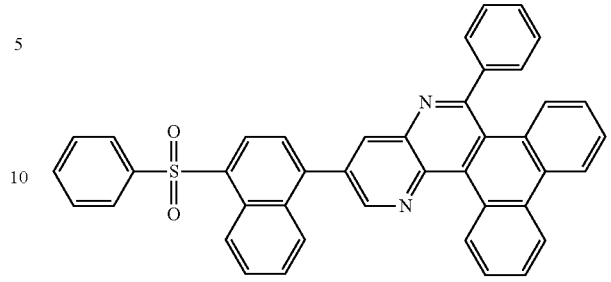
162
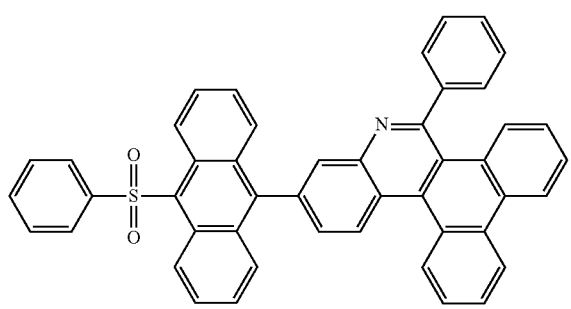
159
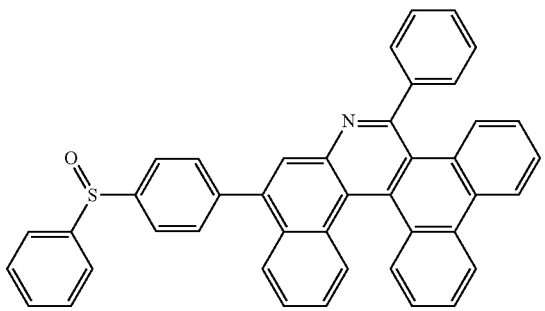
163
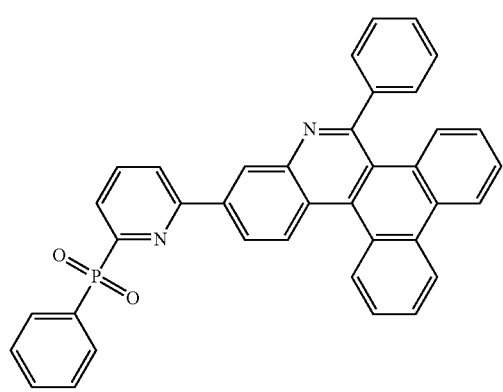
160
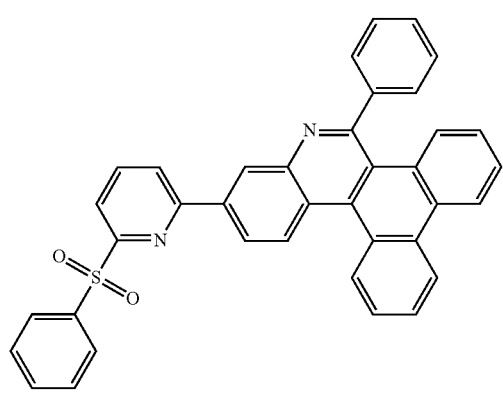
161
164
165

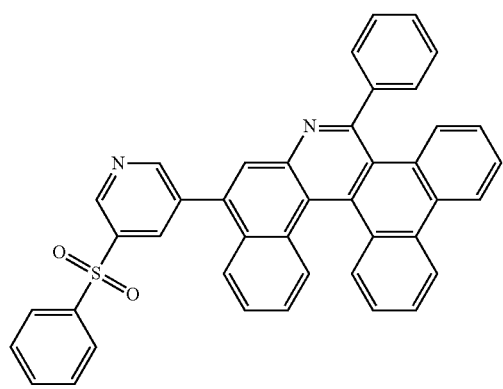
166
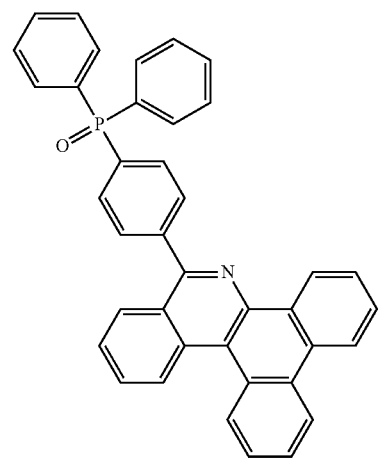
169
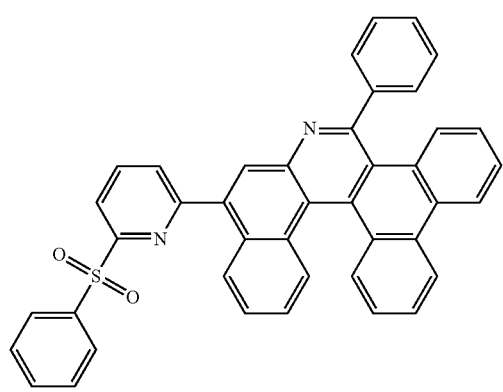
167
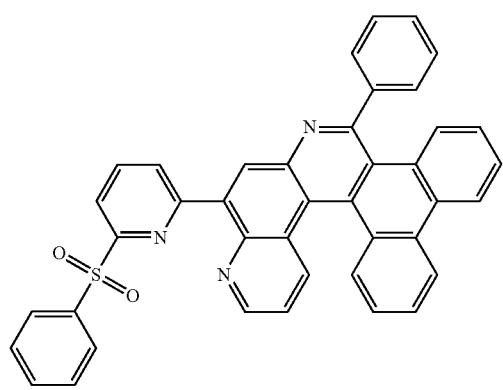
168

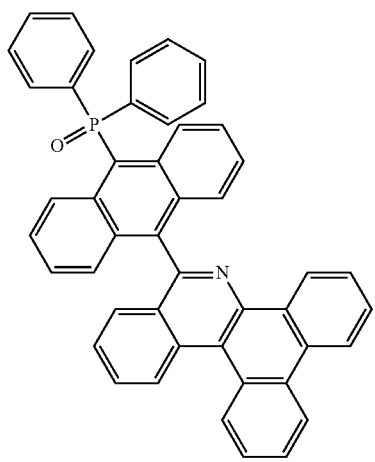
172
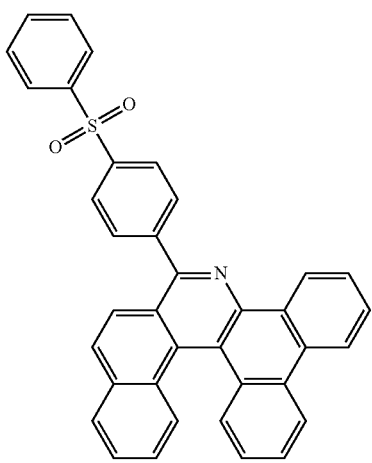
175
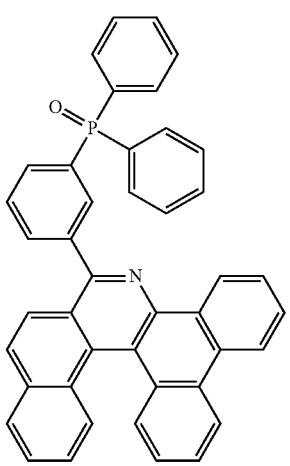
173
176
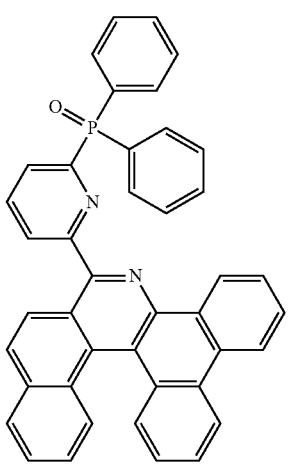
174
177

178 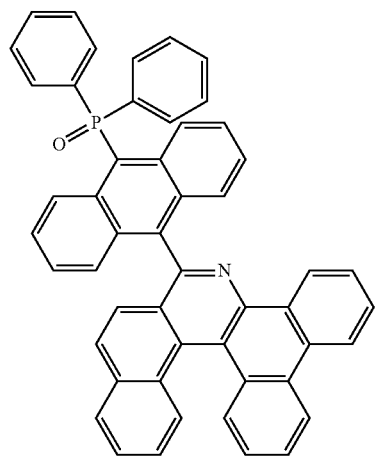
181 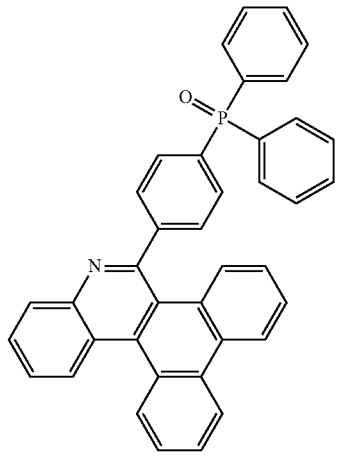
179 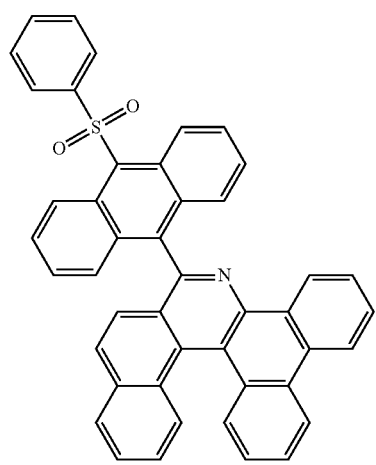
182 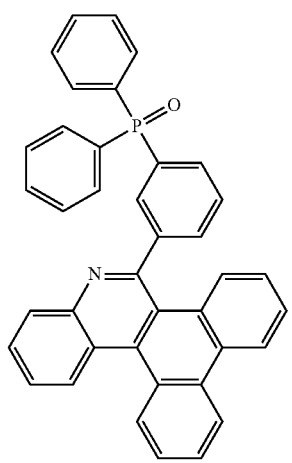
180 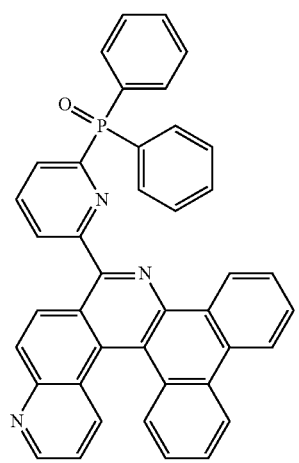
183 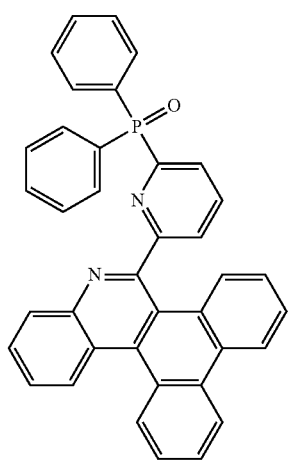

184
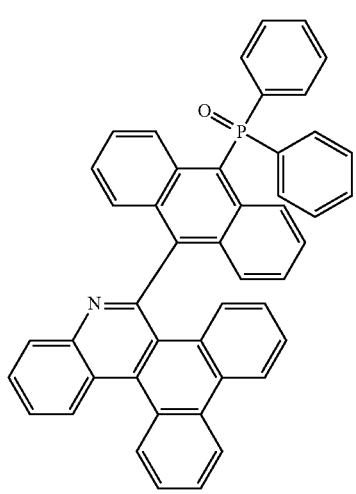
185
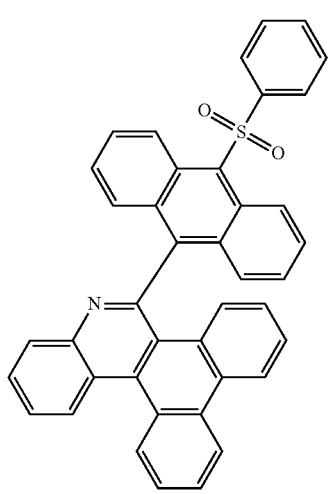
186
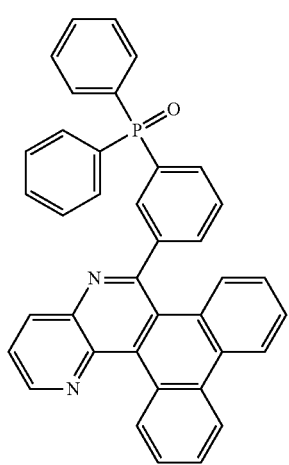
187
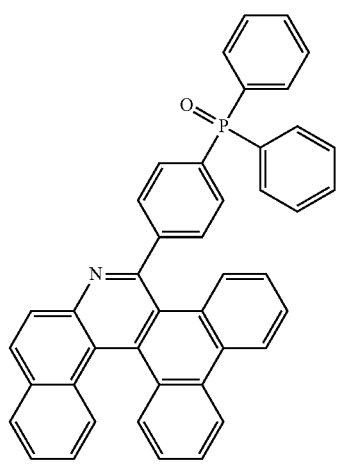
188
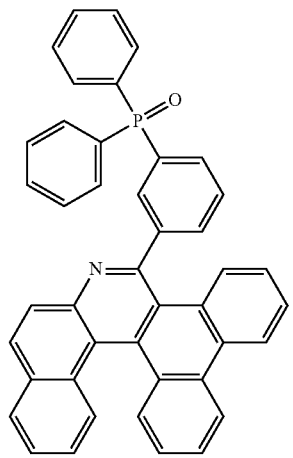
189
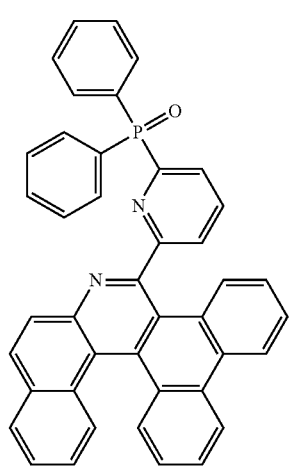

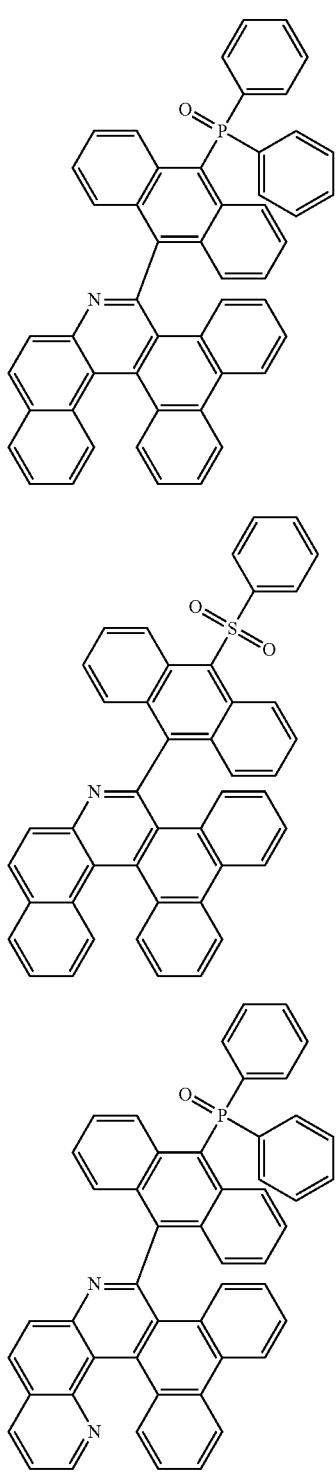

The condensed cyclic compound represented by Formula 1 has excellent charge transport characteristics and thermal stability. Accordingly, an organic light-emitting device including the condensed cyclic compound represented by Formula 1 may have a low driving voltage, high efficiency, high luminance, and a long lifespan.

A method of synthesizing the condensed cyclic compound represented by Formula 1 may be understood by referring to the following examples.

At least one of the condensed cyclic compounds represented by Formula 1 may be used between a pair of electrodes of an organic light-emitting device. In one or more embodiments, the condensed cyclic compound may be included in an electron transport region.

According to another aspect, an organic light-emitting device includes a first electrode; a second electrode facing the first electrode; and an organic layer that is disposed between the first electrode and the second electrode and includes an emission layer, wherein the organic layer includes at least one of condensed cyclic compounds represented by Formula 1.

The expression "(an organic layer) includes at least one of the condensed cyclic compounds" used herein may include a case in which "(an organic layer) includes identical condensed cyclic compounds represented by Formula 1" and a case in which "(an organic layer) includes two or more different condensed cyclic compounds represented by Formula 1."

For example, the organic layer may include, as the condensed cyclic compound, only Compound 1. In this regard, Compound 1 may exist only in an electron transport layer of the organic light-emitting device. In one or more embodiments, as the organic layer may include, as the condensed cyclic compound, Compound 1 and Compound 2. In one or more embodiments, Compound 1 and Compound 2 may both exist in an identical layer (for example, Compound 1 and Compound 2 may both exist in an electron transport layer), or may exist in different layers (for example, Compound 1 may exist in an electron transport layer and Compound 2 may exist in an electron injection layer).

The organic layer includes i) a hole transport region that is disposed between the first electrode (anode) and the emission layer and includes at least one of a hole injection layer, a hole transport layer, an emission auxiliary layer, and an electron blocking layer, and ii) an electron transport region that is disposed between the emission layer and the second electrode (cathode) and includes at least one selected from a buffer layer, a hole blocking layer, an electron control layer, an electron transport layer, and an electron injection layer. The electron transport region may include at least one condensed cyclic compound represented by Formula 1. For example, the electron transport region of the organic light-emitting device may include the electron transport layer, wherein the electron transport layer may include at least one of the condensed cyclic compound represented by Formula 1. For example, the electron transport region of the organic light-emitting device may include an electron injection layer, and the electron injection layer may include at least one of the organometallic compounds represented by Formula 1.

The organic light-emitting device may further include at least one selected from a first capping layer disposed in a pathway along which light generated in an emission layer travels toward outside through the first electrode and a second capping layer disposed in a pathway along which light generated in an emission layer travels toward outside through the second electrode, and the at least one selected from the first capping layer and the second capping layer may include at least one of the condensed cyclic compounds represented by Formula 1.

For example, the organic light-emitting device may have i) a stack structure including a first electrode, an organic layer, a second electrode, and a second capping layer which are sequentially stacked in this stated order, ii) a stack structure including a first capping layer, a first electrode, an organic layer, and a second electrode which are sequentially stacked in this stated order, or iii) a stack structure including a first capping layer, a first electrode, an organic layer, a second electrode, and a second capping layer which are sequentially stacked in this stated order, and at least one selected from the first capping layer and the second capping layer may include the condensed cyclic compound.

The term "organic layer" used herein refers to a single layer and/or a plurality of layers disposed between the first electrode and the second electrode of the organic light-emitting device. A material included in the "organic layer" is not limited to an organic material.

[Description of FIG. 1]

Figure 1:
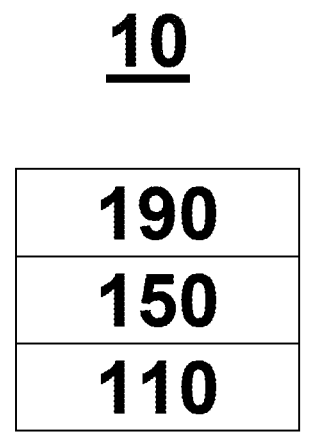

FIG. 1 is a schematic cross-sectional view of an organic light-emitting device 10 according to an embodiment. The organic light-emitting device 10 includes a first electrode 110, an organic layer 150, and a second electrode 190.

Hereinafter, the structure of the organic light-emitting device 10 according to the present embodiment and a method of manufacturing the same will be described in connection with FIG. 1.

[First Electrode 110]

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water-resistance.

The first electrode 110 may be formed by depositing or sputtering a material for forming the first electrode 110 on the substrate. When the first electrode 110 is an anode, the material for forming the first electrode 110 may be selected from materials with a high work function to facilitate hole injection.

The first electrode 110 may be a reflective electrode, a semi-reflective electrode, or a transmissive electrode. When the first electrode 110 is a transmissible electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissible electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

[Organic Layer 150]

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

[Hole Transport Region in Organic Layer 150]

The hole transport region may have i) a single-layered structure including a single layer including a single material, ii) a single-layered structure including a single layer including different materials, or iii) a multi-layered structure having a plurality of layers including different materials.

The hole transport region may include at least one layer selected from a hole injection layer (HIL), a hole transport layer (HTL), an emission auxiliary layer, and an electron blocking layer (EBL).

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/ electron blocking layer structure, wherein for each structure, constituting layers are sequentially stacked from the first electrode 110 in this stated order, but the structure of the hole transport region is not limited thereto.

The hole transport region may include at least one selected from m-MTDATA, TDATA, 2-TNATA, NPB (NPD), β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly (4-styrenesulfonate) (PEDOT/PSS), polyaniline/camphor sulfonic acid (Pani/CSA), polyaniline/poly(4-styrene-sulfonate) (Pani/PSS), a compound represented by Formula 201, and a compound represented by Formula 202:

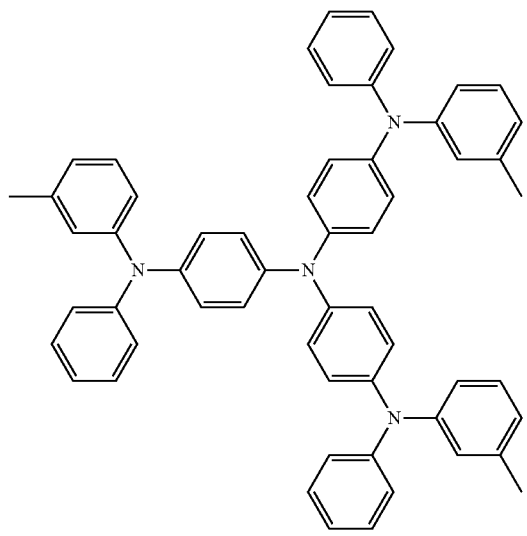

m-MTDATA

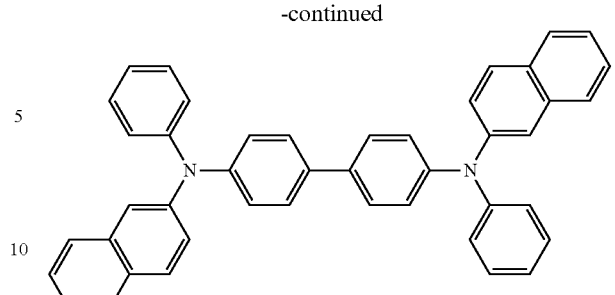
β-NPB
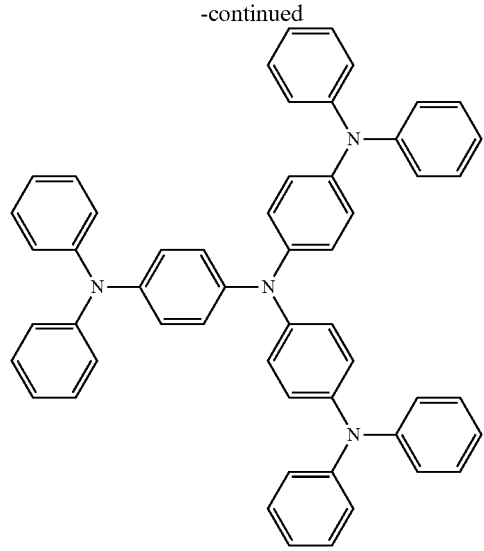
TDATA
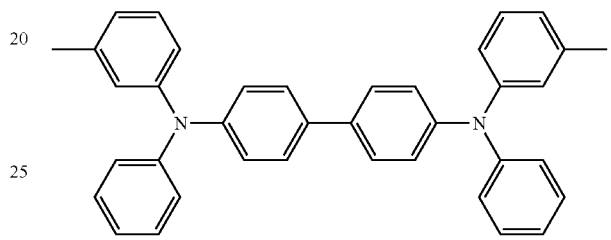
TPD
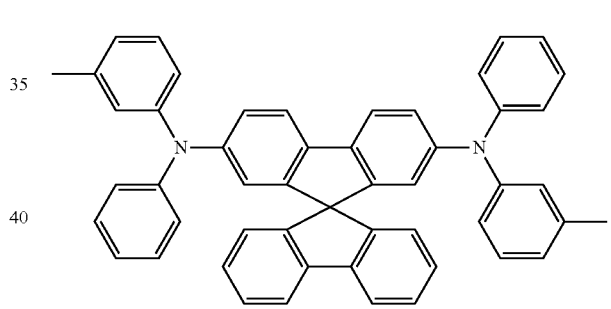
Spiro-TPD
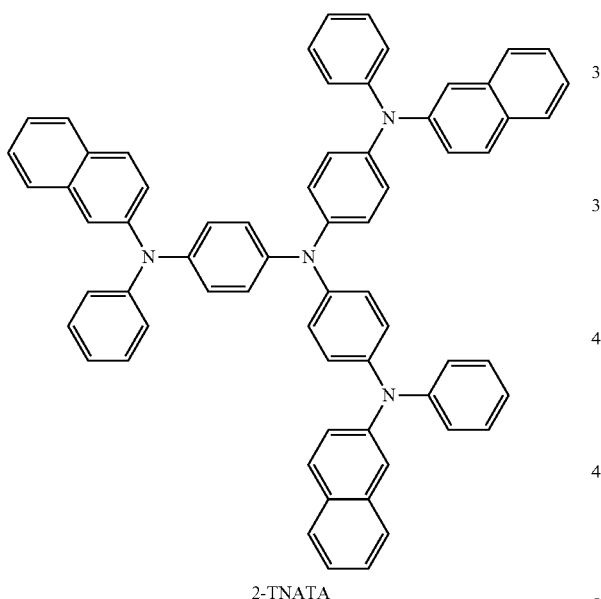
2-TNATA
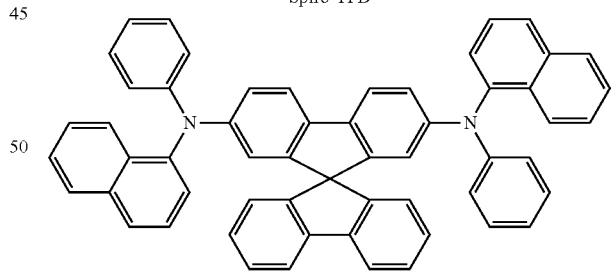
Spiro-NPB
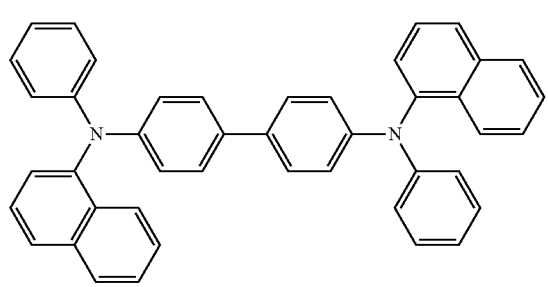
NPB
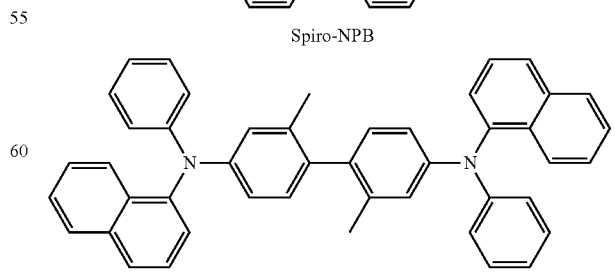
methylated NPB -continued

TAPC

HMTPD

<Formula 201>

$$R_{201}-(L_{201})_{xa1}-N\begin{matrix}(L_{202})_{xa2}-R_{202}\\ \\(L_{203})_{xa3}-R_{203}\end{matrix}$$

<Formula 202>

$$R_{201}-(L_{201})_{xa1}\quad (L_{203})_{xa3}-R_{203}$$
$$\quad\quad\quad N-(L_{205})_{xa5}-N$$
$$R_{202}-(L_{202})_{xa2}\quad (L_{204})_{xa4}-R_{204}$$

In Formulae 201 and 202, $L_{201}$ to $L_{204}$ may each independently be selected from a substituted or unsubstituted $C_3$-$C_{10}$ cycloalkylene group, substituted or unsubstituted $C_1$-$C_{10}$ heterocycloalkylene group, substituted or unsubstituted $C_3$-$C_{10}$ cycloalkenylene group, substituted or unsubstituted $C_1$-$C_{10}$ heterocycloalkenylene group, substituted or unsubstituted $C_6$-$C_{60}$ arylene group, substituted or unsubstituted $C_1$-$C_{60}$ heteroarylene group, substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, substituted or unsubstituted $C_2$-$C_{20}$ alkenylene group, substituted or unsubstituted $C_3$-$C_{10}$ cycloalkylene group, substituted or unsubstituted $C_1$-$C_{10}$ heterocycloalkylene group, substituted or unsubstituted $C_3$-$C_{10}$ cycloalkenylene group, substituted or unsubstituted $C_1$-$C_{10}$ heterocycloalkenylene group, substituted or unsubstituted $C_6$-$C_{60}$ arylene group, substituted or unsubstituted $C_1$-$C_{60}$ heteroarylene group, substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, $R_{201}$ to $R_{204}$ and $Q_{201}$ may each independently be selected from a substituted or unsubstituted $C_3$-$C_{10}$ cycloalkyl group, substituted or unsubstituted $C_1$-$C_{10}$ heterocycloalkyl group, substituted or unsubstituted $C_3$-$C_{10}$ cycloalkenyl group, substituted or unsubstituted $C_1$-$C_{10}$ heterocycloalkenyl group, substituted or unsubstituted $C_6$-$C_{60}$ aryl group, substituted or unsubstituted $C_6$-$C_{60}$ aryloxy group, substituted or unsubstituted $C_6$-$C_{60}$ arylthio group, substituted or unsubstituted $C_1$-$C_{60}$ heteroaryl group, substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one embodiment, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may be the same as described above.

In one or more embodiments, at least one of $R_{201}$ to $R_{203}$ in Formula 201 may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202, i) $R_{201}$ and $R_{202}$ may be linked via a single bond, and/or ii) $R_{203}$ and $R_{204}$ may be linked via a single bond.

In one or more embodiments, at least one of $R_{201}$ to $R_{204}$ in Formula 202 may be selected from:

a carbazolyl group; and a carbazolyl group, substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group and a dibenzothiophenyl group, but embodiments of the present disclosure are not limited thereto.

The compound represented by Formula 201 may be represented by Formula 201A:

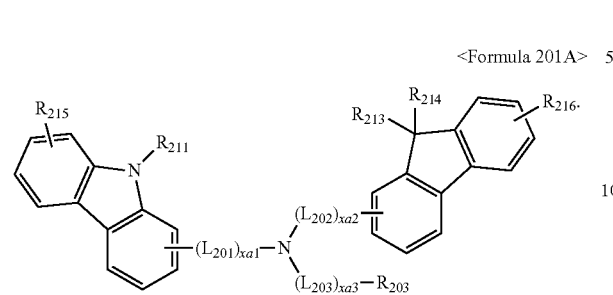

<Formula 201A>

For example, the compound represented by Formula 201 may be represented by Formula 201A(1), but embodiments of the present disclosure are not limited thereto:

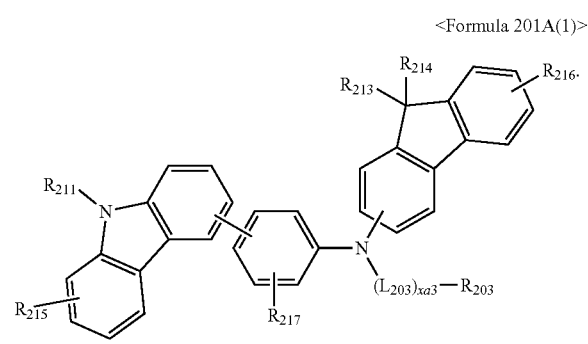

<Formula 201A(1)>

In one embodiment, the compound represented by Formula 201 may be represented by Formula 201A-1, but embodiments of the present disclosure are not limited thereto:

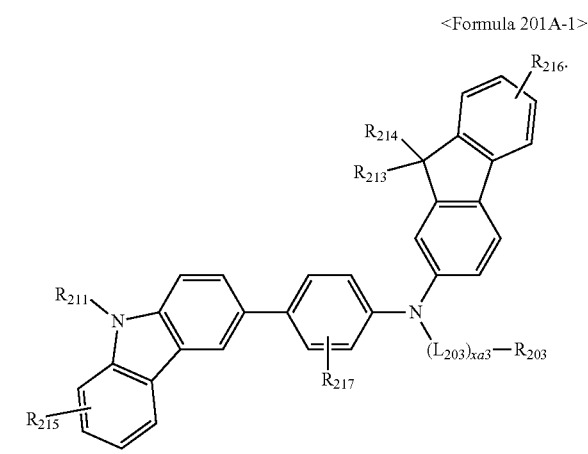

<Formula 201A-1>

The compound represented by Formula 202 may be represented by Formula 202A:

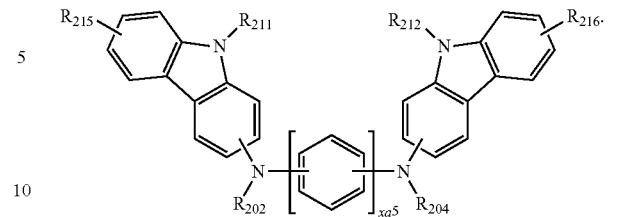

<Formula 202A>

In one or more embodiments, the compound represented by Formula 202 may be represented by Formula 202A-1:

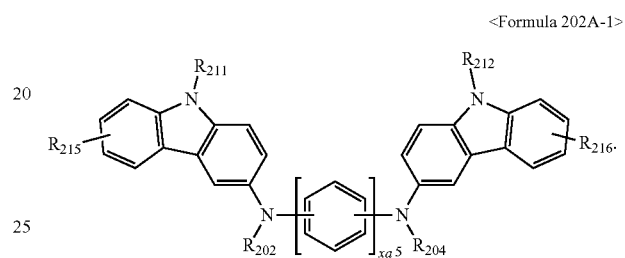

<Formula 202A-1>

In Formulae 201A, 201A(1), 201A-1, 202A, and 202A-1,
$L_{201}$ to $L_{203}$, xa1 to xa3, xa5, and $R_{202}$ to $R_{204}$ may be the same as described above, $R_{211}$ and $R_{212}$ may be the same as described in connection with $R_{203}$, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the present disclosure are not limited thereto:

97 HT1
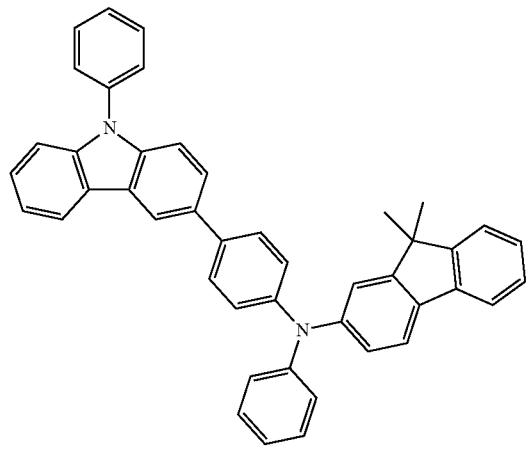
98 HT2
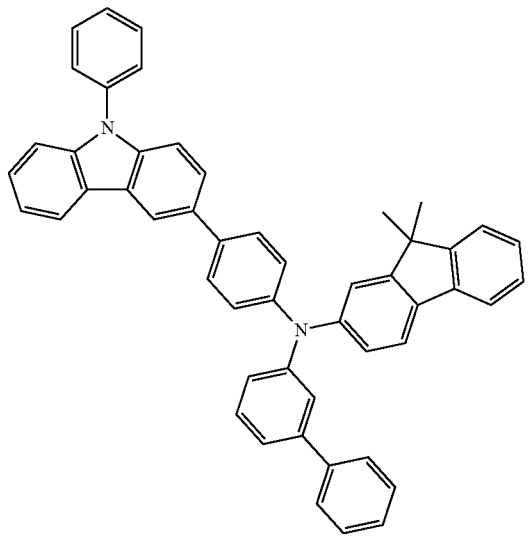
HT3
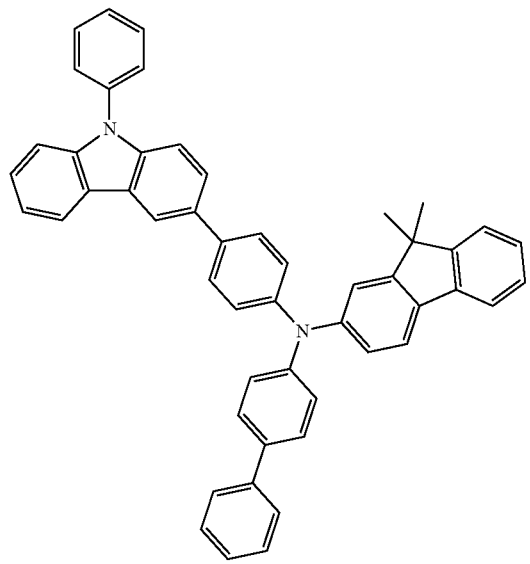
HT4
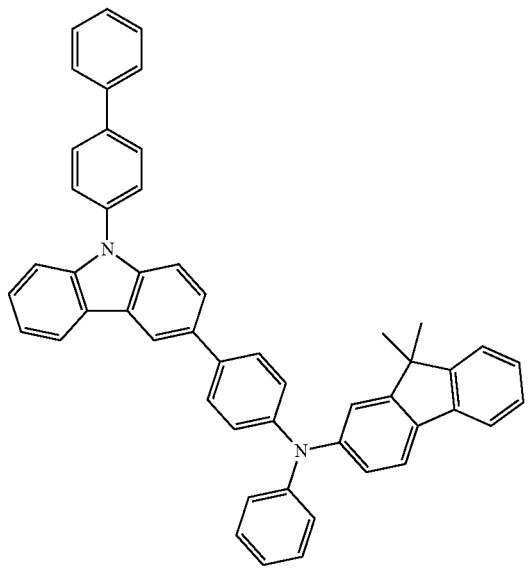

-continued
HT5
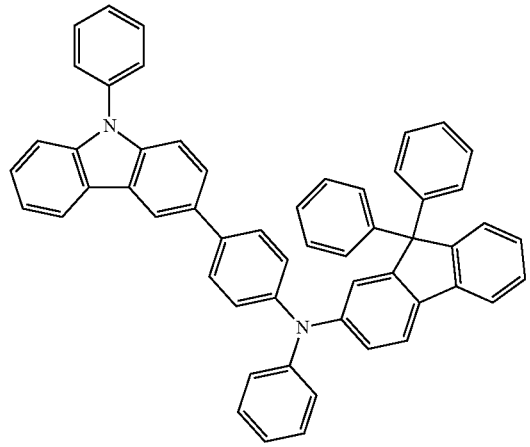
HT6
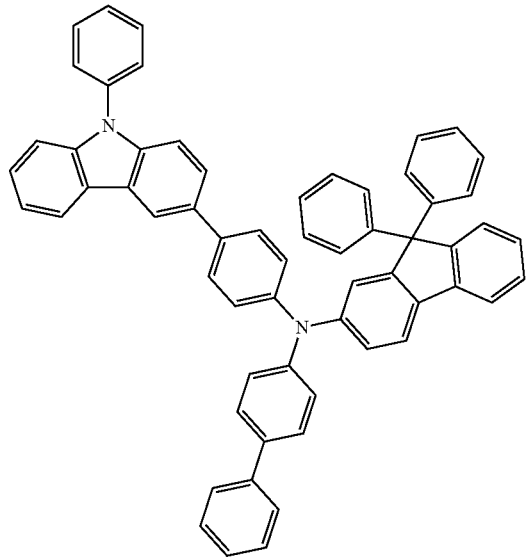
HT7
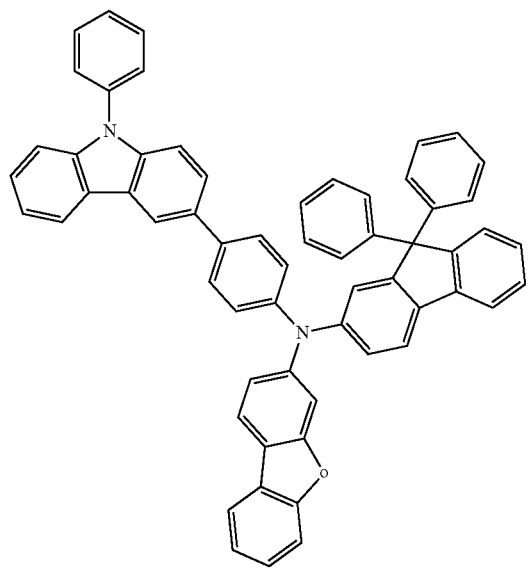
HT8
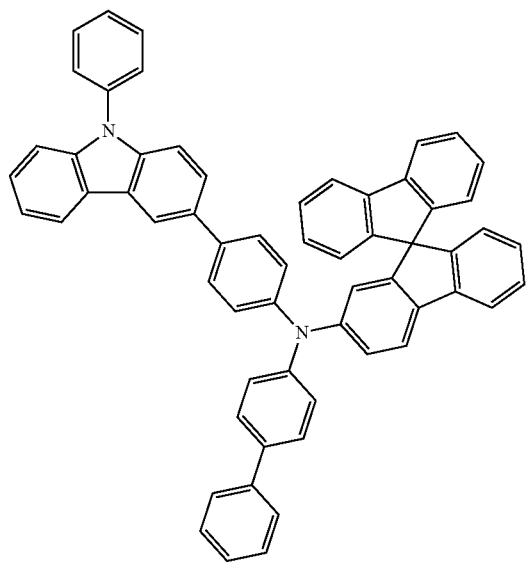

-continued
HT9
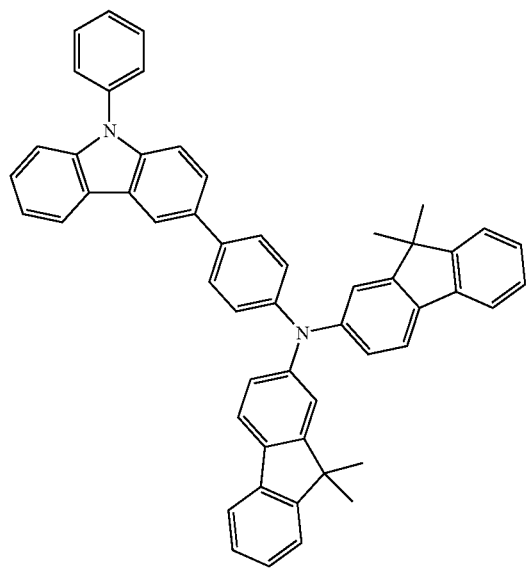
HT10
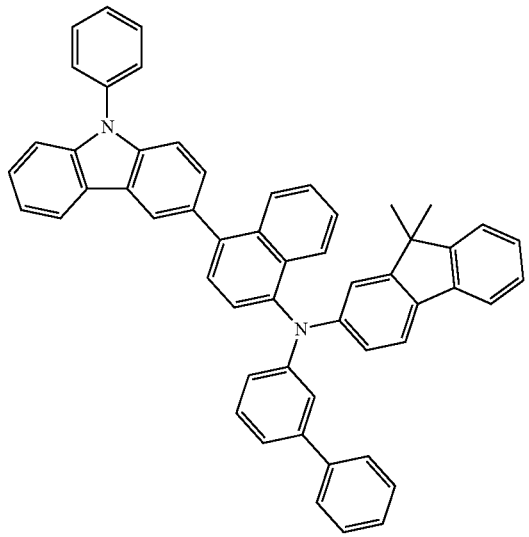
HT11
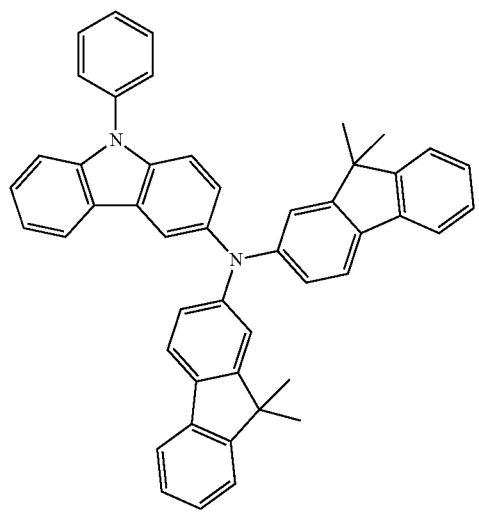
HT12
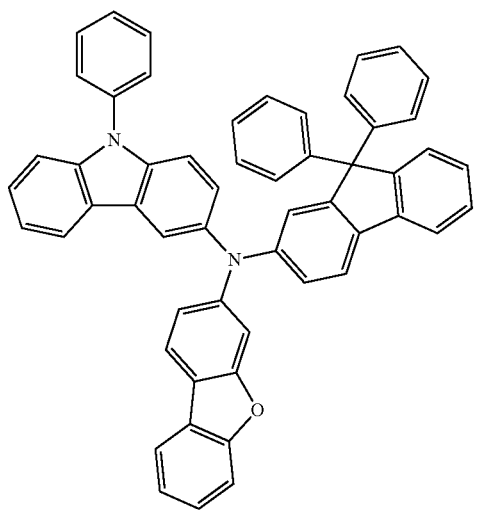

-continued
HT13
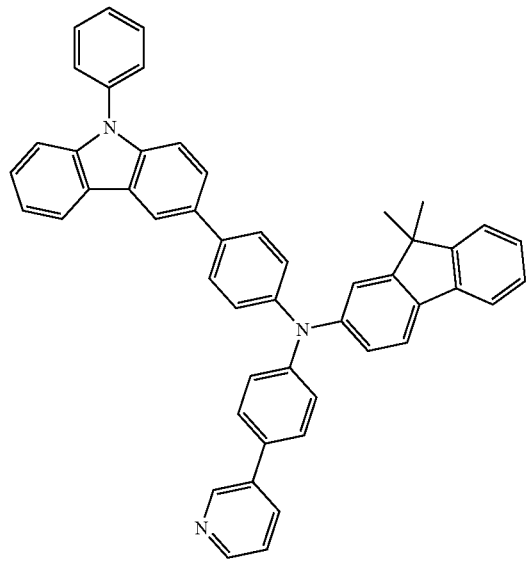
HT14
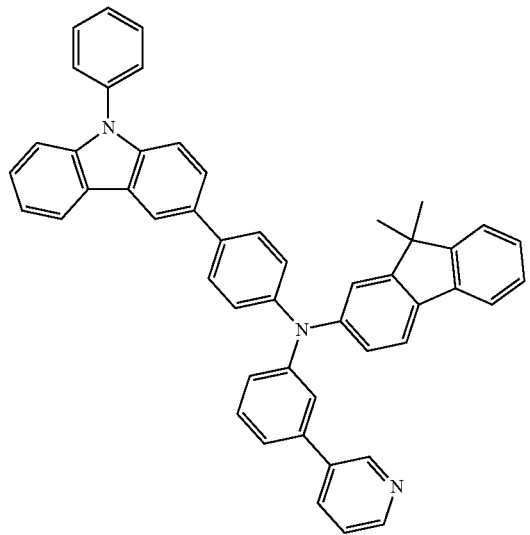
HT15
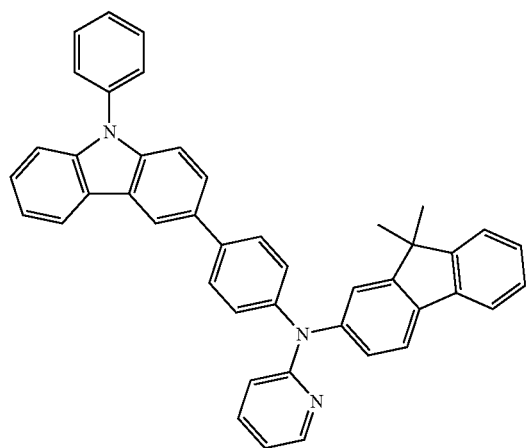
HT16
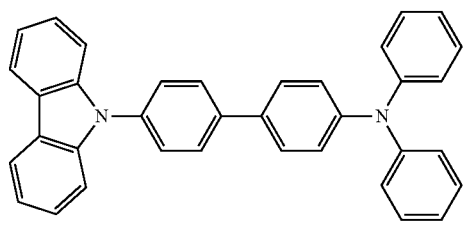
HT17
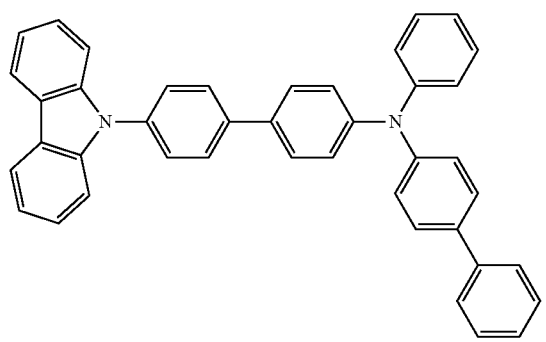
HT18
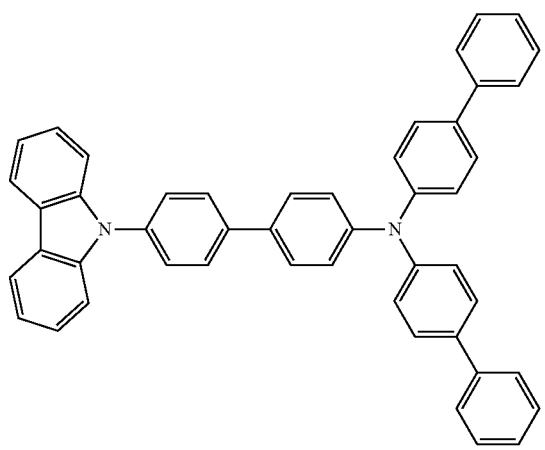

-continued
HT19
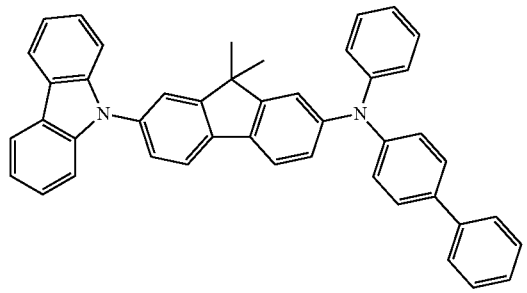
HT20
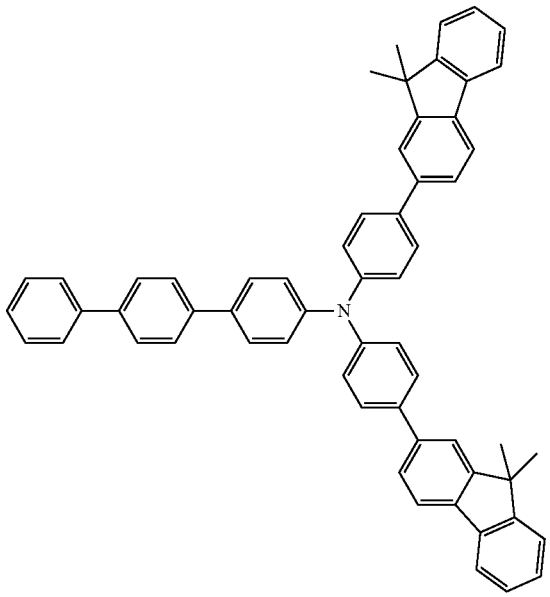
HT21
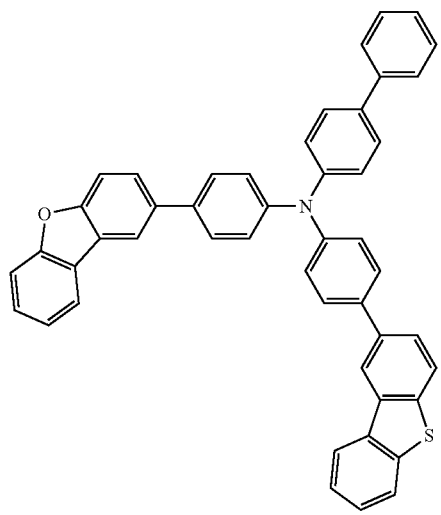
HT22
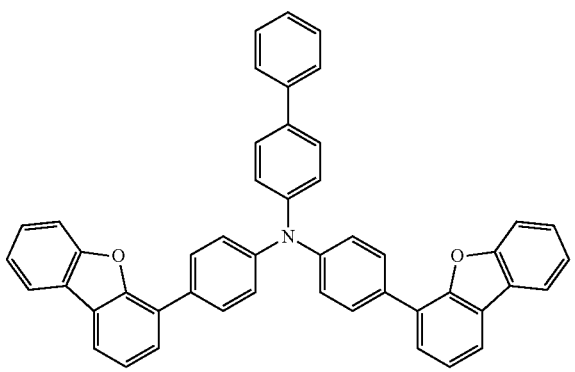
HT23
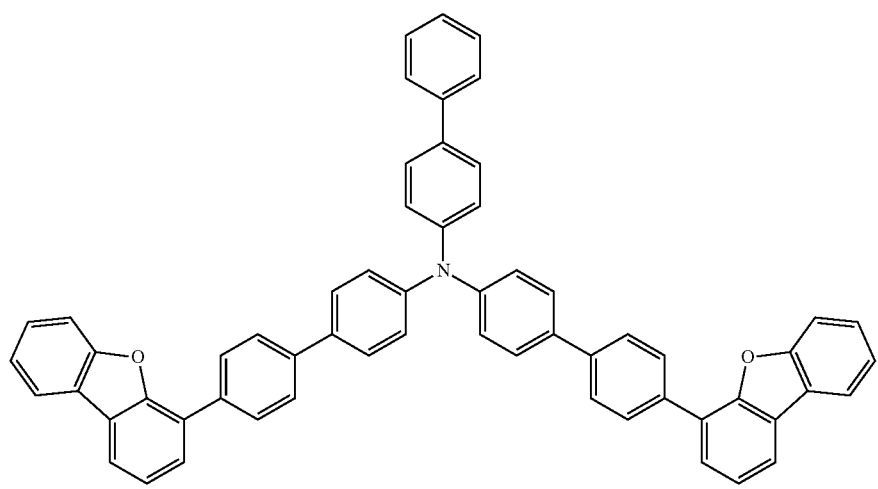

-continued
HT24
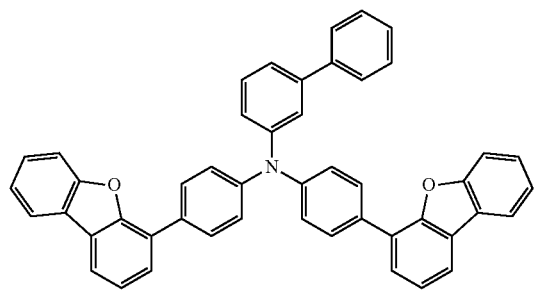
HT25
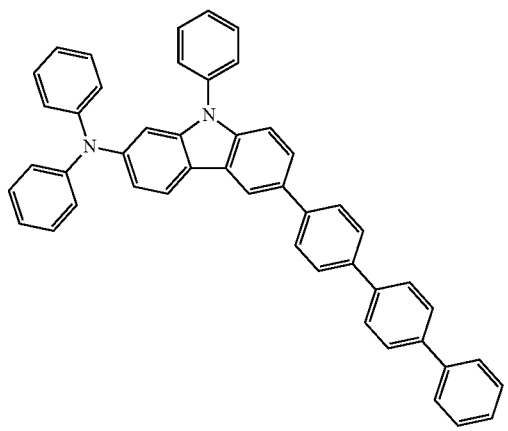
HT26
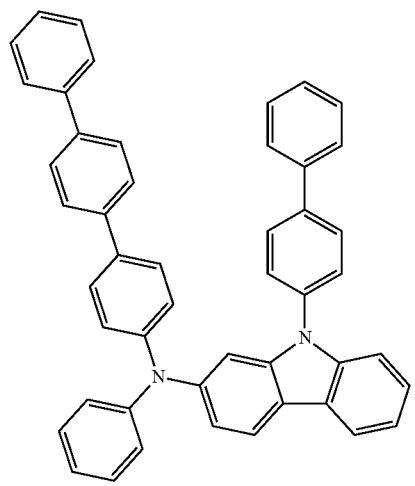
HT27
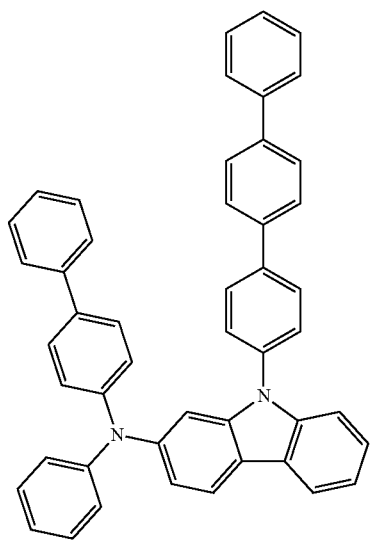
HT28
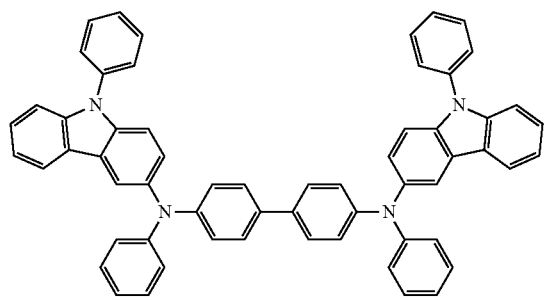
HT29
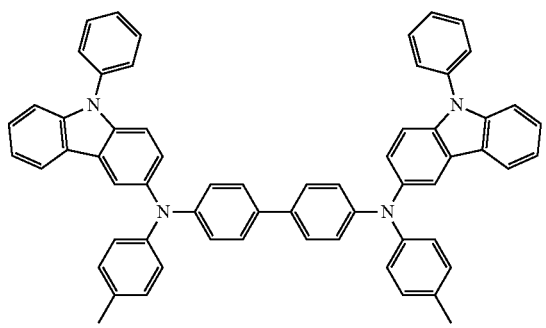

-continued
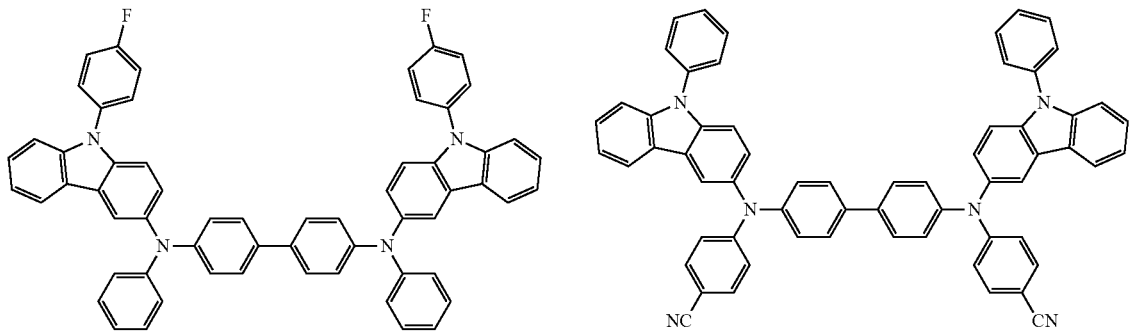
HT30
HT31
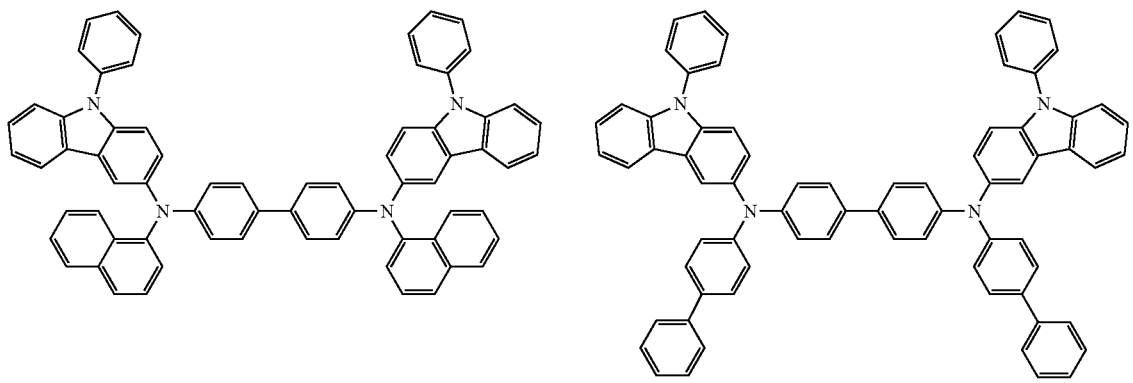
HT32
HT33
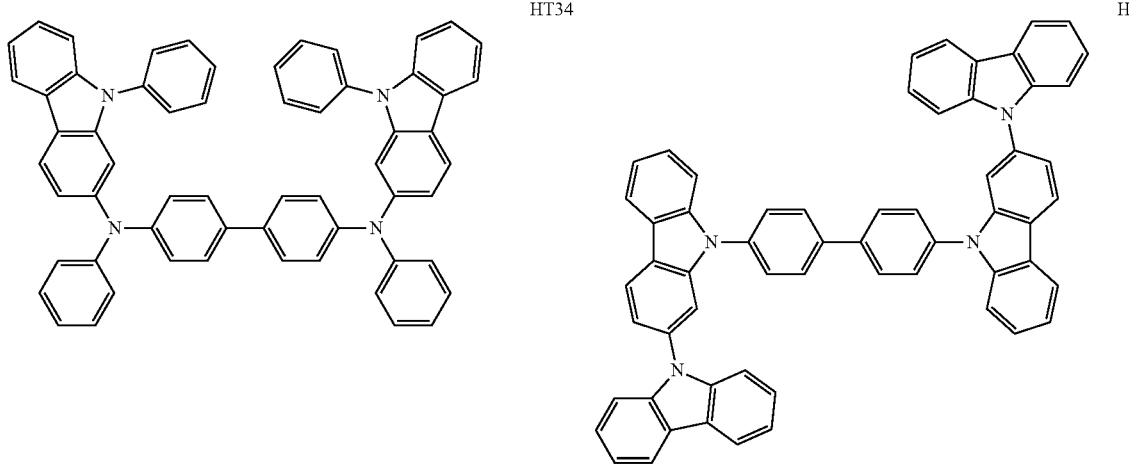
HT34
HT35
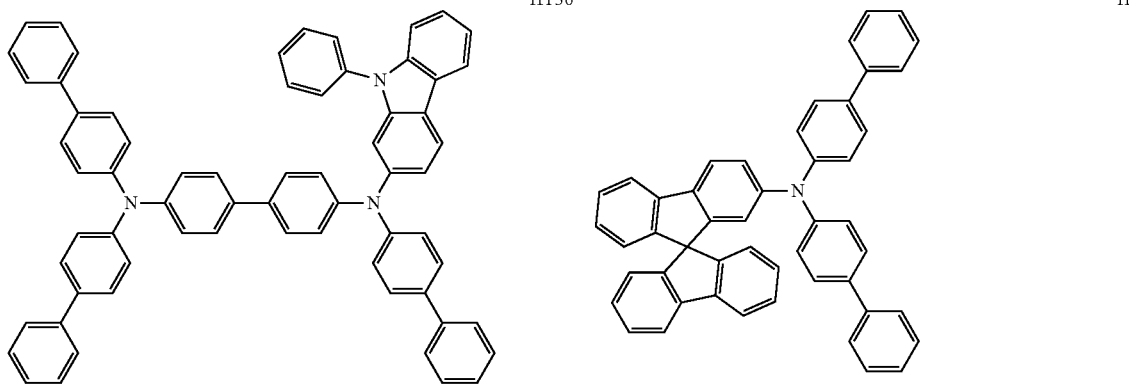
HT36
HT37

-continued

HT38
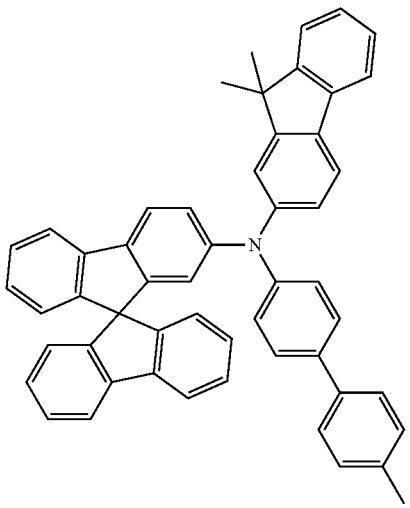

HT39
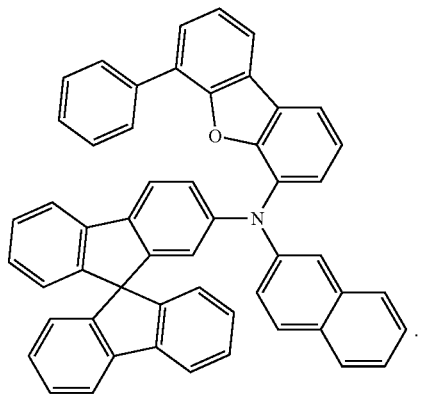

A thickness of the hole transport region may be in a range of about 100 Å to about 10,000 Å, for example, about 100 Å to about 1,000 Å. When the hole transport region includes at least one selected from a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example about 100 Å to about 1,500 Å. When the thickness of each of the hole transport region, the hole injection layer, and the hole transport layer is within these ranges, satisfactory hole transport characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may each include the materials as described above.

[p-Dopant]

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, a lowest unoccupied molecular orbital (LUMO) of the p-dopant may be −3.5 eV or less.

The p-dopant may include at least one selected from a quinone derivative, a metal oxide, and a cyano group-containing compound, but embodiments are not limited thereto.

In one embodiment, the p-dopant may include at least one selected from:

a quinone derivative, such as tetracyanoquinodimethane (TCNQ) and F4-2,3,5,6-tetrafluoro-7,7,8,8-tetracyanoquinodimethane (TCNQ);

metal oxide, such as tungsten oxide and molybdenum oxide;

1,4,5,8,9,11-hexaazatriphenylene-hexacarbonitrile (HAT-CN); and a compound represented by Formula 221, but embodiments of the present disclosure are not limited thereto:

<HAT-CN>
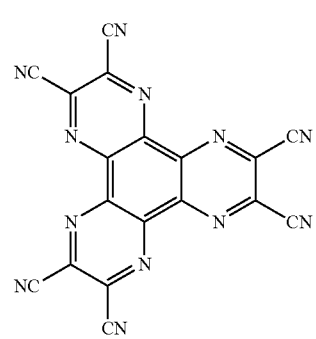

<F4-TCNQ>
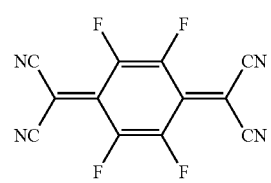

<Formula 211>
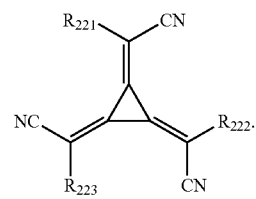

In Formula 221, $R_{221}$ to $R_{223}$ may each independently be selected from a substituted or unsubstituted $C_3$-$C_{10}$ cycloalkyl group, substituted or unsubstituted $C_1$-$C_{10}$ heterocycloalkyl group, substituted or unsubstituted $C_3$-$C_{10}$ cycloalkenyl group, substituted or unsubstituted $C_1$-$C_{10}$ heterocycloalkenyl group, substituted or unsubstituted $C_6$-$C_{60}$ aryl group, substituted or unsubstituted $C_1$-$C_{60}$ heteroaryl group, substituted or unsubstituted monovalent non-aromatic condensed polycyclic group and a substituted or unsubstituted monovalent non-aromatic condensed heteropolycyclic group, and at least one of $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

[Emission Layer in Organic Layer 150]

When the organic light-emitting device 10 is a full color organic light-emitting device, the emission layer may be patterned into a red emission layer, a green emission layer, or a blue emission layer, according to a sub pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red-light emission material, a green-light emission material, and a blue-light emission material, in which the two or more materials are mixed with each other in a single layer to emit white light.

The emission layer may include a host and a dopant. The dopant may include at least one selected from a phosphorescent dopant and a fluorescent dopant.

An amount of the dopant in the emission layer may be, in general, in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent emission characteristics may be obtained without a substantial increase in driving voltage.

[Host in Emission Layer]

The host may include a compound represented by Formula 301.

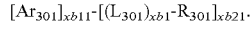  <Formula 301>

In Formula 301, $Ar_{301}$ may be selected from a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, substituted or unsubstituted $C_1$-$C_{10}$ heterocycloalkylene group, substituted or unsubstituted $C_3$-$C_{10}$ cycloalkenylene group, substituted or unsubstituted $C_1$-$C_{10}$ heterocycloalkenylene group, substituted or unsubstituted $C_6$-$C_{60}$ arylene group, substituted or unsubstituted $C_1$-$C_{60}$ heteroarylene group, substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), and xb21 may be an integer from 1 to 5, wherein $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one embodiment, $Ar_{301}$ in Formula 301 may be selected from a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

When xb11 in Formula 301 is two or more, two or more $Ar_{301}$(s) may be linked via a single bond.

In one or more embodiments, the compound represented by Formula 301 may be represented by one of Formula 301-1 or 301-2:

<Formula 301-1>

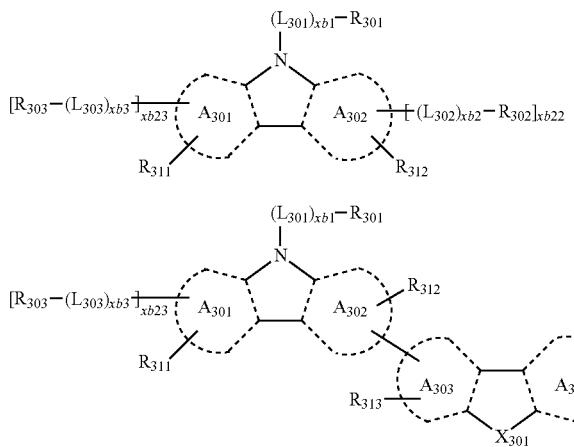

<Formula 301-2>

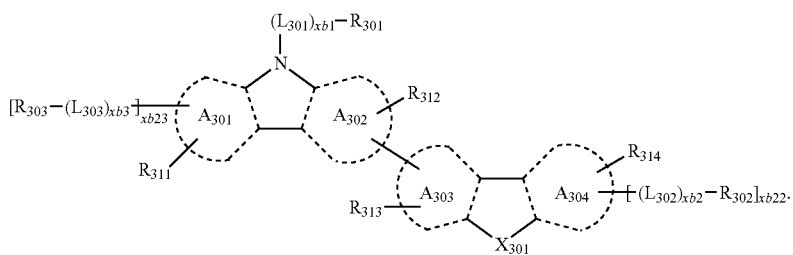

In Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or $N\text{-}[(L_{304})_{xb4}\text{-}R_{304}]$, $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si$(Q_{31})(Q_{32})(Q_{33})$, —N$(Q_{31})(Q_{32})$, —B$(Q_{31})(Q_{32})$, —C(=O)$(Q_{31})$, —S(=O)$_2(Q_{31})$, and —P(=O)$(Q_{31})(Q_{32})$, xb22 and xb23 may each independently be 0, 1, or 2, $L_{301}$, xb1, $R_{301}$, and $Q_{31}$ to $Q_{33}$ may be the same as described above, $L_{302}$ to $L_{304}$ may each independently be the same as described in connection with $L_{301}$.

Xb2 to xb4 may each independently be the same as described in connection with xb1, and $R_{302}$ to $R_{304}$ may each independently be the same as described in connection with $R_{301}$.

For example, $L_{301}$ to $L_{304}$ in Formulae 301, 301-1 and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an aza carbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may be the same as described above.

In one embodiment, $R_{301}$ to $R_{304}$ in Formulae 301, 301-1, and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an aza carbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may be the same as described above.

In one or more embodiments, the host may include an alkaline-earth metal complex. For example, the host may be selected from a Be complex (for example, Compound H55), an Mg complex, and a Zn complex.

The host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but is not limited thereto:

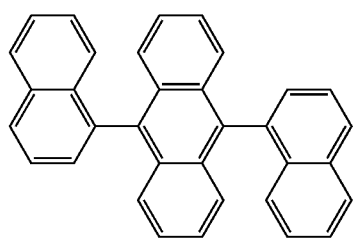

H1

119
-continued
H2
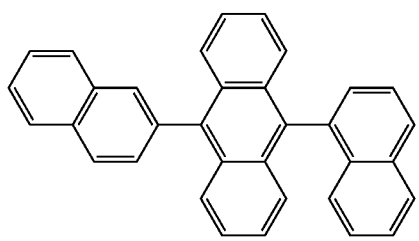
H3
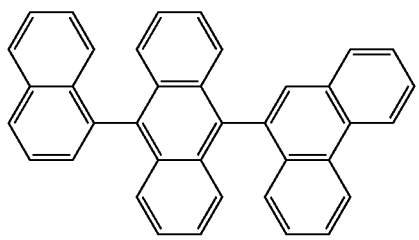
H4
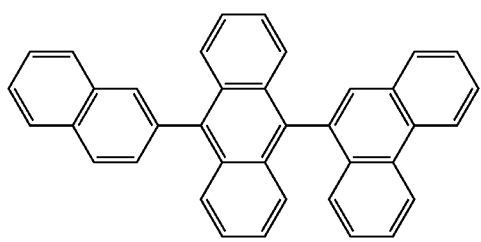
H5
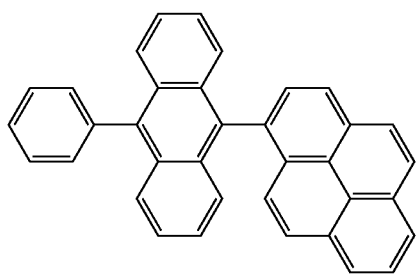
H6
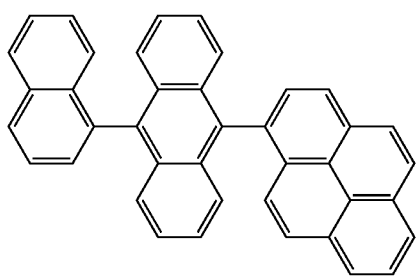
H7
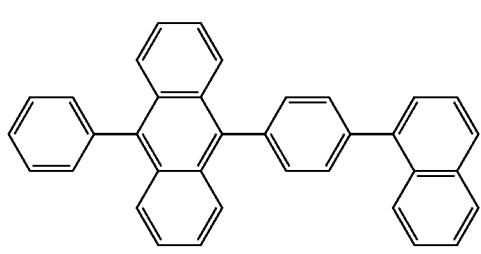
120
-continued
H8
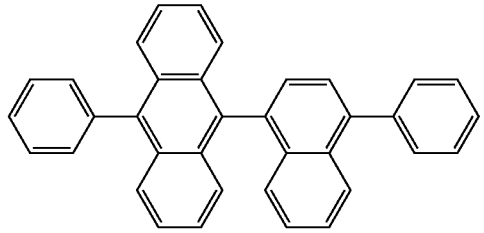
H9
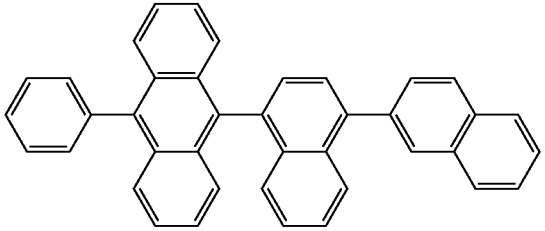
H10
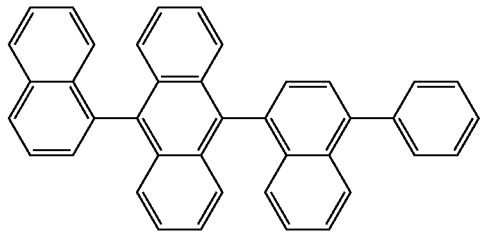
H11
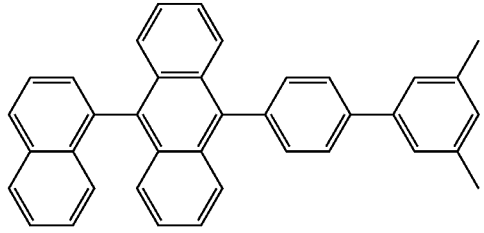
H12
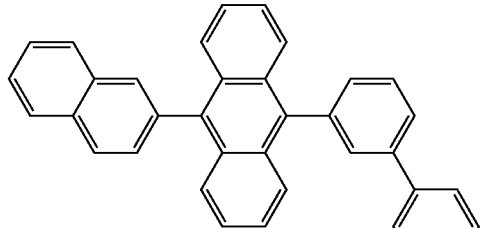
H13
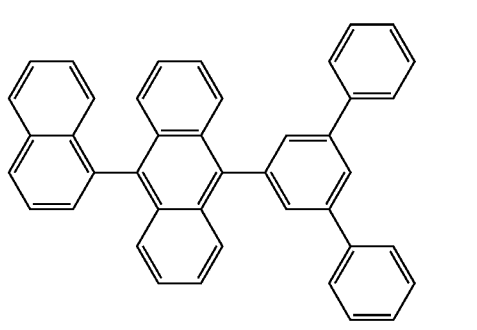

H14
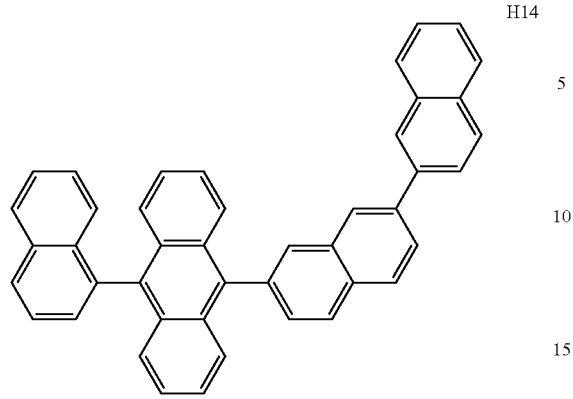
H15
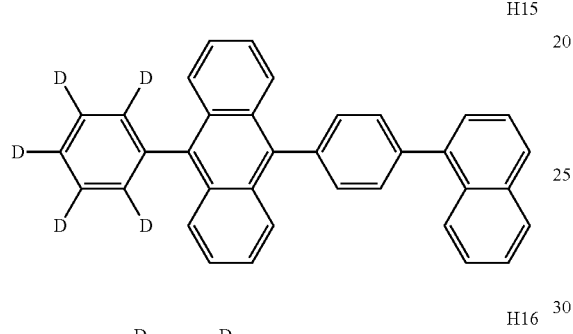
H16
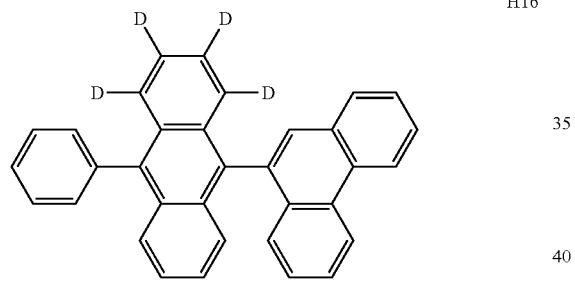
H17
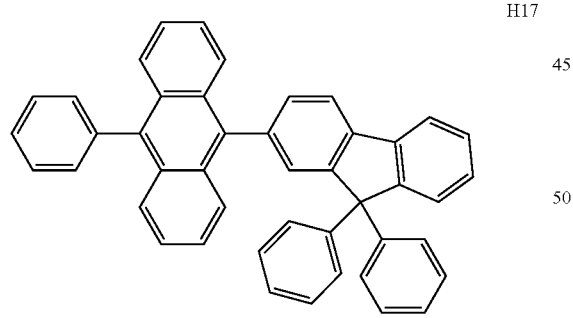
H18
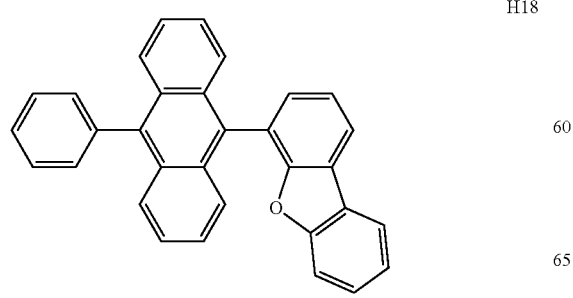
H19
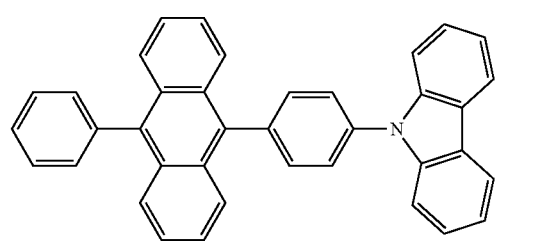
H20
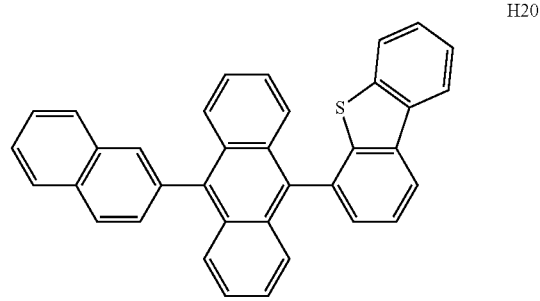
H21
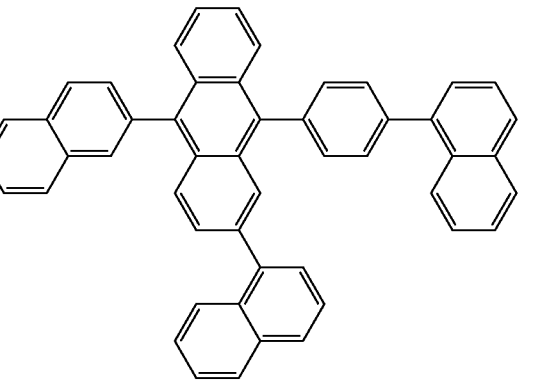
H22
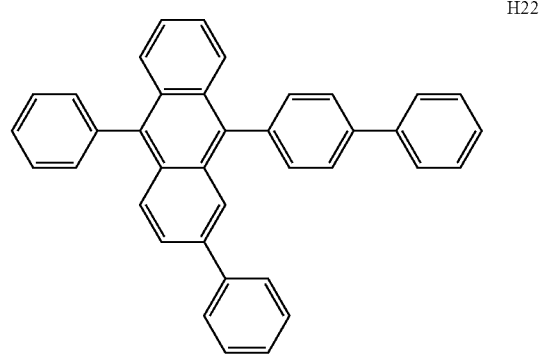

H23
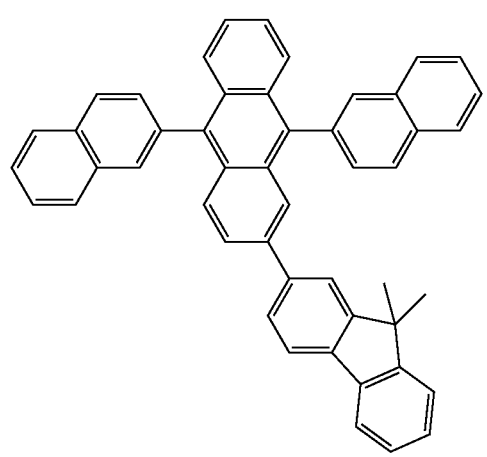
H24
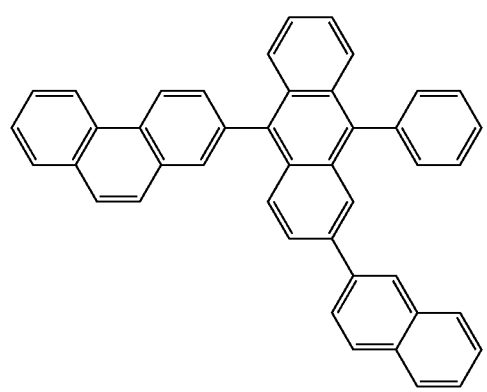
H25
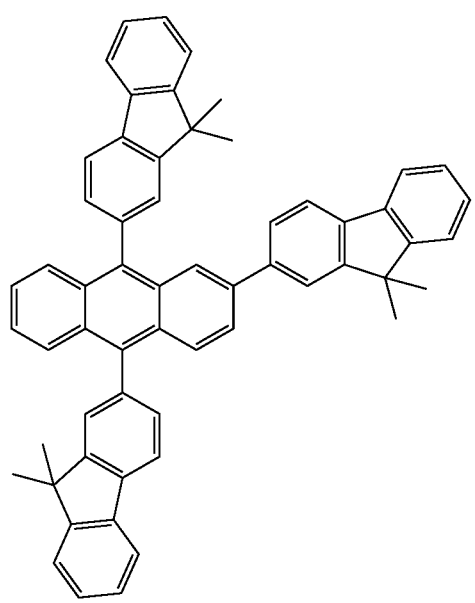
H26
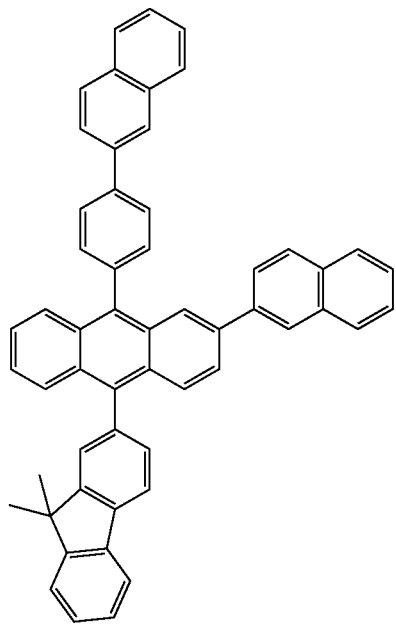
H27
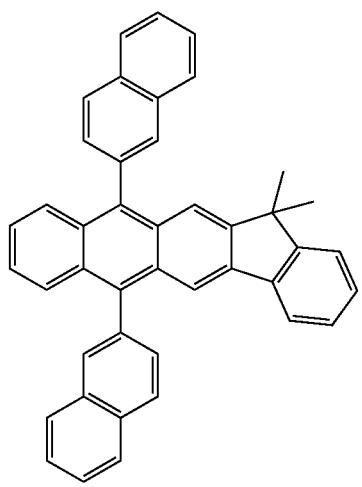
H28
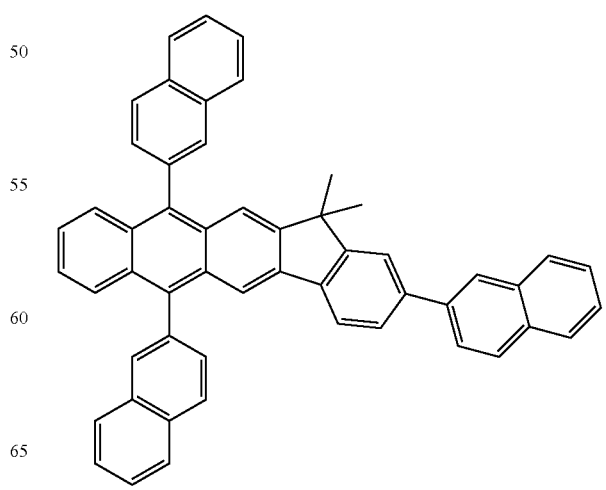

H29
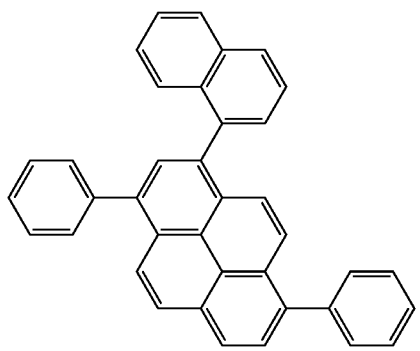
H30
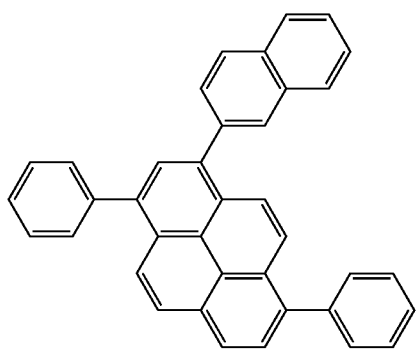
H31
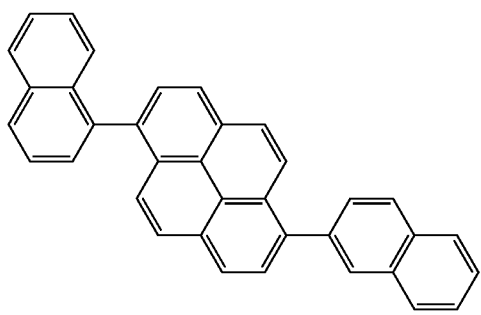
H32
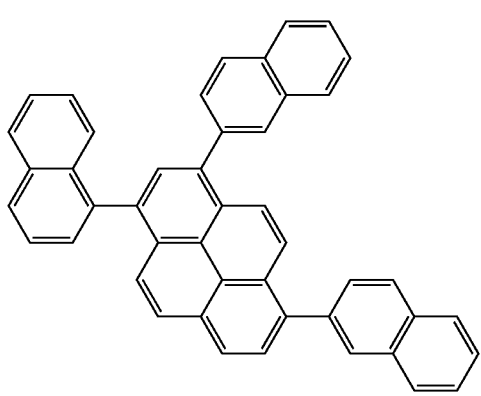
H33
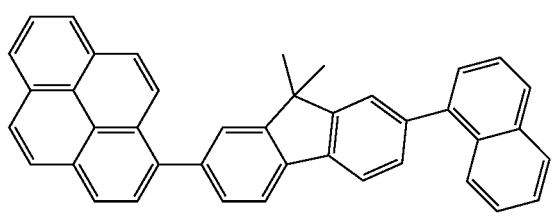
H34
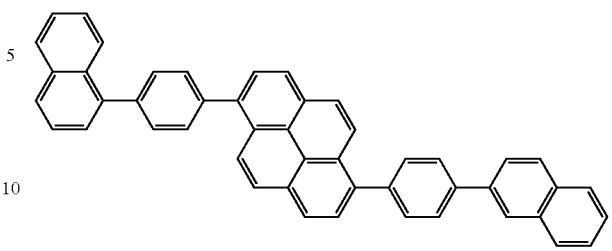
H35
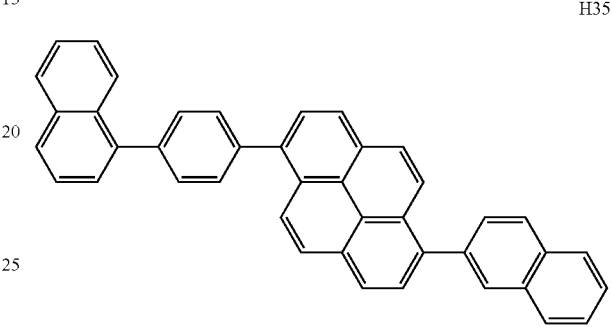
H36
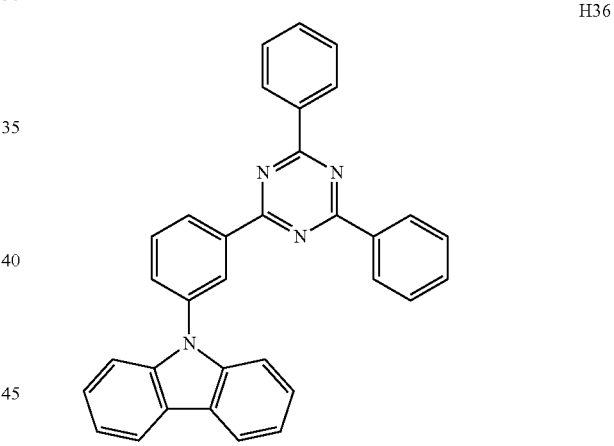
H37
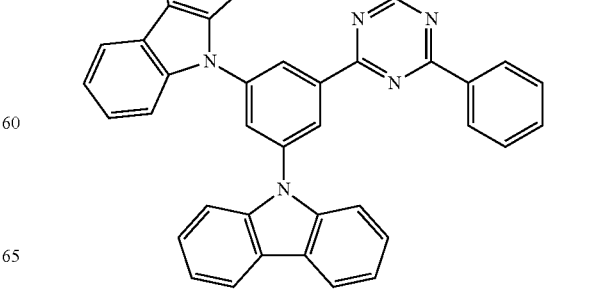

H38
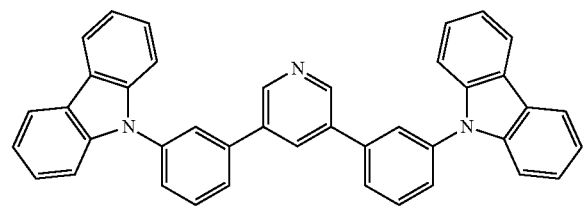
H39
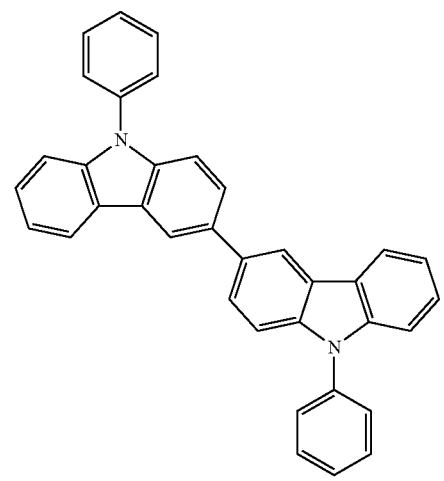
H40
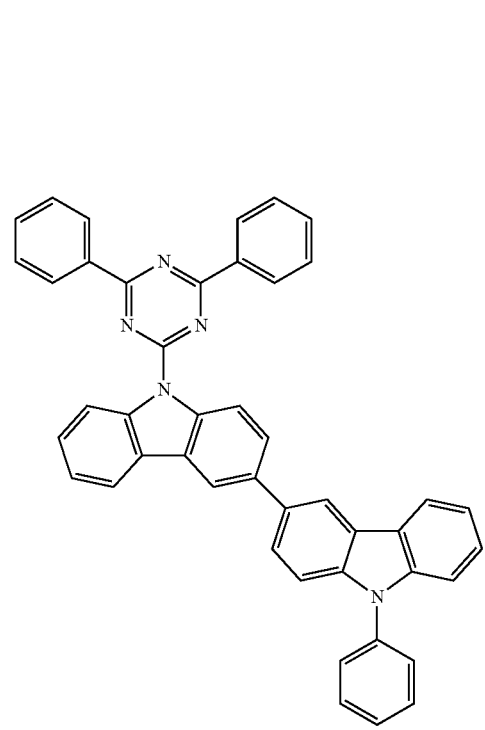
H41
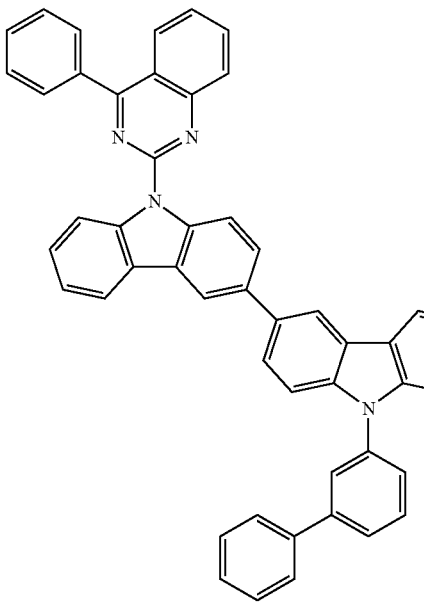
H42
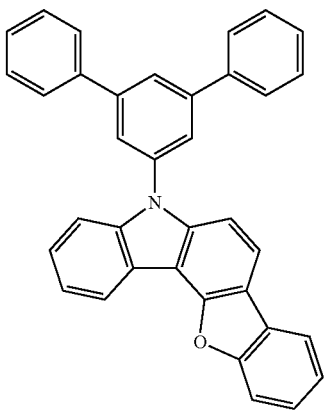
H43
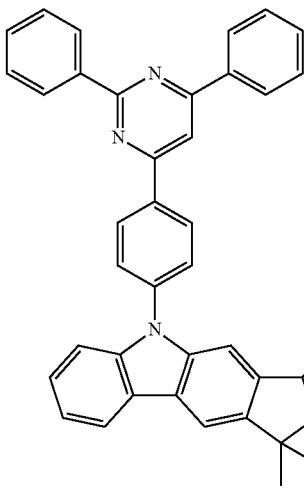

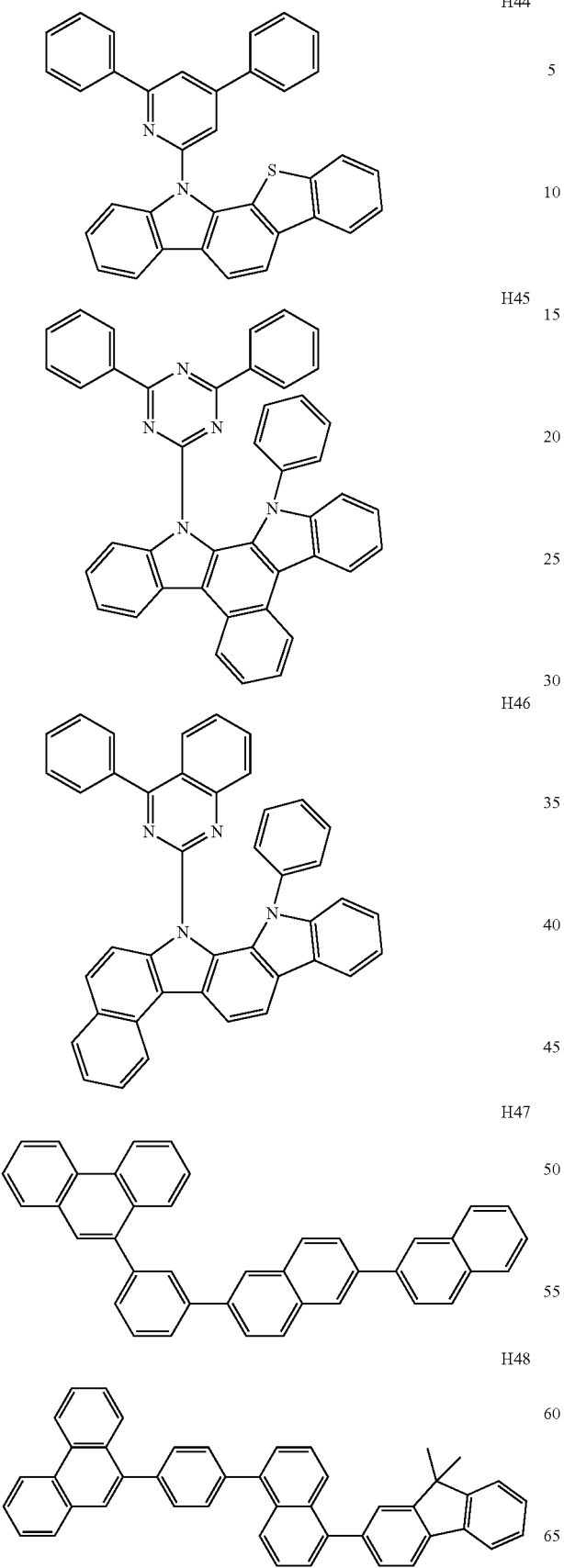
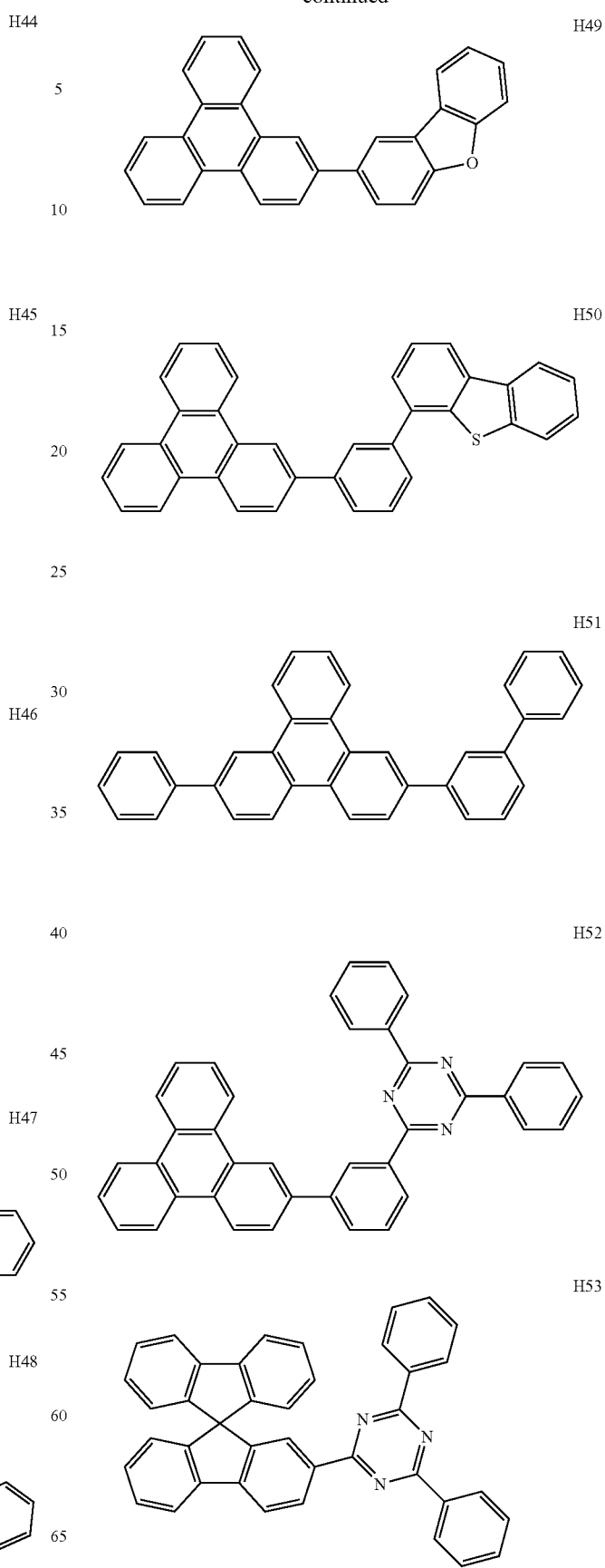

H54

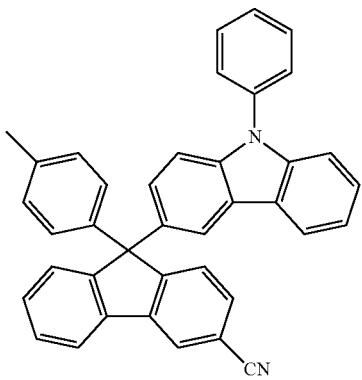

H55

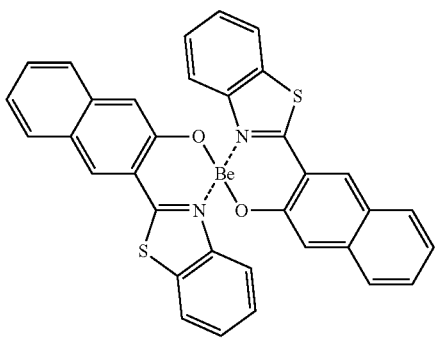

[Phosphorescent Dopant Included in Emission Layer in Organic Layer 150]

In one or more embodiments, the phosphorescent dopant may include an organometallic complex represented by Formula 401:

$$M(L_{401})_{n1}(L_{402})_{n2}$$ <Formula 401>

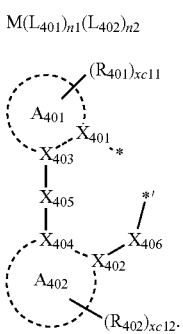

<Formula 402>

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$(S) may be identical to or different from each other, $L_{402}$ may be an organic ligand, and xc2 may be an integer from 0 to 4, wherein, when xc2 is two or more, two or more $L_{402}$(s) may be identical to or different from each other, $X_{401}$ to $X_{404}$ may each independently be nitrogen or carbon;

$X_{401}$ and $X_{403}$ may be linked via a single bond or a double bond, and $X_{402}$ and $X_{404}$ may be linked via a single bond or a double bond, $A_{401}$ and $A_{402}$ may each independently be selected from a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C($Q_{411}$)=*, $Q_{411}$ and $Q_{412}$ may be hydrogen, deuterium, $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, substituted or unsubstituted $C_1$-$C_{20}$ alkyl group, substituted or unsubstituted $C_1$-$C_{20}$ alkoxy group, substituted or unsubstituted $C_3$-$C_{10}$ cycloalkyl group, substituted or unsubstituted $C_1$-$C_{10}$ heterocycloalkyl group, substituted or unsubstituted $C_3$-$C_{10}$ cycloalkenyl group, substituted or unsubstituted $C_1$-$C_{10}$ heterocycloalkenyl group, substituted or unsubstituted $C_6$-$C_{60}$ aryl group, substituted or unsubstituted $C_6$-$C_{60}$ aryloxy group, substituted or unsubstituted $C_6$-$C_{60}$ arylthio group, substituted or unsubstituted $C_1$-$C_{60}$ heteroaryl group, substituted or unsubstituted monovalent non-aromatic condensed polycyclic group and a substituted or unsubstituted monovalent non-aromatic condensed heteropolycyclic group —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$) and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10,

* and *' in Formula 402 each indicate a binding site to M in Formula 401.

In one embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may all be nitrogen.

In one or more embodiments, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments of the present disclosure are not limited thereto.

In one or more embodiments, when xc1 in Formula 401 is two or more, two $A_{401}$(s) in two or more $L_{401}$(s) may optionally be linked via $X_{407}$, which is a linking group, or two $A_{402}$(S) in two or more $L_{401}$(s) may optionally be linked via $X_{408}$, which is a linking group (see Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C($Q_{413}$)=C($Q_{414}$)-*' (herein, $Q_{413}$ and $Q_{414}$ may each independently be selected from hydrogen, deuterium, $C_1$-$C_{20}$ alkyl group, a $C_1$-$C_{20}$ alkoxy group, a phenyl group, a biphenyl group, a terphenyl group, or a naphthyl group), but embodiments of the present disclosure are not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine, or phosphite), but embodiments of the present disclosure are not limited thereto.

In one or more embodiments, the phosphorescent dopant may be selected from, for example, Compounds PD1 to PD25, but embodiments of the present disclosure are not limited thereto:

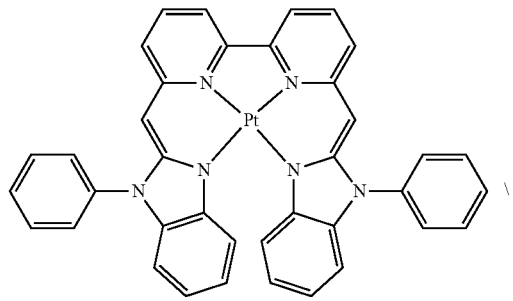
PD1

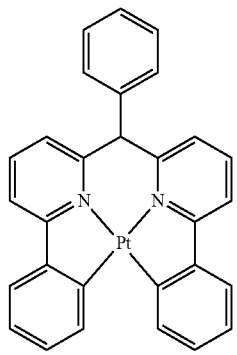
PD2

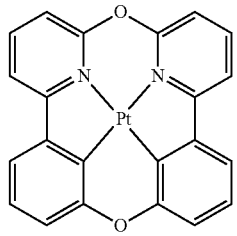
PD3

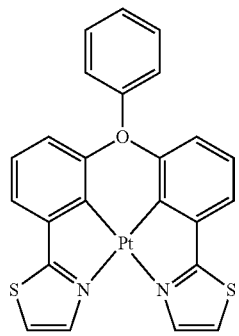
PD4

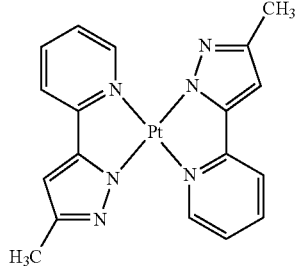
PD5

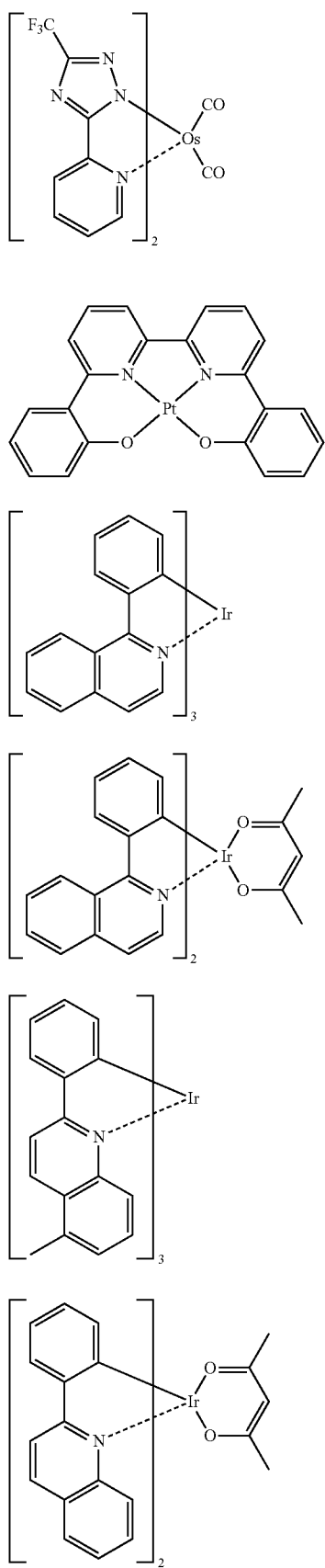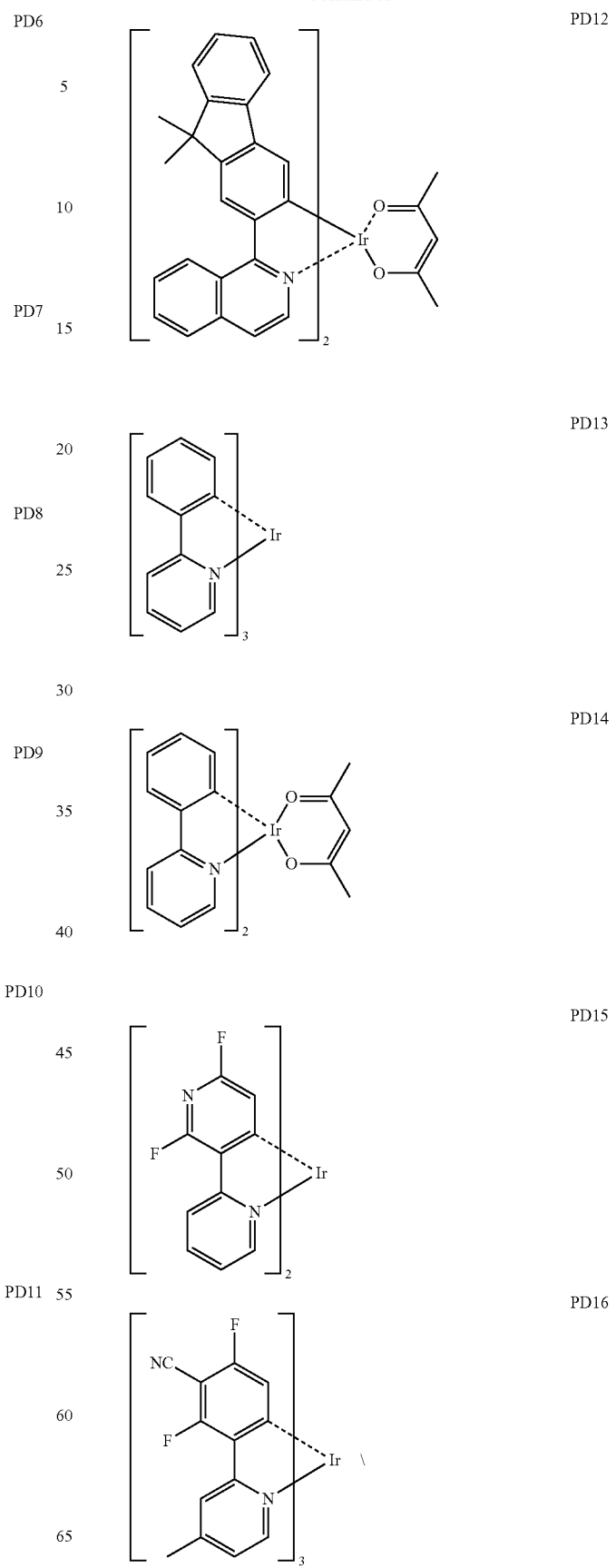

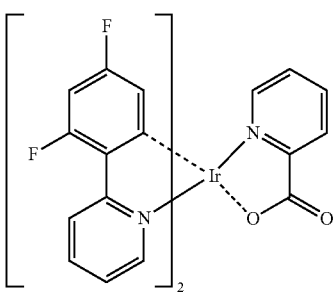
PD17
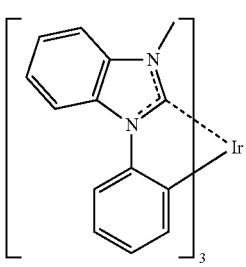
PD18
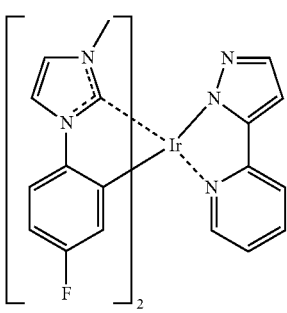
PD19
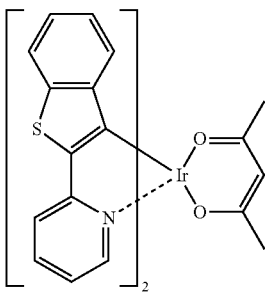
PD20
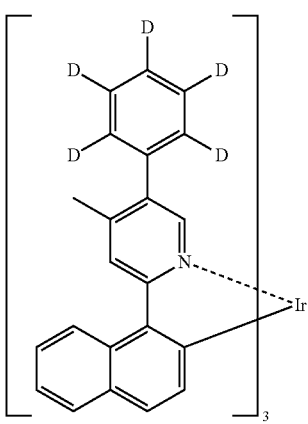
PD21
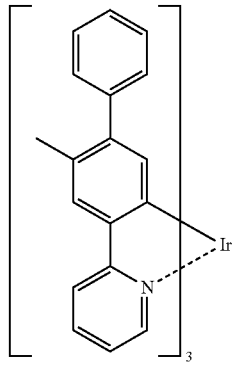
PD22
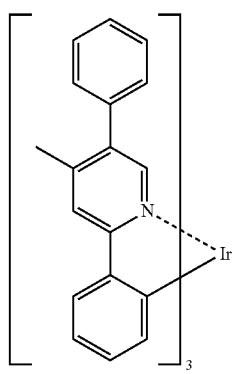
PD23
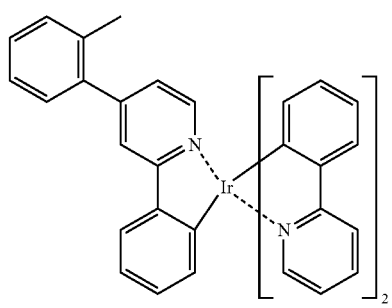
PD24
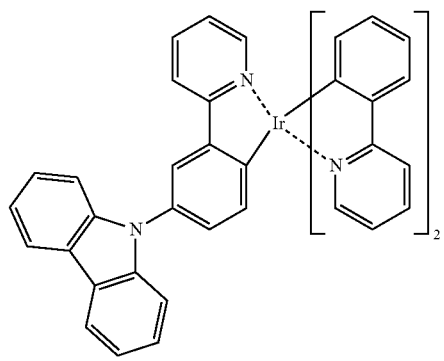
PD25
[Fluorescent Dopant in Emission Layer]
The fluorescent dopant may include an arylamine compound or a styrylamine compound.
The fluorescent dopant may include a compound represented by Formula 501:

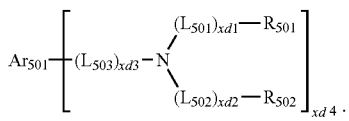
<Formula 501>

In Formula 501,

Ar$_{501}$ may be a substituted or unsubstituted C$_5$-C$_{60}$carbocyclic group or a substituted or unsubstituted C$_1$-C$_{60}$ heterocyclic group, L$_{501}$ to L$_{503}$ may each independently be selected from a substituted or unsubstituted C$_3$-C$_{10}$ cycloalkylene group, substituted or unsubstituted C$_1$-C$_{10}$ heterocycloalkylene group, substituted or unsubstituted C$_3$-C$_{10}$ cycloalkenylene group, substituted or unsubstituted C$_1$-C$_{10}$ heterocycloalkenylene group, substituted or unsubstituted C$_6$-C$_{60}$ arylene group, substituted or unsubstituted C$_1$-C$_{60}$ heteroarylene group, substituted or unsubstituted divalent non-aromatic condensed polycyclic group, and a substituted or unsubstituted divalent non-aromatic condensed heteropolycyclic group, xd1 to xd3 may each independently be an integer from 0 to 3, R$_{501}$ and R$_{502}$ may each independently be selected from a substituted or unsubstituted C$_3$-C$_{10}$ cycloalkyl group, substituted or unsubstituted C$_1$-C$_{10}$ heterocycloalkyl group, substituted or unsubstituted C$_3$-C$_{10}$ cycloalkenyl group, substituted or unsubstituted C$_1$-C$_{10}$ heterocycloalkenyl group, substituted or unsubstituted C$_6$-C$_{60}$ aryl group, substituted or unsubstituted C$_6$-C$_{60}$ aryloxy group, substituted or unsubstituted C$_6$-C$_{60}$ arylthio group, substituted or unsubstituted C$_1$-C$_{60}$ heteroaryl group, substituted or unsubstituted monovalent non-aromatic condensed polycyclic group, and a substituted or unsubstituted monovalent non-aromatic condensed heteropolycyclic group, and xd4 may be an integer from 1 to 6.

In one embodiment, Ar$_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, and a naphthyl group, In one or more embodiments, L$_{50}$ to L$_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group and a pyridinyl group.

In one or more embodiments, R$_{501}$ and R$_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a C$_1$-C$_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), wherein $Q_{31}$ to $Q_{33}$ may be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be two, but embodiments of the present disclosure are not limited thereto.

For example, the fluorescent dopant may be selected from Compounds FD1 to FD22:

FD1

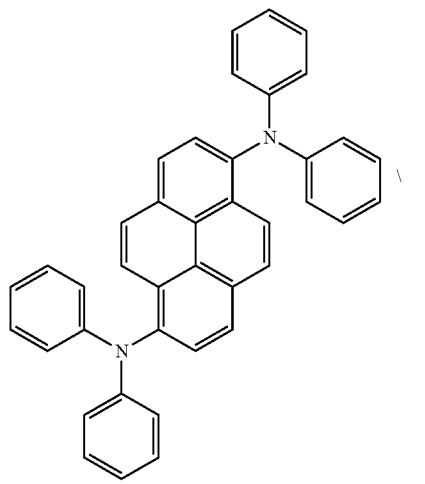

FD2

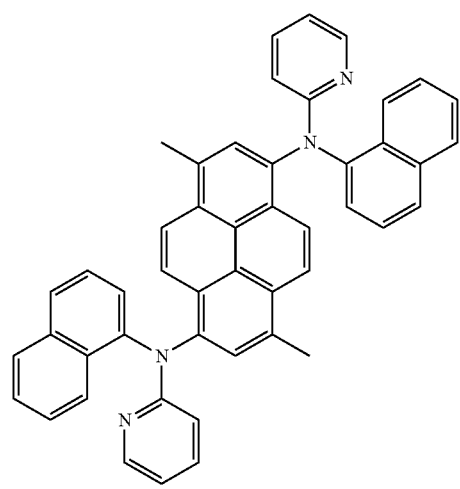

FD3

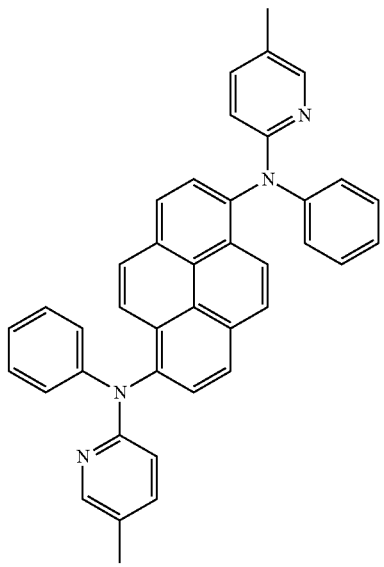

FD4

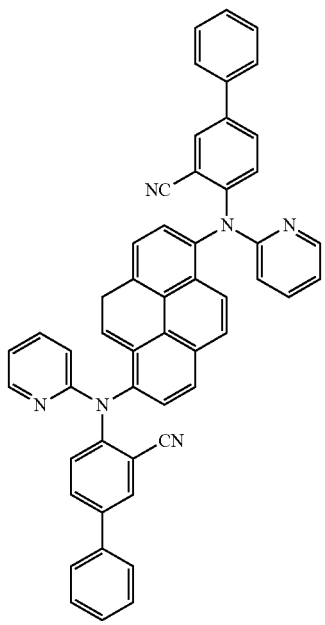

FD5
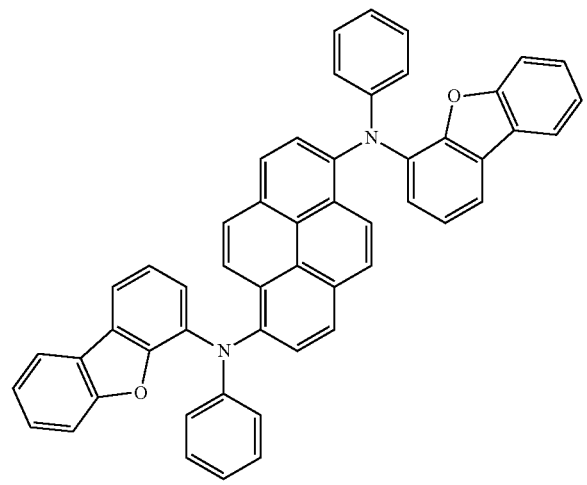
FD6
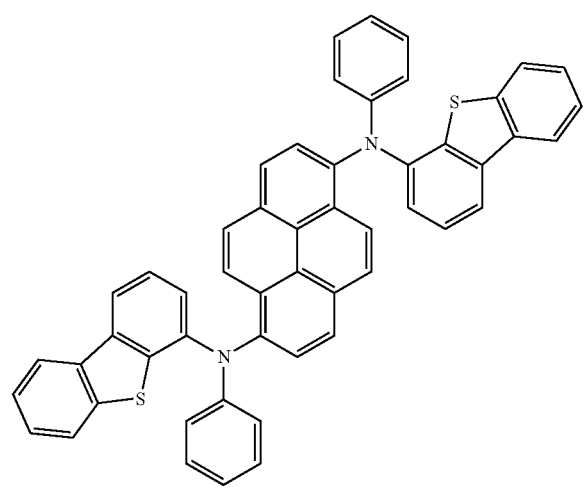
FD7
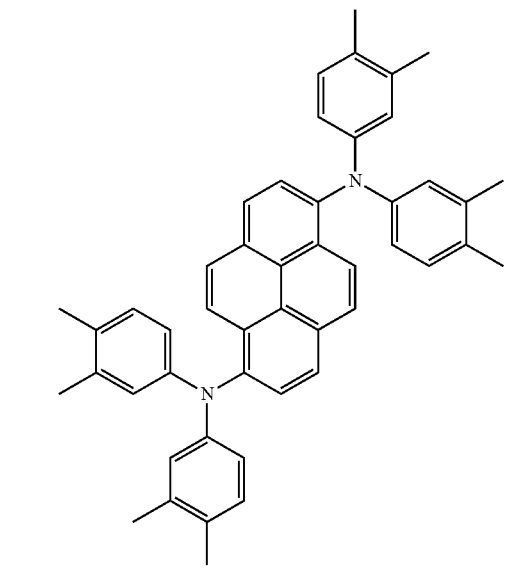
FD8
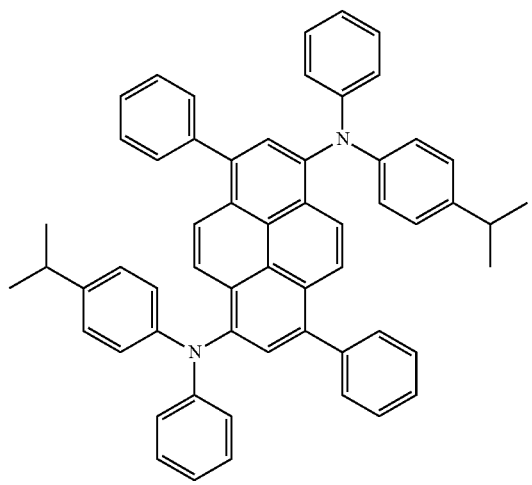
FD9
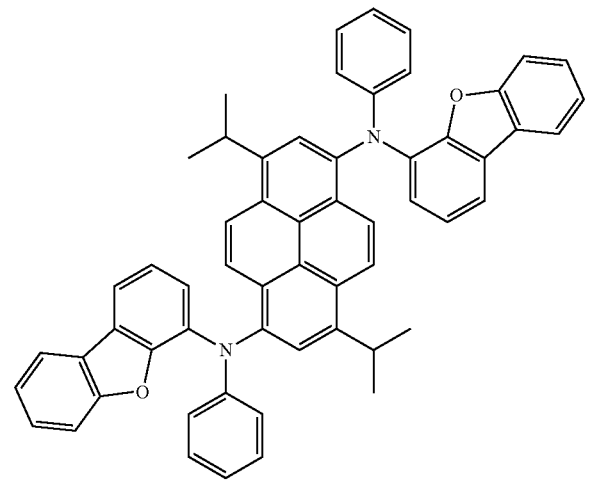
FD10
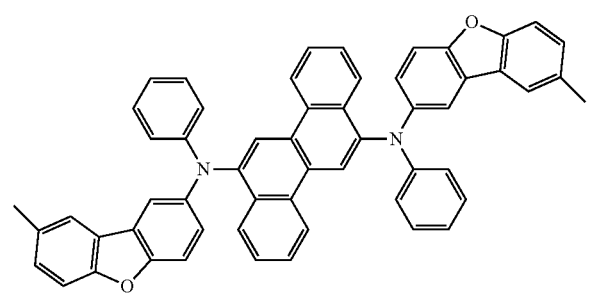
FD11
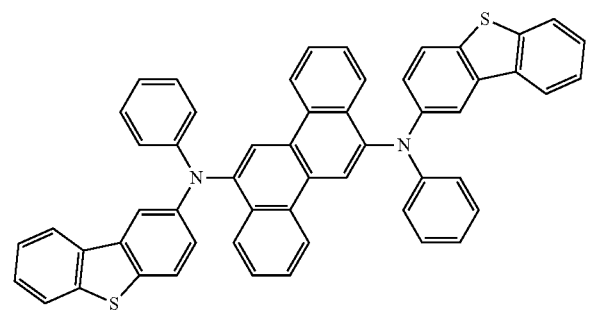

FD12
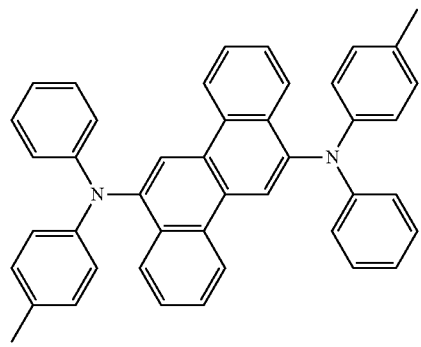
FD17
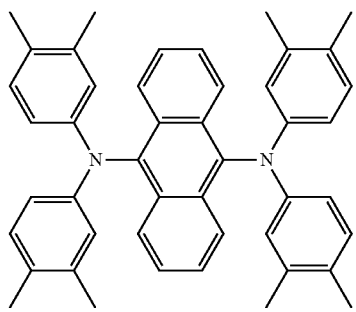
FD13
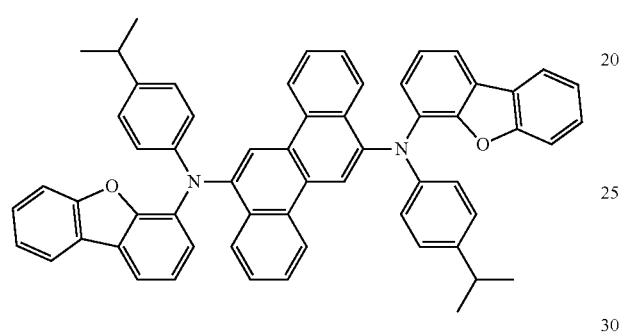
FD18
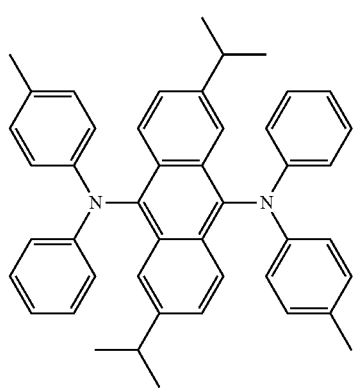
FD14
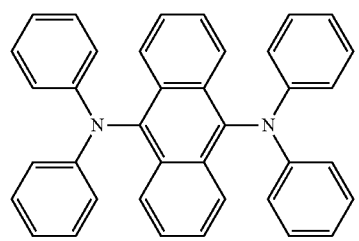
FD19
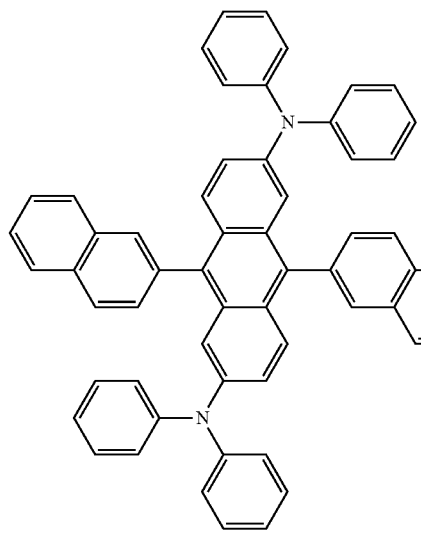
FD15
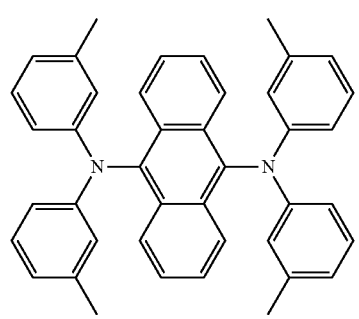
FD16
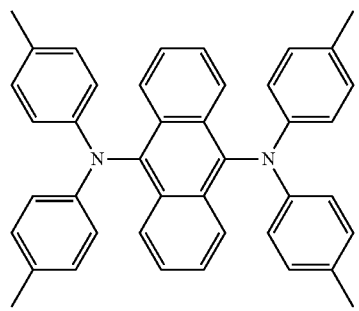
FD20
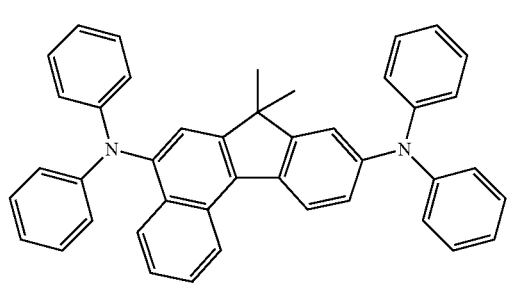

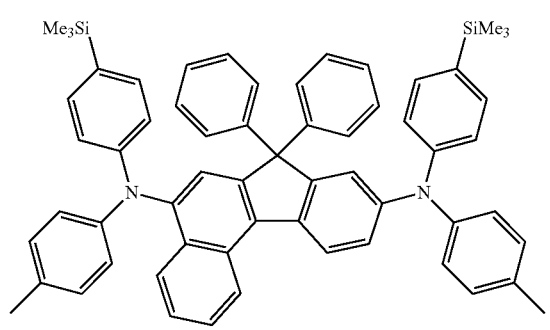
FD21
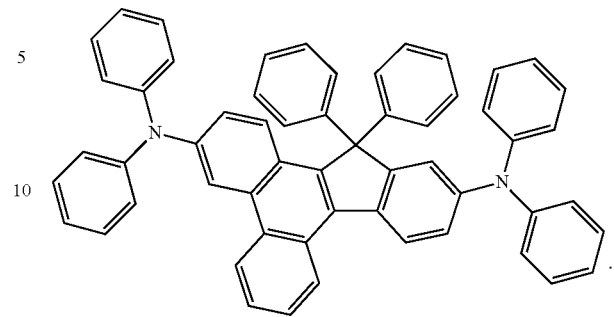
FD22
In one embodiment, the fluorescent dopant may be selected from the following compounds, but embodiments of the present disclosure are not limited thereto:
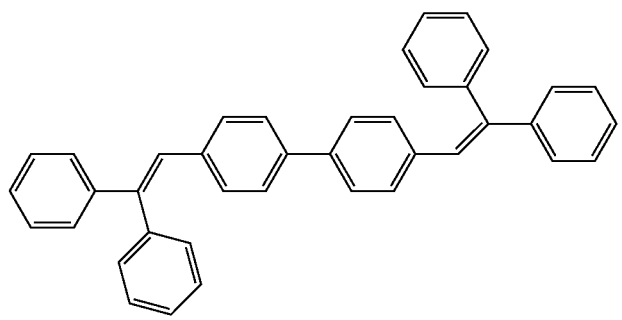
DPVBi
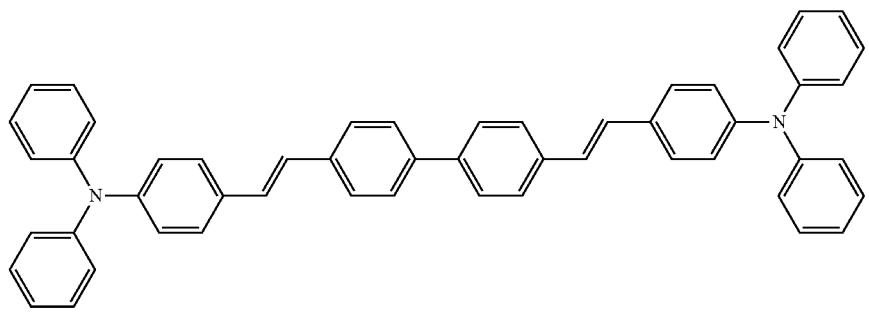
DPAVBi
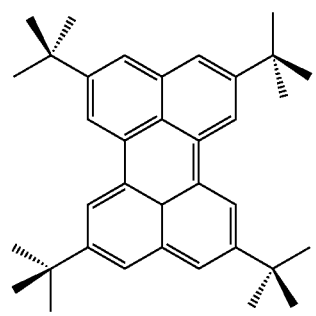
TBPe
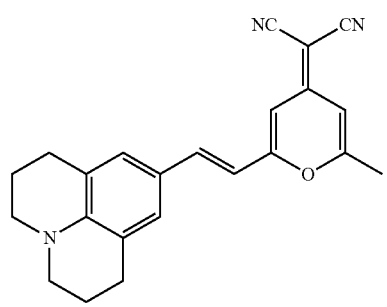
DCM

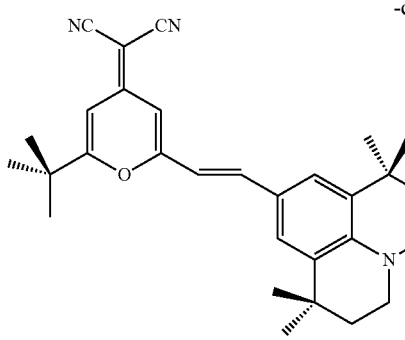

DCJTB

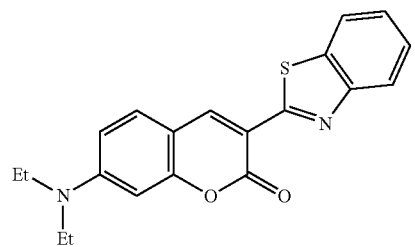

Coumarin 6

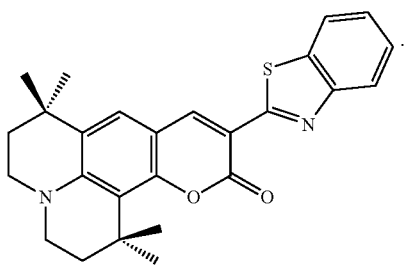

C545T

[Electron Transport Region in Organic Layer 150]

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

For example, the electron transport region (for example, a buffer layer, a hole blocking layer, an electron control layer, or an electron transport layer in the electron transport region) may include a condensed cyclic compound represented by Formula 1.

In one embodiment, the electron transport region (for example, a buffer layer, a hole blocking layer, an electron control layer, or an electron transport layer in the electron transport region) may include a metal-free compound containing at least one π electron-depleted nitrogen-containing ring.

The "π electron-depleted nitrogen-containing ring" indicates a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropoly cyclic group in which two or more 5-membered to 7-membered heteromonocyclic groups each having at least one *—N=*' moiety are condensed with each other, or iii) a heteropoly cyclic group in which at least one of 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring include an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, thiadiazol group, an imidazopyridine group, an imidazopyrimidine group, and an azacarbazole group, but are not limited thereto.

For example, the electron transport region may include a compound represented by Formula 601:

$$[Ar_{601}]_{xe11}-[(L_{601})_{xe1}-R_{601}]_{xe21}. \qquad <\text{Formula 601}>$$

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, substituted or unsubstituted $C_1$-$C_{10}$ heterocycloalkylene group, substituted or unsubstituted $C_3$-$C_{10}$ cycloalkenylene group or unsubstituted $C_1$-$C_{10}$ heterocycloalkenylene group, substituted or unsubstituted $C_6$-$C_{60}$ arylene group, substituted or unsubstituted $C_1$-$C_{60}$ heteroarylene group, substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, substituted or unsubstituted $C_1$-$C_{10}$ heterocycloalkyl group, substituted or unsubstituted $C_3$-$C_{10}$ cycloalkenyl group, substituted or unsubstituted $C_1$-$C_{10}$ heterocycloalkenyl group, substituted or unsubstituted $C_6$-$C_{60}$ aryl group, substituted or unsubstituted $C_6$-$C_{60}$ aryloxy group, substituted or unsubstituted $C_6$-$C_{60}$ arylthio group, substituted or unsubstituted $C_1$-$C_{60}$ heteroaryl group, substituted or unsubstituted monovalent non-aromatic condensed polycyclic group, substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), wherein $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one selected from $Ar_{601}$ in the number of xe11 and $R_{601}$ in the number of xe21 may include the π electron-depleted nitrogen-containing ring described above.

In one embodiment, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, naphthyridine group, a quinoxaline group, a quinazoline group, a cinnoline group, a phenanthridine group, an acridine group, phenanthroline group, phenazine group, a benzimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, naphthyridine group, a quinoxaline group, a quinazoline group, a cinnoline group, a phenanthridine group, an acridine group, phenanthroline group, phenazine group, a benzimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more $Ar_{601}$(S) may be linked via a single bond.

In one or more embodiments, $Ar_{601}$ in Formula 601 may be an anthracene group.

In one or more embodiments, the compound represented by Formula 601 may be represented by Formula 601-1:

<Formula 601-1>

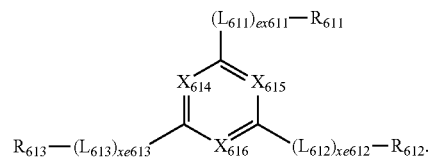

In Formula 601-1, $X_{614}$ may be N or C($R_{614}$), $X_{615}$ may be N or C($R_{615}$), $X_{616}$ may be N or C($R_{616}$), at least one of $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formulae 601 and 601-1 may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), wherein Q$_{601}$ and Q$_{602}$ are the same as described above.

The electron transport region may include at least one compound represented by Compounds ET1 to ET36, but embodiments of the present disclosure are not limited thereto:

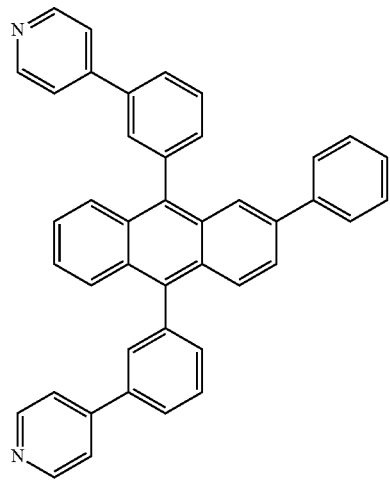

ET3

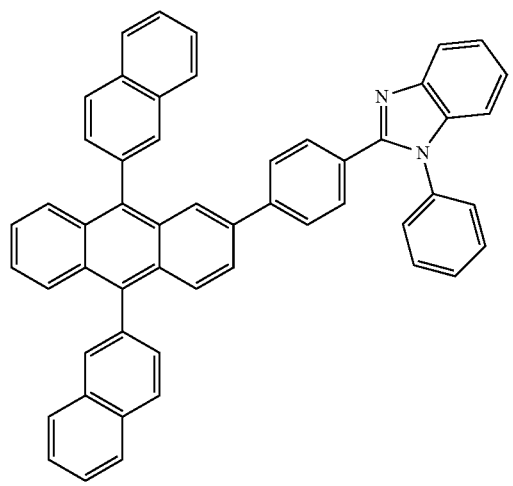

ET1

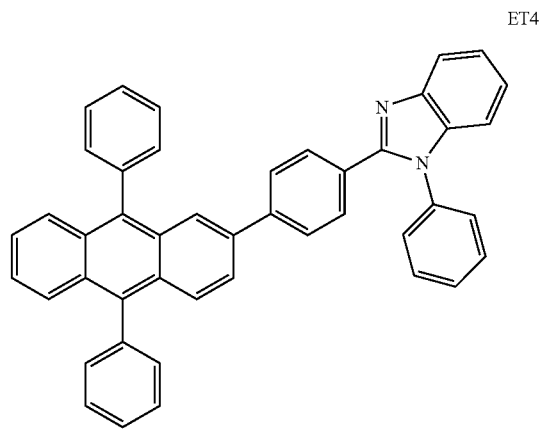

ET2

ET4

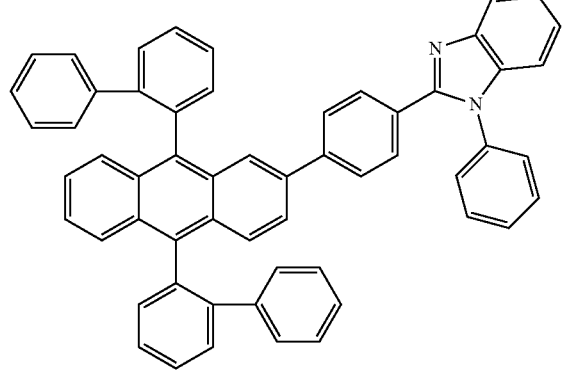

ET5

ET6
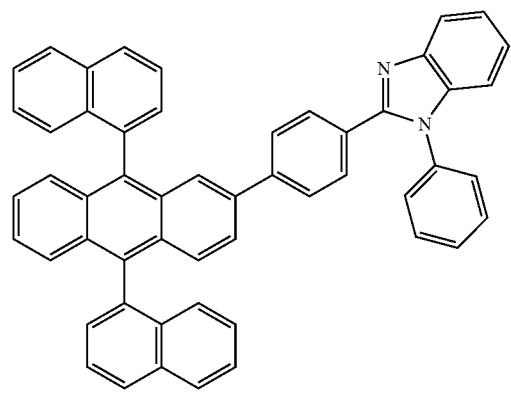
ET7
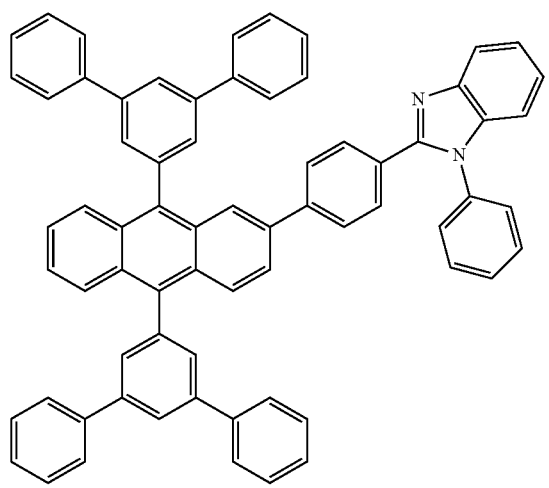
ET8
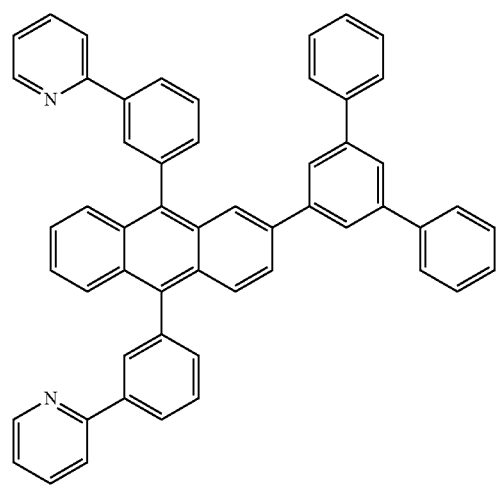
ET9
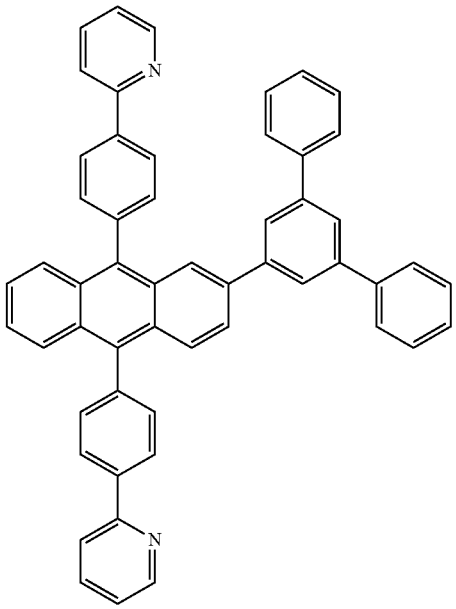
ET10
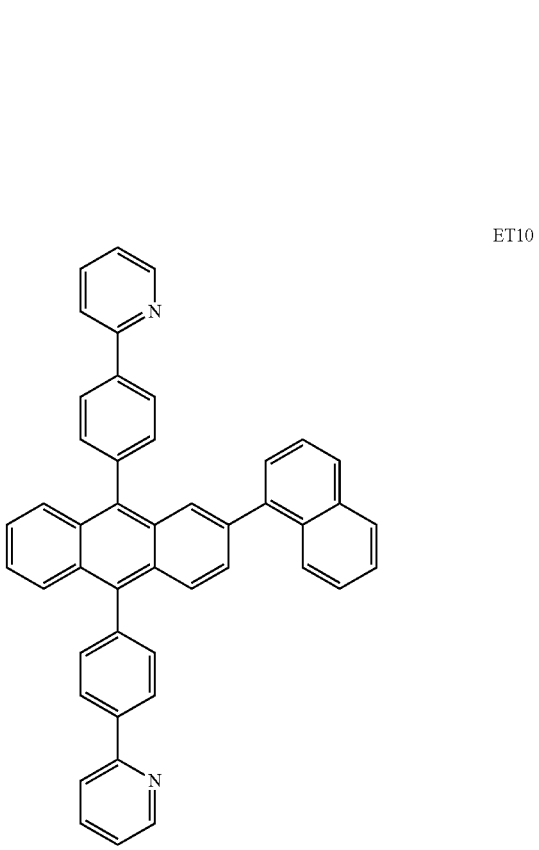

ET11
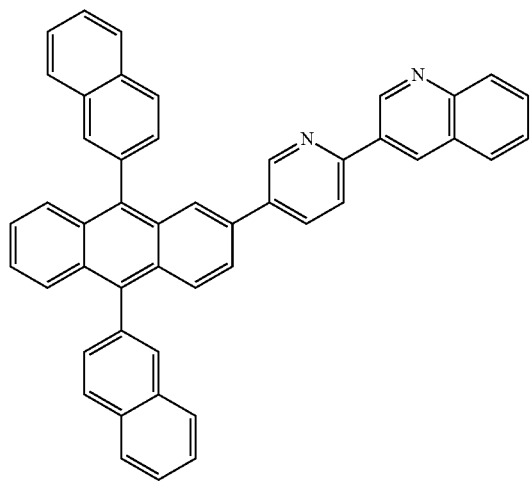
ET12
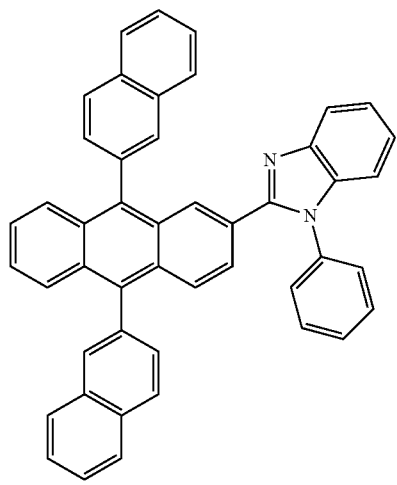
ET13
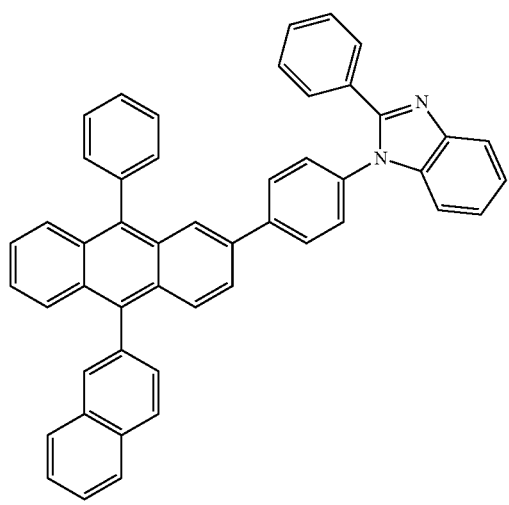
ET14
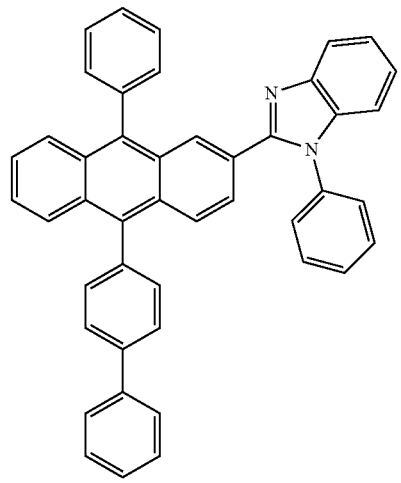
ET15
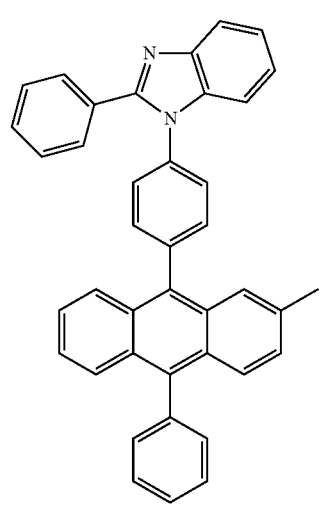
ET16
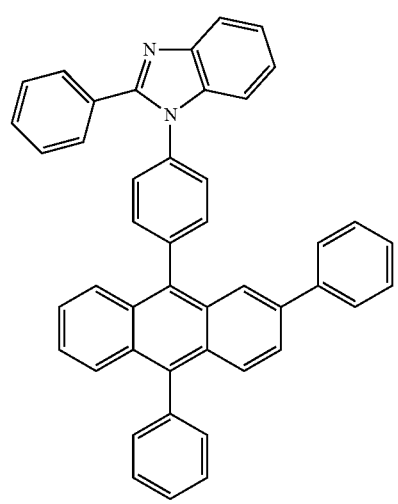

ET17
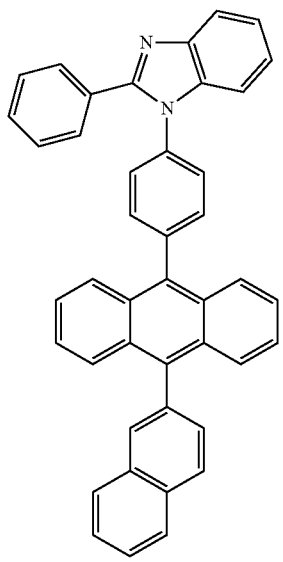
ET18
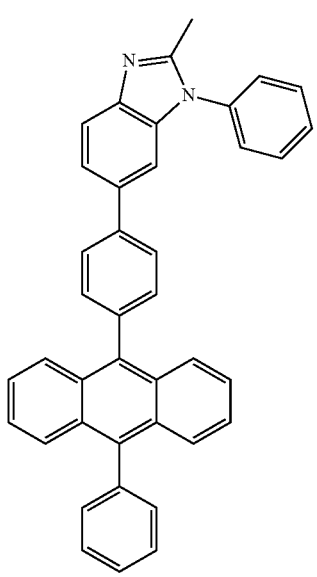
ET19
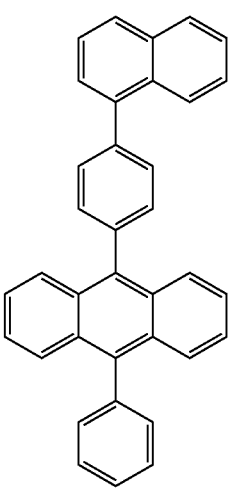
ET20
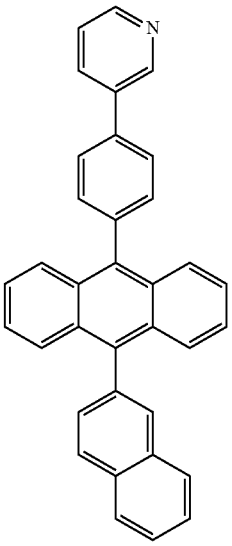
ET21
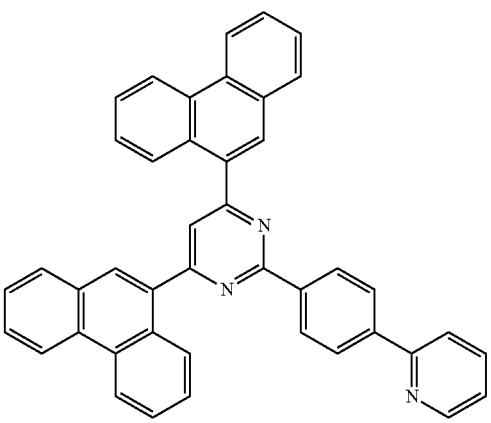
ET22

ET23
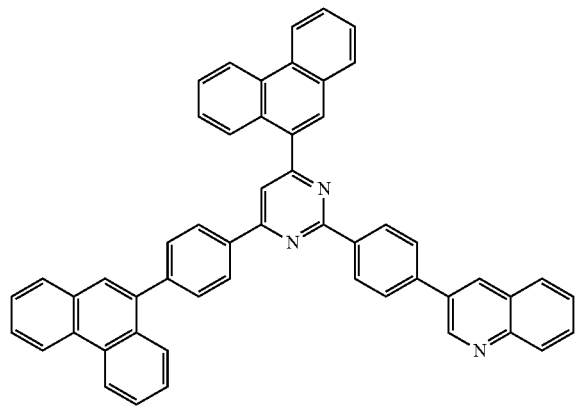
ET24
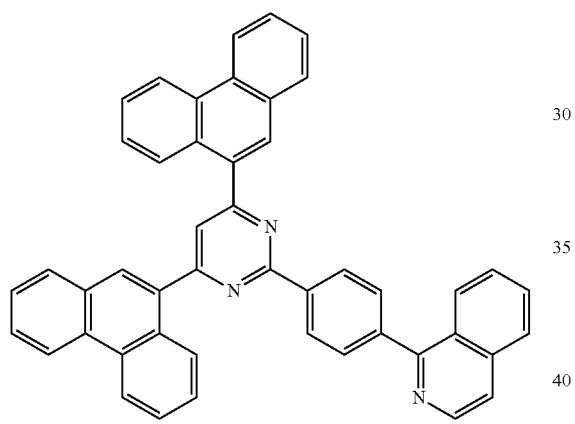
ET25
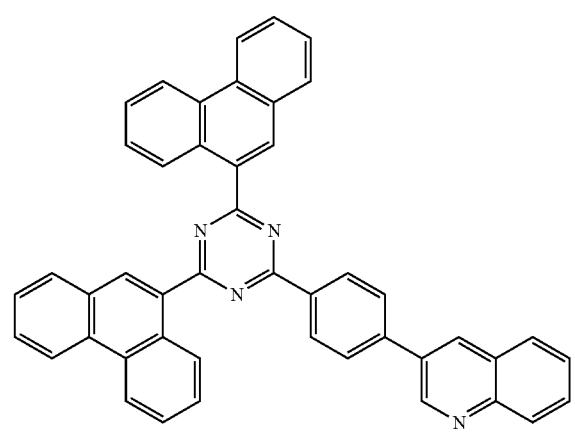
ET26
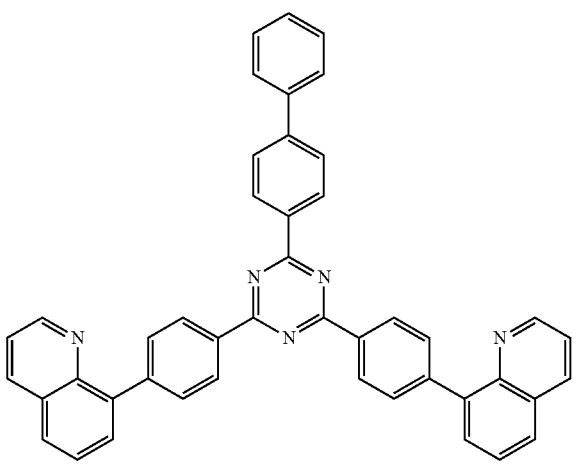
ET27
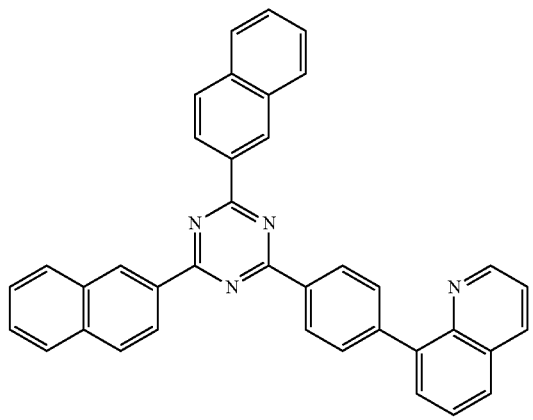
ET28
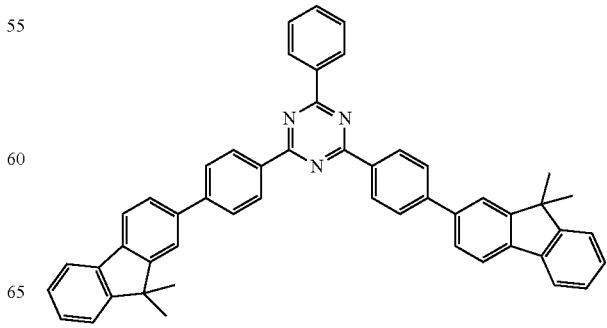

ET29
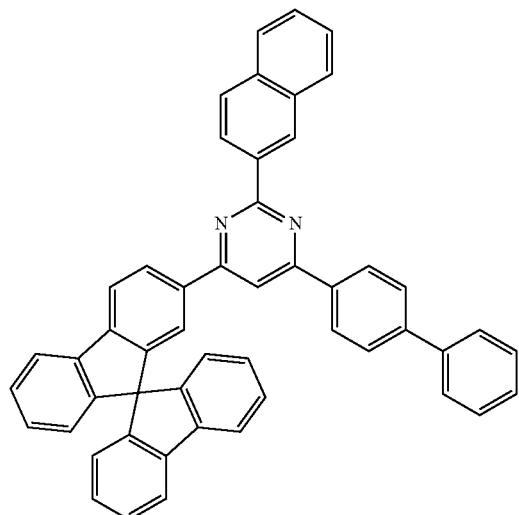
ET30
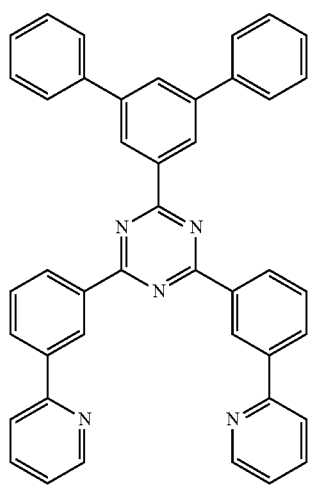
ET31
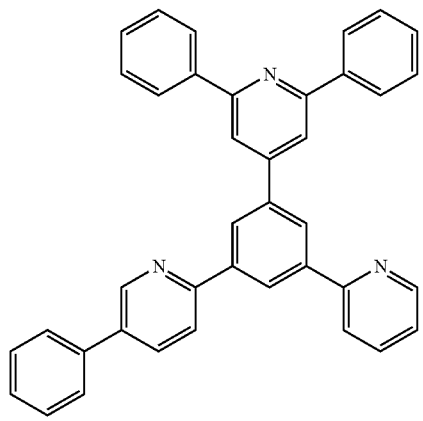
ET32
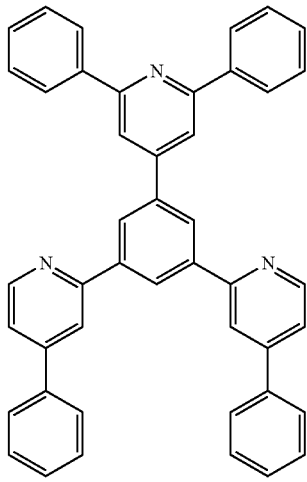
ET33
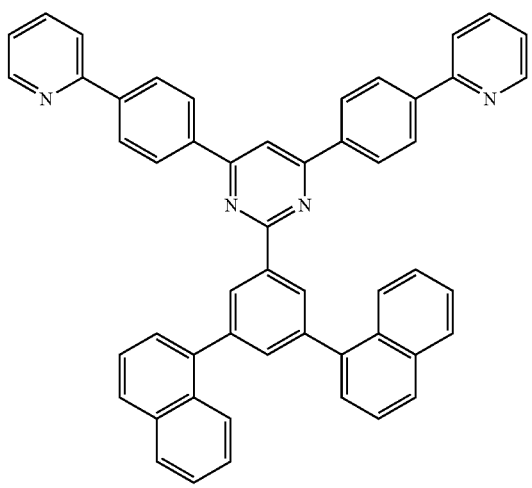
ET34
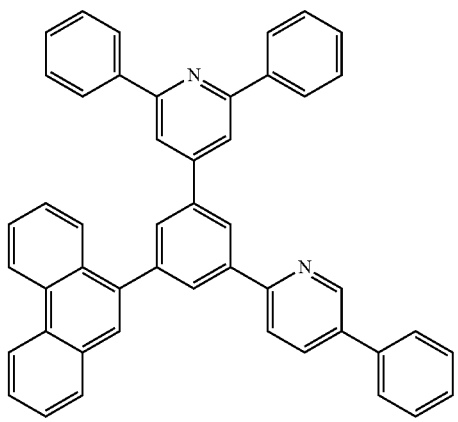

ET35

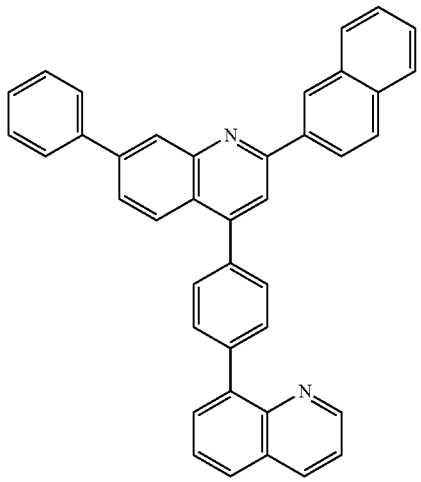

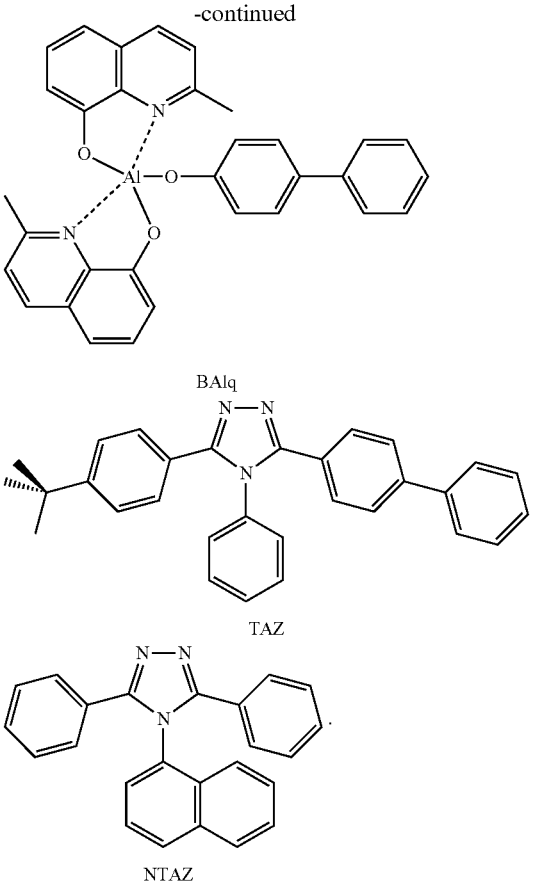

ET36

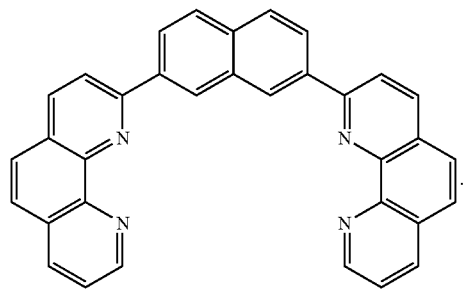

In one embodiment, the electron transport region may include at least one compound selected from 2,9-dimethyl-4,7-diphenyl-1,10-phenanthroline (BOP), 4,7-diphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), and NTAZ.

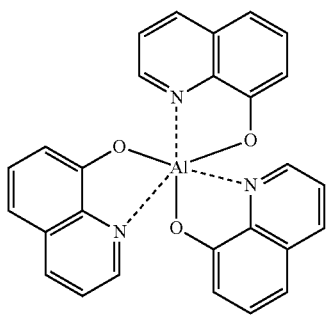

Alq$_3$

A thickness of the buffer layer, the hole blocking layer, or the electron control layer may be in a range of about 20 Å to about 1,000 Å, for example, about 30 Å to about 300 Å. When the thicknesses of the buffer layer, the hole blocking layer, and the electron control layer are within these ranges, the electron blocking layer may have excellent electron blocking characteristics or electron control characteristics without a substantial increase in driving voltage.

A thickness of the electron transport layer may be from about 100 Å to about 1,000 Å, for example, about 150 Å to about 500 Å. When the thickness of the electron transport layer is within the ranges described above, excellent electron transport characteristics may be obtained without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from an Li ion, a Na ion, a K ion, a Rb ion, and a Cs ion, and the alkaline earth-metal complex may include a metal ion selected from a Be ion, a Mg ion, a Ca ion, an Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenylan oxazole, a hydroxy phenylthiazole, a hydroxy diphenylan oxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

In one embodiment, the metal-containing material may include a Li complex. The Li complex may include, for example, Compound ET-D1 (lithium quinolate, LiQ) or ET-D2.

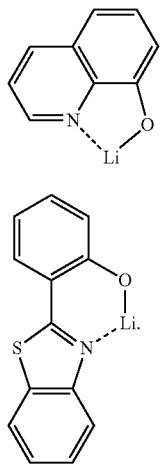

ET-D1

ET-D2

The electron transport region may include an electron injection layer that facilitates electron injection from the second electrode 190. The electron injection layer may directly contact the second electrode 190.

The electron injection layer may have i) a single-layered structure including a single layer including a single material, ii) a single-layered structure including a single layer including different materials, or iii) a multi-layered structure having a plurality of layers including different materials.

The electron injection layer may include alkali metal, alkaline earth metal, rare-earth metal, an alkali metal compound, an alkaline earth-metal compound, a rare-earth metal compound, an alkali metal complex, an alkaline earth-metal complex, a rare-earth metal complex, or any combinations thereof.

The alkali metal may be selected from Li, Na, K, Rb, and Cs. In one embodiment, the alkali metal may be Li, Na, or Cs. In one or more embodiments, the alkali metal may be Li or Cs, but embodiments of the present disclosure are not limited thereto.

The alkaline earth metal may be selected from Mg, Ca, Sr, and Ba.

The rare-earth metal may be selected from Sc, Y, Ce, Tb, Yb, and Gd.

The alkali metal compound, the alkaline earth-metal compound, and the rare-earth metal compound may be selected from oxides and halides (for example, fluorides, chlorides, bromides, or iodides) of the alkali metal, the alkaline earth-metal and rare-earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, KI, or RbI. In one embodiment, the alkali metal compound may be selected from LiF, $Li_2O$, NaF, LiI, NaI, CsI, and KI, but embodiments of the present disclosure are not limited thereto.

The alkaline earth-metal compound may be selected from alkaline earth-metal compounds, such as BaO, SrO, CaO, $Ba_xSr_{1-x}O$ (0<x<1), or $Ba_xCa_{1-x}O$ (0<x<1). In one embodiment, the alkaline earth-metal compound may be selected from BaO, SrO, and CaO, but embodiments of the present disclosure are not limited thereto.

The rare-earth metal compound may be selected from $YbF_3$, $ScF_3$, $ScO_3$, $Y_2O_3$, $Ce_2O_3$, $GdF_3$, and $TbF_3$ In one embodiment, the rare-earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare-earth metal complex may include an ion of alkali metal, alkaline earth-metal, and rare-earth metal as described above, and a ligand coordinated with a metal ion of the alkali metal complex, the alkaline earth-metal complex, and the rare-earth metal complex may each independently be selected from hydroxy quinoline, hydroxy isoquinoline, hydroxy benzoquinoline, hydroxy acridine, hydroxy phenanthridine, hydroxy phenylan oxazole, hydroxy phenylthiazole, hydroxy diphenylan oxadiazole, hydroxy diphenylthiadiazol, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may consist of alkali metal, alkaline earth metal, rare-earth metal, an alkali metal compound, an alkaline earth-metal compound, a rare-earth metal compound, an alkali metal complex, an alkaline earth-metal complex, a rare-earth metal complex, or any combinations thereof, as described above. In one or more embodiments, the electron injection layer may further include an organic material. When the electron injection layer further includes an organic material, alkali metal, alkaline earth metal, rare-earth metal, alkali metal compound, alkaline earth-metal compound, rare-earth metal compound, alkali metal complex, alkaline earth-metal complex, rare-earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. If the thickness of the electron injection layer is within the ranges described above, excellent electron injection characteristics may be obtained without a substantial increase in driving voltage.

[Second Electrode 190]

The second electrode 190 may be disposed on the organic layer 150 having such a structure. The second electrode 190 may be a cathode that is an electron injection electrode, and in this regard, as a metal for forming the second electrode 190, metal, alloy, an electrically conductive compound, and a combination thereof, each having a low work function, may be used.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The first electrode 190 may be a transmissive electrode, a semi-transmissive electrode, or a reflective electrode.

The first electrode 190 may have a single-layered structure, or a multi-layered structure including two or more layers.

Figure 3:
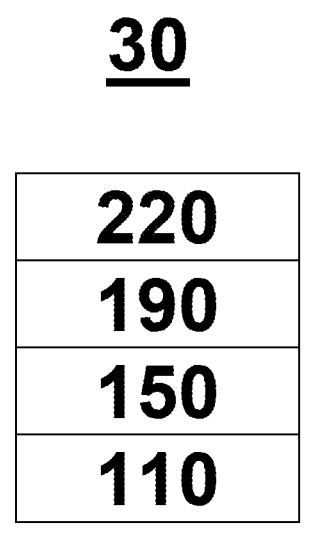
Figure 4:
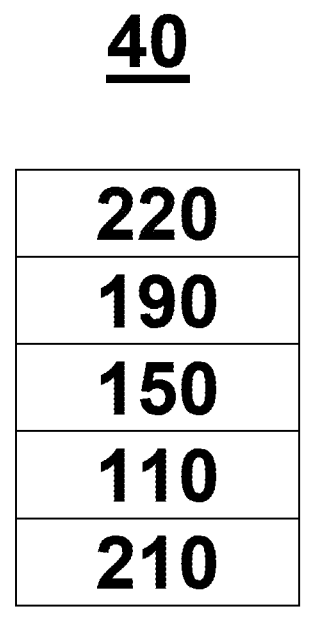

[Description of FIGS. 2 to 4]

Figure 2:
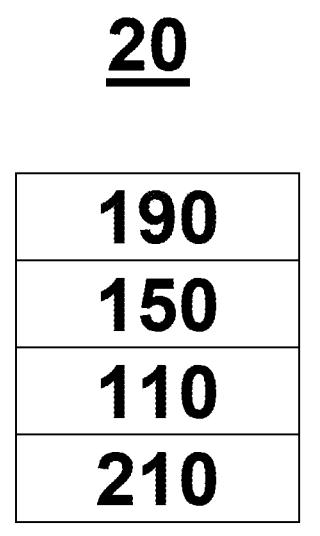

FIG. 2 is a schematic view of an organic light-emitting device 20 according to an embodiment. The organic light-emitting device 20 includes a first capping layer 210, the first electrode 110, the organic layer 150, and the second electrode 190, which are sequentially stacked in this stated order. FIG. 3 is a schematic view of an organic light-emitting device 30 according to an embodiment. The organic light-emitting device 30 includes the first electrode 110, the organic layer 150, the second electrode 190, and a second capping layer 220, which are sequentially stacked in this stated order. FIG. 4 is a schematic view of an organic light-emitting device 40 according to an embodiment. The organic light-emitting device 40 includes the first capping layer 210, the first electrode 110, the organic layer 150, the second electrode 190, and the second capping layer 220, which are sequentially stacked in this stated order.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110 and the first capping layer 210 toward the outside, wherein the first electrode 110 may be a semi-transmissive electrode or a transmissive electrode. In the organic layer 150 of each of the organic light-emitting devices 30 and 40, light generated in an emission layer may pass through the second electrode 190 and the second capping layer 220 toward the outside, wherein the second electrode 190 may be a semi-transmissive electrode or a transmissive electrode.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may include the condensed cyclic compound represented by Formula 1.

At least one selected from the first capping layer 210 and the second capping layer 220 may each independently include at least one material selected from carbocyclic compounds, heterocyclic compounds, amine-based compounds, porphyrin derivatives, phthalocyanine derivatives, naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5, but embodiments of the present disclosure are not limited thereto.

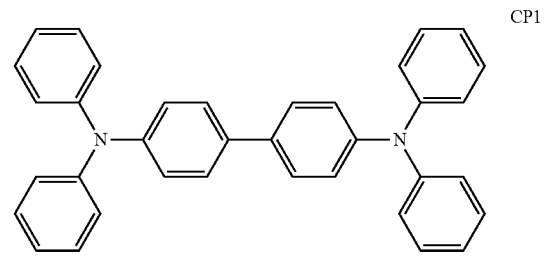

CP1

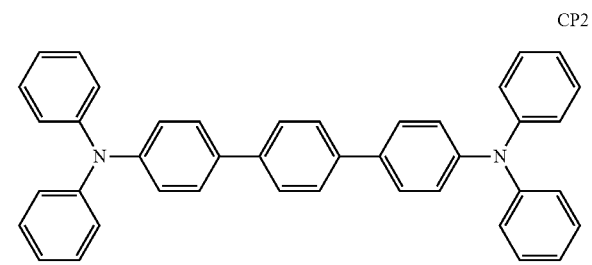

CP2

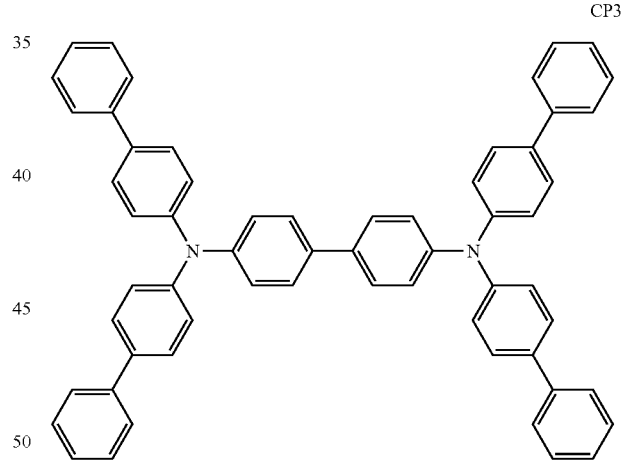

CP3

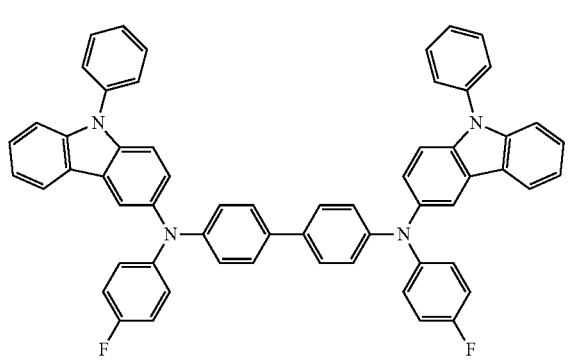

CP4

CP5

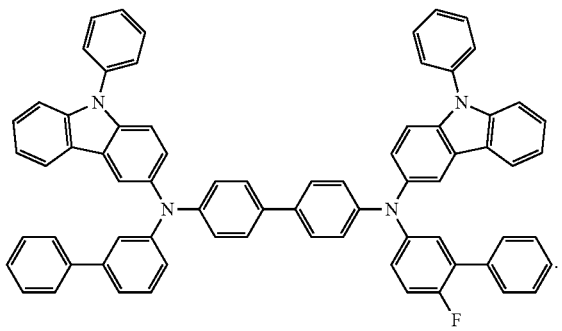

Hereinbefore, the organic light-emitting device according to an embodiment has been described in connection with FIGS. 1 to 4, but embodiments of the present disclosure are not limited thereto.

Respective layers constituting the hole transport region, an emission layer, and respective layers constituting the electron transport region may be formed in a certain region by using one or more suitable methods selected from vacuum deposition, spin coating, casting, langmuir-blodgett (LB) deposition, ink-jet printing, laser-printing, and laser-induced thermal imaging.

When the respective layers of the hole transport region, the emission layer, and the respective layers of the electron transport region are formed by deposition, the deposition may be performed at a deposition temperature of about 100 to about 500° C., at a vacuum degree of about $10^{-8}$ to about $10^{-3}$ torr, and at a deposition rate of about 0.01 to about 100 Å/sec by taking into account a material for forming a layer to be deposited, and the structure of a layer to be formed.

When respective layers constituting the hole transport region, an emission layer, and respective layers constituting the electron transport region are formed by spin coating, the spin coating may be performed at a coating speed of about 2,000 rpm to about 5,000 rpm and at a heat treatment temperature of about 80° C. to 200° C., depending on a material to be included in a layer and the structure of each layer to be formed.

[General Definition of Substituents]

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and does not have aromaticity, and examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be condensed to each other.

The term "$C_1$-$C_{60}$ heteroaryl group" as used herein refers to a monovalent group having a heterocyclic aromatic system that has at least one heteroatom selected from N, O, P, and S as a ring-forming atom, in addition to 1 to 60 carbon atoms. The term "$C_1$-$C_{60}$ heteroarylene group," as used herein, refers to a divalent group having a heterocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed to each other.

The term "$C_6$-$C_{60}$ aryloxy group" as used herein refers to —$OA_{102}$ (wherein $A_{102}$ is the $C_6$-$C_{60}$ aryl group), and the term "$C_6$-$C_{60}$ arylthio group" as used herein refers to —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) that has two or more rings condensed to each other, only carbon atoms as a ring-forming atom, and non-aromaticity in the entire molecular structure. Examples of the monovalent non-aromatic condensed polycyclic group include a fluorenyl group. The term "divalent non-aromatic condensed polycyclic group," used herein, refers to a divalent group having the same structure as the monovalent non-aromatic condensed polycyclic group.

The term "monovalent non-aromatic condensed heteropolycyclic group," used herein, refers to a monovalent group (for example, having 2 to 60 carbon atoms) that has two or more rings condensed to each other, has at least one heteroatom selected from N, O, Si, P, and S, other than carbon atoms, as a ring-forming atom, and has non-aromaticity in the entire molecular structure. Examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a monovalent group, such as a cyclic phenyl group, such as benzene, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_1$-$C_{60}$ carbocyclic group, except that, as a ring-forming atom, at least one heteroatom selected from N, O, Si, P, and S is used in addition to carbon (the number of carbon atoms may be in a range of 1 to 60).

At least one of substituent or substituents of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(\!\!=\!\!O)(Q_{11})$, —$S(\!\!=\!\!O)_2(Q_{11})$, and —$P(\!\!=\!\!O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(\!\!=\!\!O)(Q_{21})$, —$S(\!\!=\!\!O)_2(Q_{21})$, and —$P(\!\!=\!\!O)(Q_{21})(Q_{22})$; and —$Si(Q_{31})(Q_{32})(Q_{33})$, —$N(Q_{31})(Q_{32})$, —$B(Q_{31})(Q_{32})$, —$C(\!\!=\!\!O)(Q_{31})$, —$S(\!\!=\!\!O)_2(Q_{31})$, and —$P(\!\!=\!\!O)(Q_{31})(Q_{32})$, wherein $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" used herein represents a phenyl group, the term "Me" used herein represents a methyl group, the term "Et" used herein represents an ethyl group, the term "ter-Bu" or "Bu$^t$" used herein represents a tert-butyl group, and "OMe" used herein represents a methoxy group.

The term "biphenyl group" as used therein refers to "a phenyl group substituted with a phenyl group." In other words, a "biphenyl group" is a substituted phenyl group having a $C_6$-$C_{60}$ aryl group as a substituent.

The term "terphenyl group" as used herein refers to "a phenyl group substituted with a biphenyl group." The "terphenyl group" is a "substituted phenyl group" having a "$C_6$-$C_{60}$ aryl group substituted with a $C_6$-$C_{60}$ aryl group" as a substituent.

* and *' used herein, unless defined otherwise, each refer to a binding site to a neighboring atom in a corresponding formula.

Hereinafter, a compound according to embodiments and an organic light-emitting device according to embodiments will be described in detail with reference to Synthesis Examples and Examples. The wording "B was used instead of A" used in describing Synthesis Examples indicates that a molar equivalent of A was identical to a molar equivalent of B.

EXAMPLE

Synthesis Example 1: Synthesis of Compound 5

<Reaction Scheme 1>

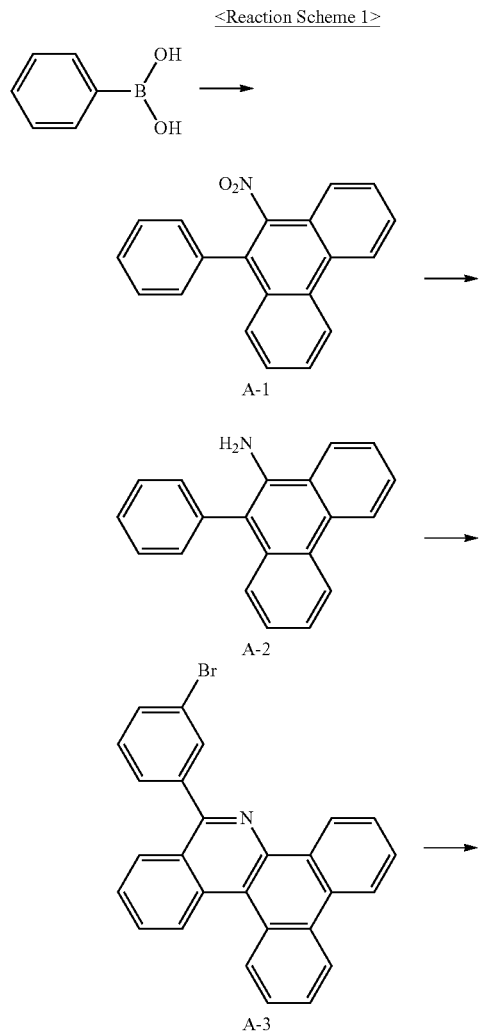

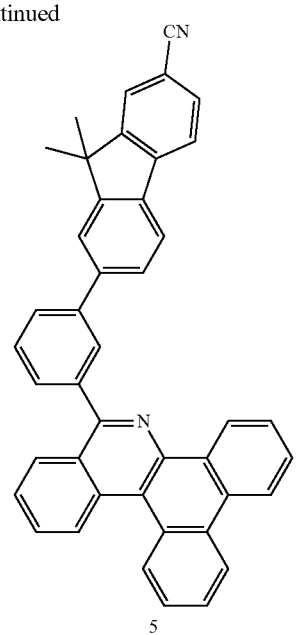

Synthesis of Intermediate A-1

Phenylboronic acid (2.44 g, 20.0 mmol), 9-bromo-10-nitrophenanthrene (6.04 g, 20.0 mmol), Pd(PPh$_3$)$_4$ (1.16 g, 1.00 mmol), tetrabutylammonium bromide (TBAB) (0.322 g, 1.00 mmol), and Na$_2$CO$_3$ (6.28 g, 60.0 mmol) were dissolved in 80 mL of a mixed solution of toluene/ethanol/H$_2$O (3/3/1), and then, stirred at a temperature of 80° C. for 16 hours. The reaction solution was cooled to room temperature, and then, an extraction process was performed three times thereon by using 60 mL of water and 60 mL of diethylether. An organic layer was dried by using MgSO$_4$, and the residue obtained by evaporating a solvent therefrom was separation-purified by silica gel column chromatography, thereby completing the preparation of 4.91 g of Intermediate A-1 (yield of 82%). The obtained compound was identified by LC-MS. $C_{20}H_{13}NO_2$: M+1 299.1

Synthesis of Intermediate A-2

Intermediate A-1 (4.91 g, 16.4 mmol), Tin (5.84 g, 49.2 mmol), and 8.2 mL (82 mmol, conc. 36.5%) of HCl were dissolved in 60 mL of ethanol, and then, stirred at a temperature of 100° C. for 8 hours. The reaction solution was cooled to room temperature, and then, 5 g of sodium hydroxide dissolved in 10 mL of water was added to a filtrate obtained by filtering under reduced pressure, and then, the result was subjected three times to an extraction process using 60 mL of water and 60 mL of dichloromethane. An organic layer obtained therefrom was dried by using MgSO$_4$, and the residue obtained by evaporating a solvent therefrom was separation-purified by silica gel column chromatography, thereby completing the preparation of 3.98 g (yield of 90%) of Intermediate A-2. The obtained compound was identified by LC-MS. $C_{20}H_{15}N$: M+1 269.1

Synthesis of Intermediate A-3

Intermediate A-2 (3.98 g, 14.7 mmol) and 3-bromobenzaldehyde (5.38 g, 29.4 mmol) were dissolved in 30 mL of trifluoroacetic acid, and then, the mixture was stirred in a seal tube at a temperature of 130° C. for 3 days. The reaction solution was cooled to room temperature, and then, the reaction was quenched by using $NaHCO_3$. The result was subjected to an extraction process using 60 mL of water and 60 mL of dichloromethane. An organic layer obtained therefrom was dried by using $MgSO_4$, and the residue obtained by evaporating a solvent therefrom was separation-purified by silica gel column chromatography, thereby completing the preparation of 3.83 g (yield of 60%) of Intermediate A-3. The obtained compound was identified by LC-MS. $C_{27}H_{16}BrN$: M+1 433.1

Synthesis of Compound 5

Intermediate A-3 (3.83 g, 8.82 mmol), 9,9-dimethyl-7-(4,4,5,5-tetramethyl-1,3,2-dioxaborolan-2-yl)-9H-fluorene-2-carbonitrile (3.05 g, 10 mmol), $Pd(PPh_3)_4$ (0.51 g, 0.44 mmol), and $K_2CO_3$ (3.66 g, 2.65 mmol) were dissolved in 60 mL of a mixed solution including $THF/H_2O$ (a volumetric ratio of 2/1), and then, the mixture was stirred at a temperature of 80° C. for 16 hours. The reaction solution was cooled to room temperature, and then, 40 mL of water was added thereto, and an extraction process was performed three times on the result by using 50 mL of ethyl ether. An organic layer obtained therefrom was dried by using $MgSO_4$, and the residue obtained by evaporating a solvent therefrom was separation-purified by silica gel column chromatography, thereby completing the preparation of 3.63 g of Compound 5 (yield of 72%). The obtained compound was identified by MS/FAB and $^1H$ NMR. $C_{43}H_{28}N_2$ cal. 572.23, found 572.22.

Synthesis Example 2: Synthesis of Compound 7

3.83 g of Compound 7 (yield of 70%) was obtained in the same manner as used to synthesize Compound 5 in Synthesis Example 1, except that 9-phenyl-6-(4,4,5,5-tetramethyl-1,3,2-dioxaborolan-2-yl)-9H-carbazole-2-carbonitrile was used instead of 9,9-dimethyl-7-(4,4,5,5-tetramethyl-1,3,2-dioxaborolan-2-yl)-9H-fluorene-2-carbonitrile. The obtained compound was identified by MS/FAB and $^1H$ NMR. $C_{46}H_{27}N_3O$ cal. 621.22, found 621.23.

Synthesis Example 3: Synthesis of Compound 12

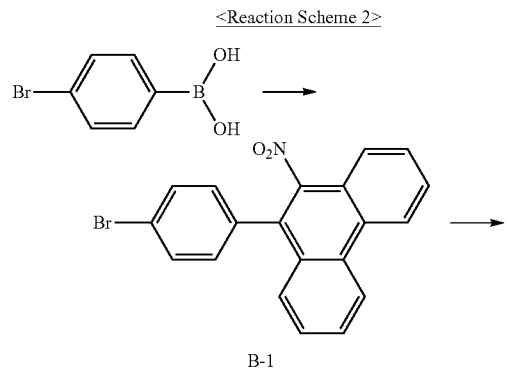

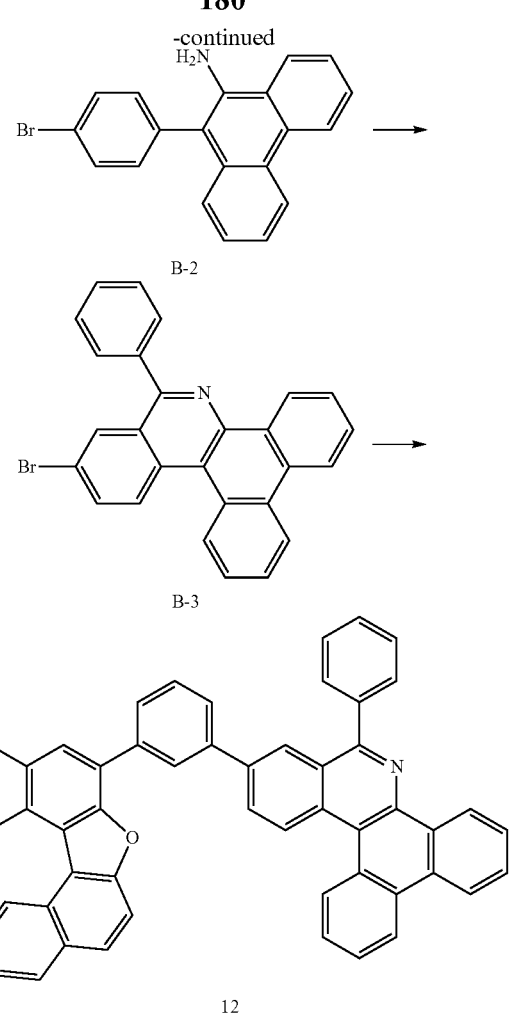

Synthesis of Intermediate B-1

6.05 g of Intermediate B-1 (yield of 80%) was obtained in the same manner as used to synthesize Intermediate A-1, except that 4-bromophenylboronic acid was used instead of phenylboronic acid. The obtained compound was identified by LC-MS. $C_{20}H_{12}NBrO_2$: M+1 377.0

Synthesis of Intermediate B-2

5.01 g of Intermediate B-2 (yield of 90%) was obtained in the same manner as used to synthesize Intermediate A-2, except that Intermediate B-1 was used instead of Intermediate A-1. The obtained compound was identified by LC-MS. $C_{20}H_{14}BrN$: M+1 347.0

Synthesis of Intermediate B-3

4.38 g of Intermediate B-3 (yield of 70%) was obtained in the same manner as used to synthesize Intermediate A-3, except that Intermediate B-2 was used instead of Intermediate A-2. The obtained compound was identified by LC-MS. $C_{27}H_{16}BrN$: M+1 433.1

Synthesis of Compound 12

4.57 g of Compound 12 (yield of 65%) was obtained in the same manner as used to synthesize Compound 5, except

Synthesis Example 4: Synthesis of Compound 19

3.98 g of Compound 19 (yield of 60%) was obtained in the same manner as used to synthesize Compound 12 in Synthesis Example 3, except that 4,4,5,5-tetramethyl-2-(10-(naphthalen-1-yl)anthracen-9-yl)-1,3,2-dioxaborolane was used instead of 2-(3-(dinaphtho[2,1-b:1',2'-d]furan-6-yl)phenyl)-4,4,5,5-tetramethyl-1,3,2-dioxaborolane. The obtained compound was identified by MS/FAB and $^1$H NMR. $C_{51}H_{31}N$ cal. 657.25, found 657.26.

Synthesis Example 5: Synthesis of Compound 30

4.27 g of Compound 30 (yield of 68%) was obtained in the same manner as in Synthesis Example 3, except that, in synthesizing Intermediate B-1, (4-bromonaphthalen-1-yl) boronic acid was used instead of 4-bromophenylboronic acid, and, in synthesizing Compound 12, 9,9-dimethyl-7-(4,4,5,5-tetramethyl-1,3,2-dioxaborolan-2-yl)-9H-fluorene-2-carbonitrile was used instead of 2-(3-(dinaphtho[2,1-b: 1',2'-d]furan-6-yl)phenyl)-4,4,5,5-tetramethyl-1,3,2-dioxaborolane. The obtained compound was identified by MS/FAB and $^1$H NMR. $C_{47}H_{30}N_2$ cal. 622.24, found 622.25.

Synthesis Example 6: Synthesis of Compound 47

4.23 g (yield of 63%) of Compound 47 was obtained in the same manner as in Synthesis Example 1, except that, in synthesizing Intermediate A-1, 2-naphthaleneboronic acid was used instead of a phenylboronic acid, and, in synthesizing Compound 5, 9-phenyl-6-(4,4,5,5-tetramethyl-1,3,2-dioxaborolan-2-yl)-9H-carbazole-2-carbonitrile was used instead of 9,9-dimethyl-7-(4,4,5,5-tetramethyl-1,3,2-dioxaborolan-2-yl)-9H-fluorene-2-carbonitrile. The obtained compound was identified by MS/FAB and $^1$H NMR. $C_{50}H_{29}N_3$ cal. 671.24, found 671.23.

Synthesis Example 7: Synthesis of Compound 56

4.36 g of Compound 56 (yield of 70%) was obtained in the same manner as used to synthesize Synthesis Example 1, except that, in synthesizing Intermediate A-1, 2-pyridineboronic acid was used instead of a phenylboronic acid, and, in synthesizing Compound 5, 2-(dinaphtho[2,1-b:1',2'-d]furan-6-yl)-4,4,5,5-tetramethyl-1,3,2-dioxaborolane was used instead of 9,9-dimethyl-7-(4,4,5,5-tetramethyl-1,3,2-dioxaborolan-2-yl)-9H-fluorene-2-carbonitrile. The obtained compound was identified by MS/FAB and $^1$H NMR. $C_{46}H_{26}N_2O$ cal. 622.20, found 622.19.

Synthesis Example 8: Synthesis of Compound 67

3.52 g of Compound 67 (yield of 60%) was obtained in the same manner as in Synthesis Example 1, except that, in synthesizing Intermediate A-1,4-pyridineboronic acid was used instead of a phenylboronic acid, in synthesizing Intermediate A-3,4-bromobenzaldehyde was used instead of 3-bromobenzaldehyde, and, in synthesizing Compound 5,3,3'-(5-(4,4,5,5-tetramethyl-1,3,2-dioxaborolan-2-yl)-1,3-phenylene)dipyridine was used instead of 9,9-dimethyl-7-(4,4,5,5-tetramethyl-1,3,2-dioxaborolan-2-yl)-9H-fluorene-2-carbonitrile. The obtained compound was identified by MS/FAB and $^1$H NMR. $C_{42}H_{26}N_4$ cal. 586.22, found 586.21.

Synthesis Example 9: Synthesis of Compound 79

4.51 g of Compound 79 (yield of 67%) was obtained in the same manner as in Synthesis Example 1, except that, in synthesizing Intermediate A-1,8-quinolineboronic acid was used instead of a phenylboronic acid, and, in synthesizing Compound 5, 9-phenyl-6-(4,4,5,5-tetramethyl-1,3,2-dioxaborolan-2-yl)-9H-carbazole-2-carbonitrile was used instead of 9,9-dimethyl-7-(4,4,5,5-tetramethyl-1,3,2-dioxaborolan-2-yl)-9H-fluorene-2-carbonitrile. The obtained compound was identified by MS/FAB and $^1$H NMR. $C_{49}H_{28}N_4$ cal. 672.23, found 672.22.

Synthesis Example 10: Synthesis of Compound 88

4.64 g of Compound 88 (yield of 69%) was obtained in the same manner as in Synthesis Example 1, except that, in synthesizing Intermediate A-1,3-isoquinolineboronic acid was used instead of phenylboronic acid, and, in synthesizing Compound 5, 2-(dinaphtho[2,1-b:1',2'-d]furan-6-yl)-4,4,5,5-tetramethyl-1,3,2-dioxaborolane was used instead of 9,9-dimethyl-7-(4,4,5,5-tetramethyl-1,3,2-dioxaborolan-2-yl)-9H-fluorene-2-carbonitrile. The obtained compound was identified by MS/FAB and $^1$H NMR. $C_{50}H_{28}N_2O$ cal. 672.22, found 672.20.

Synthesis Example 11: Synthesis of Compound 89

Intermediate B-3 (3.91 g, 9.00 mmol) prepared according to Synthesis Example 3 was dissolved in 30 mL of THF, and then, at a temperature of −80° C., n-butyllithium (3.6 mL, 2.5 M in hexane) was added thereto. After one hour, at the same temperature, chlorodiphenylphosphine (1.99 g, 9 mmol) was added to the resultant mixture. The mixture was stirred at room temperature for 3 hours, followed by adding water thereto, and then, washed three times with diethylether (30 mL). A diethylether layer obtained after the washing was dried by using MgSO$_4$, and then, dried under reduced pressure to obtain a product. Then, 30 mL of H$_2$O$_2$ was added to the product and stirred for 1 hour. Water was added to the resultant product, which was then washed three times with diethylether (30 mL). A diethylether layer obtained after the washing was dried by using MgSO$_4$, and then, dried under reduced pressure to obtain a product, which was then separation-purified by silica gel column chromatography to obtain 3.00 g of Compound 89 (yield of 60%), which was white solid. The obtained compound was identified by MS/FAB and $^1$H NMR. $C_{39}H_{26}NOP$ cal. 555.18, found 555.19.

Synthesis Example 12: Synthesis of Compound 91

Intermediate B-3 (4.35 g, 10.0 mmol) prepared according to Synthesis Example 3, diphenyl(3-(4,4,5,5-tetramethyl-1,3,2-dioxaborolan-2-yl)phenyl)phosphine oxide (4.04 g, 10.0 mmol), Pd(PPh$_3$)$_4$ (0.58 g, 0.50 mmol), and K$_2$CO$_3$ (4.15 g, 30.0 mmol) were dissolved in 60 mL of a mixed solution including THF/H$_2$O (a volumetric ratio of 2/1), and then, stirred at a temperature of 80° C. for 16 hours. The reaction solution was cooled to room temperature, followed by adding with 40 mL of water thereto, and then, washed three times with 50 mL of diethylether. A collected organic layer was dried by using MgSO$_4$, and the residue obtained by evaporating a solvent therefrom was separation-purified by silica gel column chromatography, thereby completing the preparation of 4.29 g (yield of 68%) of Compound 91. The obtained compound was identified by MS/FAB and $^1$H NMR. C$_{45}$H$_{30}$NOP cal. 631.21, found 631.22.

Synthesis Example 13: Synthesis of Compound 103

3.45 g of Compound 103 (yield of 67%) was obtained in the same manner as in Synthesis Example 11, except that, in synthesizing Intermediate B-1, (4-bromonaphthalen-1-yl) boronic acid was used instead of 4-bromophenylboronic acid. The obtained compound was identified by MS/FAB and $^1$H NMR. C$_{43}$H$_{28}$NOP cal. 605.19, found 605.18.

Synthesis Example 14: Synthesis of Compound 119

4.29 g of Compound 119 (yield of 68%) was obtained in the same manner as in Synthesis Example 12, except that, in synthesizing Compound 91,4,4,5,5-tetramethyl-2-(10-(phenylsulfonyl)anthracen-9-yl)-1,3,2-dioxaborolane was used instead of diphenyl(3-(4,4,5,5-tetramethyl-1,3,2-dioxaborolan-2-yl)phenyl)phosphine oxide The obtained compound was identified by MS/FAB and $^1$H NMR. C$_{47}$H$_{29}$NO$_2$S cal. 671.19, found 671.18.

Synthesis Example 15: Synthesis of Compound 129

<Reaction Scheme 3>

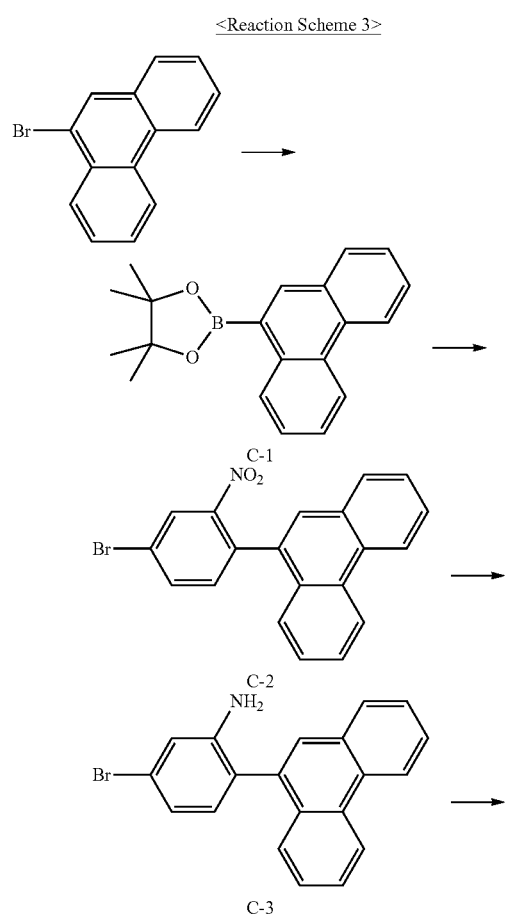

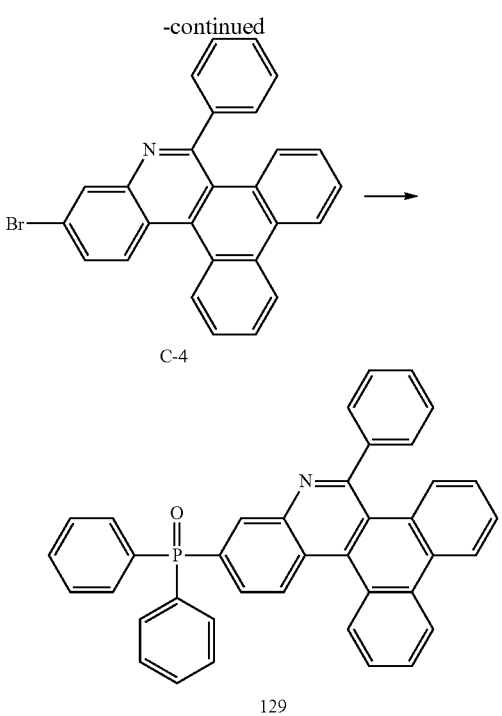

Synthesis of Intermediate C-1

9-bromophenanthrene (2.57 g, 10.0 mmol) was dissolved in 30 mL of THF, and then, at a temperature of −80° C., n-butyllithium (4.0 mL, 2.5 M in Hexane) was added thereto. After one hour, at the same temperature, 2-isopropoxy-4,4,5,5-tetramethyl-1,3,2-dioxaborolane (2.24 mL, 11 mmol) was added thereto. The resultant mixture was stirred at room temperature for 3 hours, followed by adding water thereto, and then, washed three times with 30 mL of diethylether. A diethylether layer obtained after the washing was dried by using MgSO$_4$, and then, dried under reduced pressure to obtain a product, which was then separation-purified by silica gel column chromatography to obtain 1.88 g (yield of 62%) of Intermediate C-1. The obtained compound was identified by MS/FAB and $^1$H NMR. C$_{20}$H$_{31}$BO$_2$: M+1 378.0

Synthesis of Intermediate C-2

Intermediate C-1 (3.04 g, 10.0 mmol), 1,4-dibromo-2-nitrobenzene (2.81 g, 10.0 mmol), Pd(PPh$_3$)$_4$ (0.58 g, 0.50 mmol), tetrabutylammonium bromide (TBAB) (0.161 g, 0.50 mmol), and Na$_2$CO$_3$ (3.14 g, 30.0 mmol) were dissolved in 40 mL of a mixed solution including toluene/ethanol/H$_2$O (3/3/1), and then, stirred at a temperature of 80° C. for 16 hours. The reaction solution was cooled to room temperature, and then, subjected to an extraction process three times by using 60 mL of water and 60 mL of diethylether. An organic layer obtained therefrom was dried by using MgSO$_4$, and the residue obtained by evaporating a solvent therefrom was separation-purified by silica gel column chromatography, thereby completing the preparation of 3.06 g of Intermediate C-2 (yield of 81%). The obtained compound was confirmed by LC-MS. C$_{20}$H$_{12}$NBrO$_2$: M+1 378.0

Synthesis of Intermediate C-3

Intermediate C-2 (3.78 g, 10.0 mmol), Tin (3.56 g, 30.0 mmol), and HCl 5.0 mL (50 mmol, conc. 36.5%) were dissolved in 40 mL of ethanol, and then, the mixture was stirred at a temperature of 100° C. for 8 hours. The reaction solution was cooled to room temperature, and then, 5 g of sodium hydroxide dissolved in 10 mL of water was added to a filtrate obtained by filtering the reaction solution under reduced pressure. The resultant product was subjected to an extraction process three times by using 60 mL of water and 60 mL of dichloromethane. An organic layer obtained therefrom was dried by using $MgSO_4$, and the residual obtained by evaporating a solvent therefrom was separation-purified by silica gel column chromatography, thereby completing the preparation of 2.99 g (yield of 86%) of Intermediate C-3. The obtained compound was confirmed by LC-MS. $C_{20}H_{14}BrN$: M+1 348.0

Synthesis of Intermediate C-4

Intermediate C-3 (3.48 g, 10.0 mmol) and 3-bromobenzaldehyde (3.70 g, 20.0 mmol) were dissolved in 20 mL of trifluoroacetic acid, and then, the mixture was stirred in a seal tube at a temperature of 130° C. for 3 days. The reaction solution was cooled to room temperature, followed by quenching using $NaHCO_3$. The resultant solution was subjected to an extraction process three times by using 40 mL of water and 60 mL of dichloromethane. An organic layer obtained therefrom was dried by using $MgSO_4$, and the residual obtained by evaporating a solvent therefrom was separation-purified by silica gel column chromatography, thereby completing the preparation of 2.99 g of Intermediate C-4 (yield of 69%). The obtained compound was confirmed by LC-MS. $C_{27}H_{16}BrN$: M+1 434.1

Synthesis of Compound 129

Intermediate C-4 (4.34 g, 10.00 mmol) was dissolved in 30 mL of THF, and then, at a temperature of −80° C., n-butyllithium (4.0 mL, 2.5 M in hexane) was added thereto. After one hour, at the same temperature, chlorodiphenylphosphine (2.20 g, 10 mmol) was added to the mixture. The resultant mixture was stirred at room temperature for 3 hours, followed by adding water thereto, and then, washed three times with diethylether (30 mL). A diethylether layer was dried by using $MgSO_4$, and then, dried under reduced pressure to obtain a product. Then, 30 mL of $H_2O_2$ was added thereto and stirred for 1 hour. After the stirring, water was added thereto, and the resultant product was washed three times with diethylether (30 mL). A diethylether layer obtained after the washing was dried by using $MgSO_4$, and then, dried under reduced pressure to obtain a product, which was then separation-purified by silica gel column chromatography to obtain 3.27 g of Compound 129 (yield of 59%). The obtained compound was identified by MS/FAB and $^1$H NMR. $C_{39}H_{26}NOP$ cal. 555.18, found 555.19.

Synthesis Example 16: Synthesis of Compound 134

Intermediate C-4 (4.34 g, 10.0 mmol) prepared according to Synthesis Example 15, diphenyl(10-(4,4,5,5-tetramethyl-1,3,2-dioxaborolan-2-yl)anthracen-9-yl)phosphine oxide (5.04 g, 10.0 mmol), $Pd(PPh_3)_4$ (0.58 g, 0.50 mmol), and $K_2CO_3$ (4.15 g, 30.0 mmol) were dissolved in 60 mL of a mixed solution including $THF/H_2O$ (a volumetric ratio of 2/1), and then, the mixture was stirred at a temperature of 80° C. for 16 hours. The reaction solution was cooled to room temperature, followed by adding 40 mL of water thereto, and then, subjected to an extraction process three times by using 50 mL of diethylether. A collected organic layer was dried by using $MgSO_4$, and the residual obtained by evaporating a solvent therefrom was separation-purified by silica gel column chromatography, thereby completing the preparation of 4.29 g (yield of 68%) of Compound 134. The obtained compound was identified by MS/FAB and $^1$H NMR. $C_{53}H_{34}NOP$ cal. 731.24, found 731.23.

Synthesis Example 17: Synthesis of Compound 138

4.37 g (yield of 64%) of Compound 138 was obtained in the same manner as in Synthesis Example 16, except that, in synthesizing Intermediate C-2,3,6-dibromo-2-nitropyridine was used instead of 1,4-dibromo-2-nitrobenzene, and, in synthesizing Compound 134, diphenyl(4-(4,4,5,5-tetramethyl-1,3,2-dioxaborolan-2-yl)naphthalen-1-yl)phosphine oxide was used instead of diphenyl(3-(4,4,5,5-tetramethyl-1,3,2-dioxaborolan-2-yl)phenyl)phosphine oxide. The obtained compound was identified by MS/FAB and $^1$H NMR. $C_{48}H_{31}N_2OP$ cal. 682.22, found 682.21.

Synthesis Example 18: Synthesis of Compound 143

3.88 g (yield of 64%) of Compound 143 was obtained in the same manner as in Synthesis Example 15, except that, in synthesizing Intermediate C-2,1,4-dibromo-2-nitronaphthalene was used instead of 1,4-dibromo-2-nitrobenzene. The obtained compound was identified by MS/FAB and $^1$H NMR. $C_{43}H_{28}NOP$ cal. 605.19, found 605.18.

Synthesis Example 19: Synthesis of Compound 146

4.43 g of Compound 146 (yield of 65%) was obtained in the same manner as used to synthesize Synthesis Example 16, except that, in synthesizing Intermediate C-2,1,4-dibromo-2-nitronaphthalene was used instead of 1,4-dibromo-2-nitrobenzene, and, in synthesizing Compound 134, diphenyl(5-(4,4,5,5-tetramethyl-1,3,2-dioxaborolan-2-yl)pyridin-3-yl)phosphine oxide was used instead of diphenyl(3-(4,4,5,5-tetramethyl-1,3,2-dioxaborolan-2-yl)phenyl)phosphine oxide. The obtained compound was identified by MS/FAB and $^1$H NMR. $C_{48}H_{31}N_2OP$ cal. 682.22, found 682.21.

Synthesis Example 20: Synthesis of Compound 153

4.17 g of Compound 153 (yield of 61%) was obtained in the same manner as in Synthesis Example 16, except that, in synthesizing Intermediate C-2,5,8-dibromo-6-nitroquinoline was used instead of 1,4-dibromo-2-nitrobenzene, and, in synthesizing Compound 134, diphenyl(6-(4,4,5,5-tetramethyl-1,3,2-dioxaborolan-2-yl)pyridin-2-yl)phosphine oxide was used instead of diphenyl(10-(4,4,5,5-tetramethyl-1,3,2-dioxaborolan-2-yl)anthracen-9-yl)phosphine oxide. The obtained compound was identified by MS/FAB and $^1$H NMR. $C_{47}H_{30}N_3OP$ cal. 685.22, found 685.23.

Synthesis Example 21: Synthesis of Compound 154

4.43 g (yield of 65%) of Compound 154 was obtained in the same manner as in Synthesis Example 16, except that, in synthesizing Intermediate C-2,5,8-dibromo-7-nitroquinoline was used instead of 1,4-dibromo-2-nitrobenzene, and, in synthesizing Compound 134, diphenyl(3-(4,4,5-trimethyl-1,3,2-dioxaborolan-2-yl)phenyl)phosphine oxide was used instead of diphenyl(10-(4,4,5,5-tetramethyl-1,3,2-dioxaborolan-2-yl)anthracen-9-yl)phosphine oxide. The obtained compound was identified by MS/FAB and $^1$H NMR. $C_{48}H_{31}N_2OP$ cal. 682.22, found 682.21.

Synthesis Example 22: Synthesis of Compound 168

4.12 g of Compound 168 (yield of 66%) was obtained in the same manner as in Synthesis Example 16, except that, in synthesizing Intermediate C-2, 5,8-dibromo-6-nitroquinoline was used instead of 1,4-dibromo-2-nitrobenzene, and, in synthesizing Compound 134, 2-(phenylsulfonyl)-6-(4,4,5,5-tetramethyl-1,3,2-dioxaborolan-2-yl)pyridine was used instead of diphenyl(10-(4,4,5,5-tetramethyl-1,3,2-dioxaborolan-2-yl)anthracen-9-yl)phosphine oxide. The obtained compound was identified by MS/FAB and $^1$H NMR. $C_{41}H_{25}N_3O_2S$ cal. 623.17, found 623.18.

Additional compounds were synthesized by using the same synthesis paths and methods as described above and appropriate intermediate materials. Table 1 shows $^1$H NMR and MS/FAB of these compounds are shown in Table 1.

Synthesis methods for other compounds than the compounds shown in Table 1 may be understood by one of ordinary skill in the art by referring to the synthesis paths and source materials described above.

TABLE 1

| Compound | $^1$H NMR (CDCl$_3$ 400 MHz) δ | MS/FAB found | MS/FAB calc. |
|---|---|---|---|
| 5 | δ = 9.23 (d, 1H), 8.87 (d, 1H), 8.69-8.65 (m, 2H), 8.36-8.34 (m, 1H), 8.22 (d, 1H), 7.92-7.76 (m, 7H), 7.70-7.64 (m, 3H), 7.60-7.45 (m, 4H), 7.36 (t, 1H), 7.12-7.08 (m, 1H), 1.65 (s, 6H) | 572.22 | 572.23 |
| 7 | δ = 9.22 (d, 1H), 8.86 (d, 1H), 8.69-8.66 (m, 2H), 8.57-8.55 (m, 1H), 8.23-8.21 (m, 2H), 8.08 (d, 1H), 8.03 (d, 1H), 7.92-7.76 (m, 7H), 7.70-7.48 (m, 8H), 7.41 (t, 1H), 7.32-7.28 (m, 1H), 7.13-7.09 (m, 1H) | 621.23 | 621.22 |
| 12 | δ = 9.23-9.19 (m, 1H), 8.83 (t, 2H), 8.69-8.63 (m, 4H), 8.33 (s, 1H), 8.06-7.90 (m, 7H), 7.86-7.48 (m, 15H), 7.09 (t, 1H) | 697.23 | 697.24 |
| 19 | δ = 9.22-9.20 (m, 1H), 8.82, 8.73-8.65 (m, 4H), 8.18 (d, 1H), 7.98-7.96 (m, 2H), 7.86-7.79 (m, 6H), 7.72-7.44 (m, 10H), 7.40-7.27 (m, 5H), 7.09 (t, 1H), 6.96 (t, 1H) | 657.26 | 657.25 |
| 30 | δ = 9.27 (d, 1H), 8.86 (d, 1H), 8.70 (d, 1H), 8.67 (d, 1H), 8.28 (s, 1H), 8.20-8.18 (m, 2H), 8.06-8.02 (m, 2H), 7.95-7.79 (m, 5H), 7.74-7.45 (m, 8H), 7.23 (t, 1H), 7.07 (t, 1H), 1.66 (s, 6H) | 622.25 | 622.24 |
| 47 | δ = 9.29-9.26 (m, 1H), 8.82-8.76 (m, 2H), 8.70-8.64 (m, 3H), 8.23, 8.16-8.03 (m, 5H), 7.94 (d, 1H), 7.89-7.79 (m, 6H), 7.70-7.45 (m, 8H), 7.42 (t, 1H), 7.32-7.28 (m, 1H), 7.13 (t, 1H) | 671.23 | 671.24 |
| 56 | δ = 9.31-9.28 (m, 1H), 9.01 (d, 1H), 8.89-8.76 (m, 5H), 8.60-8.56 (m, 2H), 8.39 (s, 1H), 7.96-7.87 (m, 6H), 7.83-7.78 (m, 3H), 7.72-7.48 (m, 6H), 7.37 (t, 1H) | 622.19 | 622.20 |
| 67 | δ = 9.52-9.50 (m, 1H), 9.23-9.21 (m, 1H), 8.94 (d, 2H), 8.81 (d, 1H), 8.69-8.65 (m, 4H), 8.46 (d, 1H), 8.38-8.35 (m, 2H), 8.06-8.00 (m, 3H), 7.95-7.79 (m, 8H), 7.54-7.46 (m, 3H) | 586.21 | 586.22 |
| 79 | δ = 9.53-9.51 (m, 1H), 9.18 (d, 1H), 8.80-8.70 (m, 3H), 8.46 (d, 1H), 8.27 (d, 1H), 8.23 (d, 1H), 8.08 (d, 1H), 8.04-7.94 (m, 3H), 7.86-7.76 (m, 5H), 7.70-7.48 (m, 8H), 7.41 (t, 1H), 7.31-7.28 (m, 1H), 7.16 (t, 1H) | 672.22 | 672.23 |
| 88 | δ = 9.55 (d, 1H), 9.37-8.34 (m, 1H), 8.92 (d, 1H), 8.85-8.76 (m, 3H), 8.67-8.63 (m, 2H), 8.39 (d, 1H), 8.29 (dd, 1H), 8.19 (d, 1H), 8.01-7.76 (m, 11H), 7.72-7.48 (m, 6H) | 672.20 | 672.22 |
| 89 | δ = 9.23-9.16 (m, 2H), 8.74-8.66 (m, 3H), 7.95-7.93 (m, 1H), 7.85-7.81 (m, 5H), 7.69-7.61 (m, 7H), 7.55-7.47 (m, 3H), 7.45-7.39 (m, 4H), 7.12-7.07 (m, 1H) | 555.19 | 555.18 |
| 91 | δ = 9.23-9.21 (m, 1H), 8.71-8.65 (m, 2H), 8.52-8.50 (m, 1H), 8.37-8.36 (m, 1H), 8.13-8.11 (m, 1H), 7.98-7.97 (m, 2H), 7.87-7.81 (m, 4H), 7.68-7.61 (m, 8H), 7.57-7.48 (m, 5H), 7.44-7.41 (m, 4H), 7.12-7.08 (m, 1H) | 631.22 | 631.21 |
| 103 | δ = 9.29-9.24 (m, 2H), 8.96-8.94 (m, 1H), 8.78-8.71 (m, 2H), 8.67-8.66 (m, 1H), 8.01-8.00 (m, 2H), 7.85-7.81 (m, 2H), 7.74-7.72 (m, 4H), 7.68-7.66 (m, 2H), 7.63-7.53 (m, 5H), 7.51-7.49 (m, 1H), 7.41-7.39 (m, 4H), 7.08-7.06 (m, 1H) | 605.18 | 605.19 |
| 119 | δ = 9.76-9.74 (m, 1H), 9.26-9.22 (m, 2H), 8.85-8.68 (m, 4H), 8.06-8.01 (m, 2H), 7.96-7.93 (m, 3H), 7.80-7.63 (m, 12H), 7.54-7.52 (m, 2H), 7.44-7.42 (m, 4H) | 671.18 | 671.19 |
| 129 | δ = 8.84-8.83 (m, 2H), 8.71-8.61 (m, 4H), 8.00-7.99 (m, 2H), 7.84-7.74 (m, 3H), 7.70-7.68 (m, 5H), 7.64-7.62 (m, 4H), 7.49-7.42 (m, 5H) | 555.19 | 555.18 |
| 134 | δ = 8.84-8.83 (m, 2H), 8.71-8.62 (m, 3H), 8.20-8.18 (m, 2H), 8.04-8.00 (m, 3H), 7.83-7.68 (m, 4H), 7.64-7.62 (m, 8H), 7.54-7.45 (m, 6H), 7.39-7.37 (m, 4H), 7.19-7.16 (m, 2H) | 731.23 | 731.24 |
| 138 | δ = 8.93-8.85 (m, 4H), 8.73-8.71 (m, 1H), 8.59-8.55 (m, 2H), 8.01-7.92 (m, 4H), 7.79-7.72 (m, 10H), 7.64-7.63 (m, 2H), 7.53-7.51 (m, 3H), 7.45-7.39 (m, 5H) | 682.21 | 682.22 |

TABLE 1-continued

| Compound | $^1$H NMR (CDCl$_3$ 400 MHz) δ | MS/FAB found | calc. |
|---|---|---|---|
| 143 | δ = 8.92-8.90(m, 2H), 8.85-8.69(m, 5H), 8.02-8.00(m, 2H), 7.80-7.69(m, 8H), 7.65-7.63(m, 4H), 7.55-7.53(m, 3H), 7.40-7.38(m, 4H) | 605.18 | 605.19 |
| 146 | δ = 8.93-8.85(m, 4H), 8.79-8.77(m, 2H), 8.66-8.59(m, 2H), 8.40-8.39(m, 1H), 8.02-7.97(m, 3H), 7.83-7.80(m, 6H), 7.74-7.69(m, 2H), 7.64-7.63(m, 4H), 7.50-7.48(m, 3H), 7.41-7.39(m, 4H) | 682.21 | 682.22 |
| 153 | δ = 9.76-9.74(m, 1H), 9.26-9.22(m, 2H), 8.85-8.68(m, 4H), 8.06-8.01(m, 2H), 7.96-7.93(m, 3H), 7.80-7.63(m, 12H), 7.54-7.52(m, 2H), 7.44-7.42(m, 4H) | 685.23 | 685.22 |
| 154 | δ = 9.06-9.02(m, 2H), 8.94-8.79(m, 3H), 8.65-8.63(m, 1H), 8.39-8.38(m, 1H), 8.22-8.21(m, 1H), 8.02-7.93(m, 3H), 7.80-7.74(m, 3H), 7.65-7.63(m, 9H), 7.57-7.56(m, 1H), 7.50-7.48(m, 3H), 7.44-7.41(m, 4H) | 682.21 | 682.22 |
| 168 | δ = 9.76-9.74(m, 2H), 9.26-9.25(m, 1H), 8.85-8.77(m, 3H), 8.70-8.69(m, 1H), 8.40-8.38(m, 1H), 8.15-8.14(m, 1H), 8.05-8.02(m, 4H), 7.89-7.80(m, 3H), 7.74-7.69(m, 2H), 7.65-7.55(m, 7H) | 623.18 | 623.17 |

Example 1

As a substrate and an anode, a Corning 150/cm$^2$ (1200 Å) ITO glass substrate was cut to a size of 50 mm×50 mm×0.7 mm, and then, sonicated with isopropyl alcohol and pure water, each for 5 minutes, and then, cleaned by exposure to ultraviolet light for 30 minutes, and then, to ozone. The resultant glass substrate was mounted on a vacuum deposition apparatus.

2-TNATA was vacuum-deposited on the ITO anode on the glass substrate to form a hole injection layer having a thickness of 600 Å, and then, 4,4'-bis[N-(1-naphthyl)-N-phenylamino]biphenyl (NPB) was vacuum-deposited on the hole injection layer to form a hole transport layer having a thickness of 300 Å.

9,10-di-naphthalene-2-yl-anthracene (ADN), which is a host, and 4,4'-bis[2-(4-(N,N-diphenylamino)phenyl)vinyl]biphenyl (DPAVBi), which is a dopant, were co-deposited at a weight ratio of 98 2 on the hole transport layer to form an emission layer having a thickness of 300 Å.

Compound 5 was deposited on the emission layer to form an electron transport layer having a thickness of 300 Å, LiF was deposited on the electron transport layer to form an electron injection layer having a thickness of 10 Å, and Al was vacuum-deposited on the electron injection layer to form a cathode having a thickness of 3,000 Å, thereby completing manufacture of an organic light-emitting device.

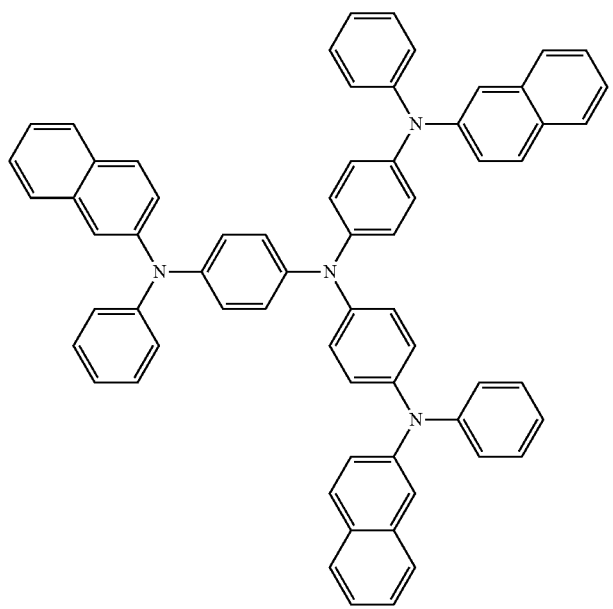

2-TNATA

-continued

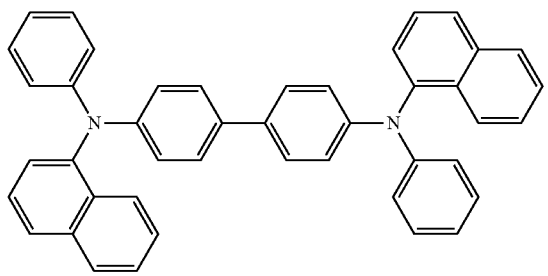

NPB

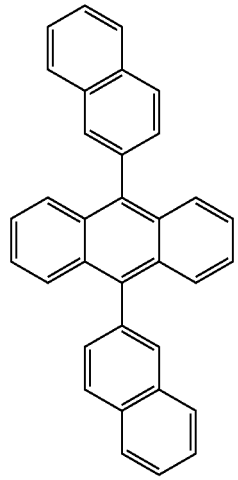

ADN

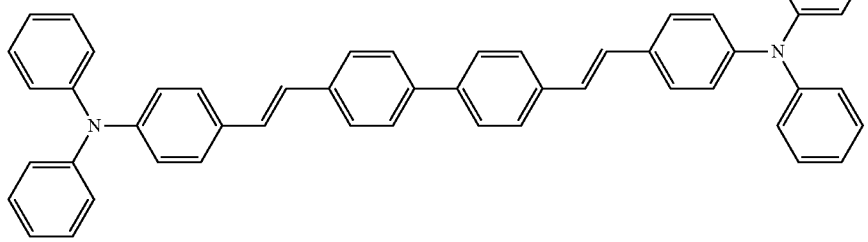

DPAVBi

Examples 2 to 22 and Comparative Examples 1 and 2

Organic light-emitting devices were manufactured in the same manner as in Example 1, except that, in forming the electron transport layer, compounds shown in Table 2 were used instead of Compound 1.

Evaluation Example 1

The driving voltage, current density, luminance, efficiency, emission color, and half lifespan of the organic light-emitting devices manufactured according to Examples 1 to 22 and Comparative Examples 1 and 2 were measured by using Keithley SMU 236 and luminance meter PR650. Results thereof are shown in Table 2.

TABLE 2

| | Material | Driving voltage (V) | Current density (mA/cm$^2$) | Luminance (cd/m$^2$) | Efficiency (cd/A) | Emission color | Half lifespan (hr @100 mA/cm$^2$) |
|---|---|---|---|---|---|---|---|
| Example 1 | Compound 5 | 3.60 | 50 | 3,425 | 7.20 | Blue | 618 |
| Example 2 | Compound 7 | 3.42 | 50 | 3,755 | 8.12 | Blue | 625 |
| Example 3 | Compound 12 | 3.54 | 50 | 3,500 | 7.53 | Blue | 656 |
| Example 4 | Compound 19 | 3.38 | 50 | 3,615 | 8.07 | Blue | 602 |
| Example 5 | Compound 30 | 3.47 | 50 | 3,830 | 8.27 | Blue | 635 |
| Example 6 | Compound 47 | 3.33 | 50 | 3,550 | 7.75 | Blue | 620 |
| Example 7 | Compound 56 | 3.46 | 50 | 3,745 | 8.03 | Blue | 635 |
| Example 8 | Compound 67 | 3.50 | 50 | 3,570 | 7.55 | Blue | 662 |
| Example 9 | Compound 79 | 3.47 | 50 | 3,600 | 8.10 | Blue | 627 |
| Example 10 | Compound 88 | 3.52 | 50 | 3,815 | 8.16 | Blue | 640 |
| Example 11 | Compound 89 | 3.60 | 50 | 3,425 | 6.85 | Blue | 618 |
| Example 12 | Compound 91 | 3.42 | 50 | 3,755 | 7.51 | Blue | 625 |
| Example 13 | Compound 103 | 3.54 | 50 | 3,500 | 7.00 | Blue | 656 |
| Example 14 | Compound 119 | 3.38 | 50 | 3,615 | 7.23 | Blue | 602 |
| Example 15 | Compound 129 | 3.47 | 50 | 3,830 | 7.66 | Blue | 635 |
| Example 16 | Compound 134 | 3.34 | 50 | 3,727 | 7.45 | Blue | 627 |
| Example 17 | Compound 138 | 3.41 | 50 | 3,750 | 7.50 | Blue | 637 |
| Example 18 | Compound 143 | 3.37 | 50 | 3,627 | 7.25 | Blue | 608 |
| Example 19 | Compound 146 | 3.52 | 50 | 3,635 | 7.27 | Blue | 650 |
| Example 20 | Compound 153 | 3.59 | 50 | 3,487 | 6.97 | Blue | 591 |

TABLE 2-continued
| | Material | Driving voltage (V) | Current density (mA/cm²) | Luminance (cd/m²) | Efficiency (cd/A) | Emission color | Half lifespan (hr @100 mA/cm²) |
|---|---|---|---|---|---|---|---|
| Example 21 | Compound 154 | 3.42 | 50 | 3,562 | 7.12 | Blue | 613 |
| Example 22 | Compound 168 | 3.48 | 50 | 3,612 | 7.22 | Blue | 647 |
| Comparative Example 1 | Compound A | 5.06 | 50 | 3,010 | 6.52 | Blue | 325 |
| Comparative Example 2 | Compound B | 4.88 | 50 | 2,948 | 5.89 | Blue | 411 |
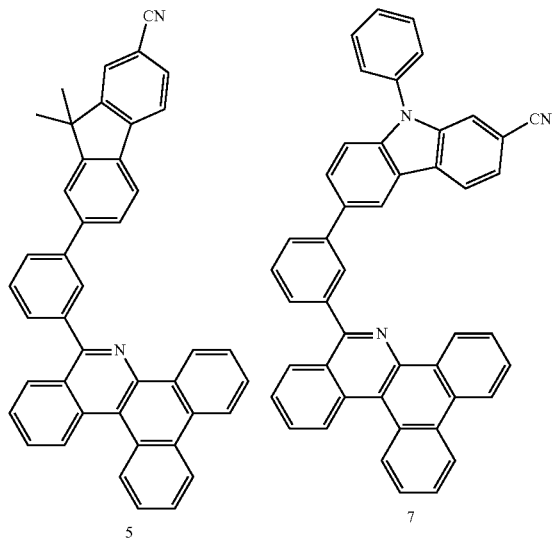
5
7
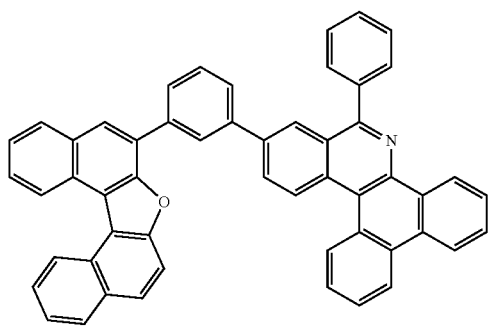
12
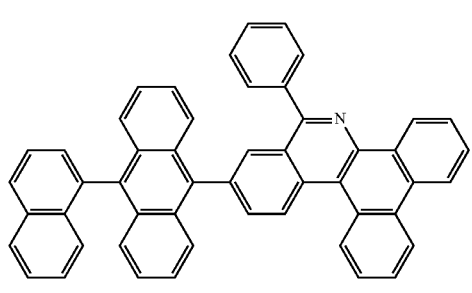
19

TABLE 2-continued
| Material | Driving voltage (V) | Current density (mA/cm$^2$) | Luminance (cd/m$^2$) | Efficiency (cd/A) | Emission color | Half lifespan (hr @100 mA/cm$^2$) |
| --- | --- | --- | --- | --- | --- | --- |
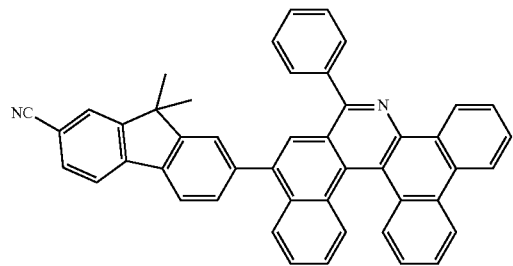
30
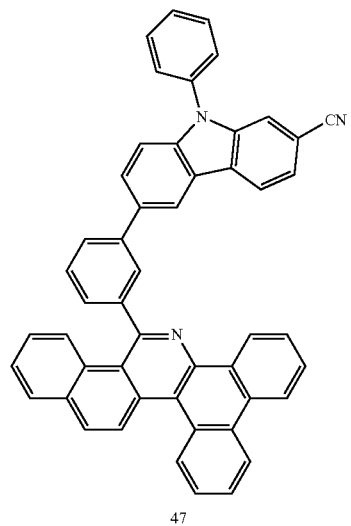 [SMILES: N#Cc1ccc2c3cc(-c4cccc(-c5nc6c7ccccc7c7ccccc7c6c6ccc7ccccc7c56)c4)ccc3n(-c3ccccc3)c2c1]
47
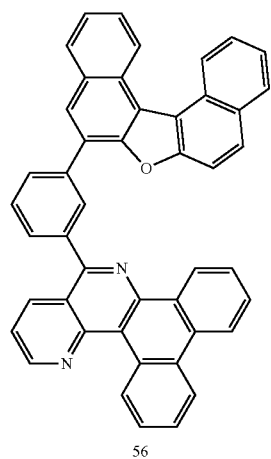 [SMILES: c1cc(-c2nc3c4ccccc4c4ccccc4c3c3ncccc23)cc(-c2cc3ccccc3c3c2oc2ccc4ccccc4c23)c1]
56

TABLE 2-continued
| Material | Driving voltage (V) | Current density (mA/cm$^2$) | Luminance (cd/m$^2$) | Efficiency (cd/A) | Emission color | Half lifespan (hr @100 mA/cm$^2$) |
| --- | --- | --- | --- | --- | --- | --- |
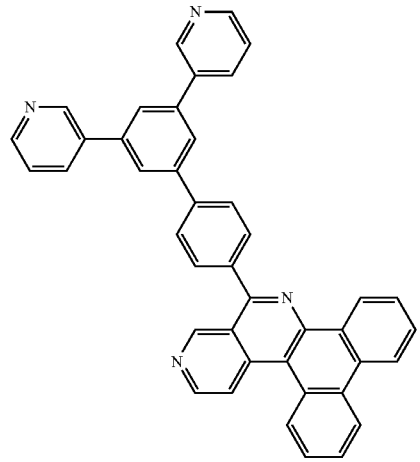
67
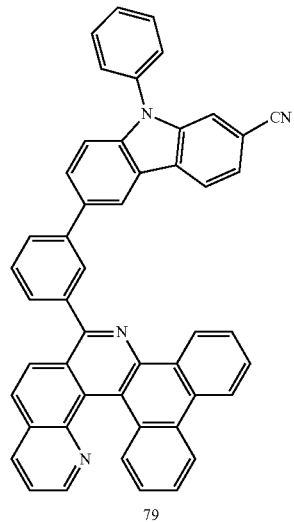 [SMILES: N#Cc1ccc2c3cc(-c4cccc(-c5nc6c7ccccc7c7ccccc7c6c6c5ccc5cccnc56)c4)ccc3n(-c3ccccc3)c2c1]
79
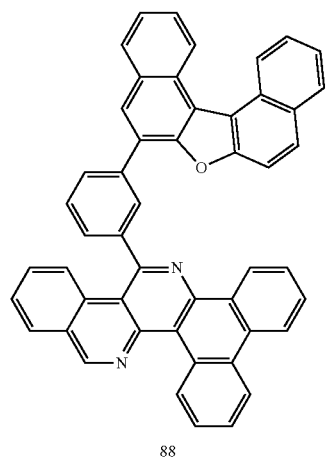 [SMILES: c1cc(-c2cc3ccccc3c3c2oc2ccc4ccccc4c23)cc(-c2nc3c4ccccc4c4ccccc4c3c3ncc4ccccc4c23)c1]
88

TABLE 2-continued

| Material | Driving voltage (V) | Current density (mA/cm²) | Luminance (cd/m²) | Efficiency (cd/A) | Emission color | Half lifespan (hr @100 mA/cm²) |
|---|---|---|---|---|---|---|
| 89 | | | | | | |
| 91 | | | | | | |
| 103 | | | | | | |
| 119 | | | | | | |
| 129 | | | | | | |

TABLE 2-continued
| Material | Driving voltage (V) | Current density (mA/cm²) | Luminance (cd/m²) | Efficiency (cd/A) | Emission color | Half lifespan (hr @100 mA/cm²) |
|---|---|---|---|---|---|---|
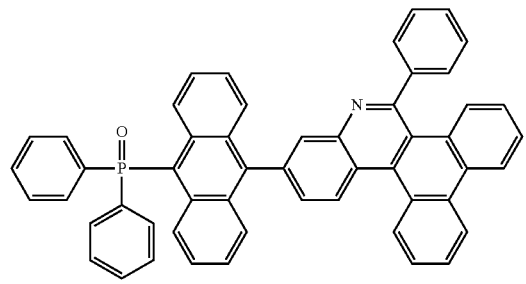
134
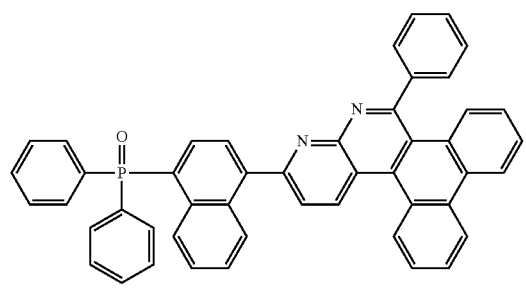
138
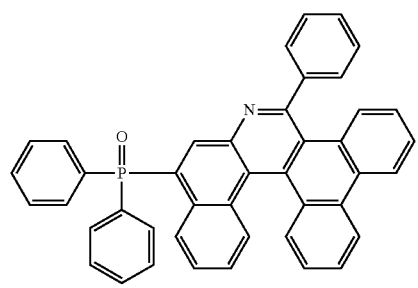
143
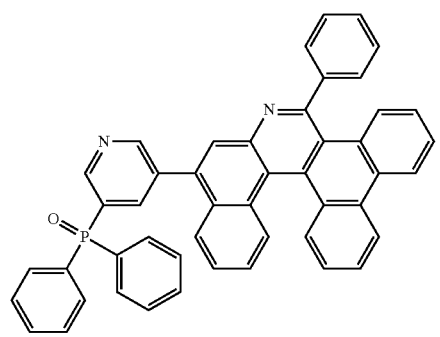
146

TABLE 2-continued
| Material | Driving voltage (V) | Current density (mA/cm$^2$) | Luminance (cd/m$^2$) | Efficiency (cd/A) | Emission color | Half lifespan (hr @100 mA/cm$^2$) |
|---|---|---|---|---|---|---|
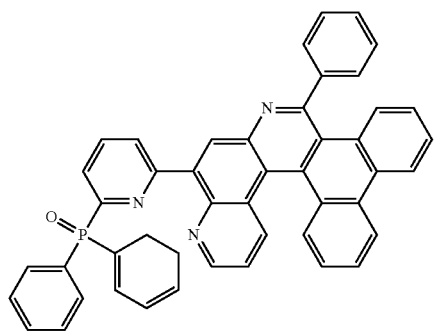
153
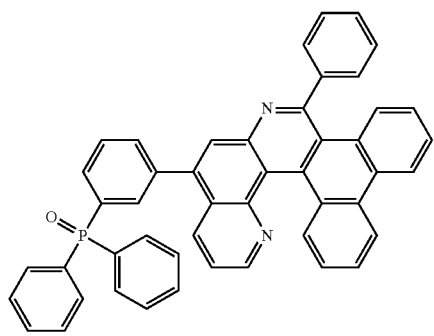
154
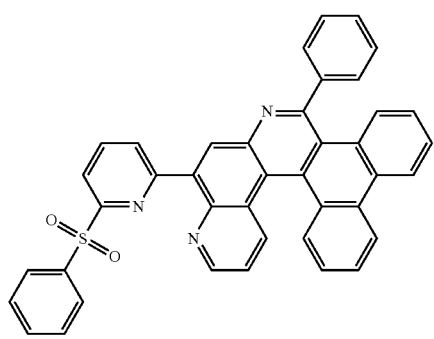
168
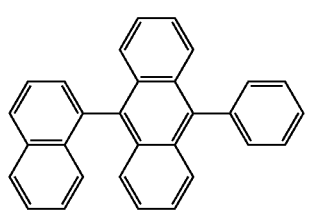
A
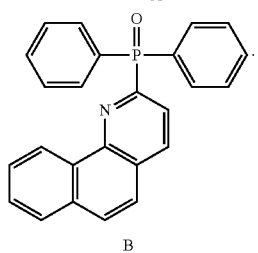
B Referring to Table 2, it was confirmed that the organic light-emitting devices of Examples 1 to 22 had better characteristics than those of Comparative Examples 1 and 2, in terms of a driving voltage, luminance, efficiency, and a half lifespan.

An organic light-emitting device including the condensed cyclic compound according to an embodiment may have a low driving voltage, high luminance, high efficiency, and a long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope as defined by the following claims.

What is claimed is:

1. A condensed cyclic compound represented by Formula 1:

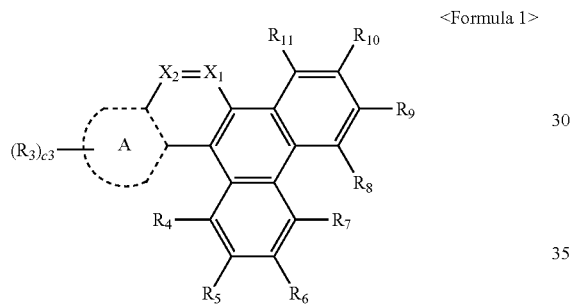

<Formula 1> wherein, in Formula 1,
ring A is selected from a benzene group, a pyridine group, a pyridazine group, a pyrimidine group, a pyrazine group, a naphthalene group, a quinoline group, an isoquinoline group, a cinnoline group, a quinazoline group, a quinoxaline group, naphthyridine group, an anthracene group, a phenanthrene group, a benzoquinoline group, a phenanthridine group, an acridine group, phenanthroline group, and a phenazine group,
$X_1$ is $C(R_1)$ and $X_2$ is N, or $X_1$ is N and $X_2$ is $C(R_2)$,
one of $R_1$ to $R_3$ is a group represented by Formula 2-5,
the remainder of $R_1$ to $R_3$ are each independently hydrogen, a substituted or unsubstituted $C_6$-$C_{60}$ aryl group, or a substituted or unsubstituted $C_1$-$C_{60}$ heteroaryl group,
$R_4$ to $R_{11}$ are each independently hydrogen or deuterium,

*-(L$_{11}$)$_{a11}$-Ar$_7$  <Formula 2-5>

$L_{11}$ is selected from a substituted or unsubstituted $C_6$-$C_{60}$ arylene group and a substituted or unsubstituted $C_1$-$C_{60}$ heteroarylene group,
a11 is 0, 1, or 2,
$Ar_7$ is selected from groups represented by Formulae 6-17 and 6-18 in case that A is a benzene group, and
$Ar_7$ is selected from groups represented by Formulae 6-12, 6-14, 6-15, 6-17, and 6-18 in case that A is selected from a pyridine group, a pyridazine group, a pyrimidine group, a pyrazine group, a naphthalene group, a quinoline group, an isoquinoline group, a cinnoline group, a quinazoline group, a quinoxaline group, naphthyridine group, an anthracene group, a phenanthrene group, a benzoquinoline group, a phenanthridine group, an acridine group, phenanthroline group, and a phenazine group:

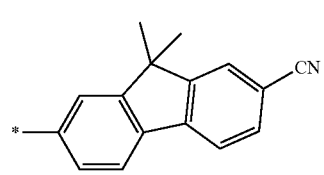

Formula 6-12

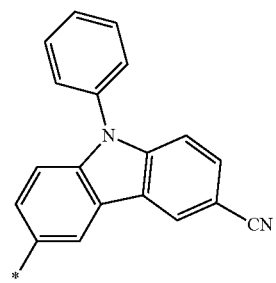

Formula 6-14

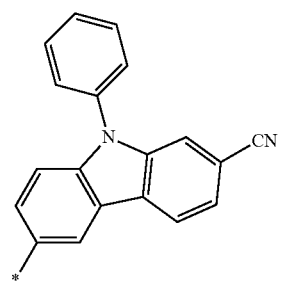

Formula 6-15

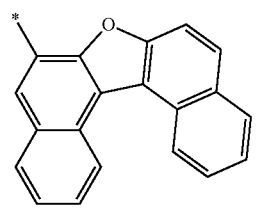

Formula 6-17

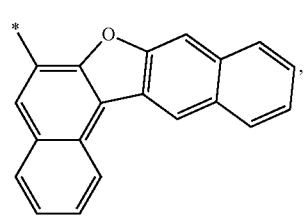

Formula 6-18 wherein, in Formulae 6-12, 6-14, 6-15, 6-17, and 6-18, * indicates a binding site to a neighboring atom,
c3 is 1, 2, 3, 4, 5, or 6,
at least one of substituents of the substituted $C_6$-$C_{60}$ arylene group, the substituted $C_1$-$C_{60}$ heteroarylene group, and the substituted $C_6$-$C_{60}$ aryl group is selected from
deuterium (-D), a cyano group, a $C_6$-$C_{60}$ aryl group, and a $C_1$-$C_{60}$ heteroaryl group, and
* indicates a binding site to a neighboring atom.

2. The condensed cyclic compound of claim 1, wherein $L_{11}$ is selected from:
a phenylene group, a pentalenylene group, an indenylene group, a naphthylene group, an azulenylene group, a heptalenylene group, an indacenylene group, an acenaphthylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzosilolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzosilolylene group, a dibenzocarbazolylene group, a thiadiazolylene group, an imidazopyridinylene group, and an imidazopyrimidinylene group, each substituted with at least one selected from deuterium, a cyano group, a phenyl group, a biphenyl group, a terphenyl group, a pentalenyl group, an indenyl group, a naphthyl group, an azulenyl group, a heptalenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, and an imidazopyridinyl group.

3. The condensed cyclic compound of claim 1, wherein $L_{11}$ is selected from groups represented by Formulae 3-1 to 3-16 and 3-19 to 3-25:

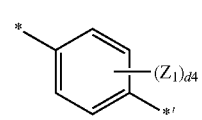

Formula 3-1

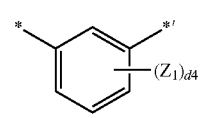

Formula 3-2

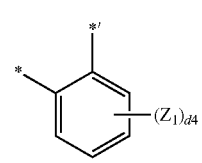

Formula 3-3

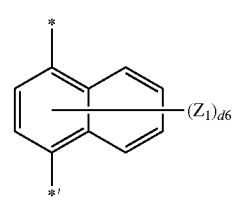

Formula 3-4

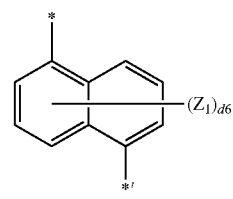

Formula 3-5

209
-continued
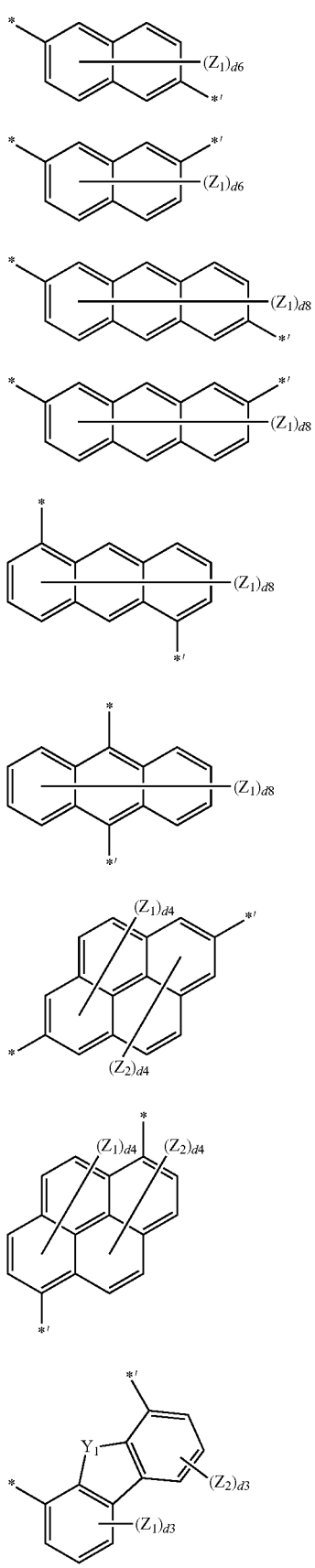
210
-continued
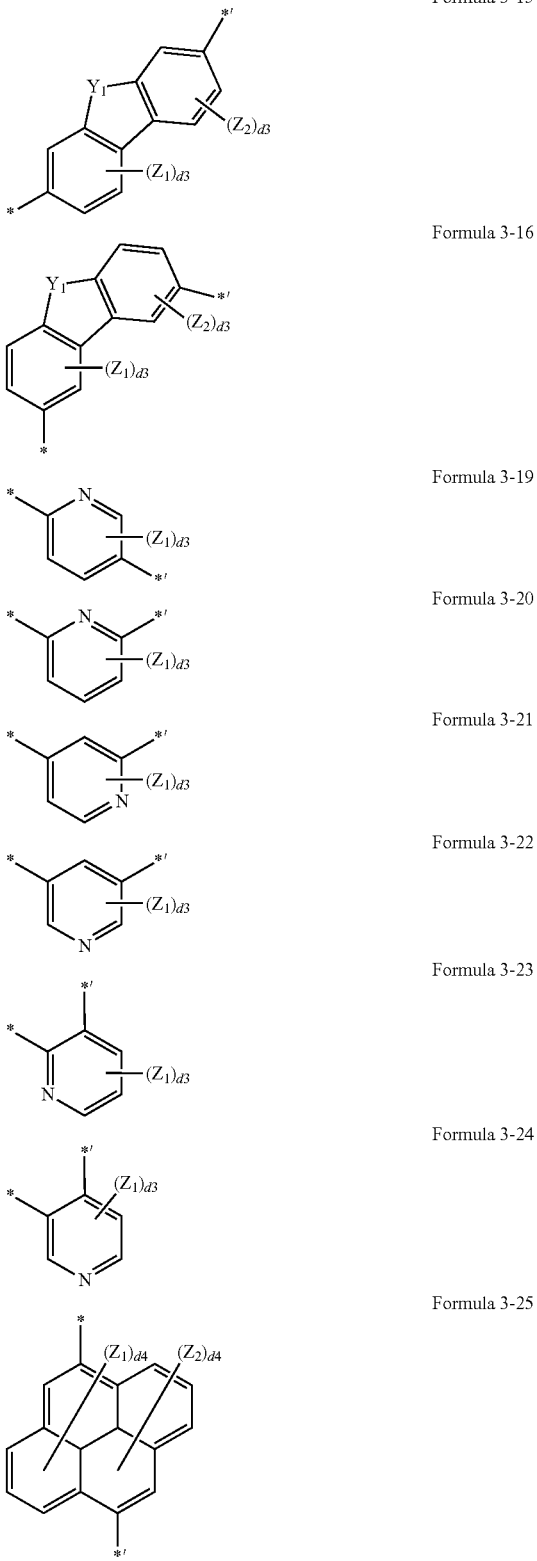
wherein, in Formulae 3-1 to 3-16 and 3-19 to 3-25,
Y is O, S, or $N(Z_7)$,
$Z_1$ to $Z_4$ and $Z_7$ hydrogen, deuterium, a cyano group, a phenyl group, a biphenyl group, a terphenyl group, a naphthyl group, a phenanthrenyl group, an anthracenyl group, a triphenylenyl group, a pyrenyl group, a chrysenyl group, a carbazolyl group, a benzocarbazolyl group, a dibenzocarbazolyl group, a pyridinyl group, a pyrazinyl group, a pyrimidinyl group, a pyridazinyl group, and a triazinyl group, d3 is an integer from 1 to 3, d4 is an integer from 1 to 4, d6 is an integer from 1 to 6, d8 is an integer from 1 to 8, and

* and *' each indicate a binding site to a neighboring atom.

4. The condensed cyclic compound of claim 1, wherein $L_{11}$ is selected from groups represented by Formulae 4-1 to 4-16:

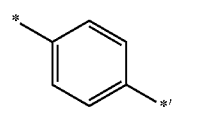
Formula 4-1

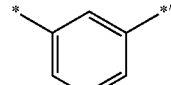
Formula 4-2

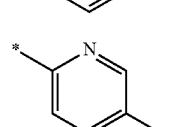
Formula 4-3

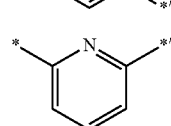
Formula 4-4

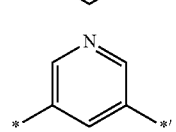
Formula 4-5

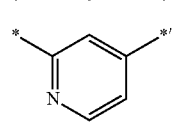
Formula 4-6

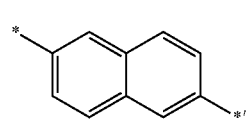
Formula 4-7

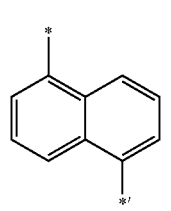
Formula 4-8

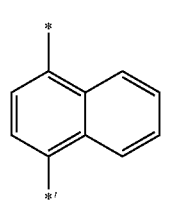
Formula 4-9

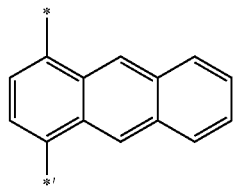
Formula 4-10

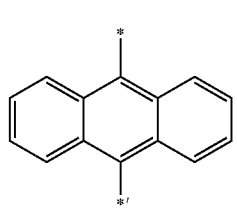
Formula 4-11

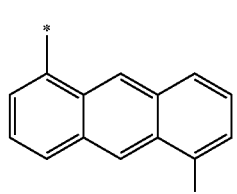
Formula 4-12

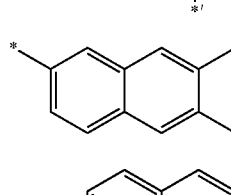
Formula 4-13

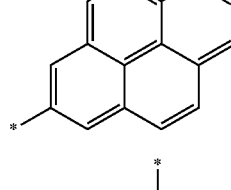
Formula 4-14

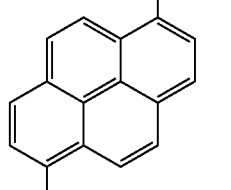
Formula 4-15

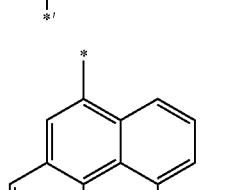
Formula 4-16 wherein, in Formulae 4-1 to 4-16, * and *' each indicate a binding site to a neighboring atom.

5. The condensed cyclic compound of claim 1, wherein $R_1$ to $R_3$ are each independently selected from:

a group represented by Formula 2-5;

a phenyl group, a biphenyl group, a terphenyl group, a naphthyl group, a phenanthrenyl group, an anthracenyl group, a triphenylenyl group, a pyrenyl group, a chrysenyl group; or a phenyl group, a biphenyl group, a terphenyl group, a naphthyl group, a phenanthrenyl group, an anthracenyl group, and a triphenylenyl group, each substituted with at least one selected from deuterium, a cyano group, a phenyl group, a biphenyl group, a terphenyl group, a naphthyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group.

6. The condensed cyclic compound of claim 1, wherein $R_1$ to $R_3$ are each independently selected from:

a group represented by Formula 2-5, a phenyl group, a biphenyl group, a terphenyl group, a naphthyl group, a phenanthrenyl group, an anthracenyl group, a triphenylenyl group, a pyrenyl group, a chrysenyl group, a carbazolyl group, a benzocarbazolyl group, and a dibenzocarbazolyl group.

7. The condensed cyclic compound of claim 1, wherein the condensed cyclic compound is represented by one of Formulae 1A to 1S:

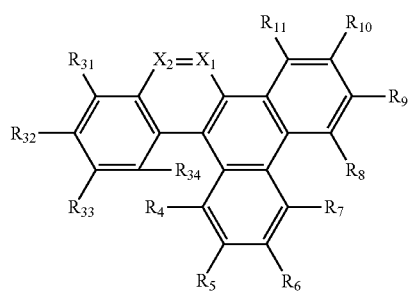

Formula 1A

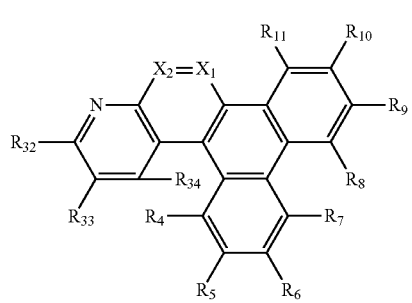

Formula 1B

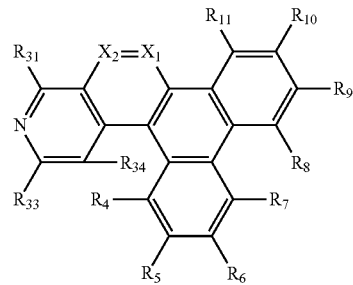

Formula 1C

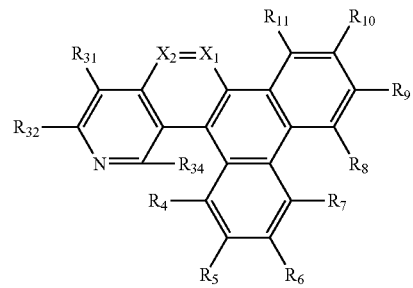

Formula 1D

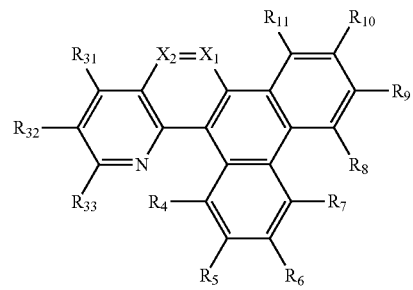

Formula 1E

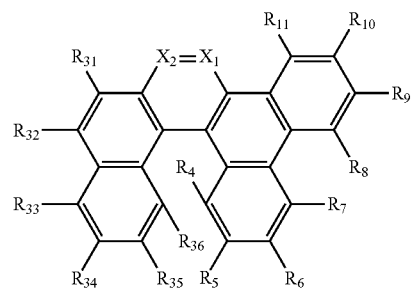

Formula 1F

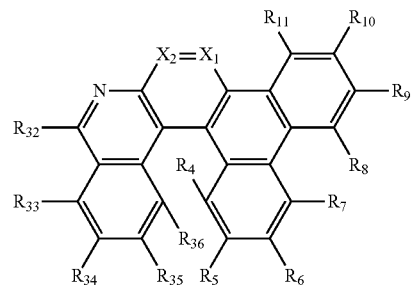

Formula 1G

Formula 1H
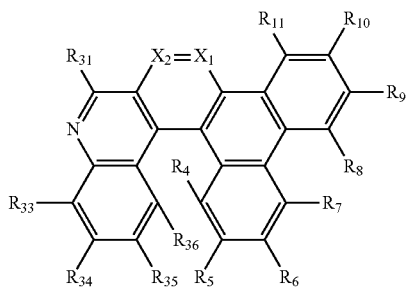
Formula 1M
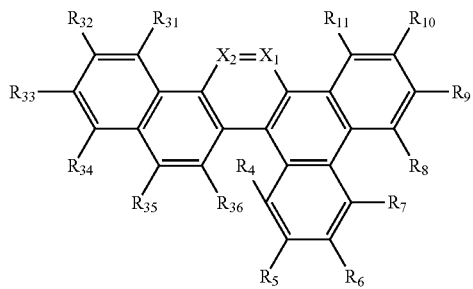
Formula 1I
Formula 1N
Formula 1J
Formula 1O
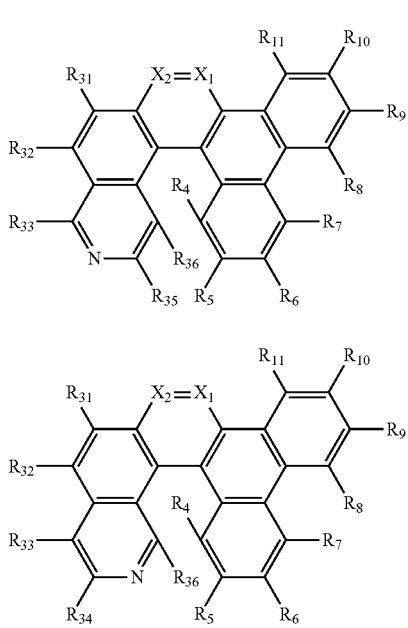
Formula 1K
Formula 1P
Formula 1L
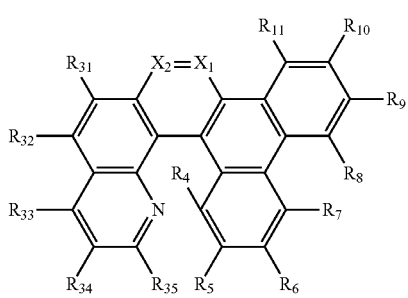
Formula 1Q -continued Formula 1R

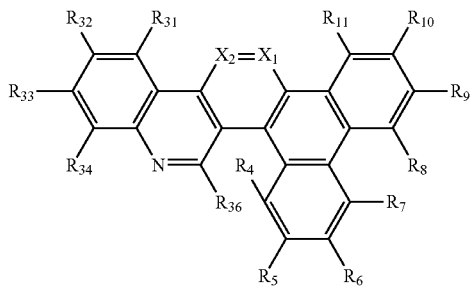

Formula 1S

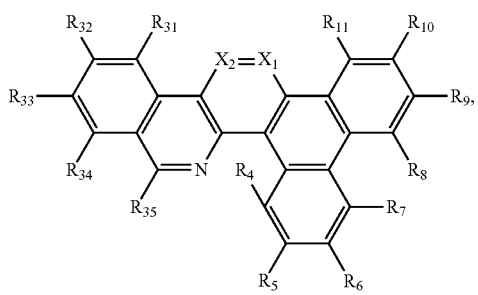

wherein, in Formulae 1A to 1S, $R_{31}$ to $R_{36}$ are the same as described in connection with $R_3$, $X_1$, $X_2$, and $R_4$ to $R_{11}$ are the same as described in in connection with Formula 1, and at least one of $R_{31}$ to $R_{36}$ are each independently a group represented by Formula 2-5.

8. The condensed cyclic compound of claim 7, wherein, in Formulae 1A to 1S, $X_1$ is N, and $X_2$ is $C(R_2)$, and $R_2$ is a group represented by Formula 2-5.

9. The condensed cyclic compound of claim 7, wherein, in Formulae 1A to 1S, $X_1$ is $C(R_1)$, $X_2$ is N, and $R_1$ is a group represented by Formula 2-5.

10. The condensed cyclic compound of claim 7, wherein, in Formulae 1A, 1B, 1D to 1G, 1I to 1N, and 1P to 1S, $X_1$ is N, $X_2$ is $C(R_2)$, and $R_{32}$ is a group represented by Formula 2-5.

11. The condensed cyclic compound of claim 7, wherein, in Formulae 1A, 1B, 1D to 1G, 1I to 1N, and 1P to 1S, $X_1$ is $C(R_1)$, $X_2$ is N, and $R_{32}$ is a group represented by Formula 2-5.

12. An organic light-emitting device comprising:

a first electrode;

a second electrode facing the first electrode; and an organic layer between the first electrode and the second electrode, the organic layer including an emission layer, wherein the organic layer is at least one condensed cyclic compound of Formula 1:

<Formula 1>

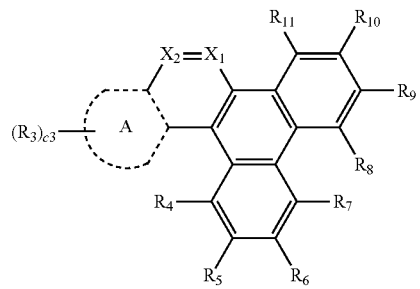

wherein, in Formula 1, ring A is selected from a benzene group, a pyridine group, a pyridazine group, a pyrimidine group, a pyrazine group, a naphthalene group, a quinoline group, an isoquinoline group, a cinnoline group, a quinazoline group, a quinoxaline group, naphthyridine group, an anthracene group, a phenanthrene group, a benzoquinoline group, a phenanthridine group, an acridine group, phenanthroline group, and a phenazine group, $X_1$ is $C(R_1)$ and $X_2$ is N, or $X_1$ is N and $X_2$ is $C(R_2)$, one of $R_1$ to $R_3$ is a group represented by Formula 2-5, the remainder of $R_1$ to $R_3$ are each independently hydrogen, a substituted or unsubstituted $C_6$-$C_{60}$ aryl group, or a substituted or unsubstituted $C_1$-$C_{60}$ heteroaryl group, $R_4$ to $R_{11}$ are each independently hydrogen or deuterium,

*$(L_{11})_{a11}$-$Ar_7$     <Formula 2-5>

$L_{11}$ is selected from a substituted or unsubstituted $C_6$-$C_{60}$ arylene group and a substituted or unsubstituted $C_1$-$C_{60}$ heteroarylene group, a11 is 0, 1, or 2, $Ar_7$ is selected from groups represented by Formulae 6-17 and 6-18 in case that A is a benzene group, and $Ar_7$ is selected from groups represented by Formulae 6-12, 6-14,6-15, 6-17, and 6-18 in case that A is selected from a pyridine group, a pyridazine group, a pyrimidine group, a pyrazine group, a naphthalene group, a quinoline group, an isoquinoline group, a cinnoline group, a quinazoline group, a quinoxaline group, naphthyridine group, an anthracene group, a phenanthrene group, a benzoquinoline group, a phenanthridine group, an acridine group, phenanthroline group, and a phenazine group:

Formula 6-12

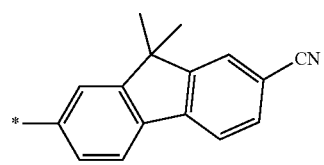

Formula 6-14

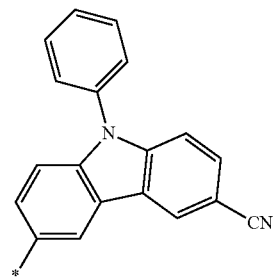

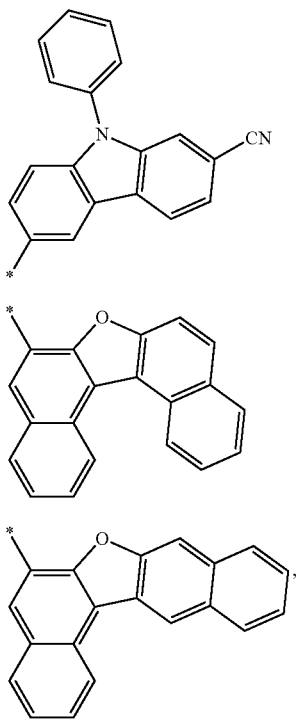

Formula 6-15

Formula 6-17

Formula 6-18

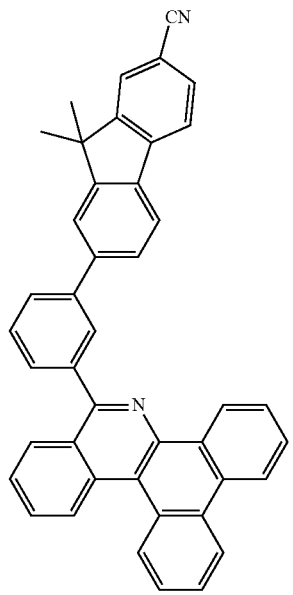

5 wherein, in Formulae 6-12, 6-14,6-15, 6-17, and 6-18, * indicates a binding site to a neighboring atom, c3 is 1, 2, 3, 4, 5, or 6, at least one of substituents of the substituted $C_6$-$C_{60}$ arylene group, the substituted $C_1$-$C_{60}$ heteroarylene group, and the substituted $C_6$-$C_{60}$ aryl group is selected from deuterium (-D), a cyano group, a $C_6$-$C_{60}$ aryl group, and a $C_1$-$C_{60}$ heteroaryl group, and

* indicates a binding site to a neighboring atom.

13. The organic light-emitting device of claim 12, wherein the first electrode is an anode,
the second electrode is a cathode,
the organic layer includes a hole transport region between the first electrode and the emission layer and an electron transport region between the emission layer and the second electrode,
the hole transport region includes at least one selected from a hole injection layer, a hole transport layer, an emission auxiliary layer, and an electron blocking layer, and
the electron transport region includes at least one selected from a buffer layer, a hole blocking layer, an electron control layer, an electron transport layer, and an electron injection layer.

14. The organic light-emitting device of claim 13, wherein the electron transport region includes an electron transport layer, and the electron transport layer includes the at least one condensed cyclic compound.

15. The organic light-emitting device of claim 13, wherein the electron transport region includes an electron injection layer, and the electron injection layer includes the at least one condensed cyclic compound.

16. A condensed cyclic compound selected from one of Compounds 5 to 14, 25 to 34, 45 to 48, 53 to 56, 61 to 64, 69 to 72, 77 to 80, and 85 to 88:

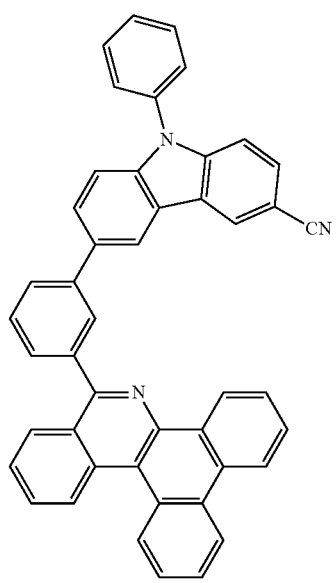

6

-continued
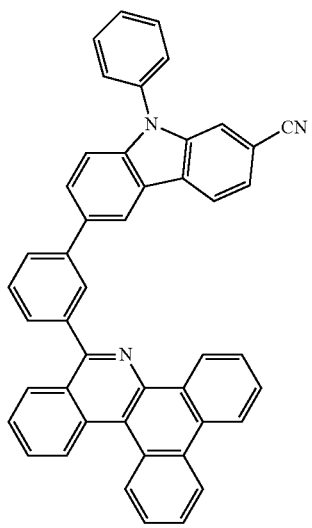
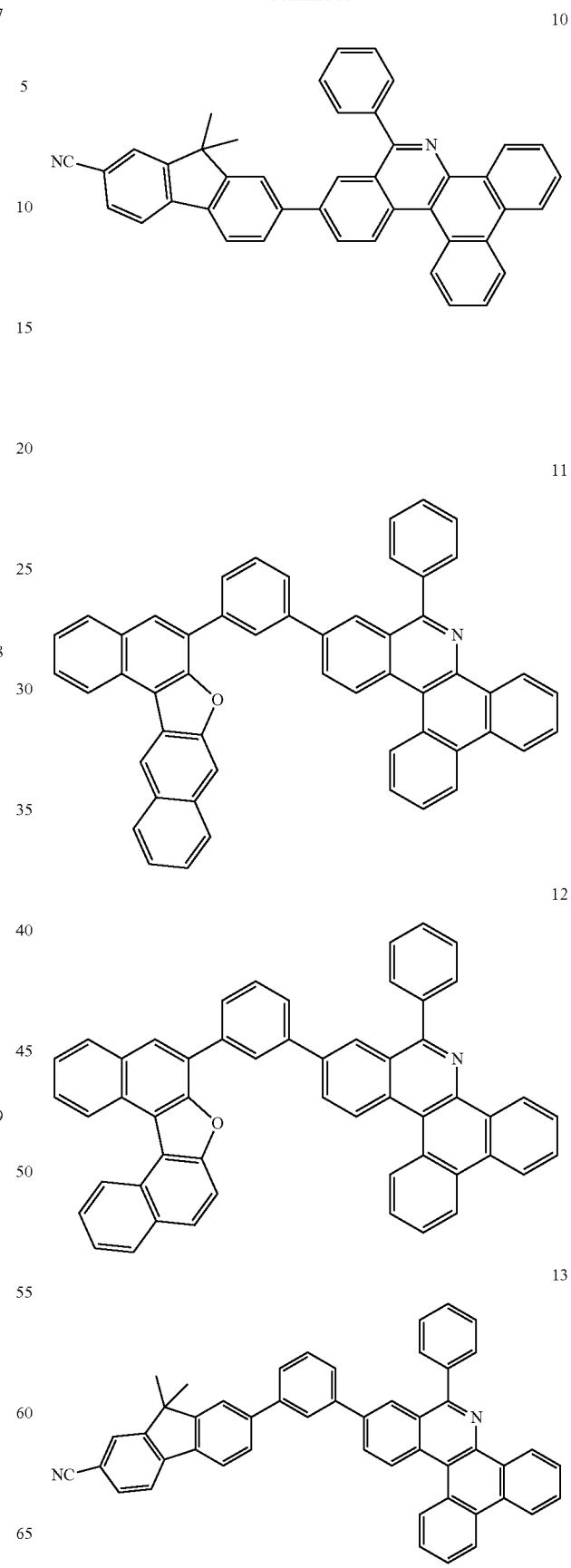

223
-continued
14
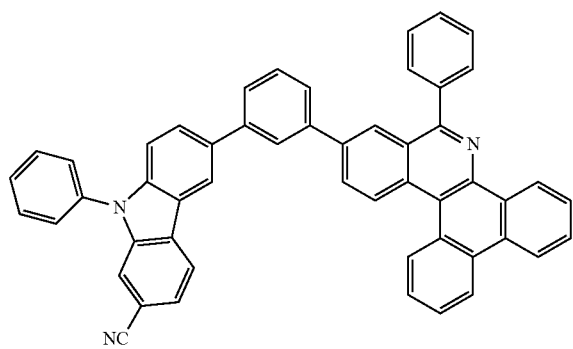
25
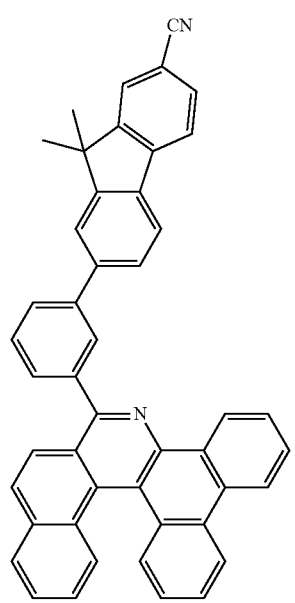
26
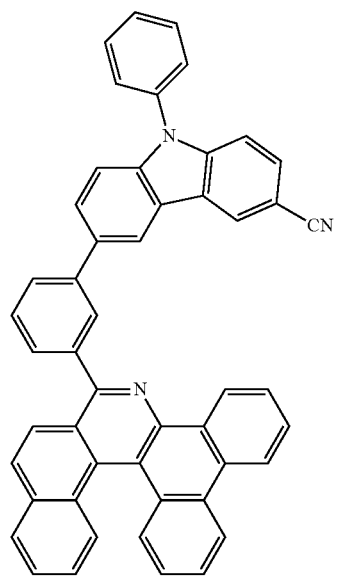
224
-continued
27
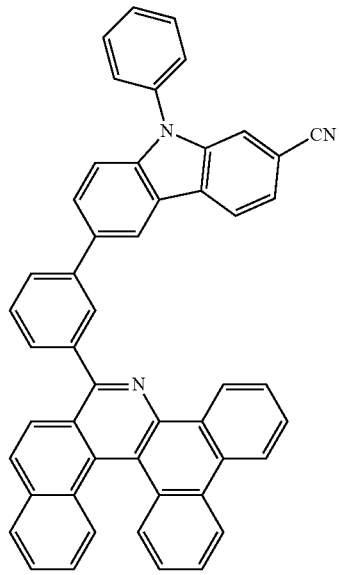
28
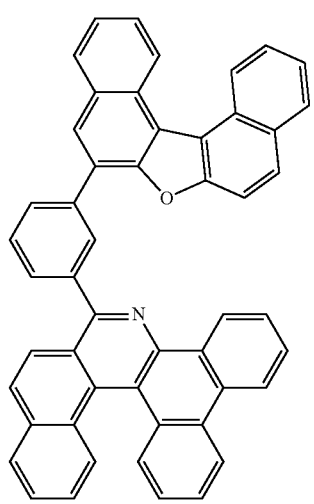
29
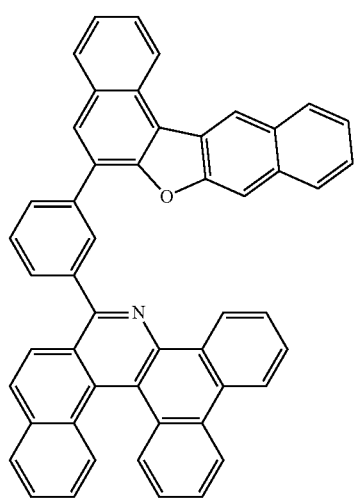

30
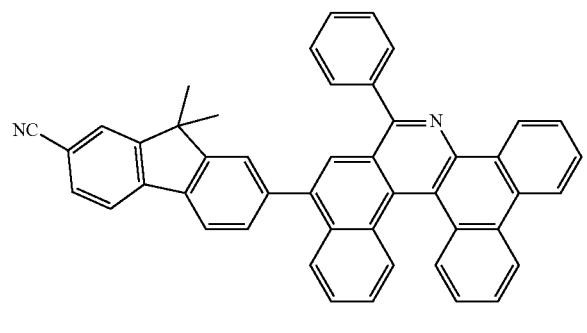
31
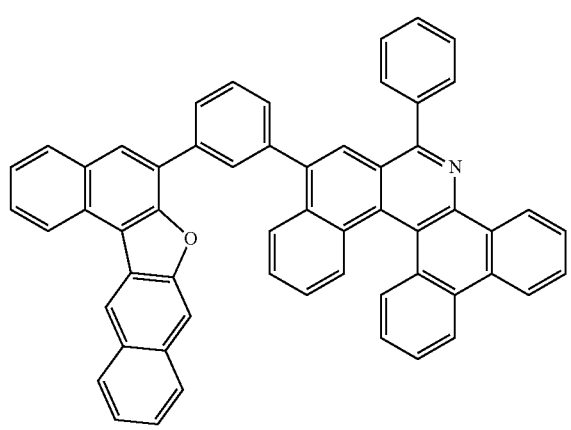
32
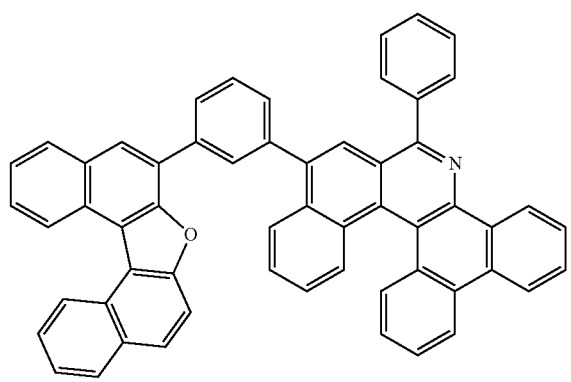
33
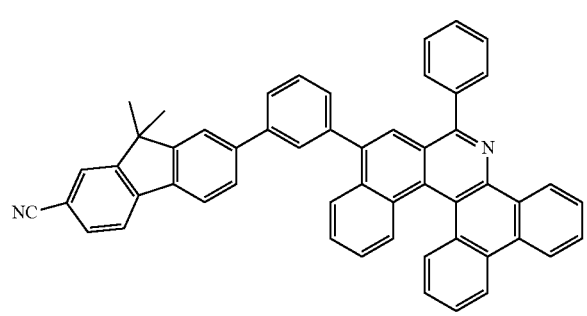
34
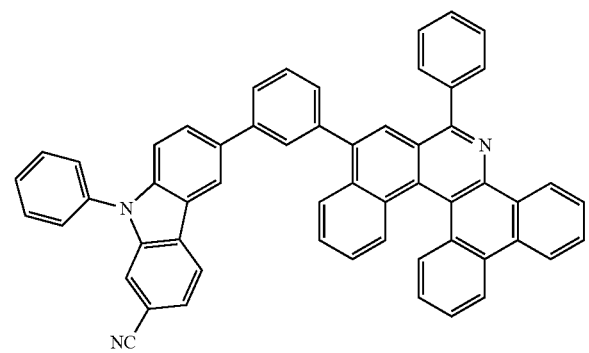
45
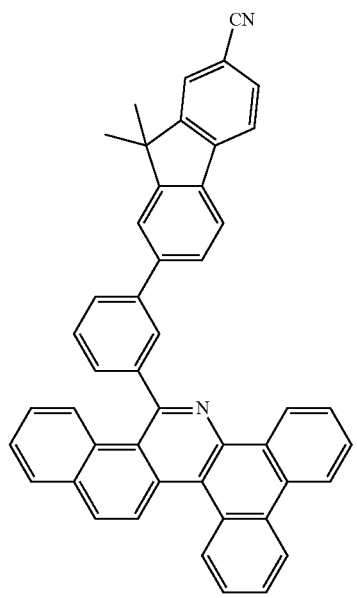
46
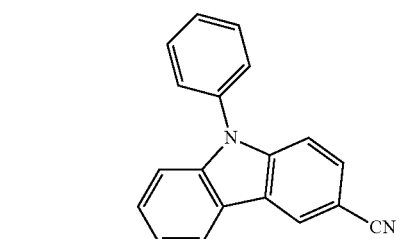
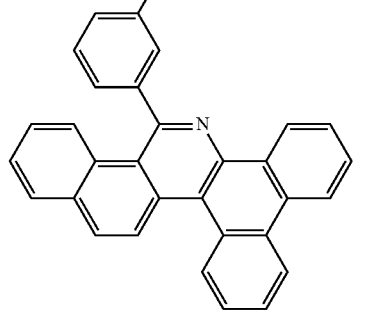

227
-continued
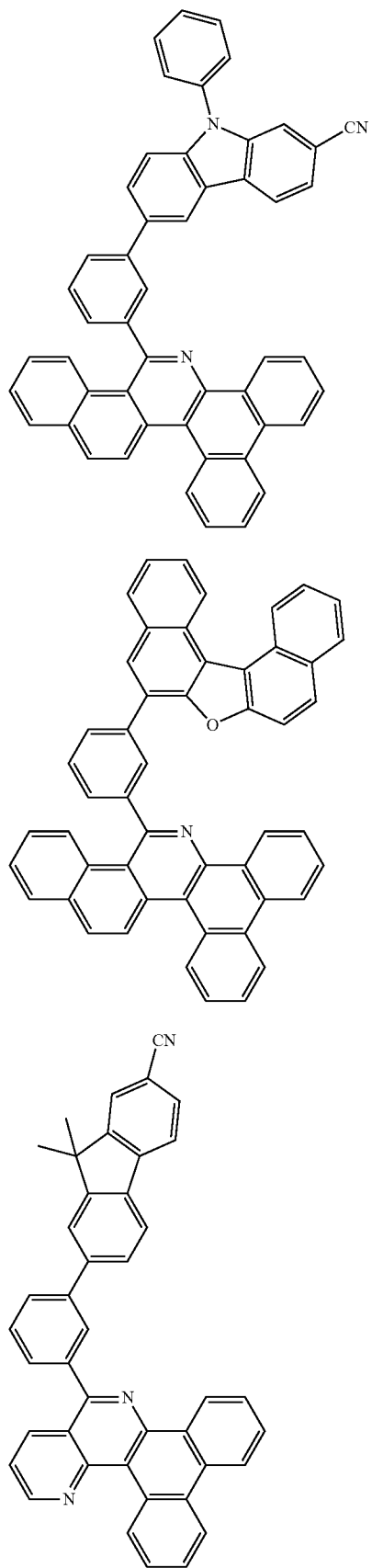
47
228
-continued
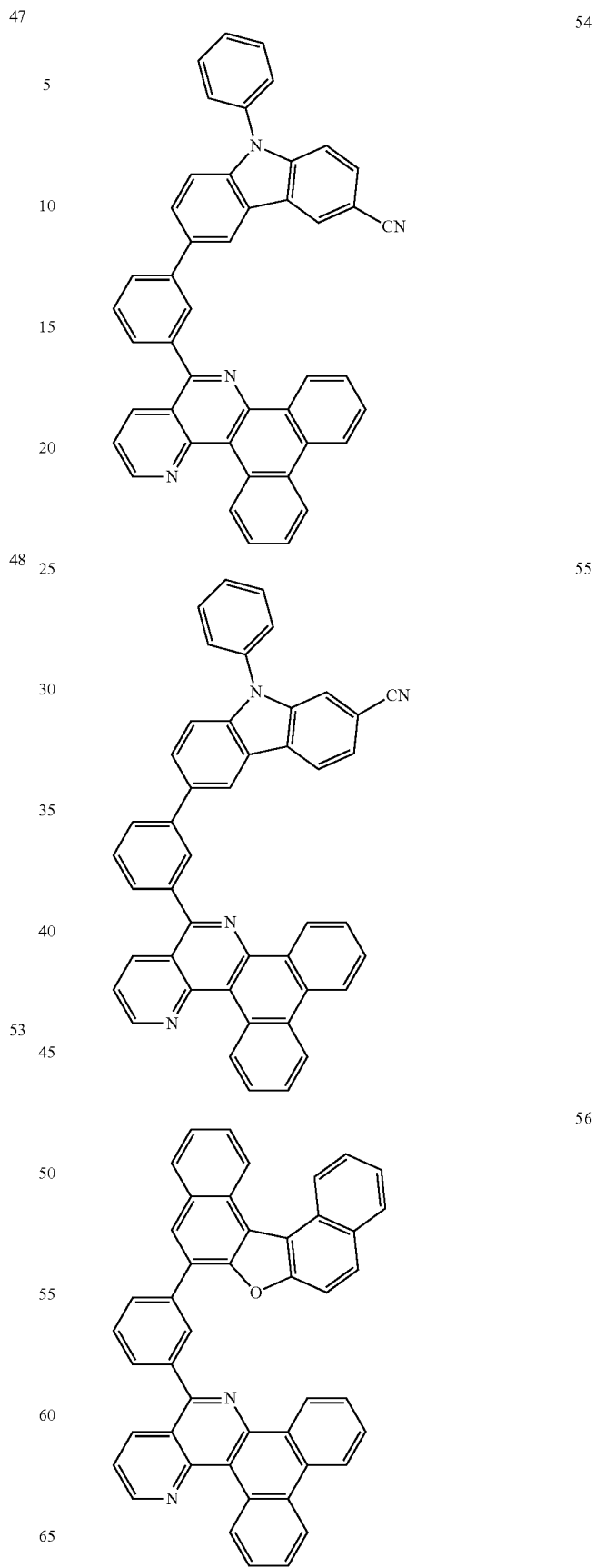

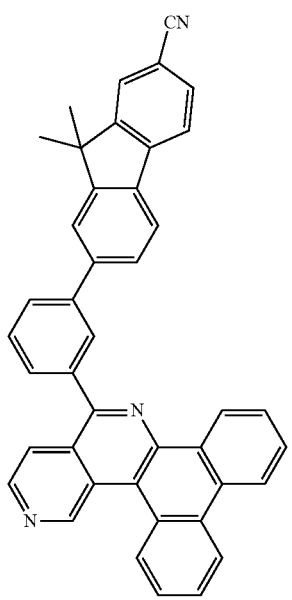
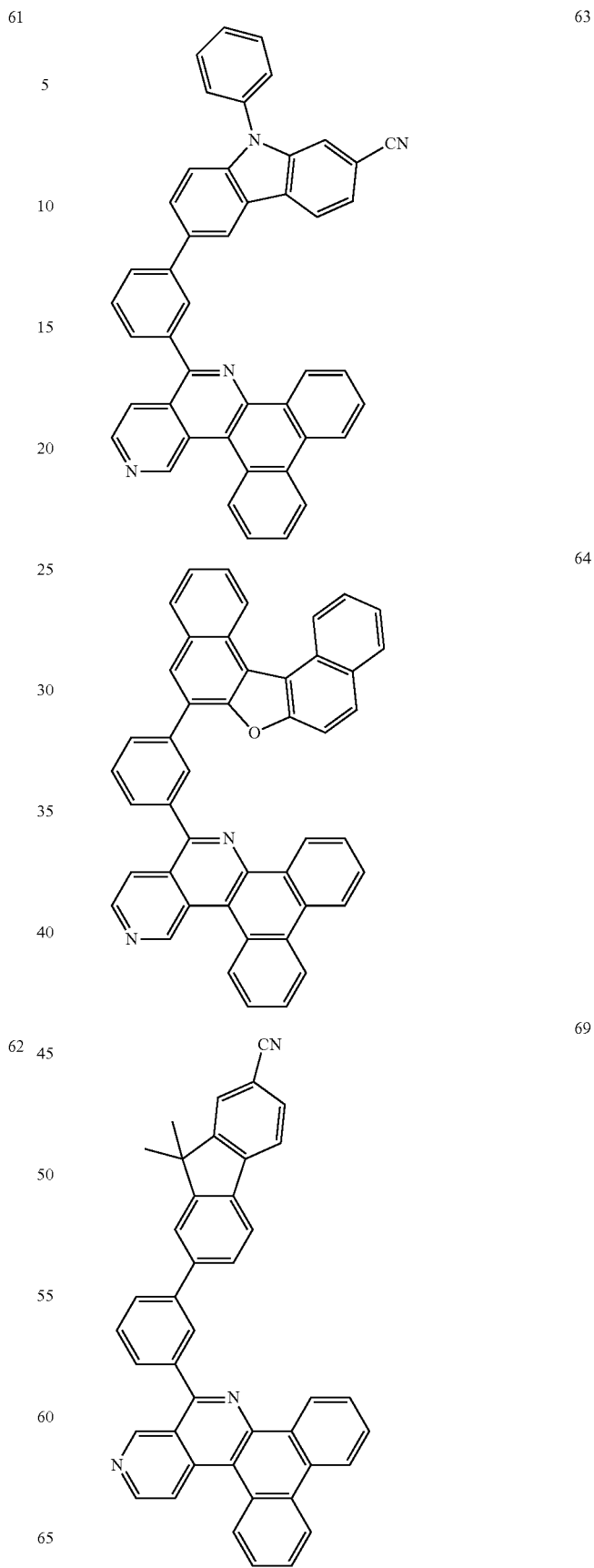

231
-continued
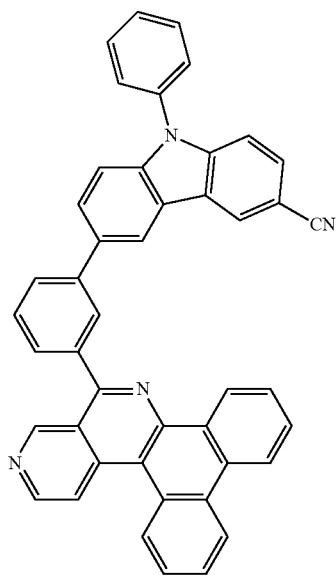
70
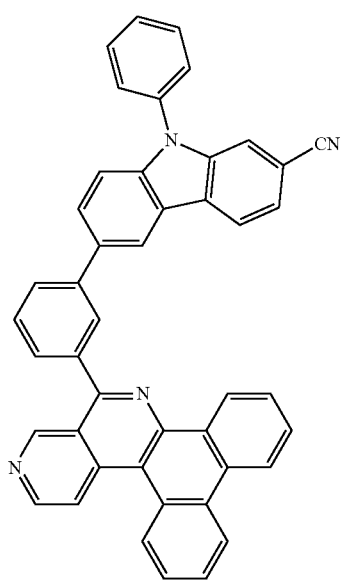
71
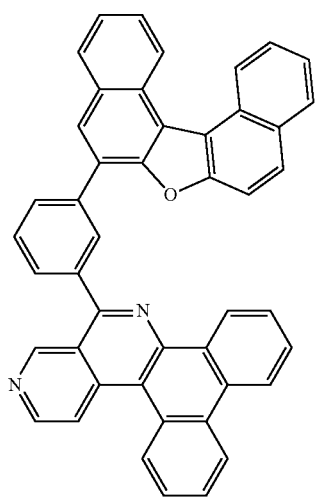
72
232
-continued
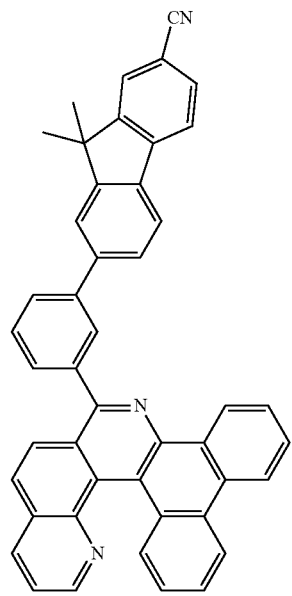
77
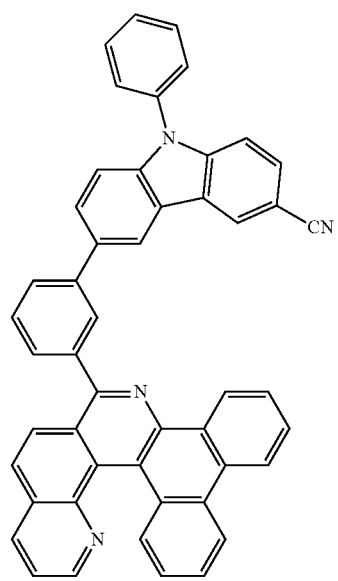
78

233
-continued
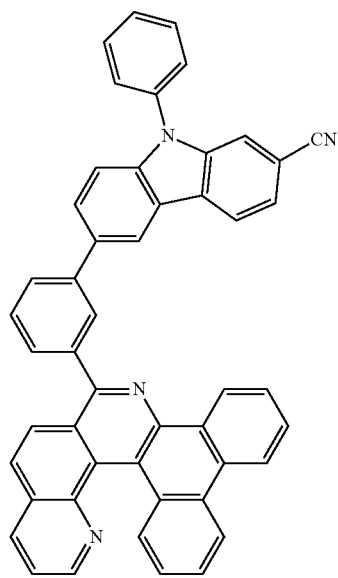
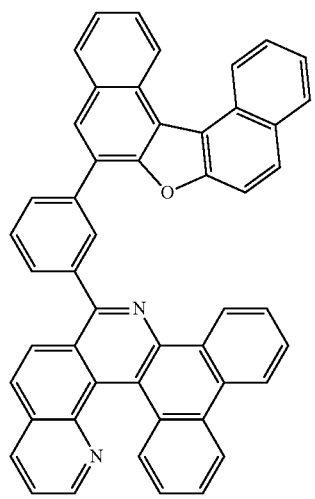
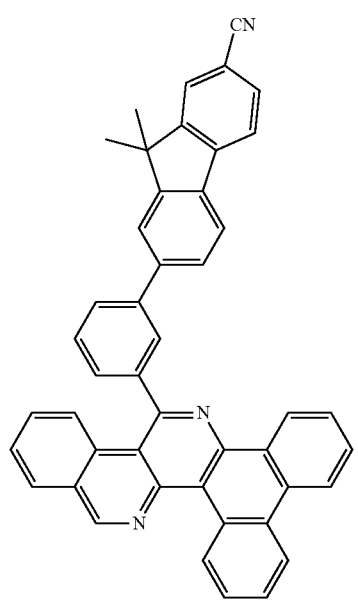
234
-continued
79
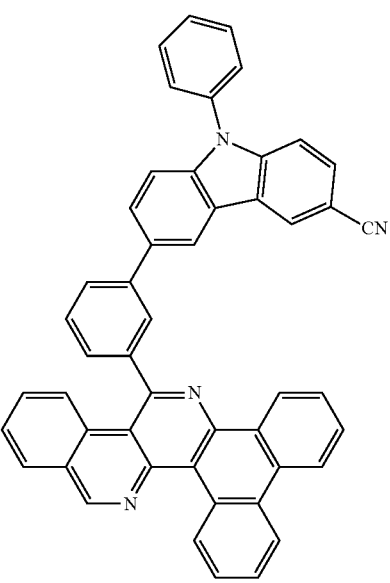
87
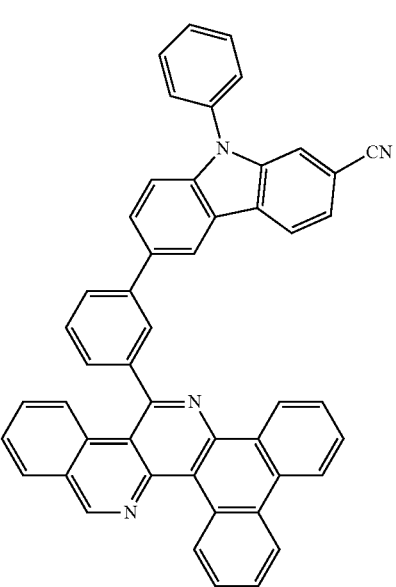

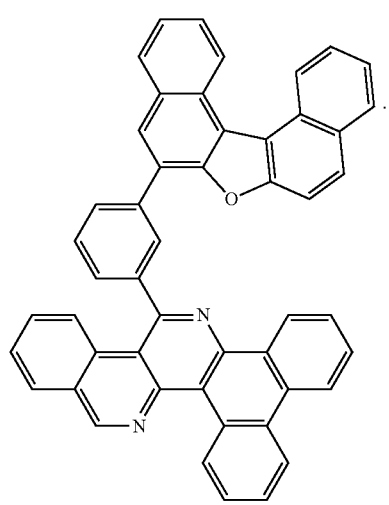
* * * * *